US010117864B2

(12) United States Patent
Beck et al.

(10) Patent No.: US 10,117,864 B2
(45) Date of Patent: Nov. 6, 2018

(54) SUBSTITUTED N-BICYCLO-2-ARYL-QUINOLIN-4-CARBOXAMIDES AND USE THEREOF

(71) Applicant: BAYER PHARMA AKTIENGESELLSCHAFT, Berlin (DE)

(72) Inventors: Hartmut Beck, Wuppertal (DE); Tobias Thaler, Wuppertal (DE); Raimund Kast, Wuppertal (DE); Mark Meininghaus, Wuppertal (DE); Carsten Terjung, Bochum (DE); Uwe Muenster, Wülfrath (DE); Britta Olenik, Bottrop (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/552,997

(22) PCT Filed: Mar. 15, 2016

(86) PCT No.: PCT/EP2016/055489
§ 371 (c)(1),
(2) Date: Aug. 23, 2017

(87) PCT Pub. No.: WO2016/146602
PCT Pub. Date: Sep. 22, 2016

(65) Prior Publication Data
US 2018/0036300 A1 Feb. 8, 2018

(30) Foreign Application Priority Data
Mar. 18, 2015 (EP) .................. 15159572

(51) Int. Cl.
A61K 31/4709 (2006.01)
C07D 215/52 (2006.01)
A61K 31/47 (2006.01)
A61K 31/16 (2006.01)
C07D 409/04 (2006.01)
C07D 405/12 (2006.01)
A61K 31/195 (2006.01)

(52) U.S. Cl.
CPC .............. A61K 31/47 (2013.01); A61K 31/16 (2013.01); A61K 31/195 (2013.01); C07D 215/52 (2013.01); C07D 405/12 (2013.01); C07D 409/04 (2013.01)

(58) Field of Classification Search
CPC .................. C07D 215/52; A61K 31/4709
See application file for complete search history.

(56) References Cited

FOREIGN PATENT DOCUMENTS

| WO | WO 95/32948 A1 | 12/1995 |
|---|---|---|
| WO | WO 96/02509 A1 | 2/1996 |
| WO | WO 97/19926 A1 | 6/1997 |
| WO | WO 00/31038 A1 | 6/2000 |
| WO | WO 2000/064877 | 11/2000 |
| WO | WO 2006/094237 A2 | 9/2006 |
| WO | WO 2011/153553 A2 | 12/2011 |
| WO | WO 2012/122370 A2 | 9/2012 |
| WO | WO 2013/074059 A2 | 5/2013 |
| WO | WO 2013/164326 A1 | 11/2013 |
| WO | WO 2014/117090 A1 | 7/2014 |

OTHER PUBLICATIONS

STN Reg Cmp No. 405070-30-6, entered into STN Apr. 10, 2002. (Year: 2002).*
Lamers et al.: Expert Opinion on Therapeutic Patents, vol. 23, No. 1, pp. 47-44 (2013).
Watanabe et al., The Journal of Biological Chemistry, 1985, vol. 260, No. 11, pp. 7035-7041.
Basu et al., Acta Chemica Scandinavica, 1992, vol. 46, pp. 108-110.
Abramovitz et al., The Journal of Biological Chemistry, 1994, vol. 269, No. 4, pp. 2632-2636.
Sugimoto et al., The Journal of Biological Chemistry, 1994, vol. 269, No. 2, pp. 1356-1360.
Kitanaka et al., Prostaglandins, 1994, vol. 48, pp. 31-41.
Woodward et al., Pharmacological Reviews, 2011, vol. 63, No. 3, pp. 471-538.
Basu, Molecules and Cells, 2010, vol. 30, pp. 383-391.
Agas et al., Journal of Cellular Physiology, 2013, 228: 25-29.
Zhang et al., Frontiers in Pharmacology, 2010, vol. 1., Article 116, pp. 1-7.
Ding et al., The International Journal of Biochemistry & Cell Biology, 2012, vol. 44, pp. 1031-1039.
Ding et al., Journal of Molecular Medicine, 2014, vol. 92, pp. 629-640.
Aihara et al., PLoS One, Jun. 2013, vol. 8, Issue 6, pp. 1-7.
O'Reilly et al., Am. J. Physiol. Lung Cell. Mol. Physiol., 2005, vol. 288, pp. L1010-L1016.
Oga et al., Nature Medicine, 2009, vol. 15, No. 12, pp. 1426-1430.
Olman, Nature Medicine, 2009, vol. 15, No. 12, pp. 1360-1361.
Kanno et al., Arthritis & Rheumatism, 2013, vol. 65, No. 2, pp. 492-502.
Bastiaansen et al. Arthritis & Rheumatism, vol. 65, No. 8, Aug. 2013, pp. 2070-2080.
Ley et al., American Journal of Respiratory Critical Care Medicine, vol. 183, pp. 431-440 (2011).
Strieter et al., Chest, vol. 136, pp. 1364-1370 (2009).
Beck et al., Pneumologe 2013, vol. 10, pp. 105-111.

(Continued)

Primary Examiner — Rebecca L Anderson
Assistant Examiner — Karen Cheng
(74) Attorney, Agent, or Firm — Nixon & Vanderhye P.C.

(57) ABSTRACT

The present application relates to novel substituted N-bicyclo-2-arylquinoline-4-carboxamide derivatives, to processes for preparation thereof, to the use thereof alone or in combinations for treatment and/or prevention of diseases, and to the use thereof for production of medicaments for treatment and/or prevention of diseases, especially for treatment and/or prevention of fibrotic and inflammatory disorders.

20 Claims, No Drawings

(56) References Cited

OTHER PUBLICATIONS

Lettieri et al., Chest, vol. 129, pp. 746-752 (2006).
Behr et al., European Respiratory Journal, 2008, vol. 31, pp. 1357-1367.
M. Humbert et al., Journal of the American College of Cardiology, 2004, vol. 23, No. 12, Suppl. S, pp. 13S-24S.
Naeije, R., Pulmonary Circulation. Diseases and their treatment, 3rd edition, Hodder Arnold Publ., 2011, S. 3.
Blanco et al., American Journal of Respiratory Critical Care Medicine, 2010, vol. 181, pp. 270-278.
D. Stolz et al., European Respiratory Journal, 2008, vol. 32, pp. 619-628.
Ghofrani et al., Herz 2005, vol. 30, pp. 296-302.
Rosenzweig, E. B., Expert Opinion on Emerging Drugs, vol. 11, No. 4, pp. 609-619, 2006.
Montani et al., Pulmonary Circulation. Diseases and their treatment, 3rd edition, 2011, S. 197-206.
Hoeper et al., Journal of the American College of Cardiology, 2009, No. 54, No. 1, Supp. S, pp. S87-S96.
Estenne et al., American Journal of Respiratory Critical Care Medicine, 2002, vol. 166, pp. 440-444.
Barnes, P.J., The New England Journal of Medicine, vol. 343, No. 4, pp. 269-280 (2000).
An International Preliminary Report on Patentability dated Mar. 15, 2016, in a corresponding PCT Application No. PCT/EP2016/055489.

* cited by examiner

SUBSTITUTED N-BICYCLO-2-ARYL-QUINOLIN-4-CARBOXAMIDES AND USE THEREOF

This application is the U.S. national phase of International Application No. PCT/EP2016/055489 filed 15 Mar. 2016, which designated the U.S. and claims priority to EP Patent Application No. 15159572.5 filed 18 Mar. 2015.

The present application relates to novel substituted N-bicyclo-2-arylquinoline-4-carboxamide derivatives, to processes for preparation thereof, to the use thereof alone or in combinations for treatment and/or prevention of diseases, and to the use thereof for production of medicaments for treatment and/or prevention of diseases, especially for treatment and/or prevention of fibrotic and inflammatory disorders.

Prostaglandin F2alpha (PGF2α) is part of the family of bioactive prostaglandins, which are derivatives of arachidonic acid. After release from membrane phospholipids by A2 phospholipases, arachidonic acid is oxidized by cyclooxygenases to prostaglandin H2 (PGH2), which is converted further by PGF synthase to PGF2α. PGF2α can also be formed enzymatically in a much smaller proportion from other prostaglandins such as PGE2 or PGD2 [Watanabe et al., *J. Biol. Chem.* 1985, 260,7035-7041]. PGF2α is not stored, but is released immediately after synthesis, as a result of which it displays its effects locally. PGF2α is an unstable molecule ($t_{1/2}$<1 minute), which is rearranged rapidly by enzymatic means in the lung, liver and kidney to give an inactive metabolite, 15-ketodihydro-PGF2α [Basu et al., *Acta Chem. Scand.* 1992, 46, 108-110]. 15-Ketodihydro-PGF2α is detectable in relatively large amounts in the plasma and later also in the urine, both under physiological and pathophysiological conditions.

The biological effects of PGF2α come about through the binding and activation of a receptor on the membrane, of the PGF2α receptor or else of what is called the FP receptor. The FP receptor is one of the G protein-coupled receptors characterized by seven transmembrane domains. As well as the human FP receptor, it is also possible to clone the FP receptors of mice and rats [Abramovitz et al., *J. Biol. Chem.* 1994, 269, 2632-2636; Sugimoto et al., *J. Biol. Chem.* 1994, 269, 1356-1360; Kitanaka et al., *Prostaglandins* 1994, 48, 31-41]. In humans there exist two isoforms of the FP receptor, FPA and FPB. The FP receptor is the least selective of the prostanoid receptors, since not only PGF2α but also PGD2 and PGE2 bind to it with nanomolar affinities [Woodward et al., *Pharmacol. Rev.* 2011, 63, 471-538]. Stimulation of the FP receptor leads primarily to Gq-dependent activation of phospholipase C, which results in release of calcium and activation of the diacylglycerol-dependent protein kinase C (PKC). The elevated intracellular calcium level leads to calmodulin-mediated stimulation of myosin light-chain kinase (MLCK). As well as coupling to the G protein Gq, the FP receptor, via G12/G13, can also stimulate the Rho/Rho kinase signal transduction cascade and, via Gi coupling, can alternatively stimulate the Raf/MEK/MAP signaling pathway [Woodward et al., *Pharmacol. Rev.* 2011, 63, 471-538].

PGF2α is involved in the regulation of numerous physiological functions, for example ovarian functions, embryonal development, changes in the endometrium, uterine contraction and luteolysis, and in the induction of contractions and birth. PGF2α is also synthesized in epithelial cells in the endometrium, where it stimulates cellular proliferation [Woodward et al., *Pharmacol. Rev.* 2011, 63, 471-538].

In addition, PGF2α is a potent stimulator of smooth muscle constriction, vascular constriction and bronchoconstriction, and is involved in acute and chronic inflammatory processes [Basu, *Mol. Cells* 2010, 30, 383-391]. In the kidney, PGF2α is involved in water absorption, natriuresis and diuresis. In the eyes, PGF2α regulates intraocular pressure. PGF2α also plays an important role in bone metabolism: Prostaglandin stimulates the sodium-dependent transport of inorganic phosphate into osteoblasts and it promotes the release of interleukin-6 and vascular endothelial growth factor (VEGF) in osteoblasts; in addition, PGF2α is a strong mitogen and a survival factor for osteoblasts [Agas et al., *J. Cell Physiol.* 2013, 228, 25-29]. In addition, it was shown that PGF2α-FP receptor activation is involved in various cardiovascular dysfunctions such as myocardial fibrosis, myocardial infarction and hypertension [Zhang et al., *Frontiers in Pharmacol.* 2010, 1, 1-7; Ding et al., *Int. J. Biochem. Cell. Biol.,* 2012, 44, 1031-1039; Ding et al., *J. Mol. Med.,* 2014, 6, 629-640]. Moreover, the PGF2α receptor (FP) is involved in joint disorders and the regulation of the signal cascade of the bone morphogenetic protein (BMP) and promotes differentiation of chondrocytes [Kim et al., *Biochim. Biophys. Acta,* 2015, 1853, 500-512]. More stable analogs of PGF2α have been developed for estrus synchronization and for influencing human reproductive functions, and also for reduction of intraocular pressure for treatment of glaucoma [Basu, *Mol. Cells* 2010, 30, 383-391].

In patients having idiopathic pulmonary fibrosis (IPF), it has been shown that the stable PGF2α metabolite 15-ketodihydro-PGF2α is significantly elevated in the plasma and that the level of 15-ketodihydro-PGF2α correlates with functional parameters, for example forced vital capacity (FVC), the diffusion distance of carbon monoxide in the lung (DLCO) and the 6-minute walk test. In addition, a relationship between elevated plasma 15-ketodihydro-PGF2α and the mortality of patients has been detected [Aihara et al., *PLoS One* 2013, 8, 1-6]. In accordance with this, it has also been shown that stimulation of human lung fibroblasts with naturally occurring silica dusts, which in humans can lead to silicosis in the event of chronic inhalation and as a result to pulmonary fibrosis, brings about significant upregulation of PGF2α synthesis [O'Reilly et al., *Am. J. Physiol. Lung Cell. Mol. Physiol.* 2005, 288, L1010-L1016]. In bleomycin-induced pulmonary fibrosis in mice, the elimination of the FP receptor by knockdown (FP −/−) led to a distinct reduction in pulmonary fibrosis compared to wild-type mice [Oga et al., *Nat. Med.* 2009, 15, 1426-1430]. In FP −/− mice, after administration of bleomycin, a significant reduction in the hydroxyproline content and reduced induction of profibrotic genes in the pulmonary tissue was observed. Moreover, lung function was distinctly improved in FP −/− mice compared to the wild-type mice. In human pulmonary fibroblasts, PGF2α stimulates proliferation and collagen production via the FP receptor. Since this occurs independently of the profibrotic mediator TGFβ, the PGF2α/FP receptor signaling cascade constitutes an independent route in the onset of pulmonary fibrosis [Oga et al., *Nat. Med.* 2009, 15, 1426-1430]. These findings show that the FP receptor is a therapeutic target protein for treatment of IPF [Olman, *Nat. Med.* 2009, 15, 1360-1361]. The involvement of PGF2α in the induction of fibrotic lesions has also been shown in cardiac mouse fibroblasts [Ding et al., *Int. J. Biochem. & Cell Biol.* 2012, 44, 1031-1039], in an animal model of scleroderma [Kanno et al., *Arthritis Rheum.* 2013, 65, 492-502] and in synoviocytes from patients with gonarthrosis [Bastiaansen et al. *Arthritis Rheum.* 2013, 65, 2070-2080].

It is therefore assumed that the FP receptor plays an important role in many disorders, injuries and pathological lesions whose etiology and/or progression is associated with inflammatory events and/or proliferative and fibroproliferative tissue and vessel remodeling. These may especially be disorders of and/or damage to the lung, the cardiovascular system or the kidney, or the disorder may be a blood disorder, a neoplastic disease or another inflammatory disorder.

Disorders of and damage to the lung which may be mentioned in this context are in particular idiopathic pulmonary fibrosis, pulmonary hypertension, bronchiolitis obliterans syndrome (BOS), chronic-obstructive pulmonary disease (COPD), asthma and cystic fibrosis. Disorders of and damage to the cardiovascular system in which the FP receptor is involved are, for example, tissue lesions following myocardial infarction and associated with heart failure. Renal disorders are, for example, renal insufficiency and kidney failure. An example of a blood disorder is sickle cell anemia. Examples of tissue degradation and remodeling in the event of neoplastic processes are the invasion of cancer cells into healthy tissue (formation of metastases) and neovascularization (neoangiogenesis). Other inflammatory diseases where the FP receptor plays a role are, for example, arthrosis and multiple sclerosis.

Idiopathic fibrosis of the lung or idiopathic pulmonary fibrosis (IPF) is a progressive lung disease which, left untreated, results in death within an average of 2.5 to 3.5 years after diagnosis. At the time of diagnosis, patients are usually more than 60 years old, men being slightly more frequently affected than women. Onset of IPF is insidious and characterized by increasing shortness of breath and a dry tickly cough. IPF is one of the group of idiopathic interstitial pneumonias (IIP), a heterogeneous group of pulmonary disorders which are characterized by fibrosis and inflammation of varying severity which can be distinguished using clinical, imaging and fine tissue criteria. Within this group, idiopathic pulmonary fibrosis is of particular significance owing to its frequency and aggressive progression [Ley et al., *Am. J. Respir. Crit. Care Med.* 2011, 183, 431-440]. IPF may either occur sporadically or be hereditary. As yet, the causes are unknown. However, in recent years there have been numerous indications that chronic damage of the alveolar epithelium leads to the release of profibrotic cytokines/mediators followed by increased fibroblast proliferation and increased collagen fiber formation, resulting in a patchy fibrosis and the typical honeycomb structure of the lung [Stricter et al., *Chest* 2009, 136, 1364-1370]. The clinical sequelae of fibrotization are a decrease in the elasticity of the pulmonary tissue, a reduced diffusing capacity and the development of severe hypoxia. With regard to lung function, a corresponding worsening of the forced vital capacity (FVC) and the diffusing capacity (DLCO) can be detected. Essential and prognostically important comorbidities of IPF are acute exacerbation and pulmonary hypertension [von der Beck et al., *Der Pneumologe* 2013, 10(2), 105-111]. The prevalence of pulmonary hypertension in interstitial pulmonary disorders is 10-40% [Lettieri et al., *Chest* 2006, 129, 746-752; Behr et al., *Eur. Respir. J.* 2008, 31, 1357-1367]. Currently, there is no curative treatment for IPF—except for lung transplantation.

Pulmonary hypertension (PH) is a progressive lung disease which, left untreated, results in death within an average of 2.8 years after diagnosis. By definition, the mean pulmonary arterial pressure (mPAP) in case of chronic pulmonary hypertension is >25 mmHg at rest or >30 mmHg under exertion (normal value <20 mmHg). The pathophysiology of pulmonary hypertension is characterized by vasoconstriction and remodeling of the pulmonary vessels. In chronic PH, there is a neomuscularization of primarily unmuscularized lung vessels, and the circumference of the vascular musculature of the vessels already muscularized increases. This increasing obliteration of the pulmonary circulation results in progressive stress on the right heart, which leads to a reduced output from the right heart and eventually ends in right heart failure [M. Humbert et al., *J. Am. Coll. Cardiol.* 2004, 43, 13S-24S]. Idiopathic (or primary) pulmonary arterial hypertension (IPAH) is a very rare disorder, whereas secondary pulmonary hypertension (non-PAH PH, NPAHPH) is very common, and it is thought that the latter is currently the third most common group of cardiovascular disorders after coronary heart disease and systemic hypertension [Naeije, in: A. J. Peacock et al. (Eds.), *Pulmonary Circulation. Diseases and their treatment*, $3^{rd}$ edition, Hodder Arnold Publ., 2011, 3]. Since 2008, pulmonary hypertension is classified in accordance with the Dana Point classification into various sub-groups according to the respective etiology [D. Montana and G. Simonneau, in: A. J. Peacock et al. (Eds.), *Pulmonary Circulation. Diseases and their treatment*, $3^{rd}$ edition, Hodder Arnold Publ., 2011, 197-206].

Despite all the advances in the therapy of PH there is as yet no prospect of cure of this serious disorder. Standard therapies available on the market (for example prostacyclin analogs, endothelin receptor antagonists, phosphodiesterase inhibitors) are able to improve the quality of life, the exercise tolerance and the prognosis of the patients. These are therapeutic principles which are administered systemically and act primarily hemodynamically by modulating vessel tone. The applicability of these medicaments is limited owing to side effects, some of which are serious, and/or complicated administration forms. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently. Currently, these standard therapeutics are approved only for the treatment of pulmonary arterial hypertension (PAH). In the case of secondary forms of PH such as PH-COPD, these therapeutic principles (for example sildenafil, bosentan) fail in clinical studies since, as a result of non-selective vasodilation, they lead to a reduction (desaturation) of the arterial oxygen content in the patients. The probable reason for this is an unfavorable effect on the ventilation-perfusion adaptation in the lung in heterogeneous lung disorders owing to the systemic administration of non-selective vasodilators [I. Blanco et al., *Am. J. Respir. Crit. Care Med.* 2010, 181, 270-278; D. Stolz et al., *Eur. Respir. J.* 2008, 32, 619-628].

Novel combination therapies are one of the most promising future therapeutic options for the treatment of pulmonary hypertension. In this connection, the finding of novel pharmacological mechanisms for the treatment of PH is of particular interest [Ghofrani et al., *Herz* 2005, 30, 296-302; E. B. Rosenzweig, *Expert Opin. Emerging Drugs* 2006, 11, 609-619; T. Ito et al., *Curr. Med. Chem.* 2007, 14, 719-733]. In particular, such novel therapeutic approaches which can be combined with the therapy concepts already on the market may form the basis of a more efficient treatment and thus be of great advantage for the patients.

In the context of the present invention, the term "pulmonary hypertension" includes both primary and secondary sub-forms (NPAHPH) as defined according to the Dana Point classification in accordance with their respective etiology [D. Montana and G. Simonneau, in: A. J. Peacock et al. (Eds.), *Pulmonary Circulation. Diseases and their treatment*, 3$^{rd}$ edition, Hodder Arnold Publ., 2011, 197-206; Hoeper et al., *J. Am. Coll. Cardiol.*, 2009, 54 (1), Suppl. S, S85-S96]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite suppressants), with disorders having a significant venous/capillary component such as pulmonary venoocclusive disorder and pulmonary capillary hemangiomatosis, or with other disorders such as disorders of the thyroid, glycogen storage diseases, Gaucher disease, hereditary teleangiectasia, hemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxemia (e.g. sleep apnea syndrome, alveolar hypoventilation, chronic high-altitude sickness, hereditary deformities). Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumor disorders, parasites, foreign bodies). Less common forms of pulmonary hypertension, such as in patients suffering from sarcoidosis, histiocytosis X or lymphangiomatosis, are summarized in group 5.

Bronchiolitis obliterans syndrome (BOS) is a chronic rejection reaction after a lung transplant. Within the first five years after a lung transplant about 50-60% of all patients are affected, and within the first nine years more than 90% of patients [Estenne et al., *Am. J. Respir. Crit. Care Med.* 2003, 166, 440-444]. The cause of the disease has not been elucidated. In spite of numerous improvements in the treatment of transplantation patients, the number of BOS cases has hardly changed over the last years. BOS is the most important long-term complication in lung transplantations and is considered to be the main reason for the fact that survival rates are still markedly below those for other organ transplantations. BOS is an inflammatory event which is associated with changes in the lung tissue affecting primarily the small respiratory passages. Damage and inflammatory changes of the epithelial cells and the subepithelial structures of the smaller respiratory passages lead, owing to ineffective regeneration of the epithelium and aberrant tissue repair, to excessive fibroproliferation. There is scarring and finally destruction of the bronchi and also clots of granulation tissue in the small respiratory passages and alveolae, occasionally with vascular involvement. The diagnosis is based on the lung function. In BOS, there is a worsening of the FEV1 compared to the average of the two best values measured postoperatively. Currently, there is no curative treatment of BOS. Some of the patients show improvements under intensified immunosuppression; patients not showing any response experience persistent deterioration, such that retransplantation is indicated.

Chronic obstructive pulmonary disease (COPD) is a slowly progressing pulmonary disease characterized by an obstruction of respiratory flow which is caused by pulmonary emphysema and/or chronic bronchitis. The first symptoms of the disease generally manifest themselves during the fourth or fifth decade of life. In the subsequent years of life, shortness of breath frequently becomes worse, and there are instances of coughing combined with copious and purulent sputum, and stenotic respiration extending as far as breathlessness (dyspnea). COPD is primarily a smokers' disease: smoking is the cause of 90% of all cases of COPD and of 80-90% of all COPD-related deaths. COPD is a big medical problem and constitutes the sixth most frequent cause of death worldwide. Of people over the age of 45, about 4-6% are affected. Although the obstruction of the respiratory flow may only be partial and temporal, COPD cannot be cured. Accordingly, the aim of treatment is to improve the quality of life, to alleviate the symptoms, to prevent acute worsening and to slow the progressive impairment of lung function. Existing pharmacotherapies, which have hardly changed over the last two or three decades, are the use of bronchodilators to open blocked respiratory passages, and in certain situations corticosteroids to control the inflammation of the lung [P. J. Barnes, *N Engl. J. Med.* 2000, 343, 269-280]. The chronic inflammation of the lung, caused by cigarette smoke or other irritants, is the driving force of the development of the disease. The basic mechanism comprises immune cells which, during the inflammatory reaction of the lung, release proteases and various cytokines which cause pulmonary emphysema and remodeling of the bronchi.

It is an object of the present invention to identify and provide novel substances that are potent, chemically and metabolically stable, non-prostanoid antagonists of the FP receptor, and are suitable as such for treatment and/or prevention particularly of fibrotic and inflammatory disorders.

WO 95/32948-A1, WO 96/02509-A1, WO 97/19926-A1 and WO 2000/031038-A1, inter alia, disclose 2-arylquinoline-4-carboxamides as NK$_3$ or dual NK$_2$/NK$_3$ antagonists suitable for treatment of disorders of the lung and central nervous system. WO 2000/064877 claims quinoline-4-carboxamide derivatives which can be used as NK$_3$ antagonists for the treatment of various disorders, inter alia of the lung and the central nervous system. WO 2006/094237-A2 discloses quinoline derivatives as sirtuin modulators which can be used for treatment of various kinds of disorders. WO 2011/153553-A2 claims various bicyclic heteroaryl compounds as kinase inhibitors for the treatment of neoplastic disorders in particular. WO 2013/074059-A2 details various quinoline-4-carboxamide derivatives which can serve as inhibitors of cytosine deaminases for boosting DNA transfection of cells. WO 2013/164326-A1 discloses N,3-diphenylnaphthalene-1-carboxamides as agonists of the EP2 prostaglandin receptor for treatment of respiratory pathway disorders. WO 2014/117090-A1 describes various 2-arylquinoline derivatives as inhibitors of metalloenzymes. WO 2012/122370-A2 discloses quinoline-4-carboxamide derivatives which can be used for the treatment of autoimmune and neoplastic disorders.

The present invention relates to compounds of the general formula (I)

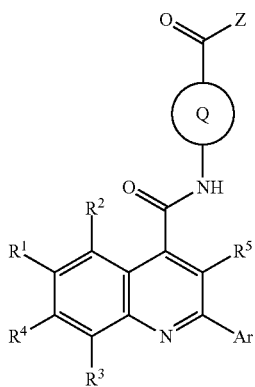

(I)

in which
the ring Q represents a group of the formula

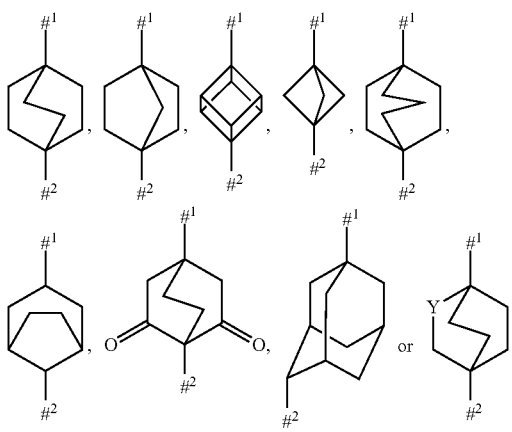

where
- #¹ represents the point of attachment to the carbonyl group,
- #² represents the point of attachment to the nitrogen atom,
- Y represents a group of the formula —O—, —CF$_2$—, —C(H)(OH)—, —CHF— or —C(=O)—
- Z represents —OH or represents a group of the formula —NH—R$^6$ or —NH—SO$_2$—R$^7$ in which
  - R$^6$ represents hydrogen, methyl or ethyl which is up to trisubstituted by fluorine, and
  - R$^7$ represents (C$_1$-C$_2$)-alkyl which is up to trisubstituted by fluorine,
- R$^1$ represents halogen, (C$_1$-C$_4$)-alkyl which is up to pentasubstituted by fluorine, methoxy which is up to trisubstituted by fluorine, (trifluoromethyl)sulfanyl, pentafluorosulfanyl, trimethylsilyl, ethynyl, cyclopropyl or cyclobutyl,
  - where cyclopropyl and cyclobutyl may be up to tetrasubstituted by fluorine,
- R$^2$, R$^3$ and R$^4$ independently of one another represent hydrogen, halogen or methyl which is up to trisubstituted by fluorine,
- R$^5$ represents halogen, (C$_1$-C$_4$)-alkyl which is up to pentasubstituted by fluorine, methoxy which is up to trisubstituted by fluorine, represents hydroxy, methylsulfanyl, cyano, ethenyl, cyclopropyl or cyclobutyl,
  - where cyclopropyl and cyclobutyl may be up to tetrasubstituted by fluorine,
  and
- Ar represents phenyl which may be up to trisubstituted by identical or different substituents from the group consisting of fluorine, chlorine, methyl, which is up to trisubstituted by fluorine, and methoxy, which is up to trisubstituted by fluorine, or represents thienyl which may be mono- or disubstituted by methyl or monosubstituted by chlorine or bromine, or represents thiazolyl or pyridyl, and the N-oxides, salts, solvates, salts of the N-oxides and solvates of the N-oxides and salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Compounds of the invention are likewise N-oxides of the compounds of the formula (I) and the salts, solvates and solvates of the salts thereof.

Preferred salts in the context of the present invention are physiologically acceptable salts of the compounds according to the invention. Also encompassed are salts which are not themselves suitable for pharmaceutical applications but can be used, for example, for the isolation, purification or storage of the compounds of the invention.

Physiologically acceptable salts of the compounds of the invention especially include the salts derived from conventional bases, by way of example and with preference alkali metal salts (e.g. sodium and potassium salts), alkaline earth metal salts (e.g. calcium and magnesium salts), zinc salts and ammonium salts derived from ammonia or organic amines having 1 to 16 carbon atoms, by way of example and with preference ethylamine, diethylamine, triethylamine, DIPEA, monoethanolamine, diethanolamine, triethanolamine, dimethylaminoethanol, diethylaminoethanol, tris(hydroxymethyl)aminomethane, choline (2-hydroxy-N,N,N-trimethylethanaminium), procaine, dicyclohexylamine, dibenzylamine, N-methylmorpholine, N-methylpiperidine, arginine, lysine and 1,2-ethylenediamine.

In addition, physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. It is possible to isolate the stereoisomerically homogeneous constituents from such mixtures of enantiomers and/or diastereomers in a known manner. Preference is given to employing chromatographic methods for this purpose, especially HPLC chromatography on achiral or chiral separation phases. In the case of carboxylic acids as intermediates or end products, separation is alternatively also possible via diastereomeric salts using chiral amine bases.

If the compounds of the invention can occur in tautomeric forms, the present invention encompasses all the tautomeric forms.

The present invention also encompasses all suitable isotopic variants of the compounds according to the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I, and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labeled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. Isotopic variants of the compounds of the invention can be prepared by commonly used processes known to those skilled in the art, for example by the methods described further down and the procedures described in the working examples, by using corresponding isotopic modifications of the respective reagents and/or starting compounds.

The present invention additionally also encompasses prodrugs of the compounds of the invention. The term "prodrugs" refers here to compounds which may themselves be biologically active or inactive, but are converted while present in the body, for example by a metabolic or hydrolytic route, to compounds of the invention.

The present invention comprises as prodrugs in particular hydrolyzable ester derivatives of the inventive carboxylic acids of the formula (I) [with Z=OH]. These are understood to mean esters which can be hydrolyzed to the free carboxylic acids, as the main biologically active compounds, in physiological media under the conditions of the biological tests described hereinbelow and in particular in vivo by an enzymatic or chemical route. $(C_1-C_4)$-Alkyl esters, in which the alkyl group can be straight-chain or branched, are preferred as such esters. Particular preference is given to methyl, ethyl or tertbutyl esters.

In the context of the present invention, unless specified otherwise, the substituents are defined as follows:

In the context of the invention, $(C_1-C_4)$-alkyl is a straight-chain or branched alkyl radical having 1 to 4 carbon atoms. Preferred examples include: methyl, ethyl, n-propyl, isopropyl, n-butyl, isobutyl, secbutyl and tert-butyl.

Halogen in the context of the invention includes fluorine, chlorine, bromine and iodine.

In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred. Particular preference is given to substitution by one substituent.

In the context of the present invention, preference is given to compounds of the formula (I)

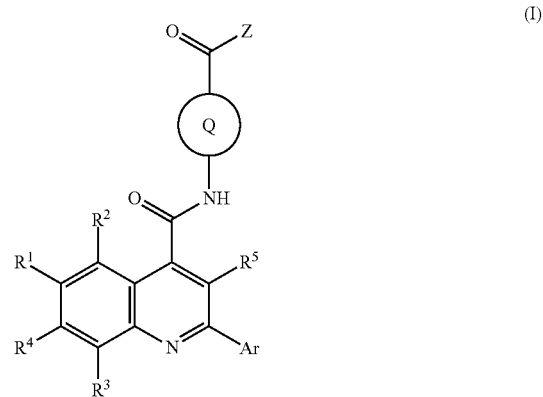

in which
the ring Q represents a group of the formula

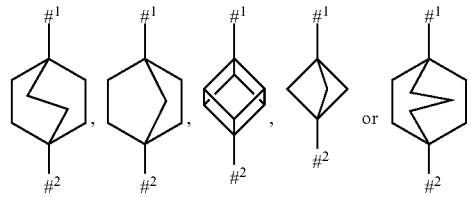

where
$\#^1$ represents the point of attachment to the carbonyl group,
$\#^2$ represents the point of attachment to the nitrogen atom,
Z represents —OH or represents a group of the formula —NH—R$^6$ or —NH—SO$_2$—R$^7$ in which
  R$^6$ represents hydrogen, methyl or ethyl which is up to trisubstituted by fluorine, and
  R$^7$ represents $(C_1-C_2)$-alkyl which is up to trisubstituted by fluorine,
R$^1$ represents halogen, $(C_1-C_4)$-alkyl which is up to pentasubstituted by fluorine, methoxy which is up to trisubstituted by fluorine, (trifluoromethyl)sulfanyl, pentafluorosulfanyl, trimethylsilyl, cyclopropyl or cyclobutyl,
  where cyclopropyl and cyclobutyl may be up to tetrasubstituted by fluorine,
R$^2$, R$^3$ and R$^4$ independently of one another represent hydrogen, halogen or methyl which is up to trisubstituted by fluorine,
R$^5$ represents halogen, $(C_1-C_4)$-alkyl which is up to pentasubstituted by fluorine, methoxy which is up to trisubstituted by fluorine, represents hydroxy, methylsulfanyl, cyclopropyl or cyclobutyl, where cyclopropyl and cyclobutyl may be up to tetrasubstituted by fluorine,
and
Ar represents phenyl which may be up to trisubstituted by identical or different substituents from the group consisting of fluorine, chlorine, methyl, which is up to trisubstituted by fluorine, and methoxy, which is up to trisubstituted by fluorine, or represents thienyl, thiazolyl or pyridyl,
and the N-oxides, salts, solvates, salts of the N-oxides and solvates of the N-oxides and salts thereof.

Preference is given in the context of the present invention to compounds of the formula (I) in which the ring Q represents a group of the formula

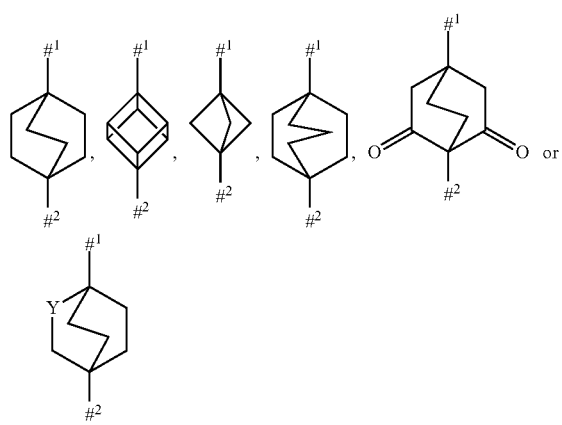

where
$\#^1$ represents the point of attachment to the carbonyl group,
$\#^2$ represents the point of attachment to the nitrogen atom,
Y represents a group of the formula —C(H)(OH)— or —CHF—
Z represents —OH,
$R^1$ represents chlorine, bromine, iodine, methyl, isopropyl, tert-butyl, difluoromethyl, trifluoromethyl, trifluoromethoxy, (trifluoromethyl)sulfanyl, trimethylsilyl, ethynyl, cyclopropyl or cyclobutyl,
$R^2$ represents hydrogen,
$R^3$ and $R^4$ independently of one another represent hydrogen, chlorine or methyl,
$R^5$ represents fluorine, chlorine, bromine, iodine, methyl, ethyl, propyl, monofluoromethyl, difluoromethyl, trifluoromethyl, methoxy, trifluoromethoxy, hydroxy, methylsulfanyl or cyclopropyl,
and
Ar represents phenyl which may be mono- or disubstituted by fluorine, represents thienyl which may be mono- or disubstituted by methyl or monosubstituted by chlorine or bromine or represents a group of the formula

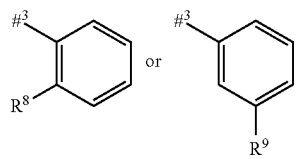

where
$\#^3$ represents the point of attachment to the quinoline ring,
$R^8$ represents chlorine or methyl, and
$R^9$ represents chlorine or methoxy,
and the salts, solvates and solvates of the salts thereof.

Preference is given in the context of the present invention to compounds of the formula (I) in which the ring Q represents a group of the formula

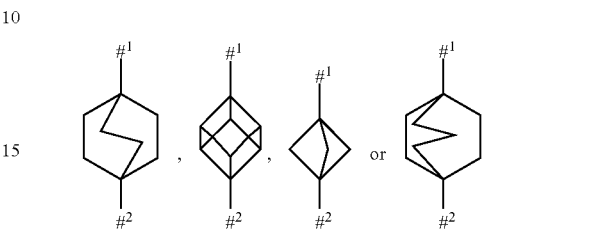

Z represents —OH,
$R^1$ represents chlorine, bromine, iodine, methyl, isopropyl, tert-butyl, difluoromethyl, trifluoromethyl, trifluoromethoxy, (trifluoromethyl)sulfanyl, trimethylsilyl, cyclopropyl or cyclobutyl,
$R^2$ represents hydrogen,
$R^3$ and $R^4$ independently of one another represent hydrogen, chlorine or methyl,
$R^5$ represents fluorine, chlorine, bromine, iodine, methyl, ethyl, propyl, monofluoromethyl, difluoromethyl, trifluoromethyl, methoxy, trifluoromethoxy, hydroxy, methylsulfanyl or cyclopropyl, and
Ar represents phenyl which may be mono- or disubstituted by fluorine, represents thienyl, or represents a group of the formula

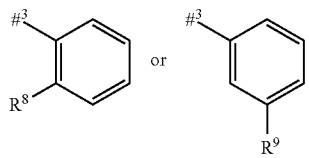

where
$\#^3$ represents the point of attachment to the quinoline ring,
$R^8$ represents chlorine or methyl, and
$R^9$ represents chlorine or methoxy,
and the salts, solvates and solvates of the salts thereof.

Particular preference in the context of the present invention is given to compounds of the formula (I) in which the ring Q represents a group of the formula

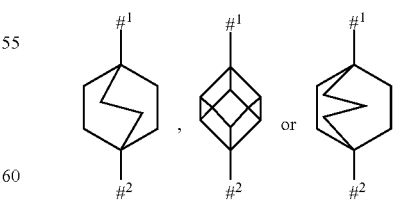

Z represents a group of the formula —OH,
$R^1$ represents chlorine, bromine, iodine, methyl, tert-butyl, difluoromethyl, trifluoromethyl, trimethylsilyl, ethynyl or cyclopropyl,
$R^2$ represents hydrogen, R³ and R⁴ independently of one another represent hydrogen, chlorine or methyl,
where at least one of the radicals R³ and R⁴ represents hydrogen, R⁵ represents fluorine, chlorine, methyl, ethyl, methoxy, hydroxy, methylsulfanyl or cyclopropyl, and Ar represents phenyl which may be monosubstituted by fluorine, and the salts, solvates and solvates of the salts thereof.

Particular preference in the context of the present invention is given to compounds of the formula (I) in which the ring Q represents a group of the formula

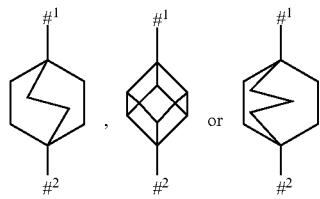

Z represents —OH,

R¹ represents chlorine, bromine, iodine, methyl, tert-butyl, difluoromethyl, trifluoromethyl, trimethylsilyl or cyclopropyl, R² represents hydrogen, R³ and R⁴ independently of one another represent hydrogen, chlorine or methyl,
where at least one of the radicals R³ and R⁴ represents hydrogen, R⁵ represents fluorine, chlorine, methyl, ethyl, methoxy, hydroxy, methylsulfanyl or cyclopropyl, and Ar represents phenyl which may be monosubstituted by fluorine, and the salts, solvates and solvates of the salts thereof.

Very particular preference in the context of the present invention is given to compounds of the formula (I) in which the ring Q represents a group of the formula

Z represents a group of the formula —OH,

R¹ represents ethynyl, bromine or iodine,

R², R³ and R⁴ each represent hydrogen,

R⁵ represents chlorine, methyl, methylsulfanyl or cyclopropyl, and

Ar represents phenyl, and the salts, solvates and solvates of the salts thereof.

Very particular preference in the context of the present invention is given to compounds of the formula (I) in which the ring Q represents a group of the formula

Z represents —OH,

R¹ represents bromine or iodine,

R², R³ and R⁴ each represent hydrogen,

R⁵ represents chlorine, methyl, methylsulfanyl or cyclopropyl, and

Ar represents phenyl, and the salts, solvates and solvates of the salts thereof.

A particular embodiment of the present invention comprises compounds of the formula (I) in which Z represents a group of the formula —OH, and the salts, solvates and solvates of the salts thereof.

A further particular embodiment of the present invention encompasses compounds of the formula (I) in which Z represents a group of the formula —NH₂, and the salts, solvates and solvates of the salts thereof.

A further particular embodiment of the present invention encompasses compounds of the formula (I) in which the ring Q represents a group of the formula

and the salts, solvates and solvates of the salts thereof.

A further particular embodiment of the present invention encompasses compounds of the formula (I) in which the ring Q represents a group of the formula

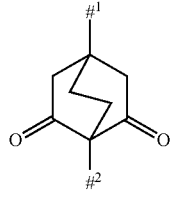

and the salts, solvates and solvates of the salts thereof.

A further particular embodiment of the present invention encompasses compounds of the formula (I) in which the ring Q represents a group of the formula

where
Y represents a group of the formula —C(H)(OH)— or —CHF—
and the salts, solvates and solvates of the salts thereof.

A further particular embodiment of the present invention encompasses compounds of the formula (I) in which the ring Q represents a group of the formula

and the salts, solvates and solvates of the salts thereof.

A further particular embodiment of the present invention encompasses compounds of the formula (I) in which the ring Q represents a group of the formula

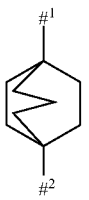

and the salts, solvates and solvates of the salts thereof.

A further particular embodiment of the present invention encompasses compounds of the formula (I) in which
$R^1$ represents chlorine, bromine, iodine, methyl, isopropyl, tert-butyl, difluoromethyl, trifluoromethyl, trifluoromethoxy, (trifluoromethyl)sulfanyl, trimethylsilyl, cyclopropyl or cyclobutyl,
$R^2$ represents hydrogen, and
$R^3$ and $R^4$ independently of one another represent hydrogen, chlorine or methyl,
where at least one of the radicals $R^3$ and $R^4$ represents hydrogen,
and the salts, solvates and solvates of the salts thereof.

A further particular embodiment of the present invention encompasses compounds of the formula (I) in which
$R^1$ represents chlorine, bromine, iodine, methyl, isopropyl, tert-butyl, difluoromethyl, trifluoromethyl, trifluoromethoxy, (trifluoromethyl)sulfanyl, trimethylsilyl, ethynyl, cyclopropyl or cyclobutyl,
$R^2$ represents hydrogen, and
$R^3$ and $R^4$ independently of one another represent hydrogen, chlorine or methyl,
where at least one of the radicals $R^3$ and $R^4$ represents hydrogen,
and the salts, solvates and solvates of the salts thereof.

A further particular embodiment of the present invention encompasses compounds of the formula (I) in which
$R^1$ represents ethynyl, and
$R^2$, $R^3$ and $R^4$ each represent hydrogen,
and the salts, solvates and solvates of the salts thereof.

A further particular embodiment of the present invention encompasses compounds of the formula (I) in which
$R^1$ represents bromine, and
$R^2$, $R^3$ and $R^4$ are each hydrogen,
and the salts, solvates and solvates of the salts thereof.

A further particular embodiment of the present invention encompasses compounds of the formula (I) in which
X represents iodine, and
$R^2$, $R^3$ and $R^4$ are each hydrogen,
and the salts, solvates and solvates of the salts thereof.

A further particular embodiment of the present invention encompasses compounds of the formula (I) in which
$R^5$ represents fluorine, chlorine, methyl, ethyl, methoxy, hydroxy, methylsulfanyl or cyclopropyl,
and the salts, solvates and solvates of the salts thereof.

A further particular embodiment of the present invention encompasses compounds of the formula (I) in which
Ar represents a group of the formula

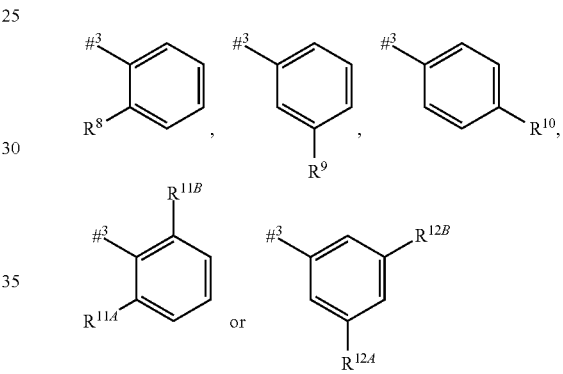

where
³ represents the point of attachment to the quinoline ring,
$R^8$ represents fluorine, chlorine or methyl, and
$R^9$ represents fluorine, chlorine or methoxy,
$R^{10}$ represents fluorine or chlorine,
$R^{11A}$, $R^{11B}$, $R^{12A}$, $R^{12B}$ each independently of one another represent fluorine, or
Ar represents thienyl,
and the salts, solvates and solvates of the salts thereof.

A further particular embodiment of the present invention encompasses compounds of the formula (I) in which
Ar represents thienyl which may be mono- or disubstituted by methyl or monosubstituted by chlorine or bromine,
and the salts, solvates and solvates of the salts thereof.

A further particular embodiment of the present invention encompasses compounds of the formula (I) in which
Ar represents phenyl which may be mono- or disubstituted by fluorine, represents thienyl, or is a group of the formula

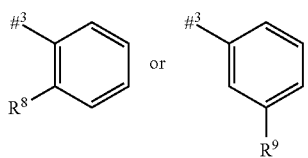

where

³ represents the point of attachment to the quinoline ring, $R^8$ represents chlorine or methyl, and $R^9$ represents chlorine or methoxy, and the salts, solvates and solvates of the salts thereof.

A further particular embodiment of the present invention encompasses compounds of the formula (I) in which Ar is phenyl which may be mono- or disubstituted identically or differently by fluorine and chlorine, or is thienyl, and the salts, solvates and solvates of the salts thereof.

A further particular embodiment of the present invention encompasses compounds of the formula (I) in which Ar represents phenyl, and the salts, solvates and solvates of the salts thereof.

The individual radical definitions specified in the respective combinations or preferred combinations of radicals are, independently of the respective combinations of the radicals specified, also replaced as desired by radical definitions of other combinations.

Very particular preference is given to combinations of two or more of the abovementioned preferred ranges and embodiments.

The radical definitions specified as preferred, particularly preferred and very particularly preferred apply both to the compounds of the formula (I) and correspondingly toward all intermediates.

The invention furthermore provides a process for preparing compounds of the formula (I) according to the invention, characterized in that a compound of the formula (II)

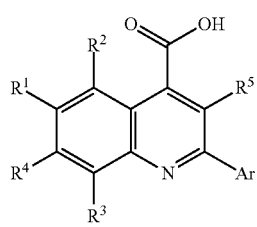

(II)

in which $R^1$, $R^2$, $R^3$, $R^4$, $R^5$ and Ar have the definitions given above, with activation of the carboxylic acid function is coupled with an amine compound of the formula (III)

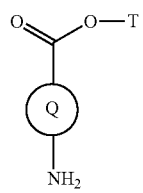

(III)

in which Q has the meaning given above, and

T represents an ester protective group, in particular $(C_1-C_4)$-alkyl, benzyl or 4-methylphenylsulfonylethyl, to give a compound of the formula (IV)

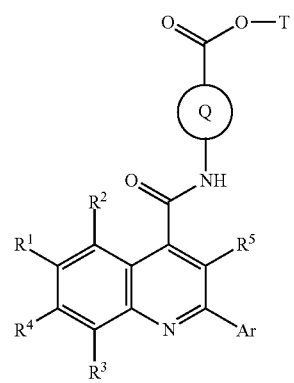

(IV)

in which $R^1$, $R^2$, $R^3$, $R^4$, $R^5$, Ar, Q and T have the meanings given above, and then the ester radical T is eliminated to give the inventive carboxylic acid of the formula (I-A)

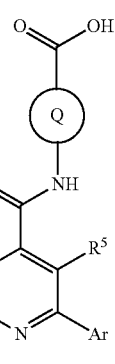

(I-A)

in which $R^1$, $R^2$, $R^3$, $R^4$, $R^5$, Ar and Q have the meanings given above, and the carboxylic acid (I-A) is optionally converted in a further step into the corresponding acid chloride of the formula (V)

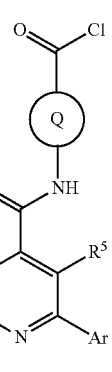

(V)

in which $R^1$, $R^2$, $R^3$, $R^4$, $R^5$, Ar and Q have the meanings given above, and the latter is subsequently reacted with a compound of the formula (VI)

in which R⁶ has the definition given above,
to give the inventive carboxamide of the formula (I-B)

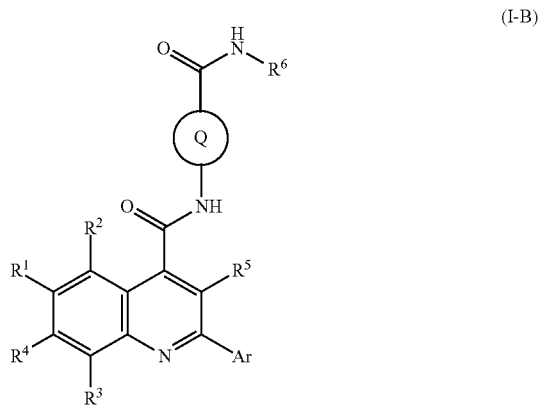

in which $R^1$, $R^2$, $R^3$, $R^4$, $R^5$, $R^6$, Ar and Q have the meanings given above,
and the compounds of the formulae (I-A) and (I-B) thus obtained are optionally converted with the appropriate (i) solvents and/or (ii) bases or acids to the solvates, salts and/or solvates of the salts thereof.

The coupling reaction (II)+(III)→(IV) [amide formation] can be effected either by a direct route with the aid of a condensing or activating agent or via the intermediate stage of a carbonyl chloride or carbonyl imidazolide obtainable from (II).

Suitable for use as condensing agents or activating agents are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, α-chlorenamines such as 1-chloro-N,N,2-trimethylprop-1-en-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (PPA), diethyl cyanophosphonate, diphenylphosphoryl azide (DPPA), bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), O-(1H-6-chlorobenzotriazol-1-yl)-1,1,3,3-tetramethyluronium tetrafluoroborate (TCTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate, or tertiary amine bases such as triethylamine, N-methylmorpholine (NMM), N-methylpiperidine (NMP), DIPEA, pyridine or 4-N,N-dimethylaminopyridine (DMAP). The condensing agent or activating agent preferably used is O-(7-azabenzotriazol-1-yl)-N,N,N',N'-tetramethyluronium hexafluorophosphate (HATU) in combination with DIPEA.

In the case of a two-stage reaction regime via the carbonyl chlorides or carbonyl imidazolides obtainable from (II), the coupling with the amine component (III) is conducted in the presence of a customary base, for example sodium carbonate or potassium carbonate, triethylamine, DIPEA, N-methylmorpholine (NMM), N-methylpiperidine (NMP), pyridine, 2,6-dimethylpyridine, 4-N,N-dimethylaminopyridine (DMAP), 1,8-diazabicyclo[5.4.0]undec-7-ene (DBU), 1,5-diazabicyclo[4.3.0]non-5-ene (DBN), sodium methoxide or potassium methoxide, sodium ethoxide or potassium ethoxide, sodium tert-butoxide or potassium tert-butoxide, or sodium hydride or potassium hydride.

The preferred coupling method is the direct reaction of (II) with the amine compound (III) with the aid of a condensing or activating agent.

Inert solvents for the coupling reactions mentioned are—according to the method used—for example ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP). It is also possible to use mixtures of such solvents. Preference is given to using N,N-dimethylformamide. The couplings are generally conducted within a temperature range from 0° C. to +130° C., preferably at +20° C. to +80° C.

The carbonyl imidazolides themselves are obtainable by known methods by reaction of (II) with N,N'-carbonyldiimidazole (CDI) at elevated temperature (+60° C. to +150° C.) in a correspondingly relatively high-boiling solvent such as N,N-dimethylformamide (DMF). The preparation of the carbonyl chlorides is accomplished in a customary manner by treating (II) with thionyl chloride or oxalyl chloride in an inert solvent such as dichloromethane.

Suitable ester protective groups T are, in general, all protective groups known to the person skilled in the art, for example suitably substituted methyl, such as methylthiomethyl (MTM), tetrahydropyranyl (THP), 2-(trimethylsilyl)ethoxymethyl (SEM), benzyloxymethyl (BOM), phenacyl and N-phthalimidomethyl, suitably 2-substituted ethyl, such as 4-methylphenylsulfonylethyl (TSE), 2,2,2-trichloroethyl, 2-(trimethylsilyl)ethyl and 2-(2'-pyridyl)ethyl (PET), allyl, benzyl, suitably substituted benzyl, such as diphenylmethyl (DPM), bis(ortho-nitrophenyl)methyl, 9-anthrylmethyl, 2,4,6-trimethylbenzyl, 4-bromobenzyl, 4-methoxybenzyl (PMB), piperonyl and suitably substituted silyl, such as triethylsilyl (TES), tert-butyldimethylsilyl (TBDMS) and di-tert-butylmethylsilyl (DTBMS); in particular and preferably, the ester protective group T used in the process according to the invention is $(C_1\text{-}C_4)$-alkyl, benzyl or 4-methylphenylsulfonylethyl.

The detachment of the ester protective group T in process step (IV)→(I-A) is conducted by customary methods, by treating the ester in an inert solvent with an acid or a base, with conversion of the salt of the carboxylic acid initially formed in the latter variant to the free carboxylic acid by subsequent treatment with acid. In the case of the tert-butyl esters, the ester cleavage is preferably effected with an acid. Methyl and ethyl ester are preferably cleaved using a base. Benzyl esters can alternatively also be cleaved by hydrogenation (hydrogenolysis) in the presence of a suitable catalyst, for example palladium on activated carbon. Silyl esters can be cleaved by treatment with acids or fluorides, e.g. tetrabutylammonium fluoride.

Suitable inert solvents for these reactions are water and the organic solvents customary for ester cleavage. These include in particular alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetonitrile, N,N-dimethylformamide or dimethyl sulfoxide. It is equally possible to use mixtures of these solvents. In the case of a basic ester hydrolysis, preference is given to using mixtures of water with tetrahydrofuran, 1,4-dioxane, methanol and/or ethanol. Preference is given to using dichloromethane in the case of the reaction with trifluoroacetic acid, and 1,4-dioxane in the case of the reaction with hydrogen chloride, in each case under anhydrous conditions.

Suitable bases for a hydrolysis reaction are the customary inorganic bases. These especially include alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to using aqueous lithium hydroxide solution or sodium hydroxide solution.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, optionally with addition of water. Preference is given to using hydrogen chloride or trifluoroacetic acid.

The ester cleavage is generally conducted within a temperature range from −20° C. to +100° C., preferably at 0° C. to +80° C.

The acid chloride (V) is prepared in a customary manner by treating the carboxylic acid (I-A) with oxalyl chloride or thionyl chloride in an inert solvent such as dichloromethane, trichloromethane or 1,2-dichloroethane, optionally with use of a small amount of N,N-dimethylformamide as catalyst. The reaction is generally conducted at a temperature of 0° C. to +30° C.

The subsequent amide formation in process step (V)+(VI)→(I-B) is usually effected in the presence of a relatively large excess of the amine component (VI). Alternatively, it is also possible to use a standard tertiary amine base as auxiliary base, for example triethylamine, DIPEA, N-methylmorpholine (NMM), N-methylpiperidine (NMP), pyridine, 2,6-dimethylpyridine or 4-N,N-dimethylaminopyridine (DMAP).

Inert solvents for this reaction are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP), or else water. It is likewise possible to use mixtures of such solvents. Preference is given to using water or a mixture of water with tetrahydrofuran, 1,4-dioxane, 1,2-dimethoxyethane or acetone. The reaction is generally conducted at a temperature of 0° C. to +40° C.

Inventive compounds of the formula (I) in which Z is a group of the formula —NH—SO$_2$—R$^7$ can be obtained in analogy to the above-described amide formation (V)+(VI)→(I-B) by base-mediated reaction of the acid chloride (V) with a compound of the formula (VI-A)

(VI-A)

in which R$^7$ has the definition given above. The reaction is preferably effected using sodium hydride as base in tetrahydrofuran or N,N-dimethylformamide as inert solvent at a temperature of 0° C. to +80° C. Further inventive compounds of the formula (I) can, if appropriate, also be prepared by transformations of functional groups of individual radicals or substituents, especially those listed under R$^1$ and R$^5$, proceeding from other compounds of the formula (I) or precursors thereof obtained by the above processes. These transformations are conducted by customary methods familiar to the person skilled in the art and include, for example, reactions such as nucleophilic or electrophilic substitution reactions, transition-metal-mediated coupling reactions, preparation and addition reactions of metal organyls (e.g. Grignard compounds or lithium organyls), oxidation and reduction reactions, hydrogenation, halogenation (e.g. fluorination, bromination), dehalogenation, amination, alkylation and acylation, the formation of carboxylic esters, carboxamides and sulfonamides, ester cleavage and hydrolysis, and the introduction and removal of temporary protecting groups.

Depending on their respective substitution pattern, the compounds of the formula (II) can be prepared by, in analogy to processes known from the literature, reacting either

[A] an isatin derivative of the formula (VII)

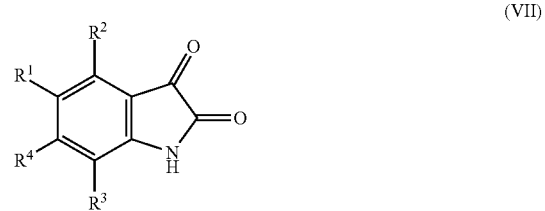

(VII)

in which R$^1$, R$^2$, R$^3$ and R$^4$ have the definitions given above in an acid- or base-mediated condensation reaction with a ketomethylene compound of the formula (VIII)

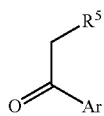
(VIII)

in which R⁵ and Ar have the definitions given above
to give the compound of the formula (II)

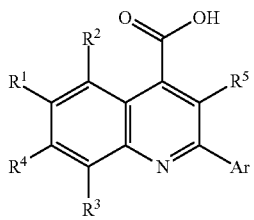
(II)

in which R¹, R², R³, R⁴, R⁵ and Ar have the definitions given above,
or
[B] an ortho-aminophenylacetic ester of the formula (IX)

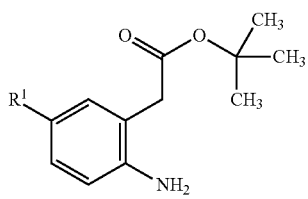
(IX)

in which R¹ has the definition given above,
is reacted in an acid-induced condensation reaction with a diketo compound of the formula (X)

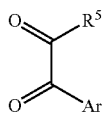
(X)

in which R⁵ and Ar have the definitions given above
to give a compound of the formula (II-A)

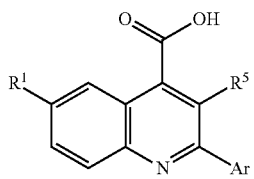
(II-A)

in which R¹, R⁵ and Ar have the definitions given above.

The condensation of the isatin derivative (VII) with the ketomethylene compound (VIII) to give the quinoline-4-carboxylic acid (II) in variant [A] can be achieved by heating the reactants in the presence of an aqueous acid, such as sulfuric acid or concentrated hydrochloric acid, or in the presence of an aqueous base, such as sodium hydroxide or potassium hydroxide solution. In the case of use of an acid, preference is given to using acetic acid as solvent for the reaction; in the case of a basic reaction regime, preference is given to using an alcoholic solvent such as methanol or ethanol. The condensation is generally conducted within a temperature range from +70° C. to +120° C. [cf., for example, K. Lackey and D. D. Sternbach, *Synthesis,* 1993, 993-997; A. N. Boa et al., *Bioorg. Med. Chem.* 2005, 13 (6), 1945-1967].

The condensation reaction according to variant [B] to give the quinoline-4-carboxylic acid (II-A) is effected in an analogous manner by heating the ortho-aminophenylacetic ester (IX) and the diketone (X) with aqueous acid, especially concentrated hydrochloric acid. The inert solvent used for the reaction here too is preferably acetic acid.

The ortho-aminophenylacetic ester (IX) itself can be obtained in accordance with a process described in the literature, by base-mediated reaction of the α-chloroacetic ester (XI)

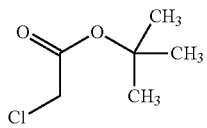
(XI)

with the nitrophenyl derivative (XII)

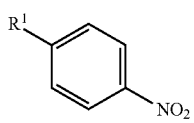
(XII)

in which R¹ has the definition given above,
to give the ortho-nitrophenylacetic ester (XIII)

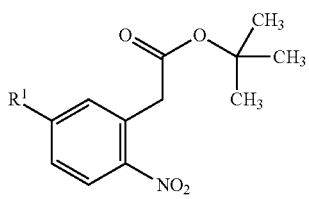
(XIII)

in which R¹ has the definition given above,
and subsequently reducing the nitro group, for example by catalytic hydrogenation [cf. P. Beier et al., *J. Org. Chem.* 2011, 76, 4781-4786].

The compounds of the formula (III) are commercially available or their preparation is described in the literature, or they can be prepared proceeding from other commercially available compounds by methods known in the literature that are familiar to those skilled in the art.

The amine functionality of the compounds of the formula (III) can be established by known Curtius rearrangement from the corresponding carboxylic acid azide. The carboxylic acid is initially converted into the acid azide following activation of the acid functionality, for example as carbonyl chloride or carboxylic anhydride, and then directly reacted with sodium azide. Alternatively, the carboxylic acid can be reacted with diphenylphosphoryl azidate (DPPA) under basic conditions, for example with triethylamine as base, and in the presence of an alcohol such as tert-butanol or benzyl alcohol, at elevated temperatures (cf. *J. Am. Chem. Soc.,* 1972, 94 (17), 6203-6205). The resulting protected amines can then be deprotected, usually, in the case of a Boc protective group, by acidic hydrolysis with addition of, for example, hydrochloric acid or trifluoroacetic acid or, in the case of a Z protective group, by hydrogenation to the corresponding amine. The temperature range for the Curtius rearrangement is usually in the range +40° C. to +120° C. It is possible to add inert solvents such as toluene or THF. Further variants of the rearrangement of carboxylic acid to amine are easily accessible to the person skilled in the art from the relevant literature.

The compounds of the formulae (VI), (VI-A), (VI-B), (VII), (VIII), (X), (XI) and (XII) are likewise commercially available or described as such in the literature, or they can be prepared in a simple manner proceeding from other commercially available compounds in analogy to methods known from the literature.

Detailed procedures and further literature references can also be found in the experimental section, in the section on the preparation of the starting compounds and intermediates.

The preparation of the compounds of the invention and their precursors can be illustrated by way of example by the following reaction schemes:

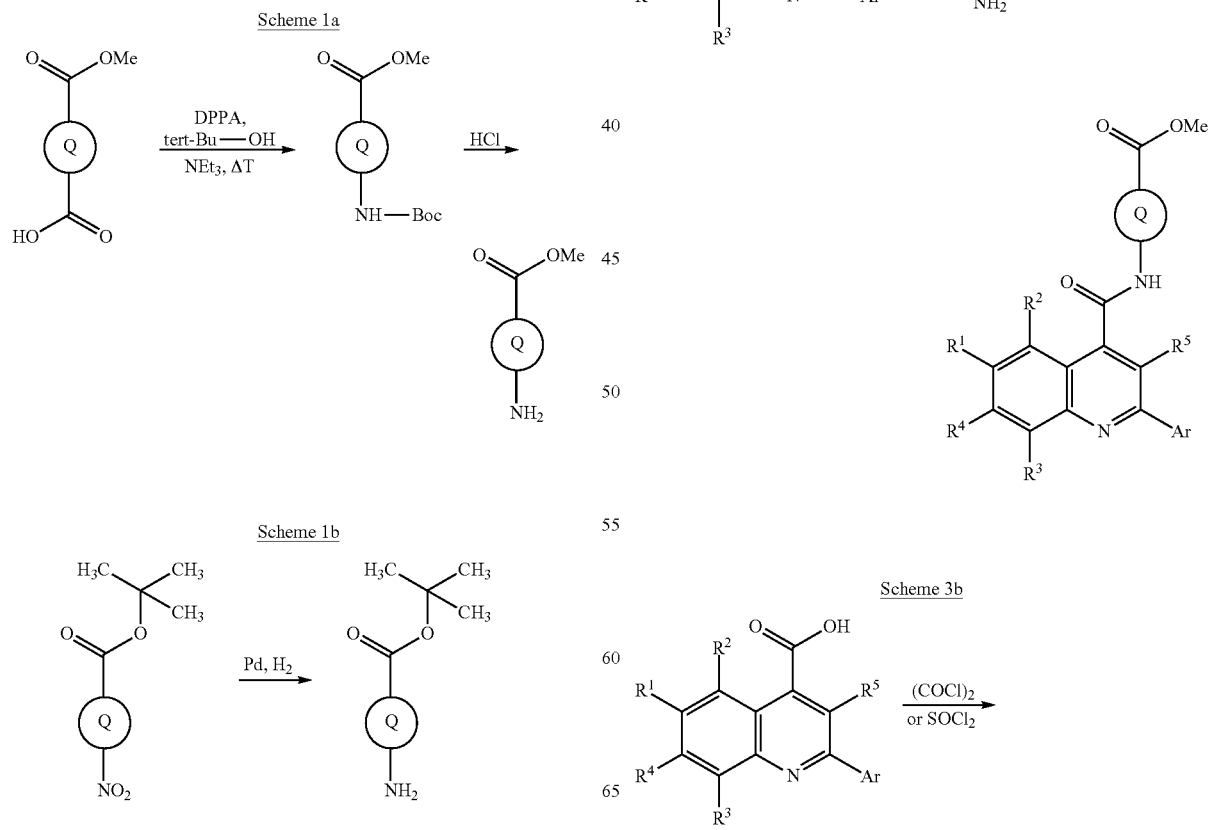

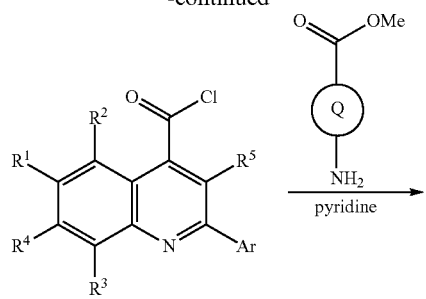
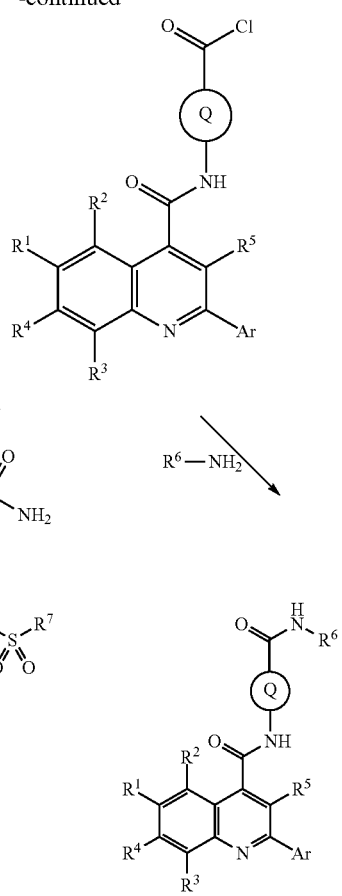
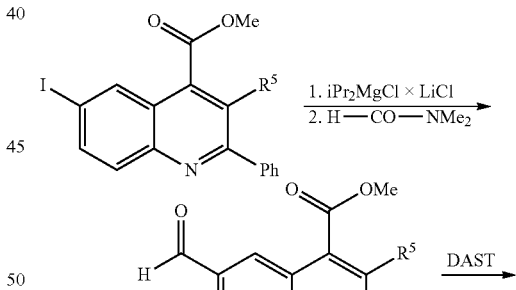
Scheme 4
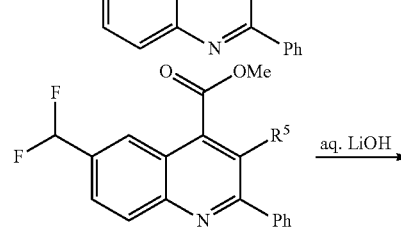
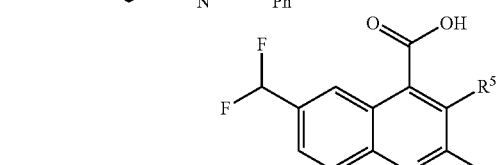
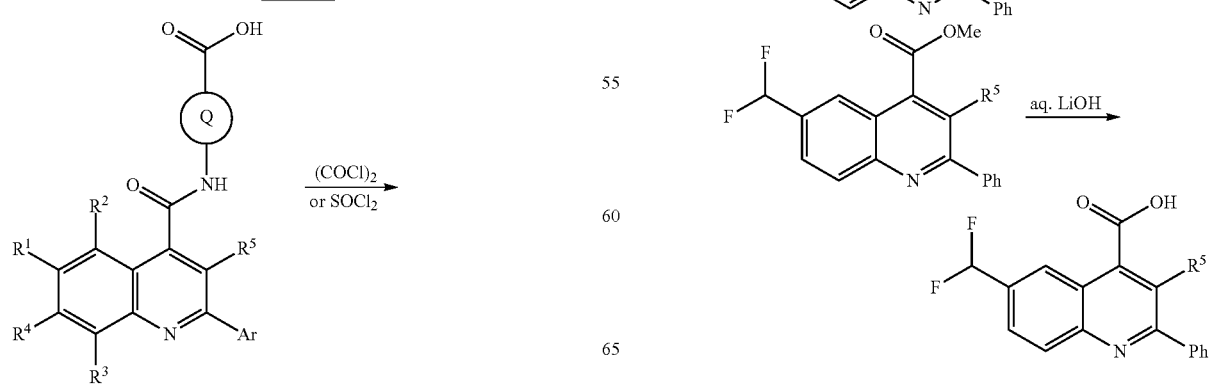

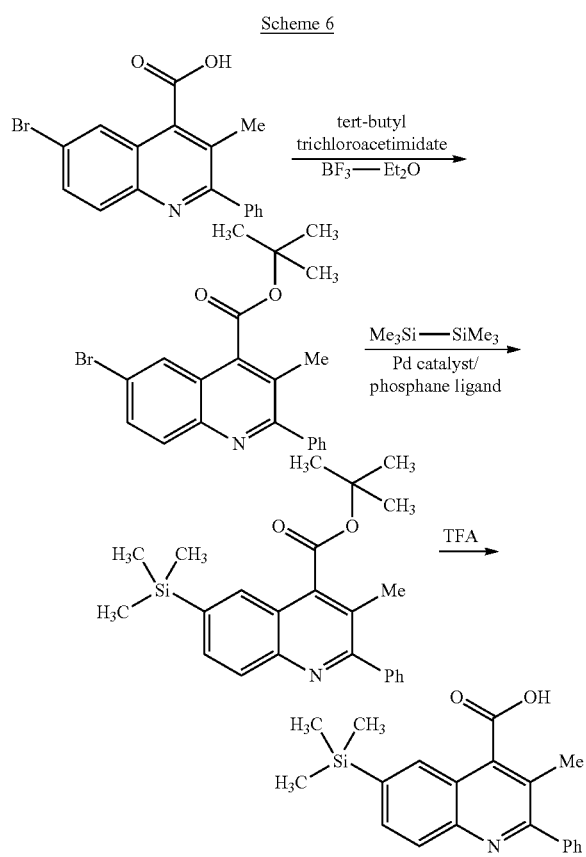

Scheme 6

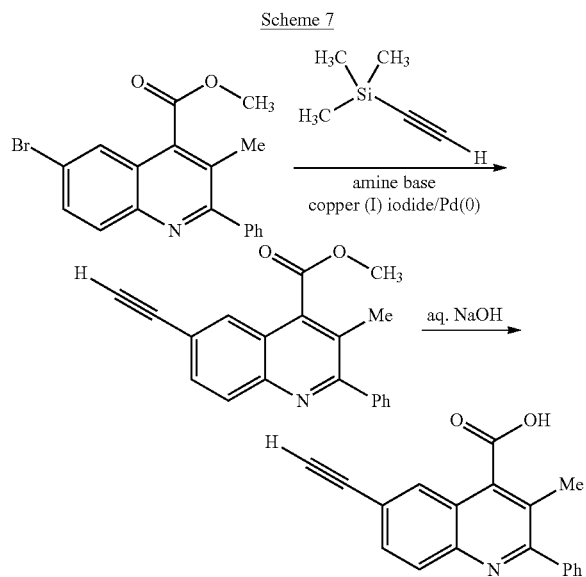

Scheme 7

The compounds of the invention have valuable pharmacological properties and can be used for treatment and/or prophylaxis of disorders in humans and animals.

The compounds of the invention are potent, chemically and metabolically stable antagonists of the FP receptor and are therefore suitable for treatment and/or prevention of disorders and pathological processes, especially those where the FP receptor is involved in the course of an inflammatory event and/or tissue or vessel reconstruction.

In the context of the present invention, these especially include disorders such as the group of the interstitial idiopathic pneumonias which includes idiopathic pulmonary fibrosis (IPF), acute interstitial pneumonia, non-specific interstitial pneumonias, lymphoid interstitial pneumonias, respiratory bronchiolitis with interstitial lung disease, cryptogenic organizing pneumonias, desquamative interstitial pneumonias and non-classifiable idiopathic interstitial pneumonias, furthermore granulomatous interstitial lung diseases, interstitial lung diseases of known etiology and other interstitial lung diseases of unknown etiology, pulmonary arterial hypertension (PAH) and other forms of pulmonary hypertension (PH), bronchiolitis obliterans syndrome (BOS), chronic-obstructive pulmonary disease (COPD), pulmonary sarcoidosis, acute respiratory distress syndrome (ARDS), acute lung injury (ALI), alpha-1-antitrypsin deficiency (AATD), pulmonary emphysema (for example pulmonary emphysema induced by cigarette smoke), cystic fibrosis (CF), inflammatory and fibrotic disorders of the kidney, chronic intestinal inflammations (IBD, Crohn's disease, ulcerative colitis), peritonitis, peritoneal fibrosis, rheumatoid disorders, multiple sclerosis, inflammatory and fibrotic skin disorders, sickle cell anemia and inflammatory and fibrotic eye disorders.

The compounds of the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds of the invention can additionally be used for treatment and/or prevention of cardiovascular disorders, for example high blood pressure (hypertension), heart failure, coronary heart disorders, stable and unstable angina pectoris, renal hypertension, peripheral and cardiovascular disorders, arrhythmias, rhythm disorders of the atria and ventricles, and conduction disorders, for example atrioventricular blocks of degrees I-III, supraventricular tachycardia, atrial fibrillation, atrial flutter, ventricular fibrillation, ventricular flutter, ventricular tachycardia, Torsade de pointes tachycardia, atrial and ventricular extrasystoles, AV-junctional extrasystoles, sick sinus syndrome, syncopes, AV nodal reentrant tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, and also for treatment and/or prevention of thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation such as, for example, pulmonary edema, cerebral edema, renal edema or edema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischemic cardiomyopathy, dilatative cardiomyopathy, hypertrophic cardiomyopathy, idiopathic cardiomyopathy, diabetic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds of the invention for treatment and/or prevention of sequelae of renal insufficiency, for example hypertension, pulmonary edema, heart failure, uremia, anemia, electrolyte disturbances (for example hyperkalemia, hyponatremia) and disturbances in bone and carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention can also be used for treatment of disorders of the female reproductive system, such as uterine myoma, endometriosis, dysmenorrhea and premature contractions. In addition, they are suitable for prophylaxis or treatment of hirsutism or hypertrichosis.

In addition, the compounds of the invention have antiinflammatory action and can therefore be used as antiinflammatory agents for the treatment and/or prevention of sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis, vulvovaginitis, rheumatoid disorders, osteoarthritis, inflammatory disorders of the central nervous system, multiple sclerosis, inflammatory skin disorders and inflammatory eye disorders.

The compounds of the invention are also suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphea, keloids, hypertrophic scarring, nevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for ageing or keratinized skin.

The compounds of the invention can also be used for treatment and/or prevention of anemias such as hemolytic anemias, in particular hemoglobinopathies such as sickle cell anemia and thalassamias, megaloblastic anemias, iron deficiency anemias, anemias owing to acute blood loss, displacement anemias and aplastic anemias.

Moreover, the compounds of the invention are suitable for treatment of cancers, for example skin cancer, brain tumors, breast cancer, bone marrow tumors, leukemias, liposarcomas, carcinomas of the gastrointestinal tract, of the liver, the pancreas, the lung, the kidney, the ureter, the prostate and the genital tract and also of malignant tumors of the lymphoproliferative system, for example Hodgkin's and non-Hodgkin's lymphoma.

In addition, the compounds of the invention can be used for treatment and/or prevention of arteriosclerosis, impaired lipid metabolism and dyslipidemias (hypolipoproteinemia, hypertriglyceridemias, hyperlipidemia, combined hyperlipidemias, hypercholesterolemia, abetalipoproteinemia, sitosterolemia), xanthomatosis, Tangier disease, adiposity, obesity, metabolic disorders (metabolic syndrome, hyperglycemia, insulin-dependent diabetes, non-insulin-dependent diabetes, gestation diabetes, hyperinsulinemia, insulin resistance, glucose intolerance and diabetic sequelae, such as retinopathy, nephropathy and neuropathy), of disorders of the gastrointestinal tract and the abdomen (glossitis, gingivitis, periodontitis, esophagitis, eosinophilic gastroenteritis, mastocytosis, Crohn's disease, colitis, proctitis, anus pruritis, diarrhea, celiac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, for example dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrheic dermatitis, sunburn, toxic dermatitis, Meleney's ulcer, dermatitis veneata, infectious dermatitis, pyrogenic dermatitis and perioral dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, for example HPV, HCMV, HIV, SARS), of disorders of the skeletal bone and the joints and also the skeletal muscle (various forms of arthritis, for example arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, hemophilic arthritis, juvenile chronic arthritis, rheumatoid arthritis and metastatic arthritis, and also Still syndrome, Felty syndrome, Sjörgen syndrome, Clutton syndrome, Poncet syndrome, Pott syndrome and Reiter syndrome, various forms of arthropathy, for example arthropathia deformans, arthropathia neuropathica, arthropathia ovaripriva, arthropathia psoriatica and arthropathia tabica, systemic scleroses, various forms of inflammatory myopathies, for example myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also Günther syndrome and Miinchmeyer syndrome), of inflammatory changes to the arteries (various forms of arteritis, for example endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, for example cataract, cachexia, osteoporosis, gout, incontinence, lepra, Sezary syndrome and paraneoplastic syndrome, in the event of rejection reactions after organ transplants and for wound healing and angiogenesis particularly in the case of chronic wounds.

Owing to their profile of biochemical and pharmacological properties, the compounds of the invention are particularly suitable for treatment and/or prevention of interstitial lung diseases, especially idiopathic pulmonary fibrosis (IPF), and also of pulmonary hypertension (PH), bronchiolitis obliterans syndrome (BOS), inflammatory and fibrotic skin and eye disorders and fibrotic disorders of the internal organs.

The aforementioned well-characterized diseases in humans can also occur with comparable etiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a method of treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders. Preferred examples of combination active ingredients suitable for this purpose include:

organic nitrates and NO donors, for example sodium nitroprusside, nitroglycerin, isosorbide mononitrate, isosorbide dinitrate, molsidomine or SIN-1, and inhaled NO;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;

NO- and heme-independent activators of soluble guanylate cyclase (sGC), such as in particular the compounds described in WO 01/19355, WO 01/19776, WO 01/19778, WO 01/19780, WO 02/070462 and WO 02/070510;

NO-independent but heme-dependent stimulators of soluble guanylate cyclase (sGC), such as in particular riociguat and the compounds described in WO 00/06568, WO 00/06569, WO 02/42301, WO 03/095451, WO 2011/147809, WO 2012/004258, WO 2012/028647 and WO 2012/059549;

prostacyclin analogs and IP receptor agonists, by way of example and with preference iloprost, beraprost, treprostinil, epoprostenol or selexipag;

edothelin receptor antagonists, by way of example and with preference bosentan, darusentan, ambrisentan or sitaxsentan;

compounds which inhibit human neutrophile elastase (HNE), by way of example and with preference sivelestat or DX-890 (reltran);

compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptors, by way of example and with preference antagonists of the 5-HT$_{2B}$ receptor such as PRX-08066;

antagonists of growth factors, cytokines and chemokines, by way of example and with preference antagonists of TGF-β, CTGF, IL-1, IL-4, IL-5, IL-6, IL-8, IL-13 and integrins;

Rho kinase-inhibiting compounds, by way of example and with preference fasudil, Y-27632, SLx-2119, BF-66851, BF-66852, BF-66853, KI-23095 or BA-1049;

compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, by way of example and with preference etomoxir, dichloroacetate, ranolazine or trimetazidine;

anti-obstructive agents as used, for example, for treatment of chronic obstructive pulmonary disease (COPD) or bronchial asthma, by way of example and with preference from the group of the inhalatively or systemically administered agonists of the β-adrenergic receptor (β-mimetics) and the inhalatively administered antimuscarinergic substances;

antiinflammatory, immunomodulating, immunosuppressive and/or cytotoxic agents, by way of example and with preference from the group of the systemically or inhalatively administered corticosteroids and also acetylcysteine, montelukast, azathioprine, cyclophosphamide, hydroxycarbamide, azithromycin, pirfenidone or etanercept;

antifibrotic agents, by way of example and with preference adenosine A2b receptor antagonists, sphingosine-1-phosphate receptor 3 (S1P3) antagonists, autotaxin inhibitors, lysophosphatidic acid receptor 1 (LPA-1) and lysophosphatidic acid receptor 2 (LPA-2) antagonists, lysyl oxidase (LOX) inhibitors, lysyl oxidase-like 2 inhibitors, CTGF inhibitors, IL-4 antagonists, IL-13 antagonists, α$_v$β$_6$-integrin antagonists, TGF-β antagonists, inhibitors of the Wnt signaling pathway or CCR2 antagonists;

antithrombotic agents, by way of example and with preference from the group of platelet aggregation inhibitors, the anticoagulants and the profibrinolytic substances;

hypotensive active compounds, by way of example and with preference from the group of the calcium antagonists, angiotensin AII antagonists, ACE inhibitors, vasopeptidase inhibitors, endothelin antagonists, renin inhibitors, α-receptor blockers, β-receptor blockers, mineralocorticoid receptor antagonists and also the diuretics;

lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-α, PPAR-γ and/or PPAR-δ agonists, cholesterol absorption inhibitors, lipase inhibitors, polymeric bile acid adsorbents, bile acid reabsorption inhibitors and lipoprotein(a) antagonists; and/or chemotherapeutics like those employed, for example, for the therapy of neoplasms in the lung or other organs.

In a preferred embodiment of the invention, the compounds of the invention are administered in combination with a β-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, beclomethasone, betamethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, α-receptor blockers, β-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an $α_1$-receptor blocker, by way of example and with preference prazosin.

In a preferred embodiment of the invention, the compounds of the invention are administered in combination with a β-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan or embursatan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-α, PPAR-γ and/or PPAR-δ agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-γ agonist, by way of example and with preference pioglitazone or rosiglitazone.

In a preferred embodiment of the invention, the compounds of the invention are administered in combination with a PPAR-δ agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

Particular preference is given to combinations of the compounds of the invention with one or more further active ingredients selected from the group consisting of PDE 5 inhibitors, sGC activators, sGC stimulators, prostacyclin analogs, IP receptor agonists, endothelin antagonists, compounds that inhibit the signal transduction cascade and pirfenidone.

The present invention further provides medicaments which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral, intravenous and intrapulmonary (inhalative) administration.

The compounds of the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavor and/or odor correctors.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight. In the case of intrapulmonary administration, the amount is generally about 0.1 to 50 mg per inhalation.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

Abbreviations and Acronyms
abs. absolute
aq. aqueous, aqueous solution
br. broad (in NMR signal)
Ex. Example
c concentration
approx. circa, about
cat. catalytic
CDI N,N'-carbonyldiimidazole
d doublet (in NMR)
d day (s)
TLC thin layer chromatography
dd doublet of doublet (in NMR)
DAST N,N-diethylaminosulfur trifluoride
DIPEA N,N-diisopropylethylamine
DMF N,N-dimethylformamide
DMSO dimethyl sulfoxide
DPPA diphenyl phosphorazidate
dppf 1,1'-bis(diphenylphosphino)ferrocene
dt doublet of triplet (in NMR)
of th. of theory (in chemical yield)
ee enantiomeric excess
ent enantiomerically pure, enantiomer
eq. equivalent(s)
ESI electrospray ionization (in MS)
ESIpos Electrospray ionization with positive ionization (in MS)
GC gas chromatography
GC/MS gas chromatography-coupled mass spectrometry
h hour(s)
HATU O-(7-azabenzotriazol-1-yl)-N,N,N',N'-tetramethyluronium hexafluorophosphate
HPLC high-pressure, high-performance liquid chromatography
conc. concentrated (in the case of a solution)
LC liquid chromatography
LC/MS liquid chromatography-coupled mass spectrometry
Lit. literature (reference)
m multiplet (in NMR)
M molar (in solution)

Me methyl
min minute(s)
MPLC medium-pressure liquid chromatography (on silica gel; also referred to as flash chromatography)
MS mass spectrometry
NMR nuclear magnetic resonance spectrometry
q (or quart) quartet (in NMR)
qd quartet of doublets (in NMR)
quant. quantitative (in chemical yield)
quint quintet (in NMR)
rac racemic, racemate
$R_f$ retention index (in TLC)
RP reverse phase (in HPLC)
RT room temperature
$R_t$ retention time (in HPLC, LC/MS)
s singlet (in NMR)
sept septet (in NMR)
SFC supercritical liquid chromatography
t triplet (in NMR)
td triplet of doublets (in NMR)
TFA trifluoroacetic acid
THF tetrahydrofuran
UV ultraviolet spectrometry
v/v volume to volume ratio (of a solution)
tog. together HPLC and LC/MS methods:

Method 1 (LC/MS):
Instrument: Waters Acquity SQD UPLC System; column: Waters Acquity UPLC HSS T3 1.8 µm, 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2 (Preparative HPLC):
Column: Chromatorex C18, 125×40 mm; mobile phase A: water+0.05% TFA, mobile phase B: acetonitrile; gradient: 0.0 min 20% B→4.0 min 20% B→30 min 95% B→35 min 95% B→36 min 20% B; flow rate: 50 ml/min. UV detection: 210 nm.

Method 3 (Preparative HPLC):
Column: Reprosil C18, 10 µm, 125×30 mm; mobile phase: acetonitrile/water with 0.1% TFA; gradient: 0-5.00 min 10:90, sample injection at 3.00 min, 5.50-17.65 min to 95:5; 17.66-19.48 min 95:5; 19.48-19.66 min to 10:90; 19.68-20.00 min 10:90. UV detection: 210 nm.

Method 4 (Preparative HPLC):
Column: Reprosil C18, 10 µm, 250×40 mm; mobile phase: acetonitrile/water with 0.1% TFA; gradient: 0-6.00 min 10:90, sample injection at 3.00 min, 6.00-27.00 min to 95:5; 27.00-38.00 min 95:5; 38.00-39.00 min to 10:90; 39.00-40.20 min 10:90. UV detection: 210 nm.

Method 5 (Preparative HPLC):
Column: Chromatorex C18, 125 mm, 125×40 mm; mobile phase: acetonitrile/water with 0.05% TFA; gradient: 0-4.00 min 10:90, sample injection at 3.00 min, 4.00-30.00 min to 95:5; 30.00-35.00 min 95:5; 35.00-36.00 min to 10:90; 36.00-36.10 min 10:90. UV detection: 210 nm.

Method 6 (GC-MS):
Instrument: Thermo Scientific DFS; Thermo Scientific Trace GC Ultra; column: Restek RTX-35, 15 m×200 µm×0.33 µm; constant helium flow rate: 1.20 ml/min; oven: 60° C.; inlet: 220° C.; gradient: 60° C., 30° C./min→300° C. (maintain for 3.33 min).

Method 7 (LC/MS):
Instrument: Agilent MS Quad 6150; HPLC: Agilent 1290; column: Waters Acquity UPLC HSS T3 1.8 µm, 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 8 (LC/MS):
Instrument: Waters Acquity SQD UPLC; column: Waters Acquity UPLC HSS T3 1.8 µm, 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 9 (LC/MS):
Instrument: Thermo Scientific UltiMate 3000; column: Waters HSS T3, 2.1×75 mm, C18 1.8 µm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/Optimum Integration Path 210-300 nm.

Further Details:

The percentages in the example and test descriptions which follow are, unless indicated otherwise, percentages by weight; parts are parts by weight. Solvent ratios, dilution ratios and concentration data for liquid/liquid solutions are based in each case on volume.

In the case of purifications of compounds of the invention by preparative HPLC by the above-described methods in which the eluents contain additives, for example trifluoroacetic acid, formic acid or ammonia, the compounds of the invention can be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

Purity figures are generally based on corresponding peak integrations in the LC/MS chromatogram, but may additionally also have been determined with the aid of the $^1$H NMR spectrum. If no purity is indicated, the purity is generally 100% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

The descriptions of the coupling patterns of $^1$H NMR signals that follow have in some cases been taken directly from the suggestions of the ACD SpecManager (ACD/Labs Release 12.00, Product version 12.5) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the center of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

Melting points and melting point ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Compounds and Intermediates

Example 1A

Methyl 4-[(tert-butoxycarbonyl)amino]cubane-1-carboxylate

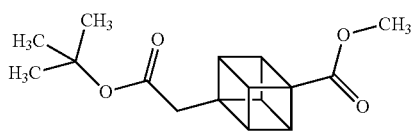 [SMILES: COC(=O)C12C3C4C1C1C2C3C41CC(=O)OC(C)(C)C]

At RT, 0.57 ml (2.55 mmol) of diphenylphosphoryl azide (DPPA) was slowly added dropwise to a mixture of 500 mg (2.43 mmol) of 4-(methoxycarbonyl)cubane-1-carboxylic acid (preparation described in *Synthesis* 1995, 5, 501-502) in 10 ml of tert-butanol and 0.36 ml (2.55 mmol) of triethylamine. The reaction mixture was stirred at 110° C. overnight and, after cooling to RT, saturated sodium sulfite solution was added slowly. After addition of ethyl acetate, the phases were separated and the organic phase was washed with water, dried over sodium sulfate, filtered and concentrated. The residue was purified by column chromatography (silica gel, mobile phase cyclohexane/ethyl acetate 5:1). This gave 189 mg (23% of theory, purity 82%) of the title compound.

$^1$H-NMR (400 Mhz, DMSO-d$_6$): δ [ppm]=7.8-7.5 (br. m, 1 H), 3.97 (br. s, 6 H), 3.61 (s, 3 H), 1.38 (s, 9 H).

GC/MS (Method 6): R$_t$=6.40 min, m/z=221 [M−C$_4$H]$^+$.

Example 2A

Methyl 4-aminocubane-1-carboxylate hydrochloride

185 mg (0.55 mmol, purity 82%) of the compound from Example 1A were initially charged in 3 ml of a 4 M hydrogen chloride solution in dioxane, and the mixture was stirred at RT overnight. The mixture was concentrated and the residue was dried under reduced pressure. This gave 141 mg (99% of theory, purity 99%) of the title compound.

$^1$H-NMR (400 Mhz, DMSO-d$_6$): δ [ppm]=8.81 (br. s, 3H), 4.11 (s, 6H), 3.63 (s, 3H).

LC/MS (Method 1, ESIpos): R$_t$=0.18 min, m/z=178 [M−HCl+H]$^+$.

Example 3A

6-Bromo-3-methyl-2-phenylquinoline-4-carboxylic acid

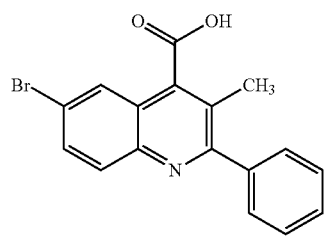 [SMILES: Cc1c(-c2ccccc2)nc2ccc(Br)cc2c1C(=O)O]

1.2 liters of acetic acid were added to 100.0 g (398.16 mmol, 90% purity) of 5-bromo-1H-indole-2,3-dione and 59.4 g (442.41 mmol) of 1-phenylpropan-1-one, and the mixture was stirred at 75° C. for 20 min. Thereafter, 400 ml of conc. hydrochloric acid were added to the reaction mixture, and stirring of the mixture was continued at 105° C. overnight. The reaction solution was then added to a mixture of 10 liters of 1 N hydrochloric acid, 9.2 liters of water and 840 ml of conc. hydrochloric acid while stirring. 1 liter of ice-water was added to the mixture, and the precipitate was filtered off with the aid of a frit. The filter residue was washed twice with 500 ml of water, then extracted by stirring twice with 150 ml each time of a 3:1 mixture of tert-butyl methyl ether and acetone and filtered again. The residue was extracted by stirring three times more with 100 ml each time of tert-butyl methyl ether and finally dried under reduced pressure. This gave 117.96 g (78% of theory; purity 100%) of the title compound.

$^1$H-NMR (400 Mhz, DMSO-d$_6$): δ [ppm]=14.39 (br. s, 1H), 8.01 (d, 1H), 7.94-7.90 (m, 2H), 7.63-7.61 (m, 2H), 7.56-7.49 (m, 3H), 2.40 (s, 3H).

LC/MS (Method 1, ESIpos): R$_t$=0.76 min, m/z=343 [M+H]$^+$.

Example 4A 6,7-Dichloro-3-methyl-2-phenylquinoline-4-carboxylic acid

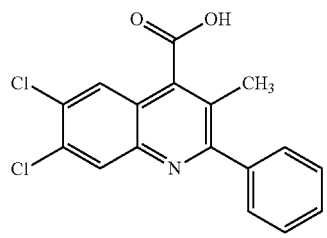 [SMILES: Cc1c(-c2ccccc2)nc2cc(Cl)c(Cl)cc2c1C(=O)O]

10.0 g (46.29 mmol) of a regioisomer mixture of 4,5-dichloro-1H-indole-2,3-dione and 5,6-dichloro-1H-indole-2,3-dione [about 1:1, preparation described in *J. Med. Chem.* 2004, 47 (4), 935-946] were initially charged in 136 ml of acetic acid, and 6.21 g (46.29 mmol) of 1-phenylpropan-1-one were added. The reaction mixture was stirred at 75° C.

for 5 min. Then 42 ml of conc. hydrochloric acid were added, and stirring of the mixture was continued at 105° C. overnight. Subsequently, the reaction solution was introduced cautiously into water while stirring. The precipitate formed was filtered off and prepurified by column chromatography (silica gel, mobile phase: ethyl acetate/methanol 10:1). The product mixture obtained in this manner was dissolved in 120 ml of a hot acetonitrile/methanol/water/trifluoroacetic acid mixture and separated into the regioisomers by preparative HPLC [column: Kinetix C18, 5 μm, 100×21.2 mm; flow rate: 25 ml/min; detection: 210 nm; injection volume: 1.0 ml; temperature: 35° C.; mobile phase: 45% water/50% acetonitrile/5% formic acid (1% in water), isocratic; run time: 4.3 min]. This gave 380 mg (2.2% of theory, purity 90%) of the title compound.

$^1$H-NMR (400 Mhz, DMSO-d$_6$): δ [ppm]=14.54 (br. s, 1H), 8.37 (s, 1H), 8.00 (s, 1H), 7.68-7.58 (m, 2H), 7.58-7.47 (m, 3H), 2.40 (s, 3H).

LC/MS (Method 1, ESIpos): R$_t$=0.99 min, m/z=332 [M+H]$^+$.

Example 5A 6-tert-Butyl-3-methyl-2-phenylquinoline-4-carboxylic acid

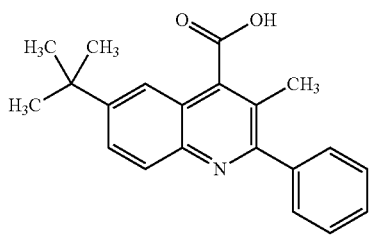 [SMILES: Cc1c(-c2ccccc2)nc2ccc(C(C)(C)C)cc2c1C(=O)O]

5.00 g (24.60 mmol) of 5-tert-butyl-1H-indole-2,3-dione were initially charged in 50 ml of acetic acid, and 3.30 g (24.60 mmol) of 1-phenylpropan-1-one were added. The reaction mixture was stirred at 75° C. for 5 min. Subsequently, 18 ml of concentrated hydrochloric acid were added, and the mixture was stirred at 105° C. overnight. After cooling to RT, the reaction mixture was added to 1 liter of 1 M hydrochloric acid and the precipitated solids were filtered off. The solids were washed with water, dried under air and then stirred with 50 ml of acetonitrile. The solids were filtered off again and dried under air and finally under reduced pressure. This gave 4.85 g (61% of theory; purity 99%) of the title compound.

$^1$H-NMR (400 Mhz, DMSO-d$_6$): δ [ppm]=14.09 (br. s, 1H), 7.99 (d, 1H), 7.92 (dd, 1H), 7.66 (d, 1H), 7.62-7.57 (m, 2H), 7.55-7.45 (m, 3H), 2.37 (s, 3H), 1.39 (s, 9H).

LC/MS (Method 1, ESIpos): R$_t$=0.69 min, m/z=320 [M+H]$^+$.

Example 6A

6-Bromo-2-(2-fluorophenyl)-3-methylquinoline-4-carboxylic acid

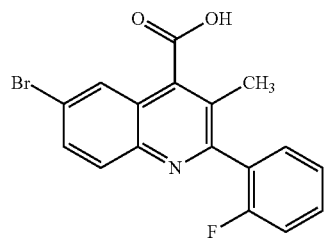 [SMILES: Cc1c(-c2ccccc2F)nc2ccc(Br)cc2c1C(=O)O]

1.00 g (4.42 mmol) of 5-bromo-1H-indole-2,3-dione were initially charged in 12.0 ml of acetic acid, and 673 mg (4.42 mmol) of 1-(2-fluorophenyl)propan-1-one were added. The reaction mixture was stirred at 75° C. for 5 min. Subsequently, 4.0 ml of conc. hydrochloric acid were added, and stirring of the mixture was continued at 105° C. overnight. After cooling to RT, the reaction mixture was added to 200 ml of 1 M hydrochloric acid and the precipitated solids were filtered off. The solids were washed with water, dried under reduced pressure and then stirred with dichloromethane. The solvent was removed by suction and the residue was dried under reduced pressure. This gave 649 mg (37% of theory, purity 90%) of the title compound.

LC/MS (Method 1, ESIpos): R$_t$=0.90 min, m/z=360/362 [M+H]$^+$.

Example 7A

6-Bromo-2-(3-fluorophenyl)-3-methylquinoline-4-carboxylic acid

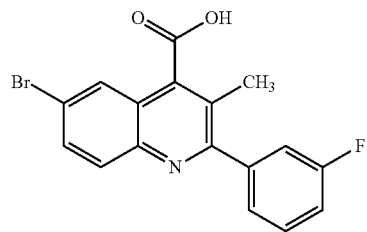 [SMILES: Cc1c(-c2cccc(F)c2)nc2ccc(Br)cc2c1C(=O)O]

1.00 g (4.42 mmol) of 5-bromo-1H-indole-2,3-dione were initially charged in 12.0 ml of acetic acid, and 673 mg (4.42 mmol) of 1-(3-fluorophenyl)propan-1-one were added. The reaction mixture was stirred at 75° C. for 5 min. Subsequently, 4.0 ml of conc. hydrochloric acid were added, and stirring of the mixture was continued at 105° C. overnight. After cooling to RT, the reaction mixture was added to 200 ml of 1 M hydrochloric acid and the precipitated solids were filtered off. The solids were washed with water and dried under reduced pressure. This gave 1.20 g (63% of theory; purity 83%) of the title compound.

LC/MS (Method 1, ESIpos): R$_t$=0.94 min, m/z=360/362 [M+H]$^+$.

Example 8A

6-Bromo-2-(4-fluorophenyl)-3-methylquinoline-4-carboxylic acid

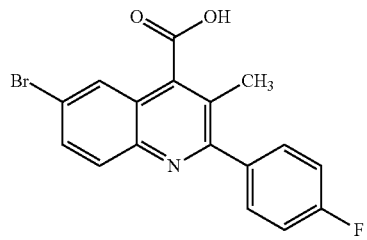 [SMILES: Cc1c(-c2ccc(F)cc2)nc2ccc(Br)cc2c1C(=O)O]

1.00 g (4.42 mmol) of 5-bromo-1H-indole-2,3-dione were initially charged in 12.0 ml of acetic acid, and 673 mg (4.42 mmol) of 1-(4-fluorophenyl)propan-1-one were added. The reaction mixture was stirred at 75° C. for 5 min. Subsequently, 4.0 ml of conc. hydrochloric acid were added, and stirring of the mixture was continued at 105° C. overnight. After cooling to RT, the reaction mixture was added to 200 ml of 1 M hydrochloric acid and the precipitated solids were filtered off. The solids were washed with water and dried under reduced pressure. This gave 1.29 g (73% of theory; purity 90%) of the title compound.

LC/MS (Method 1, ESIpos): $R_t$=0.88 min, m/z=360/362 [M+H]$^+$.

Example 9A

6-Bromo-2-(3,5-difluorophenyl)-3-methylquinoline-4-carboxylic acid

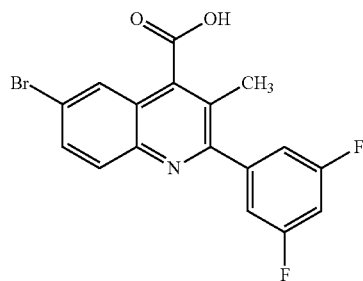 [SMILES: Cc1c(-c2cc(F)cc(F)c2)nc2ccc(Br)cc2c1C(=O)O]

300 mg (1.33 mmol) of 5-bromo-1H-indole-2,3-dione were initially charged in 2 ml of 20% strength aqueous ethanol solution, and 565 mg (3.31 mmol) of 1-(3,5-difluorophenyl)propan-1-one and 238 mg (4.25 mmol) of potassium hydroxide were added. The reaction mixture was then heated in the microwave (Biotage) at 180° C. for 20 min. After cooling to RT, the mixture was added to 100 ml of 1 M hydrochloric acid. The precipitated solid was then filtered off, washed with water and dried under reduced pressure. This gave 490 mg (69% of theory, purity 71%) of the title compound.

LC/MS (Method 1, ESIpos): $R_t$=1.01 min, m/z=378/380 [M+H]$^+$.

Example 10A

6-Bromo-2-(2-chlorophenyl)-3-methylquinoline-4-carboxylic acid

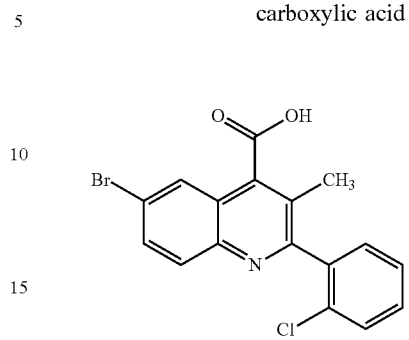

1.00 g (4.42 mmol) of 5-bromo-1H-indole-2,3-dione was initially charged in 12.0 ml of acetic acid, and 746 mg (4.42 mmol) of 1-(2-chlorophenyl)propan-1-one were added. The reaction mixture was stirred at 75° C. for 5 min. Subsequently, 4.0 ml of concentrated hydrochloric acid were added, and the mixture was stirred at 105° C. overnight. After cooling to RT, the reaction mixture was added to 200 ml of 1 M hydrochloric acid. The precipitated solid was then filtered off, washed with water and dried under reduced pressure. This gave 1.07 g (40% of theory; purity 63%) of the title compound.

LC/MS (Method 1, ESIpos): $R_t$=0.94 min, m/z=376/378 [M+H]$^+$.

Example 11A

6-Bromo-2-(3-chlorophenyl)-3-methylquinoline-4-carboxylic acid

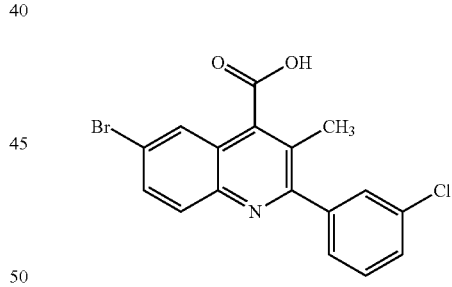

1.00 g (4.42 mmol) of 5-bromo-1H-indole-2,3-dione was initially charged in 12.0 ml of acetic acid, and 746 mg (4.42 mmol) of 1-(3-chlorophenyl)propan-1-one were added. The reaction mixture was stirred at 75° C. for 5 min. Subsequently, 4.0 ml of concentrated hydrochloric acid were added, and the mixture was stirred at 105° C. overnight. After cooling to RT, the reaction mixture was added to 200 ml of 1 M hydrochloric acid. The precipitated solid was then filtered off, washed with water and dried under reduced pressure. This gave 1.26 g (49% of theory; purity 65%) of the title compound.

LC/MS (Method 1, ESIpos): $R_t$=1.02 min, m/z=376/378 [M+H]$^+$.

Example 12A

6-Bromo-3-fluoro-2-phenylquinoline-4-carboxylic acid

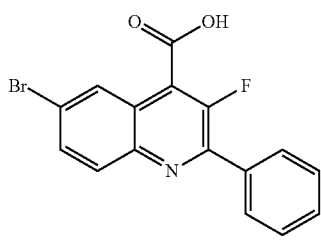 [SMILES: O=C(O)c1c(F)c(-c2ccccc2)nc2ccc(Br)cc12]

1.75 g (6.97 mmol, 90% purity) of 5-bromo-1H-indole-2,3-dione were initially charged in 15 ml of acetic acid, and 0.96 g (6.97 mmol) of 2-fluoro-1-phenylethanone was added. The reaction mixture was stirred at 75° C. for 5 min. Subsequently, 5 ml of conc. hydrochloric acid were added, and stirring of the mixture was continued at 115° C. overnight. After cooling to RT, the reaction mixture was added to 100 ml of 1 M hydrochloric acid. The precipitated solid was then filtered off, washed twice with 10 ml of water and dried under reduced pressure. The residue was purified by preparative HPLC (Method 3). This gave 501 mg (20% of theory, purity 98%) of the title compound.

$^1$H-NMR (400 Mhz, DMSO-$d_6$): δ [ppm]=14.66 (br. s, 1H), 8.21 (d, 1H), 8.11 (d, 1H), 8.04-7.96 (m, 3H), 7.62-7.56 (m, 3H).

LC/MS (Method 1, ESIpos): $R_t$=0.98 min, m/z=346/348 [M+H]$^+$.

Example 13A

6-Iodo-3-methyl-2-phenylquinoline-4-carboxylic acid

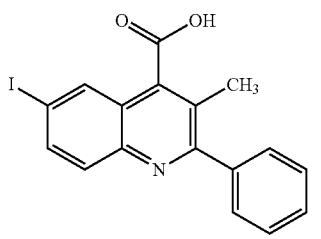 [SMILES: Cc1c(-c2ccccc2)nc2ccc(I)cc2c1C(=O)O]

20.0 g (73.25 mmol) of 5-iodo-1H-indole-2,3-dione were initially charged in 200 ml of acetic acid, and 9.83 g (73.25 mmol) of 1-phenylpropan-1-one were added. The reaction mixture was stirred at 75° C. for 5 min. Subsequently, 66 ml of conc. hydrochloric acid were added, and stirring of the mixture was continued at 105° C. overnight. After cooling to RT, the reaction mixture was, with stirring, carefully introduced into water. The precipitate formed was then filtered off and washed twice with water and twice with a little tert-butyl methyl ether and dried under reduced pressure. The residue was purified by preparative HPLC (Method 3). After drying under reduced pressure overnight, 11.10 g (32% of theory, 82% purity) of the title compound were obtained.

$^1$H-NMR (400 Mhz, DMSO-$d_6$): δ [ppm]=14.36 (br. s, 1H), 8.13 (d, 1H), 8.05 (dd, 1H), 7.84 (d, 1H), 7.66-7.57 (m, 2H), 7.57-7.41 (m, 3H), 2.39 (s, 3H).

LC/MS (Method 1, ESIpos): $R_t$=0.78 min, m/z=390 [M+H]$^+$.

Example 14A

Methyl 6-iodo-3-methyl-2-phenylquinoline-4-carboxylate

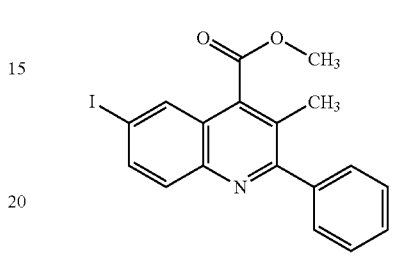

22.4 g (57.5 mmol) of the compound from Example 13A were initially charged together with 28.1 g (86.23 mmol) of cesium carbonate in 224 ml of acetonitrile under argon. 3.6 ml (57.5 mmol) of iodomethane were added at RT. The reaction mixture was warmed to 40° C. and stirred for 1 h. Subsequently, a further 3.6 ml (57.5 mmol) of iodomethane were added, and the mixture was stirred at 40° C. for another 2 h. The reaction mixture was then cooled to RT, and ethyl acetate and water were added. The phases were separated, and the organic phase was washed once with saturated sodium carbonate solution. A precipitate was formed, which was filtered off through kieselguhr. The filtrate was dried over sodium sulfate, filtered and concentrated under reduced pressure. The residue was purified by column chromatography (silica gel, mobile phase cyclohexane/ethyl acetate 10:1). Drying under reduced pressure gave 12.7 g (55% of theory, 96% purity) of the title compound.

$^1$H-NMR (400 Mhz, DMSO-$d_6$): δ [ppm]=8.12 (d, 1H), 8.06 (dd, 1H), 7.84 (d, 1H), 7.64-7.59 (m, 2H), 7.57-7.47 (m, 3H), 4.07 (s, 3H), 2.35 (s, 3H).

LC/MS (Method 1, ESIpos): $R_t$=1.26 min, m/z=404 [M+H]$^+$.

Example 15A

Methyl 6-cyclopropyl-3-methyl-2-phenylquinoline-4-carboxylate

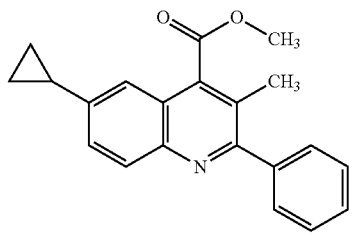 [SMILES: COC(=O)c1c(C)c(-c2ccccc2)nc2ccc(C3CC3)cc12]

Under argon, a mixture of 200 mg (0.50 mmol) of the compound from Example 14A, 67 mg (0.65 mmol) of cyclopropylboric acid hydrate, 5.6 mg (0.025 mmol) of palladium acetate, 18 mg (0.05 mmol) of tricyclohexylphosphonium tetrafluoroborate and 421 mg (1.98 mmol) of potassium phosphate in 2 ml of toluene and 0.1 ml of water was heated under reflux for 6 h. After cooling to RT, ethyl acetate and water were added to the mixture, and the phases were separated. The organic phase was dried over sodium sulfate, filtered and concentrated under reduced pressure and the residue was purified by preparative HPLC (Method 2). This gave 88 mg (55% of theory, purity 99%) of the title compound.

$^1$H-NMR (400 Mhz, DMSO-$d_6$): δ [ppm]=7.94 (dd, 1H), 7.65-7.56 (m, 2H), 7.55-7.47 (m, 3H), 7.45 (br. s, 1H), 7.41 (d, 1H), 4.06 (s, 3H), 2.32 (s, 3H), 2.25-2.11 (m, 1H), 1.13-0.98 (m, 2H), 0.88-0.75 (m, 2H).

LC/MS (Method 1, ESIpos): $R_t$=1.20 min, m/z=318 [M+H]$^+$.

Example 16A

6-Cyclopropyl-3-methyl-2-phenylquinoline-4-carboxylic acid

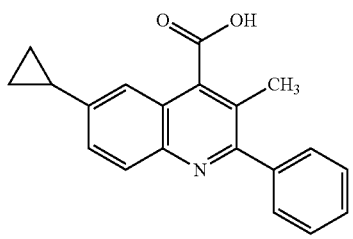 [SMILES: Cc1c(-c2ccccc2)nc2ccc(C3CC3)cc2c1C(=O)O]

82 mg (0.26 mmol) of the compound from Example 15A were dissolved in 4.0 ml of a THF/methanol mixture (5:1), and 1.30 ml (1.30 mmol) of a 1 M lithium hydroxide solution were added. The reaction mixture was stirred at 50° C. overnight. After cooling to RT, the mixture was adjusted to pH 1-2 using 4 M hydrochloric acid and, without further work-up, was purified by preparative HPLC (Method 2). This gave 71 mg (84% of theory, purity 94%) of the title compound.

$^1$H-NMR (400 Mhz, DMSO-$d_6$): δ [ppm]=14.11 (br. s, 1H), 7.93 (d, 1H), 7.63-7.56 (m, 2H), 7.55-7.45 (m, 4H), 7.42 (dd, 1H), 2.36 (s, 3H), 2.24-2.14 (m, 1H), 1.13-1.02 (m, 2H), 0.84-0.77 (m, 2H).

LC/MS (Method 1, ESIpos): $R_t$=0.56 min, m/z=304 [M+H]$^+$.

Example 17A

Methyl 6-cyclobutyl-3-methyl-2-phenylquinoline-4-carboxylate

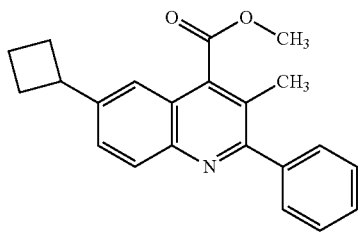 [SMILES: COC(=O)c1c(C)c(-c2ccccc2)nc2ccc(C3CCC3)cc12]

Under argon, 0.99 ml (2.48 mmol) of a 0.5 M solution of bromo(cyclobutyl)zinc in THF were added to a mixture of 500 mg (1.24 mmol) of the compound from Example 14A, 51 mg (0.062 mmol) of PdCl$_2$-dppf dichloromethane complex and 14.2 mg (0.07 mmol) of copper(I) iodide in 10 ml of anhydrous THF, and the mixture was stirred at RT overnight. Subsequently, another 1.50 ml (3.72 mmol) of the 0.5 M solution of bromo(cyclobutyl)zinc in THF were added, and the mixture was once more stirred at RT overnight. Ethyl acetate and water were then added to the mixture, and the phases were separated. The aqueous phase was acidified slightly using ammonium chloride and extracted three times with ethyl acetate. The combined organic phases were dried over sodium sulfate, filtered and concentrated and the residue was purified by column chromatography (silica gel, mobile phase cyclohexane/ethyl acetate 10:1). This gave 236 mg (54% of theory, purity 95%) of the title compound.

$^1$H-NMR (400 Mhz, DMSO-$d_6$): δ [ppm]=8.01 (d, 1H), 7.76 (d, 1H), 7.64-7.57 (m, 2H), 7.56-7.46 (m, 3H), 7.43 (s, 1H), 4.06 (s, 3H), 3.83-3.68 (m, 1H), 2.45-2.31 (m, 2H), 2.33 (s, 3H), 2.26-2.12 (m, 2H), 2.12-1.96 (m, 1H), 1.94-1.82 (m, 1H).

LC/MS (Method 1, ESIpos): $R_t$=1.35 min, m/z=332 [M+H]$^+$.

Example 18A

6-Cyclobutyl-3-methyl-2-phenylquinoline-4-carboxylic acid

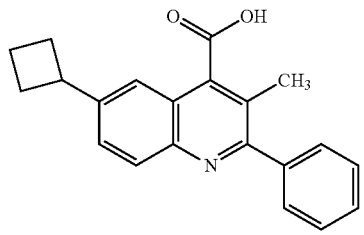 [SMILES: Cc1c(-c2ccccc2)nc2ccc(C3CCC3)cc2c1C(=O)O]

229 mg (0.69 mmol) of the compound from Example 17A were dissolved in 10.6 ml of a THF/methanol mixture (5:1), and 3.45 ml (3.45 mmol) of a 1 M lithium hydroxide solution were added. The reaction mixture was stirred at 60° C. for 36 h. After cooling to RT, the mixture was adjusted to pH 1-2 using 4 M hydrochloric acid and, without further work-up, was purified by preparative HPLC (Method 2). This gave 241 mg (">100%" of theory, purity 99%, with solvent) of the title compound.

$^1$H-NMR (400 Mhz, DMSO-$d_6$): δ [ppm]=8.01 (d, 1H), 7.74 (d, 1H), 7.62 (d, 2H), 7.58-7.47 (m, 4H), 3.83-3.71 (m, 1H), 2.46-2.38 (m, 2H), 2.38 (s, 3H), 2.24-2.12 (m, 2H), 2.12-1.99 (m, 1H), 1.94-1.81 (m, 1H).

LC/MS (Method 1, ESIpos): $R_t$=0.68 min, m/z=318 [M+H]$^+$.

Example 19A tert-Butyl 6-bromo-3-methyl-2-phenylquinoline-4-carboxylate

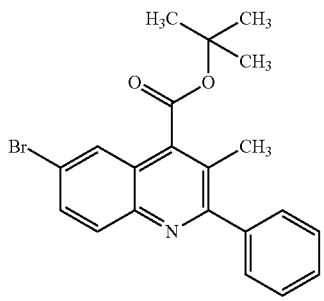 [SMILES: Cc1c(-c2ccccc2)nc2ccc(Br)cc2c1C(=O)OC(C)(C)C]

5.11 g (23.38 mmol) of tert-butyl trichloroacetimidate, followed by 166 mg (1.17 mmol) of boron trifluoride/diethyl ether complex, were added to a mixture of 2.00 g (5.85 mmol) of the compound from Example 3A in 100 ml of THF, and the mixture was stirred at RT for 2 h. Dichloromethane was then added, and the mixture was washed with water. The aqueous phase was extracted once with dichloromethane. The combined organic phases were dried over magnesium sulfate, filtered and concentrated under reduced pressure and the residue was pre-purified by column chromatography (100 g of silica gel, Biotage, mobile phase cyclohexane/ethyl acetate 85:15). The pre-purified product was then applied to Isolute® and purified again by column chromatography (100 g of silica gel, Biotage, mobile phase cyclohexane/ethyl acetate 85:15). This gave 1.66 g (70% of theory; purity 98%) of the title compound.

$^1$H-NMR (400 Mhz, DMSO-$d_6$): δ [ppm]=8.02 (d, 1H), 7.94 (d, 1H), 7.84 (d, 1H), 7.65-7.58 (m, 2H), 7.57-7.49 (m, 3H), 2.39 (s, 3H), 1.67 (s, 9H).

LC/MS (Method 1, ESIpos): $R_t$=1.47 min, m/z=398/400 [M+H]$^+$.

Example 20A tert-Butyl 3-methyl-2-phenyl-6-(trimethylsilyl)quinoline-4-carboxylate

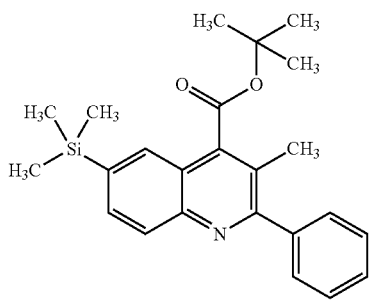 [SMILES: Cc1c(-c2ccccc2)nc2ccc([Si](C)(C)C)cc2c1C(=O)OC(C)(C)C]

Under argon and at RT, 73 mg (0.20 mmol) of allylpalladium(II) chloride dimer, 112 mg (0.40 mmol) of (2-hydroxyphenyl)diphenylphosphine, 193 mg (4.82 mmol) of sodium hydroxide and 142 mg (0.44 mmol) of tetrabutylammonium bromide were added to a mixture of 1.60 g (4.02 mmol) of the compound from Example 19A and 647 mg (4.42 mmol) of hexamethyldisilane in 10 ml of toluene and 10 ml of water, and the mixture was stirred at 100° C. overnight. After cooling to RT, the mixture was admixed with ethyl acetate and washed with water. The aqueous phase was extracted once with ethyl acetate. The combined organic phases were washed once with saturated sodium chloride solution, dried over magnesium sulfate, filtered and concentrated and the residue was purified by column chromatography (100 g of silica gel Biotage, mobile phase cyclohexane/ethyl acetate 95:5). This gave 841 mg (53% of theory, purity 100%) of the title compound.

$^1$H-NMR (400 Mhz, DMSO-$d_6$): δ [ppm]=8.03 (d, 1H), 7.92 (d, 1H), 7.87 (s, 1H), 7.64-7.58 (m, 2H), 7.56-7.47 (m, 3H), 2.37 (s, 3H), 1.67 (s, 9H).

LC/MS (Method 1, ESIpos): $R_t$=1.57 min, m/z=392 [M+H]$^+$.

Example 21A

3-Methyl-2-phenyl-6-(trimethylsilyl)quinoline-4-carboxylic acid

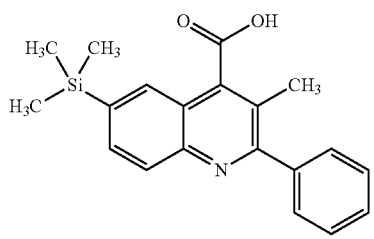 [SMILES: Cc1c(-c2ccccc2)nc2ccc([Si](C)(C)C)cc2c1C(=O)O]

10 ml of TFA were added to a mixture of 835 mg (2.13 mmol) of the compound from Example 20A in 20 ml of dichloromethane, and the mixture was stirred at RT overnight. After removal of volatile constituents on a rotary evaporator, the residue was stirred with a little water and the solid formed was filtered off, washed twice with water and dried under reduced pressure. This gave 710 mg (93% of theory, purity 94%) of the title compound.

$^1$H-NMR (400 Mhz, DMSO-$d_6$): δ [ppm]=14.20 (br. s, 1H), 8.04 (d, 1H), 7.93-7.89 (m, 2H), 7.64-7.59 (m, 2H), 7.57-7.47 (m, 3H), 2.39 (s, 3H).

LC/MS (Method 1, ESIpos): $R_t$=0.79 min, m/z=336 [M+H]$^+$.

Example 22A

Methyl 6-formyl-3-methyl-2-phenylquinoline-4-carboxylate

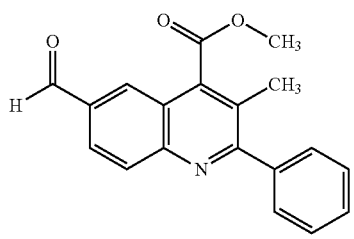 [SMILES: COC(=O)c1c(C)c(-c2ccccc2)nc2ccc(C(F)F)cc12]

5.0 g (12.4 mmol) of the compound from example 14A were dissolved in 98 ml of anhydrous THF under argon, and the mixture was cooled to −50° C. This was followed by successive dropwise addition of 35.4 ml (37.2 mmol) of a 1.05 M solution of isopropylmagnesium chloride/lithium chloride complex in THF and 3.2 ml (37.2 mmol) of 1,4-dioxane. The reaction mixture was stirred at −50° C. for 1 h and then cooled to −78° C. Then 9.5 ml (124 mmol) of absolute DMF were added dropwise. The reaction mixture was brought to RT while stirring overnight, and ethyl acetate and water were then added. The phases were separated, and the organic phase was washed once with water, dried over sodium sulfate, filtered and concentrated. In the attempt to purify the residue by column chromatography (silica gel, eluent: cyclohexane/ethyl acetate 6:1), the product precipitated out on the column. The chromatographic purification was then stopped and the silica gel was stirred with ethyl acetate. After filtration, the filtrate was concentrated. The residue was stirred in methanol, and the solid was filtered off and dried under reduced pressure. This gave 2.29 g (59% of theory, purity 98%) of the title compound.

$^1$H-NMR (400 Mhz, DMSO-d$_6$): δ [ppm]=10.24 (s, 1H), 8.44 (d, 1H), 8.24-8.12 (m, 2H), 7.71-7.60 (m, 2H), 7.59-7.47 (m, 3H), 4.12 (s, 3H), 2.40 (s, 3H).

LC/MS (Method 1, ESIpos): R$_t$=1.06 min, m/z=306 [M+H]$^+$.

Example 23A

Methyl 6-(difluoromethyl)-3-methyl-2-phenylquinoline-4-carboxylate

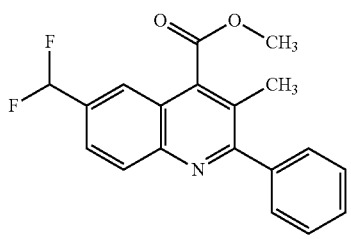

1.0 g (3.2 mmol) of the compound from Example 22A were dissolved in 40 ml of dichloromethane. The mixture was cooled to −78° C., and 1.4 g (7.86 mmol, 90% purity) of N,N-diethylaminosulfur trifluoride (DAST) were added slowly. The reaction mixture was stirred overnight, in the course of which it warmed up to RT, and then saturated aqueous sodium hydrogencarbonate solution was added. The phases were separated, and the aqueous phase was extracted three times with ethyl acetate. The combined organic phases were dried over sodium sulfate, filtered and concentrated. The residue was purified by column chromatography (silica gel, mobile phase cyclohexane/ethyl acetate 5:1). After the solvent had been removed, the residue was dried under reduced pressure. This gave 737 mg (69% of theory, purity >99%) of the title compound.

$^1$H-NMR (400 Mhz, DMSO-d$_6$): δ [ppm]=8.21 (d, 1H), 8.02 (br. s, 1H), 7.95 (d, 1H), 7.69-7.61 (m, 2H), 7.59-7.48 (m, 3H), 7.28 (t, 1H), 4.09 (s, 3H), 2.38 (s, 3H).

LC/MS (Method 1, ESIpos): R$_t$=1.15 min, m/z=328 [M+H]$^+$.

Example 24A

Methyl 6-(difluoromethyl)-3-methyl-2-phenylquinoline-4-carboxylate

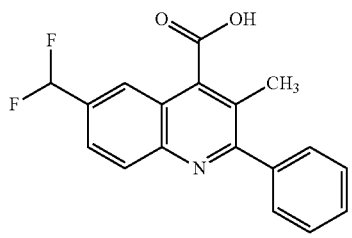 [SMILES: Cc1c(-c2ccccc2)nc2ccc(C(F)F)cc2c1C(=O)O]

100 mg (0.31 mmol) of the compound from Example 23A were dissolved in 5 ml of a THF/methanol mixture (5:1), and 1.53 ml (1.53 mmol) of a 1 M solution of lithium hydroxide in water were added. The reaction mixture was stirred at 50° C. for 7 h and then cooled to RT, and ethyl acetate and water were added. The phases were separated, and the aqueous phase was adjusted to pH 1-2 with 1 M hydrochloric acid and extracted three times with ethyl acetate. The combined organic extracts were dried over sodium sulfate, filtered and concentrated. The residue was stirred in a pentane/tert-butyl methyl ether mixture, and the solids were filtered off and dried under reduced pressure. This gave 61 mg (96% of theory, purity 99%) of the title compound.

$^1$H-NMR (400 Mhz, DMSO-d$_6$): δ [ppm]=14.37 (br. s, 1H), 8.20 (d, 1H), 8.02 (d, 1H), 7.92 (dd, 1H), 7.67-7.61 (m, 2H), 7.59-7.49 (m, 3H), 7.33 (t, 1H), 2.42 (s, 3H).

LC/MS (Method 1, ESIpos): R$_t$=0.72 min, m/z=314 [M+H]$^+$.

Example 25A

Methyl 6-(difluoromethyl)-3-methyl-2-phenylquinoline-4-carboxylate

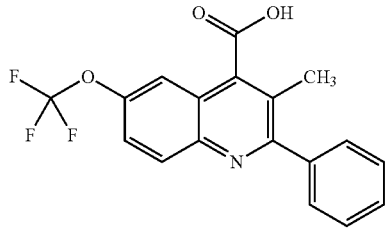 [SMILES: Cc1c(-c2ccccc2)nc2ccc(OC(F)(F)F)cc2c1C(=O)O]

1.45 g (10.82 mmol) of 1-phenylpropan-1-one were added to a mixture of 2.5 g (10.82 mmol) of 5-(trifluoromethoxy)-1H-indole-2,3-dione in 25 ml of acetic acid. After stirring at 75° C. for 5 min, 8 ml of conc. hydrochloric acid were added, and the mixture was then stirred at 110° C. for 5 h. After cooling to RT (and storage at RT overnight), the mixture was introduced into 500 ml of 1 M hydrochloric acid while stirring. After a few minutes, the solids formed were filtered off, washed twice with water and dried under reduced pressure. This gave 3.16 g (77% of theory; purity 92%) of the title compound.

$^1$H-NMR (400 Mhz, DMSO-d$_6$): δ [ppm]=14.41 (br. s, 1H), 8.21 (d, 1H), 7.80 (dd, 1H), 7.69 (d, 1H), 7.66-7.58 (m, 2H), 7.57-7.47 (m, 3H), 2.41 (s, 3H).

Example 26A

Methyl 3-methyl-2-phenyl-6-[(trifluoromethyl)sulfanyl]quinoline-4-carboxylate

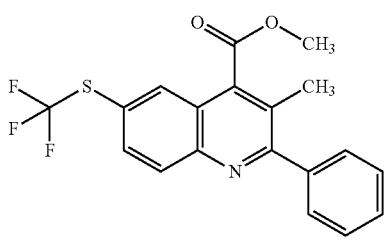 [SMILES: COC(=O)c1c(C)c(-c2ccccc2)nc2ccc(SC(F)(F)F)cc12]

A mixture of 500 mg (3.04 mmol) of copper(I) trifluoromethanethiolate and 480 mg (3.04 mmol) of 2,2'-bipyridine in 12.5 ml of acetonitrile was stirred under argon and at RT, 1.25 g (3.04 mmol) of the compound from Example 14A were then added and the mixture was subsequently stirred in a microwave apparatus at 140° C. for 6 h. A further 500 mg (3.04 mmol) of copper(I) trifluoromethanethiolate, 480 mg (3.04 mmol) of 2,2'-bipyridine and 1.25 g (3.04 mmol) of the compound from Example 14A were reacted in the same manner. After cooling to RT, the two mixtures were combined, and ethyl acetate and water were then added. After phase separation, the aqueous phase was extracted three times with ethyl acetate, and the combined organic phases were dried over sodium sulfate, filtered and concentrated. The residue was purified by column chromatography (silica gel, mobile phase cyclohexane/ethyl acetate 10:1). This gave 1.86 g (60% of theory; purity 74%) of the title compound.

$^1$H-NMR (400 Mhz, DMSO-$d_6$): δ [ppm]=8.21 (d, 1H), 8.15 (d, 1H), 8.01 (dd, 1H), 7.70-7.60 (m, 2H), 7.59-7.47 (m, 3H), 4.09 (s, 3H), 2.38 (s, 3H).

LC/MS (Method 1, ESIpos): $R_t$=1.31 min, m/z=378 [M+H]$^+$.

Example 27A

3-Methyl-2-phenyl-6-[(trifluoromethyl)sulfanyl]quinoline-4-carboxylic acid

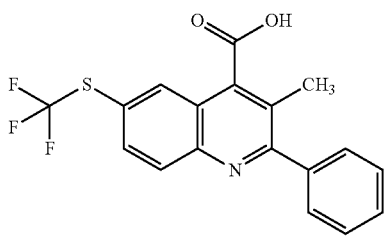 [SMILES: Cc1c(-c2ccccc2)nc2ccc(SC(F)(F)F)cc2c1C(=O)O]

1.68 g (3.30 mmol, purity 74%) of the compound from Example 26A were divided into two portions of 840 mg (1.65 mmol) each, and 14.8 ml (14.8 mmol) of a 1 M sodium hydroxide solution were added to each portion. The reaction mixtures were each stirred in a microwave apparatus at 160° C. for 6 h and, after cooling to RT, combined. Ethyl acetate and water were then added to the combined mixture, and the phases were separated. The aqueous phase was extracted three times with ethyl acetate, then adjusted to pH 1-2 with 1 M hydrochloric acid and once more extracted three times with ethyl acetate. The combined organic phases were dried over sodium sulfate, filtered and concentrated and the residue was purified by preparative HPLC (Method 2). This gave 730 mg (43% of theory, purity 70%) of the title compound.

$^1$H-NMR (400 Mhz, DMSO-$d_6$): δ [ppm]=14.50 (br. s, 1H), 8.19 (d, 1H), 8.15 (d, 1H), 8.00 (dd, 1H), 7.68-7.60 (m, 2H), 7.59-7.48 (m, 3H), 2.42 (s, 3H).

LC/MS (Method 1, ESIpos): $R_t$=0.92 min, m/z=364 [M+H]$^+$.

Example 28A

6-Bromo-3,8-dimethyl-2-phenylquinoline-4-carboxylic acid

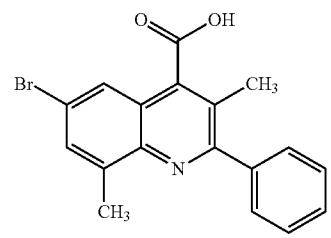

3.00 g (12.50 mmol) of 5-bromo-7-methyl-1H-indole-2,3-dione were initially charged in 34 ml of acetic acid, and 1.68 g (12.50 mmol) of 1-phenylpropan-1-one were added. The reaction mixture was stirred at 75° C. for 5 min. Subsequently, 11 ml of conc. hydrochloric acid were added, and stirring of the mixture was continued at 115° C. overnight. After cooling to RT, the reaction mixture was added to 200 ml of 1 M hydrochloric acid, and the precipitated solid was filtered off, twice washed with 10 ml of water and dried under reduced pressure. This gave 3.02 g (64% of theory; purity 94%) of the title compound.

$^1$H-NMR (400 Mhz, DMSO-$d_6$): δ [ppm]=14.31 (br. s, 1H), 7.83 (s, 1H), 7.77-7.63 (m, 3H), 7.57-7.49 (m, 3H), 2.70 (s, 3H), 2.41 (s, 3H).

LC/MS (Method 1, ESIpos): $R_t$=1.15 min, m/z=356/358 [M+H]$^+$.

Example 29A 6,8-Dichloro-3-methyl-2-phenylquinoline-4-carboxylic acid

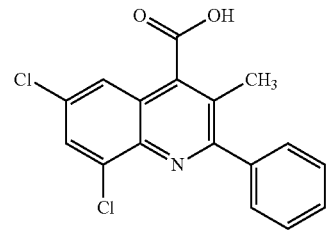 [SMILES: Cc1c(-c2ccccc2)nc2c(Cl)cc(Cl)cc2c1C(=O)O]

LC/MS (Method 1, ESIpos): $R_t$=0.97 min, m/z=348 [M+H]$^+$.

1.0 g (4.64 mmol) of 5,7-dichloro-1H-indole-2,3-dione were initially charged in 12.6 ml of acetic acid, and 0.62 g (4.64 mmol) of 1-phenylpropan-1-one were added. The reaction mixture was stirred at 75° C. for 5 min. Thereafter, 4.2 ml of conc. hydrochloric acid were added, and stirring of the mixture was continued at 105° C. overnight. Subsequently, the reaction solution was introduced cautiously into water while stirring. The precipitate formed was filtered off. This gave, after drying under reduced pressure overnight, 1.61 g (93% of theory, 90% purity) of the title compound.

$^1$H-NMR (400 Mhz, DMSO-$d_6$): δ [ppm]=14.56 (br. s, 1H), 8.13 (br. s, 1H), 7.77 (br. s, 1H), 7.72-7.35 (m, 5H), 2.43 (s, 3H).

LC/MS (Method 1, ESIpos): $R_t$=1.02 min, m/z=332 [M+H]$^+$.

Example 30A 3,6,7-Trimethyl-2-phenylquinoline-4-carboxylic acid

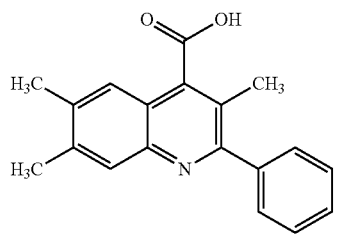 [SMILES: Cc1cc2nc(-c3ccccc3)c(C)c(C(=O)O)c2cc1C]

1.08 g (6.14 mmol) of 5,6-dimethyl-1H-indole-2,3-dione were initially charged in 12.6 ml of acetic acid, and 0.82 g (6.14 mmol) of 1-phenylpropan-1-one were added. The reaction mixture was stirred at 75° C. for 5 min. Thereafter, 5.6 ml of conc. hydrochloric acid were added, and stirring of the mixture was continued at 105° C. overnight. After cooling to RT, the reaction solution was introduced into water, and ethyl acetate was added. After phase separation, the aqueous phase was extracted with ethyl acetate, and the combined organic phases were dried over sodium sulfate, filtered and concentrated. The aqueous phase was likewise concentrated and the two residues were combined. The combined residue was then purified by column chromatography (silica gel, mobile phase ethyl acetate/methanol 5:1). The product-containing fractions were combined and concentrated and the residue was triturated in a pentane/tert-butyl methyl ether/methanol mixture. The solids were filtered off and dried under reduced pressure. This gave 0.60 g (27% of theory; purity 82%) of the title compound.

$^1$H-NMR (400 Mhz, DMSO-$d_6$): δ [ppm]=12.21 (br. s, 1H), 7.69 (s, 1H), 7.61 (s, 1H), 7.55-7.41 (m, 5H), 2.41 (s, 3H), 2.38 (s, 3H), 2.28 (s, 3H).

LC/MS (Method 1, ESIpos): $R_t$=0.52 min, m/z=292 [M+H]$^+$.

Example 31A

6-Bromo-3-methyl-2-(2-methylphenyl)quinoline-4-carboxylic acid

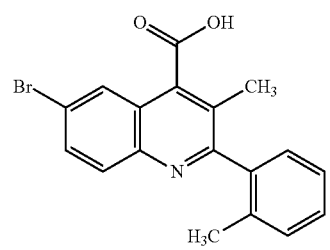 [SMILES: Cc1ccccc1-c1nc2ccc(Br)cc2c(C(=O)O)c1C]

1.17 g (5.19 mmol) of 5-bromo-1H-indole-2,3-dione were initially charged in 14.1 ml of acetic acid, and 0.77 g (5.19 mmol) of 1-(2-methylphenyl)propan-1-one were added. The reaction mixture was stirred at 75° C. for 5 min. Thereafter, 4.7 ml of conc. hydrochloric acid were added, and stirring of the mixture was continued at 105° C. overnight. The reaction solution was then divided into two microwave vessels and successively heated in a microwave apparatus at 150° C. for 4.5 h. After cooling to RT, the mixture was introduced into water and the precipitate formed was filtered off. Filtrate and precipitate were then re-combined and purified by column chromatography (silica gel, mobile phase ethyl acetate/methanol 5:1). This gave 490 mg (23% of theory, purity 93%) of the title compound.

$^1$H-NMR (400 Mhz, DMSO-$d_6$): δ [ppm]=8.07 (d, 1H), 7.86 (d, 1H), 7.78 (dd, 1H), 7.40-7.24 (m, 3H), 7.18 (d, 1H), 2.08 (s, 3H), 2.00 (s, 3H).

LC/MS (Method 1, ESIpos): $R_t$=0.76 min, m/z=356/358 [M+H]$^+$.

Example 32A

6-Bromo-2-(2,6-difluorophenyl)-3-methylquinoline-4-carboxylic acid

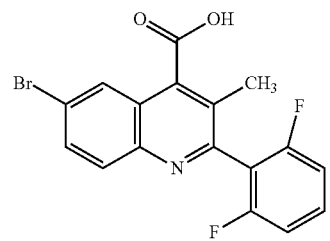 [SMILES: Cc1c(-c2c(F)cccc2F)nc2ccc(Br)cc2c1C(=O)O]

2.0 g (7.96 mmol, purity 90%) of 5-bromo-1H-indole-2,3-dione were initially charged in 22 ml of acetic acid, and 1.35 g (7.96 mmol) of 1-(2,6-difluorophenyl)propan-1-one were added. The reaction mixture was stirred at 75° C. for 5 min. Subsequently, 7.3 ml of conc. hydrochloric acid were added, and stirring of the mixture was continued at 105° C. overnight. After cooling to RT, the reaction mixture was slowly added to water. After addition of ethyl acetate, the phases were separated and the aqueous phase was extracted three times with ethyl acetate. The combined organic phases were dried over sodium sulfate, filtered and concentrated. The aqueous phase was likewise concentrated and the two residues were combined and pre-purified by column chromatography (silica gel, ethyl acetate/methanol gradient). The pre-purified product was dissolved in a mixture of acetonitrile, methanol, water and TFA and purified by preparative HPLC (column: Kinetix C18, 5 μm, 100 mm×21.5 mm; flow rate: 25 ml/min; detection: 210 nm; gradient water/acetonitrile/(water+1% formic acid) 60:35:5→25:70:5; run time 6 min). This gave 56 mg (2% of theory, purity 100%) of the title compound.

LC/MS (Method 1, ESIpos): $R_t$=1.16 min, m/z=378/380 [M+H]$^+$.

Example 33A

6-Bromo-2-(3-methoxyphenyl)-3-methylquinoline-4-carboxylic acid

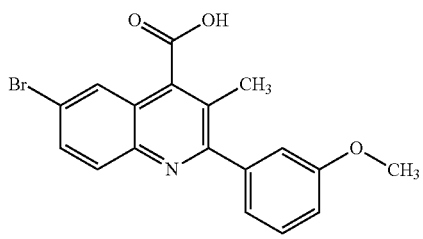 [SMILES: COc1cccc(-c2nc3ccc(Br)cc3c(C(=O)O)c2C)c1]

6.26 g (27.7 mmol) of 5-bromo-1H-indole-2,3-dione were added to a solution of 9.32 g (166 mmol) of potassium hydroxide in 55 ml of ethanol and 16 ml of water. 5.0 g (30.4 mmol) of 1-(3-methoxyphenyl)propan-1-one were added and the reaction mixture was stirred under reflux for 3 h. After cooling to RT, the mixture was concentrated, 75 ml of water were added and the mixture was stirred at RT for 30 min. The mixture was then cooled to 0° C. and adjusted to a pH of about 3 using 11 ml (166 mmol) of conc. hydrochloric acid. The precipitate present was filtered off, washed with water and air-dried. This gave 9.46 g (81% of theory; purity 88%) of the title compound. 100 mg of this product batch were re-purified by preparative HPLC (Method 4). This gave 33 mg (purity 90%) of the title compound.

$^1$H-NMR (400 Mhz, DMSO-d$_6$): δ [ppm]=14.34 (br. s, 1H), 8.01 (d, 1H), 7.96-7.88 (m, 2H), 7.47-7.40 (m, 1H), 7.17-7.12 (m, 2H), 7.10-7.03 (m, 1H), 3.82 (s, 3H), 2.39 (s, 3H).

LC/MS (Method 1, ESIpos): $R_t$=0.75 min, m/z=372/374 [M+H]$^+$.

Example 34A

6-Bromo-3-(methylsulfanyl)-2-phenylquinoline-4-carboxylic acid

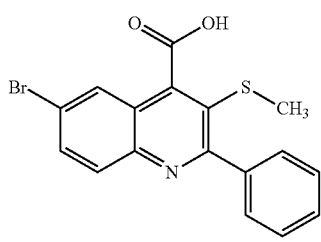 [SMILES: CSc1c(-c2ccccc2)nc2ccc(Br)cc2c1C(=O)O]

5.00 g (22.12 mmol) of 5-bromo-1H-indole-2,3-dione were initially charged in 60 ml of acetic acid, and 3.68 g (22.12 mmol) of 2-(methylsulfanyl)-1-phenylethanone were added. The reaction mixture was stirred at 75° C. for 5 min. Subsequently, 20 ml of conc. hydrochloric acid were added, and stirring of the mixture was continued at 115° C. overnight. After cooling to RT, the reaction mixture was diluted with 300 ml of water and adjusted to pH 2 with conc. hydrochloric acid. The mixture was extracted twice with 50 ml of ethyl acetate, and the combined organic phases were dried over sodium sulfate, filtered and concentrated. The residue was purified by preparative HPLC (column: Chromatorex Spring Column C18, 10 μm, 290 mm×100 mm; flow rate: 250 ml/min; detection: 210 nm; injection volume 30 ml, temperature: 22° C.; gradient acetonitrile/(water+0.1% formic acid) 20:80→90:10; run time 39.5 min). 2.07 g (24% of theory, 95% purity) of the title compound was obtained.

$^1$H-NMR (400 Mhz, DMSO-d$_6$): δ [ppm]=14.46 (br. s, 1H), 8.04 (d, 1H), 8.00 (dd, 1H), 7.88 (d, 1H), 7.77-7.71 (m, 2H), 7.55-7.49 (m, 3H), 2.03 (s, 3H).

LC/MS (Method 1, ESIpos): $R_t$=0.93 min, m/z=374/376 [M+H]$^+$.

Example 35A

6-Bromo-3-ethyl-2-phenylquinoline-4-carboxylic acid

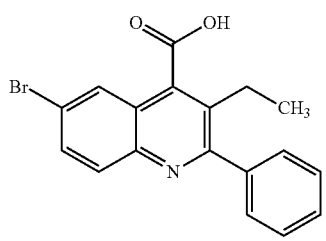 [SMILES: CCc1c(-c2ccccc2)nc2ccc(Br)cc2c1C(=O)O]

1.00 g (4.42 mmol) of 5-bromo-1H-indole-2,3-dione were initially charged in 12.0 ml of acetic acid, and 656 mg (4.42 mmol) of 1-phenylbutan-1-one were added. The reaction mixture was stirred at 75° C. for 5 min. Subsequently, 4.0 ml of conc. hydrochloric acid were added, and stirring of the mixture was continued at 105° C. overnight. After cooling to RT, the reaction mixture was added to 200 ml of 1 M hydrochloric acid and the precipitated solids were filtered off with suction. The solids were washed with water and dried under reduced pressure. This gave 1.20 g (55% of theory; purity 72%) of the title compound.

LC/MS (Method 1, ESIpos): $R_t$=0.88 min, m/z=357 [M+H]$^+$.

Example 36A

6-Bromo-3-cyclopropyl-2-phenylquinoline-4-carboxylic acid

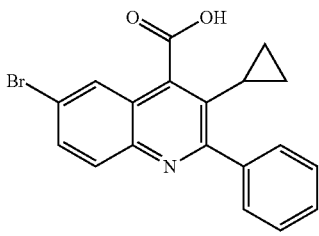 [SMILES: O=C(O)c1c(C2CC2)c(-c2ccccc2)nc2ccc(Br)cc12]

Method A:

1.75 g (6.97 mmol, 90% purity) of 5-bromo-1H-indole-2,3-dione were initially charged in 15 ml of acetic acid, and 1.12 g (6.97 mmol) of 2-cyclopropyl-1-phenylethanone (preparation described in WO2009/143049 A1, p. 182) were added. The reaction mixture was stirred at 75° C. for 5 min. Subsequently, 5 ml of conc. hydrochloric acid were added, and stirring of the mixture was continued at 110° C. for 2.5 h and then at RT overnight. The reaction mixture was then added to 100 ml of 1 M hydrochloric acid, and the precipitated solid was filtered off, twice washed with 10 ml of water and dried under reduced pressure. This gave 2.23 g of a crude product. 200 mg of this crude product were purified by preparative HPLC (Method 4). This gave 43 mg (1.5% of theory (based on 6.97 mmol of starting material), 93% purity) of the title compound.

Method B:

At RT, 1.95 g (12.18 mmol) of 2-cyclopropyl-1-phenylethanone (preparation described in WO2009/143049 A1, p. 182) and 2.05 g (36.56 mmol) of potassium hydroxide were added to a solution of 2.03 g (8.12 mmol, purity 90%) of 5-bromo-1H-indole-2,3-dione in 20 ml of ethanol. The reaction mixture was stirred at bath temperature 100° C. for 1 h. After cooling to RT, 300 ml of water were added and the mixture was adjusted to pH 2 with conc. hydrochloric acid. The mixture was extracted twice with 20 ml of ethyl acetate, and the combined organic phases were dried over sodium sulphate, filtered and concentrated. The residue was suspended in a mixture of 30 ml of DMSO and 10 ml of acetonitrile and the solid was filtered off and dried under reduced pressure, giving 107 mg (4%, purity 100%) of a first batch of the title compound. The filtrate was concentrated, and the residue was purified by preparative HPLC (Method 3), giving 750 mg (25%, purity 100%) of a second batch of the title compound.

$^1$H-NMR (400 Mhz, DMSO-$d_6$): δ [ppm]=14.22 (br. s, 1H), 8.01 (d, 1H), 7.97 (d, 1H), 7.93 (dd, 1H), 7.76-7.71 (m, 2H), 7.54-7.46 (m, 3H), 2.38-2.28 (m, 1H), 0.76-0.66 (m, 2H), 0.33-0.25 (m, 2H).

LC/MS (Method 1, ESIpos): $R_t$=0.91 min, m/z=368/370 [M+H]$^+$.

Example 37A

6-Bromo-3-chloro-2-phenylquinoline-4-carboxylic acid

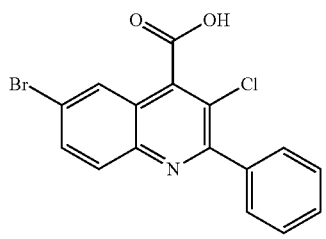 [SMILES: O=C(O)c1c(Cl)c(-c2ccccc2)nc2ccc(Br)cc12]

10.00 g (44.24 mmol) of 5-bromo-1H-indole-2,3-dione were initially charged in 120 ml of acetic acid, and 6.84 g (44.24 mmol) of 2-chloro-1-phenylethanone were added. The reaction mixture was stirred at 75° C. for 5 min. Subsequently, 5 ml of conc. hydrochloric acid were added, and stirring of the mixture was continued at 105° C. overnight. After cooling to RT, the reaction mixture was added to 200 ml of 1 M hydrochloric acid, and the precipitated solid was filtered off, twice washed with water and dried under reduced pressure. The residue was stirred in 50 ml of acetonitrile, and the solid was filtered off and dried under reduced pressure. This gave 5.60 g (29% of theory; purity 82%) of the title compound.

LC/MS (Method 1, ESIpos): $R_t$=0.88 min, m/z=362/364 [M+H]$^+$.

Example 38A

6-Bromo-2-phenyl-3-propylquinoline-4-carboxylic acid

300 mg (1.33 mmol) of 5-bromo-1H-indole-2,3-dione were initially charged in 3.6 ml of acetic acid, and 237 mg (1.46 mmol) of 1-phenylpentan-1-one were added. The reaction mixture was stirred at 75° C. for 5 min. Subsequently, 1.2 ml of conc. hydrochloric acid were added, and stirring of the mixture was continued at 105° C. overnight. After cooling to RT, the reaction mixture was added to 200 ml of 1 M hydrochloric acid and the precipitated solids were filtered off with suction. The solids were washed with water and dried under reduced pressure. This gave 246 mg (35% of theory, purity 70%) of the title compound.

LC/MS (Method 1, ESIpos): $R_t$=0.97 min, m/z=371 [M+H]$^+$.

Example 39A

3-Chloro-6-iodo-2-phenylquinoline-4-carboxylic acid

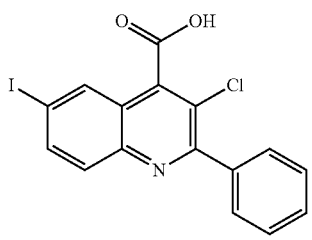 [SMILES: O=C(O)c1c(Cl)c(-c2ccccc2)nc2ccc(I)cc12]

10.00 g (36.63 mmol) of 5-iodo-1H-indole-2,3-dione were initially charged in 100 ml of acetic acid, and 5.66 g (36.63 mmol) of 2-chloro-1-phenylethanone were added. The reaction mixture was stirred at 75° C. for 5 min. Subsequently, 5 ml of conc. hydrochloric acid were added, and stirring of the mixture was continued at 105° C. overnight. After cooling to RT, the reaction mixture was added to 200 ml of 1 M hydrochloric acid, and the precipitated solid was filtered off, twice washed with water and dried under reduced pressure. The residue was stirred in 50 ml of acetonitrile, and the solid was filtered off and dried under reduced pressure. This gave 4.45 g (16% of theory; purity 54%) of the title compound.

LC/MS (Method 1, ESIpos): $R_t$=0.94 min, m/z=409 [M+H]$^+$.

Example 40A

3-Cyclopropyl-6-iodo-2-phenylquinoline-4-carboxylic acid

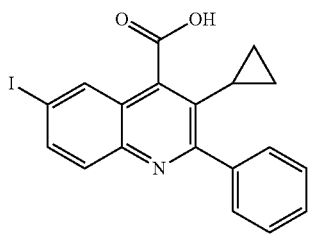 [SMILES: O=C(O)c1c(C2CC2)c(-c2ccccc2)nc2ccc(I)cc12]

At RT, 4.91 g (87.49 mmol) of potassium hydroxide were added to a mixture of 5.17 g (29.16 mmol, purity 90%) of 2-cyclopropyl-1-phenylethanone and 5.47 g (19.44 mmol, purity 97%) of 5-iodo-1H-indole-2,3-dione in 48 ml of ethanol, and the mixture was stirred at a bath temperature of 100° C. for 1 h. After cooling to RT, 300 ml of water were added and the mixture was adjusted to pH 2 by addition of conc. hydrochloric acid. The solid present was filtered off and washed with 50 ml of water. The filtrate was extracted with 50 ml of ethyl acetate, dried over sodium sulfate, filtered and concentrated, giving a residue. Solid and residue were combined, dissolved with heating in a mixture of 30 ml of methanol and 70 ml of THF and purified by preparative HPLC (column: Chromatorex Spring Column C18, 10 μm, 290 mm×100 mm; flow rate: 250 ml/min; detection: 210 nm; injection volume 30 ml; temperature: 22° C.; gradient acetonitrile/(water+0.1% formic acid) 20:80→90:10; run time 39.5 min). This gave 2.88 g (36% of theory; purity 97%) of the title compound.

$^1$H-NMR (400 Mhz, DMSO-d$_6$): δ [ppm]=14.22 (br. s, 1H), 8.17 (d, 1H), 8.05 (dd, 1H), 7.84 (d, 1H), 7.76-7.68 (m, 2H), 7.55-7.44 (m, 3H), 2.39-2.26 (m, 1H), 0.75-0.67 (m, 2H), 0.32-0.24 (m, 2H).

LC/MS (Method 1, ESIpos): $R_t$=0.97 min, m/z=416 [M+H]$^+$.

Example 41A

3-Methyl-2-phenyl-6-(trifluoromethyl)quinoline-4-carboxylic acid

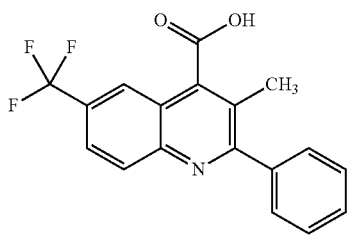 [SMILES: Cc1c(-c2ccccc2)nc2ccc(C(F)(F)F)cc2c1C(=O)O]

1.00 g (4.65 mmol) of 5-(trifluoromethyl)-1H-indole-2,3-dione were initially charged together with 12.6 ml of acetic acid and 624 mg (4.65 mmol) of 1-phenylpropan-1-one, and the reaction mixture was stirred at 75° C. for 5 min. Then 4.2 ml of conc. hydrochloric acid were added, and stirring of the mixture was continued at 105° C. overnight. After cooling to RT, the reaction mixture was added to 200 ml of 1 M hydrochloric acid and the precipitated solids were filtered off. The solids were washed with water and dried under reduced pressure. This gave 1.17 g (75% of theory; purity 100%) of the title compound.

LC/MS (Method 1, ESIpos): $R_t$=0.91 min, m/z=332 [M+H]$^+$.

Example 42A

6-Bromo-3-hydroxy-2-phenylquinoline-4-carboxylic acid

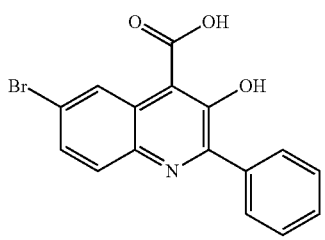 [SMILES: O=C(O)c1c(O)c(-c2ccccc2)nc2ccc(Br)cc12]

5.00 g (22.12 mmol) of 5-bromo-1H-indole-2,3-dione were initially charged in 60 ml of acetic acid, and 3.94 g (22.12 mmol) of 2-acetoxyacetophenone were added. The reaction mixture was stirred at 75° C. for 5 min. Subsequently, 20 ml of conc. hydrochloric acid were added, and stirring of the mixture was continued at 105° C. overnight. After cooling to RT, the reaction mixture was added to 200 ml of 1 M hydrochloric acid. The precipitated solid was then filtered off and dried under reduced pressure. The residue was dissolved in 250 ml of a hot THF/DMF mixture, filtered and purified by preparative HPLC (column: Chromatorex Spring Column C18, 10 μm, 290 mm×100 mm; flow rate: 250 ml/min; detection: 210 nm; injection volume 30 ml, temperature: 22° C.; gradient acetonitrile/(water+0.1% formic acid) 20:80→90:10; run time 36.5 min). This gave 930 mg (11% of theory, purity 87%) of the title compound.

LC/MS (Method 8, ESIpos): $R_t$=2.86 min, m/z=344/346 [M+H]$^+$.

Example 43A

Methyl 4-{[(6-bromo-3-methyl-2-phenylquinolin-4-yl)carbonyl]amino}bicyclo[2.2.2]octane-1-carboxylate

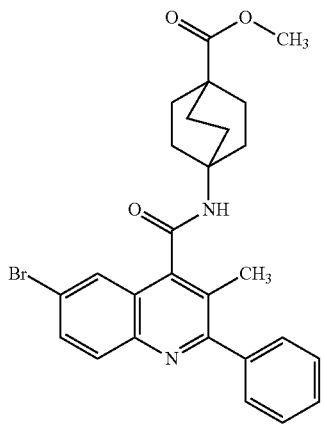 [SMILES: COC(=O)C12CCC(NC(=O)c3c(C)c(-c4ccccc4)nc4ccc(Br)cc34)(CC1)CC2]

At RT, 214 mg (1.17 mmol) of methyl 4-aminobicyclo[2.2.2]octane-1-carboxylate, 333 mg (0.88 mmol) of HATU and 0.20 ml (1.17 mmol) of DIPEA were added successively to a solution of 200 mg (0.58 mmol) of the compound from Example 3A in 3 ml of DMF. The mixture was then stirred at 60° C. overnight. After cooling to RT, the mixture was purified directly (without further work-up) by preparative HPLC (Method 2). This gave 269 mg (90% of theory, purity 99%) of the title compound.

$^1$H-NMR (400 Mhz, DMSO-d$_6$): δ [ppm]=8.48 (s, 1H), 7.97 (d, 1H), 7.88 (dd, 1H), 7.83 (d, 1H), 7.65-7.42 (m, 5H), 3.59 (s, 3H), 2.32 (s, 3H), 2.12-1.95 (m, 6H), 1.94-1.76 (m, 6H).

LC/MS (Method 1, ESIpos): $R_t$=1.20 min, m/z=507/509 [M+H]$^+$.

Example 44A

Methyl 4-{[(6-chloro-3-methyl-2-phenylquinolin-4-yl)carbonyl]amino}bicyclo[2.2.2]octane-1-carboxylate

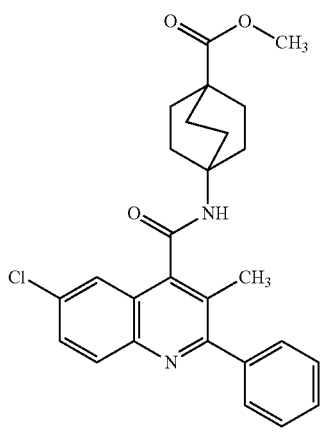 [SMILES: COC(=O)C12CCC(NC(=O)c3c(C)c(-c4ccccc4)nc4ccc(Cl)cc34)(CC1)CC2]

At RT, 258 mg (1.41 mmol) of methyl 4-aminobicyclo[2.2.2]octane-1-carboxylate, 402 mg (1.06 mmol) of HATU and 182 mg (1.41 mmol) of DIPEA were added to a solution of 210 mg (0.71 mmol) of 6-chloro-3-methyl-2-phenylquinoline-4-carboxylic acid in 5 ml of DMF. The mixture was then stirred at 60° C. for 1 h. After cooling to RT, the mixture was added to 20 ml of a 10% strength citric acid solution. The resulting precipitate was filtered off, washed with water and dried under reduced to pressure. This gave 326 mg (97% of theory, purity 98%) of the title compound.

$^1$H-NMR (400 Mhz, DMSO-d$_6$): δ [ppm]=8.48 (s, 1H), 8.05 (d, 1H), 7.77 (dd, 1H), 7.66 (d, 1H), 7.60-7.47 (m, 5H), 3.59 (s, 3H), 2.32 (s, 3H), 2.09-2.00 (m, 6H), 1.91-1.82 (m, 6H).

LC/MS (Method 1, ESIpos): $R_t$=1.22 min, m/z=463 [M+H]$^+$.

Example 45A

Methyl 4-{[(6,7-dichloro-3-methyl-2-phenylquinolin-4-yl)carbonyl]amino}bicyclo[2.2.2]octane-1-carboxylate

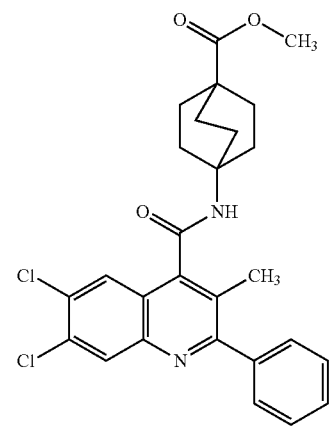 [SMILES: COC(=O)C12CCC(NC(=O)c3c(C)c(-c4ccccc4)nc4cc(Cl)c(Cl)cc34)(CC1)CC2]

At RT, 40 mg (0.18 mmol) of methyl 4-aminobicyclo[2.2.2]octane-1-carboxylate hydrochloride, 103 mg (0.27 mmol) of HATU and 0.06 ml (0.36 mmol) of DIPEA were added successively to a solution of 60 mg (0.18 mmol) of the compound from Example 4A in 1 ml of DMF. The mixture was then stirred at 60° C. overnight. After cooling to RT, the mixture was purified directly (without further work-up) by preparative HPLC (Method 2). This gave 45 mg (48% of theory, purity 95%) of the title compound.

$^1$H-NMR (400 Mhz, DMSO-d$_6$): δ [ppm]=8.51 (s, 1H), 8.34 (s, 1H), 7.82 (s, 1H), 7.62-7.44 (m, 5H), 3.59 (s, 3H), 2.32 (s, 3H), 2.08-1.97 (m, 6H), 1.92-1.82 (m, 6H).

LC/MS (Method 1, ESIpos): $R_t$=1.29 min, m/z=497 [M+H]$^+$.

Example 46A

Methyl 4-{[(6-tert-butyl-3-methyl-2-phenylquinolin-4-yl)carbonyl]amino}bicyclo[2.2.2]octane-1-carboxylate

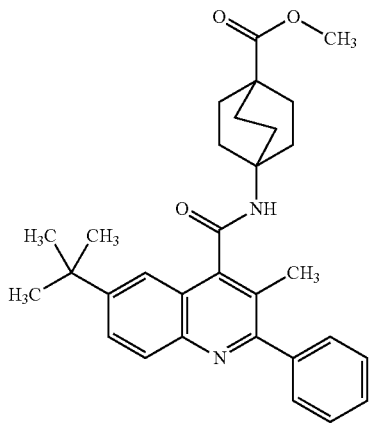 [SMILES: COC(=O)C12CCC(NC(=O)c3c(C)c(-c4ccccc4)nc4ccc(C(C)(C)C)cc34)(CC1)CC2]

At RT, 241 mg (1.32 mmol) of methyl 4-aminobicyclo[2.2.2]octane-1-carboxylate, 375 mg (0.99 mmol) of HATU and 0.23 ml (1.32 mmol) of DIPEA were added successively to a solution of 210 mg (0.66 mmol) of the compound from Example 5A in 5 ml of DMF. The mixture was then stirred at 60° C. overnight. After cooling to RT, the mixture was added with stirring to 20 ml of a 10% strength citric acid solution. The resulting solid was then filtered off, washed three times with water and once with pentane and then dried under reduced pressure. This gave 314 mg (93% of theory, purity 95%) of the title compound.

$^1$H-NMR (400 Mhz, DMSO-d$_6$): δ [ppm]=8.46 (s, 1H), 7.98 (d, 1H), 7.93 (d, 1H), 7.70 (d, 1H), 7.60-7.46 (m, 5H), 3.59 (s, 3H), 2.31 (s, 3H), 2.10-2.00 (m, 6H), 1.91-1.82 (m, 6H), 1.38 (s, 9H).

LC/MS (Method 1, ESIpos): R$_t$=1.22 min, m/z=485 [M+H]$^+$.

Example 47A

Methyl 4-({[6-bromo-3-methyl-2-(2-thienyl)quinolin-4-yl]carbonyl}amino)bicyclo[2.2.2]octane-1-carboxylate

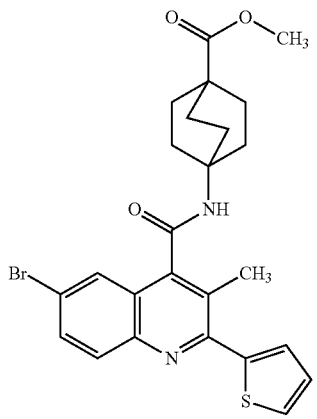 [SMILES: COC(=O)C12CCC(NC(=O)c3c(C)c(-c4cccs4)nc4ccc(Br)cc34)(CC1)CC2]

At RT, 76 mg (0.35 mmol) of methyl 4-aminobicyclo[2.2.2]octane-1-carboxylate hydrochloride, 164 mg (0.43 mmol) of HATU and 0.15 ml (0.86 mmol) of DIPEA were added successively to a solution of 100 mg (0.29 mmol) of 6-bromo-3-methyl-2-(2-thienyl)quinoline-4-carboxylic acid in 1 ml of DMF. The mixture was then stirred at 60° C. overnight. After cooling to RT, the mixture was purified directly (without further work-up) by preparative HPLC (Method 2). This gave 92 mg (51% of theory, purity 82%) of the title compound.

$^1$H-NMR (400 Mhz, DMSO-d$_6$): δ [ppm]=8.49 (s, 1H), 7.92 (d, 1H), 7.85 (dd, 1H), 7.81-7.76 (m, 2H), 7.75 (d, 1H), 7.24 (dd, 1H), 3.60 (s, 3H), 2.59 (s, 3H), 2.15-1.95 (m, 6H), 1.95-1.72 (m, 6H).

LC/MS (Method 1, ESIpos): R$_t$=1.22 min, m/z=513/515 [M+H]$^+$.

Example 48A

Methyl 4-({[6-bromo-2-(2-fluorophenyl)-3-methylquinolin-4-yl]carbonyl}amino)bicyclo[2.2.2]octane-1-carboxylate

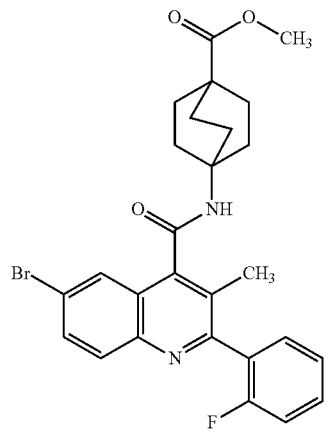 [SMILES: COC(=O)C12CCC(NC(=O)c3c(C)c(-c4ccccc4F)nc4ccc(Br)cc34)(CC1)CC2]

At RT, 15 mg (0.07 mmol) of methyl 4-aminobicyclo[2.2.2]octane-1-carboxylate hydrochloride, 32 mg (0.08 mmol) of HATU and 0.04 ml (0.22 mmol) of DIPEA were added to a solution of 20 mg (0.06 mmol) of the compound from Example 6A in 0.6 ml of DMF, and the mixture was stirred at 60° C. overnight. After cooling to RT, water and ethyl acetate were added to the mixture and the aqueous phase was extracted three times with ethyl acetate. The combined organic phases were washed with saturated aqueous sodium carbonate solution and dried over sodium sulfate, and the solvents were removed on a rotary evaporator. The residue was purified by column chromatography (silica gel, mobile phase cyclohexane/ethyl acetate 2:1). This gave 19 mg (64% of theory, purity >99%) of the title compound.

LC/MS (Method 1, ESIpos): R$_t$=1.20 min, m/z=525/527 [M+H]$^+$.

Example 49A

Methyl 4-({[6-bromo-2-(3-fluorophenyl)-3-methylquinolin-4-yl]carbonyl}amino)bicyclo[2.2.2]octane-1-carboxylate

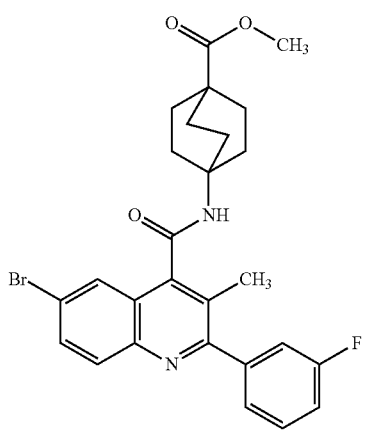 [SMILES: COC(=O)C12CCC(NC(=O)c3c(C)c(-c4cccc(F)c4)nc4ccc(Br)cc34)(CC1)CC2]

At RT, 61 mg (0.28 mmol) of methyl 4-aminobicyclo[2.2.2]octane-1-carboxylate hydrochloride, 158 mg (0.42 mmol) of HATU and 0.15 ml (0.83 mmol) of DIPEA were added successively to a solution of 100 mg (0.28 mmol) of the compound from Example 7A in 1 ml of DMF. The mixture was then stirred at 60° C. overnight. After cooling to RT, the mixture was purified directly (without further work-up) by preparative HPLC (Method 2). This gave 72 mg (44% of theory, purity 90%) of the title compound.

$^1$H-NMR (400 Mhz, DMSO-$d_6$): δ [ppm]=8.48 (s, 1H), 7.99 (d, 1H), 7.89 (dd, 1H), 7.83 (d, 1H), 7.63-7.52 (m, 1H), 7.46-7.38 (m, 2H), 7.38-7.30 (m, 1H), 3.59 (s, 3H), 2.33 (s, 3H), 2.08-1.96 (m, 6H), 1.92-1.77 (m, 6H).

LC/MS (Method 1, ESIpos): R$_t$=1.22 min, m/z=525/527 [M+H]$^+$.

Example 50A

Methyl 4-({[6-bromo-2-(4-fluorophenyl)-3-methylquinolin-4-yl]carbonyl}amino)bicyclo[2.2.2]octane-1-carboxylate

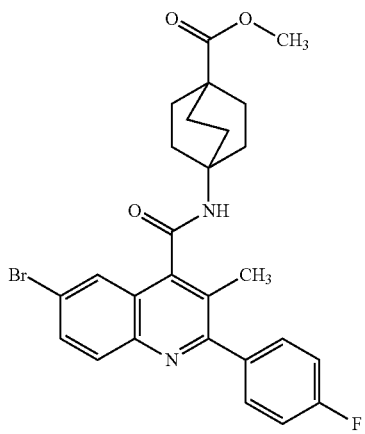 [SMILES: COC(=O)C12CCC(NC(=O)c3c(C)c(-c4ccc(F)cc4)nc4ccc(Br)cc34)(CC1)CC2]

At RT, 61 mg (0.28 mmol) of methyl 4-aminobicyclo[2.2.2]octane-1-carboxylate hydrochloride, 158 mg (0.42 mmol) of HATU and 0.15 ml (0.83 mmol) of DIPEA were added successively to a solution of 100 mg (0.28 mmol) of the compound from Example 8A in 1 ml of DMF. The mixture was then stirred at 60° C. overnight. After cooling to RT, the mixture was purified directly (without further work-up) by preparative HPLC (Method 2). This gave 68 mg (46% of theory, purity 98%) of the title compound.

$^1$H-NMR (400 Mhz, DMSO-$d_6$): δ [ppm]=8.47 (s, 1H), 7.97 (d, 1H), 7.88 (dd, 1H), 7.82 (d, 1H), 7.72-7.58 (m, 2H), 7.42-7.26 (m, 2H), 3.59 (s, 3H), 2.33 (s, 3H), 2.11-1.97 (m, 6H), 1.93-1.76 (m, 6H).

LC/MS (Method 1, ESIpos): R$_t$=1.22 min, m/z=525/527 [M+H]$^+$.

Example 51A

Methyl 4-({[6-bromo-2-(4-difluorophenyl)-3-methylquinolin-4-yl]carbonyl}amino)bicyclo[2.2.2]octane-1-carboxylate

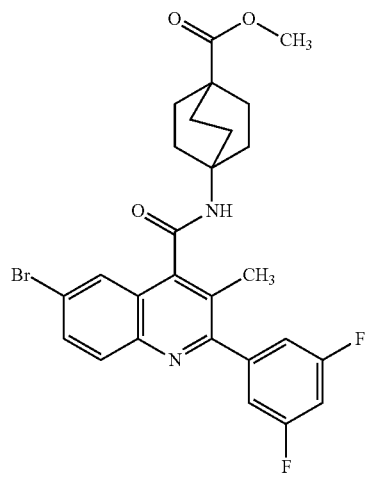 [SMILES: COC(=O)C12CCC(NC(=O)c3c(C)c(-c4cc(F)cc(F)c4)nc4ccc(Br)cc34)(CC1)CC2]

At RT, 58 mg (0.26 mmol) of methyl 4-aminobicyclo[2.2.2]octane-1-carboxylate hydrochloride, 151 mg (0.40 mmol) of HATU and 0.14 ml (0.79 mmol) of DIPEA were added successively to a solution of 100 mg (0.26 mmol) of the compound from Example 9A in 1 ml of DMF. The mixture was then stirred at 60° C. overnight. After cooling to RT, the mixture was purified directly (without further work-up) by preparative HPLC (Method 2). This gave 68 mg (43% of theory, purity 91%) of the title compound.

$^1$H-NMR (400 Mhz, DMSO-$d_6$): δ [ppm]=8.47 (s, 1H), 8.00 (d, 1H), 7.91 (dd, 1H), 7.84 (d, 1H), 7.42 (tt, 1H), 7.37-7.26 (m, 2H), 3.59 (s, 3H), 2.34 (s, 3H), 2.08-1.96 (m, 6H), 1.94-1.77 (m, 6H).

LC/MS (Method 1, ESIpos): R$_t$=1.26 min, m/z=543/545 [M+H]$^+$.

Example 52A

Methyl 4-({[6-bromo-2-(2-chlorophenyl)-3-methylquinolin-4-yl]carbonyl}amino)bicyclo[2.2.2]octane-1-carboxylate

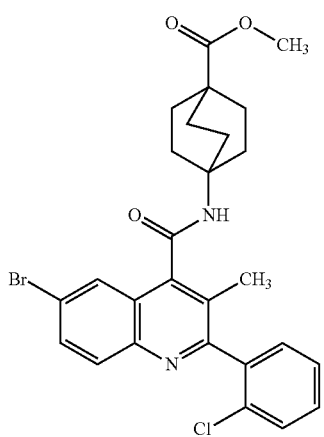 [SMILES: COC(=O)C12CCC(NC(=O)c3c(C)c(-c4ccccc4Cl)nc4ccc(Br)cc34)(CC1)CC2]

At RT, 58 mg (0.27 mmol) of methyl 4-aminobicyclo[2.2.2]octane-1-carboxylate hydrochloride, 151 mg (0.40 mmol) of HATU and 0.14 ml (0.80 mmol) of DIPEA were added successively to a solution of 100 mg (0.27 mmol) of the compound from Example 10A in 1 ml of DMF. The mixture was then stirred at 60° C. overnight. After cooling to RT, the mixture was purified directly (without further work-up) by preparative HPLC (Method 2). This gave 61 mg (40% of theory, purity 93%) of the title compound.

$^1$H-NMR (400 Mhz, DMSO-$d_6$): δ [ppm]=8.53 (br. s, 1H), 7.98 (d, 1H), 7.90 (dd, 1H), 7.86 (d, 1H), 7.63 (d, 1H), 7.59-7.47 (m, 2H), 7.39 (br. s, 1H), 3.59 (s, 3H), 2.13 (s, 3H), 2.08-1.97 (m, 6H), 1.93-1.75 (m, 6 H).

LC/MS (Method 1, ESIpos): $R_t$=1.23 min, m/z=541/543 [M+H]$^+$.

Example 53A

Methyl 4-({[6-bromo-2-(3-chlorophenyl)-3-methylquinolin-4-yl]carbonyl}amino)bicyclo[2.2.2]octane-1-carboxylate

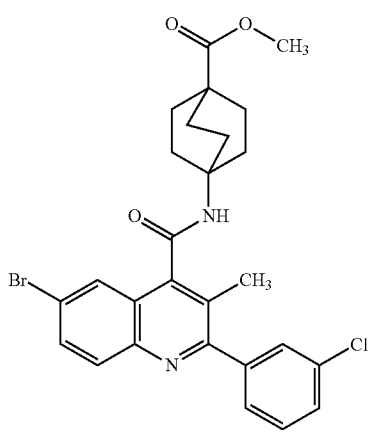 [SMILES: COC(=O)C12CCC(NC(=O)c3c(C)c(-c4cccc(Cl)c4)nc4ccc(Br)cc34)(CC1)CC2]

At RT, 58 mg (0.27 mmol) of methyl 4-aminobicyclo[2.2.2]octane-1-carboxylate hydrochloride, 151 mg (0.40 mmol) of HATU and 0.14 ml (0.80 mmol) of DIPEA were added successively to a solution of 100 mg (0.27 mmol) of the compound from Example 11A in 1 ml of DMF. The mixture was then stirred at 60° C. overnight. After cooling to RT, the mixture was purified directly (without further work-up) by preparative HPLC (Method 2). This gave 80 mg (54% of theory, purity 98%) of the title compound.

$^1$H-NMR (400 Mhz, DMSO-$d_6$): δ [ppm]=8.46 (s, 1H), 7.99 (d, 1H), 7.89 (dd, 1H), 7.84 (d, 1H), 7.62 (d, 1H), 7.60-7.50 (m, 3H), 3.59 (s, 3H), 2.33 (s, 3H), 2.10-1.98 (m, 6H), 1.92-1.79 (m, 6H).

LC/MS (Method 1, ESIpos): $R_t$=1.29 min, m/z=541/543 [M+H]$^+$.

Example 54A

Methyl 4-{[[(6-bromo-3-fluoro-2-phenylquinolin-4-yl)carbonyl]amino}-3-fluorobenzoate

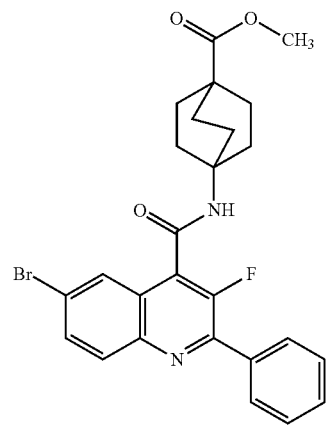 [SMILES: COC(=O)C12CCC(NC(=O)c3c(F)c(-c4ccccc4)nc4ccc(Br)cc34)(CC1)CC2]

At RT, 159 mg (0.87 mmol) of methyl 4-aminobicyclo[2.2.2]octane-1-carboxylate, 247 mg (0.65 mmol) of HATU and 112 mg (0.87 mmol) of DIPEA were added to a solution of 150 mg (0.43 mmol) of the compound from Example 12A in 4 ml of DMF, and the mixture was then stirred at 60° C. for 1 h. After cooling to RT, the mixture was added to 20 ml of a 10% strength citric acid solution. The resulting precipitate was then filtered off, washed with water and dried under reduced pressure. This gave 222 mg (97% of theory, purity 97%) of the title compound.

$^1$H-NMR (400 Mhz, DMSO-$d_6$): δ [ppm]=8.65 (s, 1H), 8.08 (d, 1H), 8.04-7.97 (m, 2H), 7.95 (dd, 1H), 7.91 (d, 1H), 7.63-7.53 (m, 3H), 3.59 (s, 3H), 2.08-1.98 (m, 6H), 1.91-1.82 (m, 6H).

LC/MS (Method 1, ESIpos): Rt=1.26 min, m/z=511/513 [M+H]$^+$.

Example 55A

Methyl 4-{[(6-iodo-3-methyl-2-phenylquinolin-4-yl)carbonyl]amino}bicyclo[2.2.2]octane-1-carboxylate

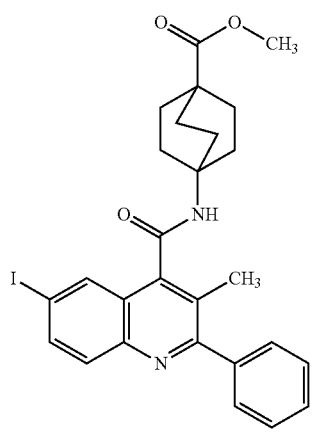 [SMILES: COC(=O)C12CCC(NC(=O)c3c(C)c(-c4ccccc4)nc4ccc(I)cc34)(CC1)CC2]

150 mg (0.38 mmol; purity 90%) of the compound from Example 13A were initially charged in 1.8 ml of DMF. Successively, 91 mg (0.42 mmol) of methyl 4-aminobicyclo[2.2.2]octane-1-carboxylate hydrochloride, 198 mg (0.52 mmol) of HATU and 0.24 ml (1.54 mmol) of DIPEA were added to the solution, and the mixture was subsequently stirred at 60° C. overnight. After cooling to RT, the mixture, without further work-up, was purified by preparative HPLC (Method 2). This gave 136 mg (66% of theory, purity 94%) of the title compound.

$^1$H-NMR (400 Mhz, DMSO-d$_6$): δ [ppm]=8.46 (s, 1H), 8.06 (d, 1H), 8.00 (dd, 1H), 7.80 (d, 1H), 7.60-7.55 (m, 2H), 7.55-7.46 (m, 3H), 3.59 (s, 3H), 2.31 (s, 3H), 2.10-1.97 (m, 6H), 1.93-1.79 (m, 6H).

LC/MS (Method 1, ESIpos): R$_t$=1.25 min, m/z=555 [M+H]$^+$.

Example 56A

Methyl 4-{[(6-cyclopropyl-3-methyl-2-phenylquinolin-4-yl)carbonyl]amino}bicyclo[2.2.2]octane-1-carboxylate

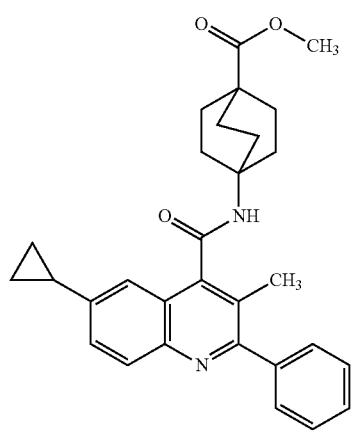 [SMILES: COC(=O)C12CCC(NC(=O)c3c(C)c(-c4ccccc4)nc4ccc(C5CC5)cc34)(CC1)CC2]

70 mg (0.23 mmol) of the compound from Example 16A were initially charged in 1.0 ml of DMF. Successively, 61 mg (0.28 mmol) of methyl 4-aminobicyclo[2.2.2]octane-1-carboxylate hydrochloride, 132 mg (0.35 mmol) of HATU and 0.16 ml (0.92 mmol) of DIPEA were added to the solution, and the mixture was subsequently stirred at 60° C. overnight. After cooling to RT, the mixture, without further work-up, was purified by preparative HPLC (Method 2). This gave 68 mg (60% of theory, purity 95%) of the title compound.

$^1$H-NMR (400 Mhz, DMSO-d$_6$): δ [ppm]=8.42 (s, 1H), 7.92 (d, 1H), 7.62-7.49 (m, 5H), 7.47 (dd, 1H), 7.43 (d, 1H), 3.59 (s, 3H), 2.30 (s, 3H), 2.21-2.11 (m, 1H), 2.10-2.01 (m, 6H), 1.91-1.83 (m, 6H), 1.14-1.06 (m, 2H), 0.77 (br. s, 2H).

LC/MS (Method 1, ESIpos): R$_t$=1.17 min, m/z=469 [M+H]$^+$.

Example 57A

Methyl 4-{[(6-cyclobutyl-3-methyl-2-phenylquinolin-4-yl)carbonyl]amino}bicyclo[2.2.2]octane-1-carboxylate

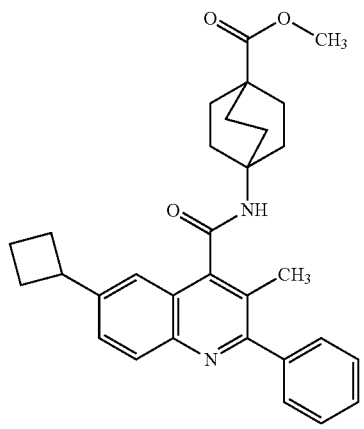 [SMILES: COC(=O)C12CCC(NC(=O)c3c(C)c(-c4ccccc4)nc4ccc(C5CCC5)cc34)(CC1)CC2]

227 mg (0.71 mmol) of the compound from Example 18A were initially charged in 3.0 ml of DMF. Successively, 188 mg (0.86 mmol) of methyl 4-aminobicyclo[2.2.2]octane-1-carboxylate hydrochloride, 408 mg (1.07 mmol) of HATU and 0.50 ml (2.86 mmol) of DIPEA were added to the solution, and the mixture was subsequently stirred at 60° C. overnight. After cooling to RT, the mixture, without further work-up, was purified by preparative HPLC (Method 2). This gave 173 mg (48% of theory, purity 95%) of the title compound.

$^1$H-NMR (400 Mhz, DMSO-d$_6$): δ [ppm]=8.45 (s, 1H), 7.99 (d, 1H), 7.70 (d, 1H), 7.62-7.46 (m, 6H), 3.80-3.70 (m, 1H), 3.59 (s, 3H), 2.46-2.36 (m, 2H), 2.31 (s, 3H), 2.21-2.08 (m, 3H), 2.07-1.97 (m, 6H), 1.95-1.72 (m, 7H).

LC/MS (Method 1, ESIpos): R$_t$=1.27 min, m/z=483 [M+H]$^+$.

Example 58A

Methyl 4-({[3-methyl-2-phenyl-6-(trimethylsilyl)quinolin-4-yl]carbonyl}amino)bicyclo[2.2.2]octane-1-carboxylate

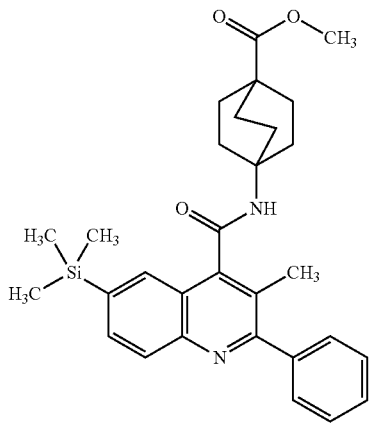 [SMILES: COC(=O)C12CCC(NC(=O)c3c(C)c(-c4ccccc4)nc4ccc([Si](C)(C)C)cc34)(CC1)CC2]

At RT, 262 mg (1.19 mmol) of methyl 4-aminobicyclo[2.2.2]octane-1-carboxylate hydrochloride, 340 mg (0.89 mmol) of HATU and 231 mg (1.79 mmol) of DIPEA were added to a solution of 200 mg (0.60 mmol) of the compound from Example 21A in 5 ml of DMF, and the mixture was stirred at 60° C. overnight. Subsequently, a further 90 mg (0.27 mmol) of the compound from Example 21A, 115 mg (0.30 mmol) of HATU and 77 mg (0.60 mmol) of DIPEA were added, and the mixture was stirred at 60° C. for a further 5 h. After cooling to RT, the mixture was purified by preparative HPLC (Method 3). This gave 209 mg (70% of theory, purity 100%) of the title compound.

$^1$H-NMR (400 Mhz, DMSO-$d_6$): δ [ppm]=8.46 (s, 1H), 8.01 (d, 1H), 7.94 (s, 1H), 7.92-7.87 (m, 1H), 7.61-7.47 (m, 5H), 3.59 (s, 3H), 2.32 (s, 3H), 2.10-2.01 (m, 6H), 1.91-1.81 (m, 6H), 0.36-0.30 (m, 9H).

LC/MS (Method 1, ESIpos): $R_t$=1.29 min, m/z=501 [M+H]$^+$.

Example 59A

Methyl 4-({[6-(difluoromethyl)-3-methyl-2-phenylquinolin-4-yl]carbonyl}amino)bicyclo[2.2.2]octane-1-carboxylate

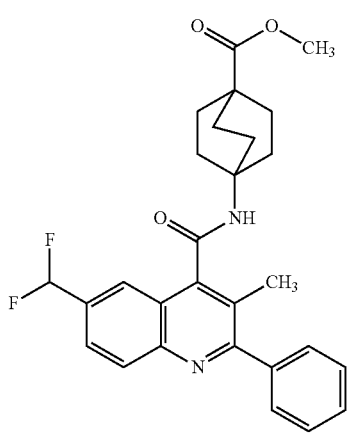 [SMILES: COC(=O)C12CCC(NC(=O)c3c(C)c(-c4ccccc4)nc4ccc(C(F)F)cc34)(CC1)CC2]

188 mg (0.60 mmol) of the compound from Example 24A were initially charged in 2.0 ml of DMF. Successively, 158 mg (0.72 mmol) of methyl 4-aminobicyclo[2.2.2]octane-1-carboxylate hydrochloride, 342 mg (0.90 mmol) of HATU and 0.42 ml (2.40 mmol) of DIPEA were added to the solution, and the mixture was subsequently stirred at 60° C. overnight. After cooling to RT, ethyl acetate and water were added to the mixture, and the phases were separated. The organic phase was washed once with water, dried over sodium sulfate, filtered and concentrated and the residue was purified by column chromatography (80 g of silica gel Biotage Chromabond, mobile phase cyclohexane/ethyl acetate 2:1). This gave 117 mg (41% of theory, purity 99%) of the title compound.

LC/MS (Method 1, ESIpos): $R_t$=1.10 min, m/z=479 [M+H]$^+$.

Example 60A

Methyl 4-({[3-methyl-2-phenyl-6-(trifluoromethoxy)quinolin-4-yl]carbonyl}amino)bicyclo[2.2.2]octane-1-carboxylate

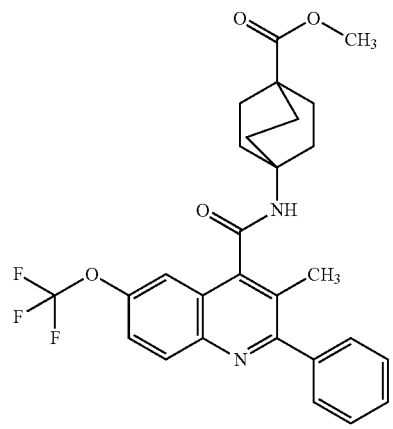 [SMILES: COC(=O)C12CCC(NC(=O)c3c(C)c(-c4ccccc4)nc4ccc(OC(F)(F)F)cc34)(CC1)CC2]

150 mg (0.43 mmol) of the compound from Example 25A were initially charged in 1.0 ml (13.7 mmol) of thionyl chloride and stirred at RT overnight. The reaction mixture was then concentrated under reduced pressure and the residue, after drying under reduced pressure, was taken up in 1 ml of anhydrous THF. The suspension present was added slowly to a mixture of 0.3 ml (1.73 mmol) of DIPEA and 114 mg (0.52 mmol) of methyl 4-aminobicyclo[2.2.2]octane-1-carboxylate hydrochloride in 2.0 ml of anhydrous THF, and the reaction mixture was stirred at RT overnight. The mixture was then adjusted to pH 2 by addition of 4 M hydrochloric acid and purified by preparative HPLC (Method 2). This gave 87 mg (38% of theory, purity 97%) of the title compound.

$^1$H-NMR (400 Mhz, DMSO-$d_6$): δ [ppm]=8.50 (s, 1H), 8.17 (d, 1H), 7.75 (dd, 1H), 7.62-7.47 (m, 6H), 3.59 (s, 3H), 2.33 (s, 3H), 2.11-1.95 (m, 6H), 1.93-1.77 (m, 6H).

LC/MS (Method 1, ESIpos): $R_t$=1.31 min, m/z=513 [M+H]$^+$.

Example 61A

Methyl 4-[({3-methyl-2-phenyl-6-[(trifluoromethyl)sulfanyl]quinolin-4-yl}carbonyl)amino]bicyclo[2.2.2]octane-1-carboxylate

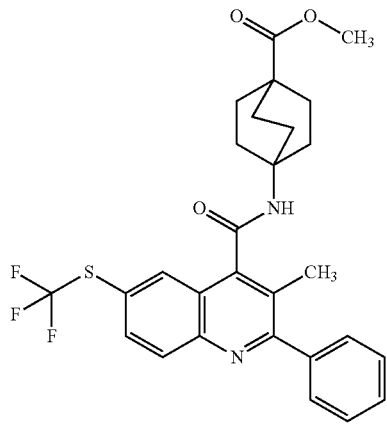 [SMILES: COC(=O)C12CCC(NC(=O)c3c(C)c(-c4ccccc4)nc4ccc(SC(F)(F)F)cc34)(CC1)CC2]

350 mg (0.67 mmol; purity 70%) of the compound from Example 27A were initially charged in 2.5 ml of DMF. Successively, 178 mg (0.81 mmol) of methyl 4-aminobicyclo[2.2.2]octane-1-carboxylate hydrochloride, 385 mg (1.01 mmol) of HATU and 0.47 ml (2.70 mmol) of DIPEA were added to the solution, and the mixture was subsequently stirred at 60° C. overnight. After cooling to RT, ethyl acetate and water were added to the mixture. The phases were separated, and the organic phase was washed with saturated sodium carbonate solution and dried over sodium sulfate, filtered and concentrated. The residue was purified by preparative HPLC (Method 2). This gave 314 mg (77% of theory, purity 87%) of the title compound.

$^1$H-NMR (400 Mhz, DMSO-$d_6$): δ [ppm]=8.52 (s, 1H), 8.15 (d, 1H), 8.08 (d, 1H), 7.96 (dd, 1H), 7.62-7.48 (m, 5H), 3.59 (s, 3H), 2.34 (s, 3H), 2.09-1.98 (m, 6H), 1.93-1.81 (m, 6H).

LC/MS (Method 1, ESIpos): $R_t$=1.28 min, m/z=529 [M+H]$^+$.

Example 62A

Methyl 4-{[(6-bromo-3,8-dimethyl-2-phenylquinolin-4-yl)carbonyl]amino}bicyclo[2.2.2]octane-1-carboxylate

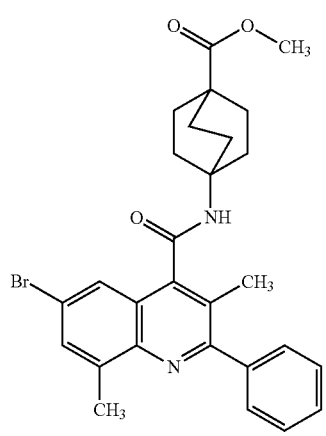 [SMILES: COC(=O)C12CCC(NC(=O)c3c(C)c(-c4ccccc4)nc4c(C)cc(Br)cc34)(CC1)CC2]

At RT, 96 mg (0.44 mmol) of methyl 4-aminobicyclo[2.2.2]octane-1-carboxylate hydrochloride, 226 mg (0.60 mmol) of HATU and 159 mg (1.23 mmol) of DIPEA were added to a solution of 150 mg (0.40 mmol, purity 94%) of the compound from Example 28A in 3 ml of DMF, and the mixture was stirred at 60° C. for 7 h. After cooling to RT, the mixture was introduced into 50 ml of a 10% strength citric acid solution, and the precipitate formed was filtered off, washed with water and dried under reduced pressure. This gave 215 mg (52% of theory, purity about 50%) of the title compound.

LC/MS (Method 1, ESIpos): $R_t$=1.32 min, m/z=521/523 [M+H]$^+$.

Example 63A

Methyl 4-{[(6,8-dichloro-3-methyl-2-phenylquinolin-4-yl)carbonyl]amino}bicyclo[2.2.2]octane-1-carboxylate

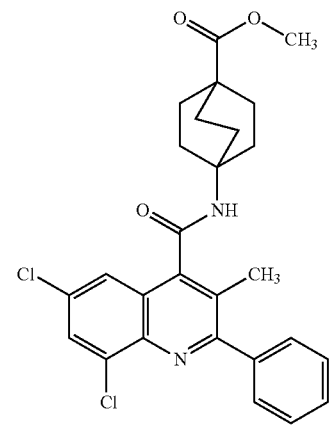 [SMILES: COC(=O)C12CCC(NC(=O)c3c(C)c(-c4ccccc4)nc4c(Cl)cc(Cl)cc34)(CC1)CC2]

150 mg (0.41 mmol; purity 90%) of the compound from Example 29A were initially charged in 1.8 ml of DMF. Successively, 107 mg (0.49 mmol) of methyl 4-aminobicyclo[2.2.2]octane-1-carboxylate hydrochloride, 232 mg (0.61 mmol) of HATU and 0.28 ml (1.63 mmol) of DIPEA were added to the solution, and the mixture was subsequently stirred at 60° C. overnight. After cooling to RT, the mixture, without further work-up, was purified by preparative HPLC (Method 2). This gave 145 mg (64% of theory, purity 90%) of the title compound.

$^1$H-NMR (400 Mhz, DMSO-$d_6$): δ [ppm]=8.50 (s, 1H), 8.10 (d, 1H), 7.66-7.59 (m, 3H), 7.59-7.48 (m, 3H), 3.59 (s, 3H), 2.36 (s, 3H), 2.15-1.94 (m, 6H), 1.94-1.75 (m, 6H).

LC/MS (Method 1, ESIpos): $R_t$=1.37 min, m/z=497 [M+H]$^+$.

Example 64A

Methyl 4-{[(3,6,7-trimethyl-2-phenylquinolin-4-yl)carbonyl]amino}bicyclo[2.2.2]octane-1-carboxylate

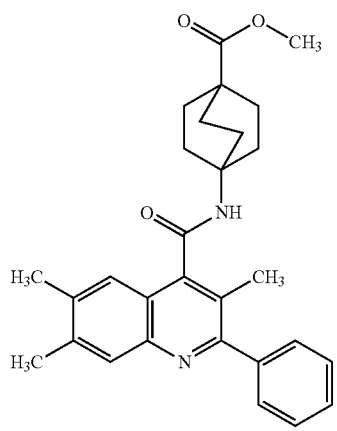 [SMILES: COC(=O)C12CCC(NC(=O)c3c(C)c(-c4ccccc4)nc4cc(C)c(C)cc34)(CC1)CC2]

300 mg (0.84 mmol; purity 82%) of the compound from Example 30A were initially charged in 4.1 ml of DMF. Successively, 223 mg (1.01 mmol) of methyl 4-aminobicyclo[2.2.2]octane-1-carboxylate hydrochloride, 482 mg (1.27 mmol) of HATU and 0.59 ml (3.38 mmol) of DIPEA were added to the solution, and the mixture was subsequently stirred at 60° C. overnight. After cooling to RT, the mixture, without further work-up, was purified by preparative HPLC (Method 2). This gave 182 mg (37% of theory, purity 78%) of the title compound.

$^1$H-NMR (400 Mhz, DMSO-d$_6$): δ [ppm]=8.34 (s, 1H), 7.77 (s, 1H), 7.60-7.35 (m, 6H), 3.59 (s, 3H), 2.43 (s, 3H), 2.42 (s, 3H), 2.28 (s, 3H), 2.13-1.99 (m, 6H), 1.92-1.76 (m, 6H).

LC/MS (Method 1, ESIpos): R$_t$=1.14 min, m/z=457 [M+H]$^+$.

Example 65A

Methyl 4-({[6-bromo-3-methyl-2-(2-methylphenyl)quinolin-4-yl]carbonyl}amino)bicyclo[2.2.2]octane-1-carboxylate

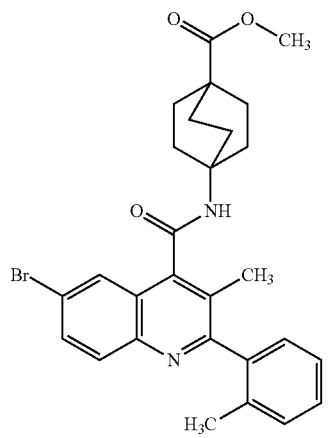 [SMILES: COC(=O)C12CCC(NC(=O)c3c(C)c(-c4ccccc4C)nc4ccc(Br)cc34)(CC1)CC2]

150 mg (0.37 mmol; purity 88%) of the compound from Example 31A were initially charged in 1.5 ml of DMF. Successively, 111 mg (0.50 mmol) of methyl 4-aminobicyclo[2.2.2]octane-1-carboxylate hydrochloride, 240 mg (0.63 mmol) of HATU and 0.29 ml (1.68 mmol) of DIPEA were added to the solution, and the mixture was subsequently stirred at 60° C. overnight. After cooling to RT, the mixture, without further work-up, was purified by preparative HPLC (Method 2). This gave 146 mg (75% of theory, purity 99%) of the title compound.

$^1$H-NMR (400 Mhz, DMSO-d$_6$): δ [ppm]=8.50 (s, 1H), 7.95 (d, 1H), 7.88 (dd, 1H), 7.85 (d, 1H), 7.42-7.28 (m, 3H), 7.18 (d, 1H), 3.59 (s, 3H), 2.09 (s, 3H), 2.08-1.97 (m, 9H), 1.92-1.81 (m, 6H).

LC/MS (Method 1, ESIpos): R$_t$=1.23 min, m/z=521/523 [M+H]$^+$.

Example 66A

Methyl 4-({[6-bromo-2-(2,6-difluorophenyl)-3-methylquinolin-4-yl]carbonyl}amino)bicyclo[2.2.2]octane-1-carboxylate

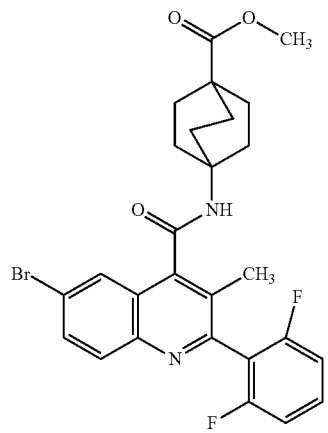 [SMILES: COC(=O)C12CCC(NC(=O)c3c(C)c(-c4c(F)cccc4F)nc4ccc(Br)cc34)(CC1)CC2]

56 mg (0.15 mmol) of the compound from Example 32A were initially charged in 1.8 ml of DMF. Successively, 39 mg (0.18 mmol) of methyl 4-aminobicyclo[2.2.2]octane-1-carboxylate hydrochloride, 85 mg (0.22 mmol) of HATU and 0.10 ml (0.59 mmol) of DIPEA were added to the solution, and the mixture was subsequently stirred at 60° C. overnight. After cooling to RT, the mixture, without further work-up, was purified by preparative HPLC (Method 2). This gave 59 mg (73% of theory, purity 99%) of the title compound.

LC/MS (Method 1, ESIpos): R$_t$=1.21 min, m/z=543/545 [M+H]$^+$.

Example 67A

Methyl 4-({[6-bromo-2-(3-methoxyphenyl)-3-methylquinolin-4-yl]carbonyl}amino)bicyclo[2.2.2]octane-1-carboxylate

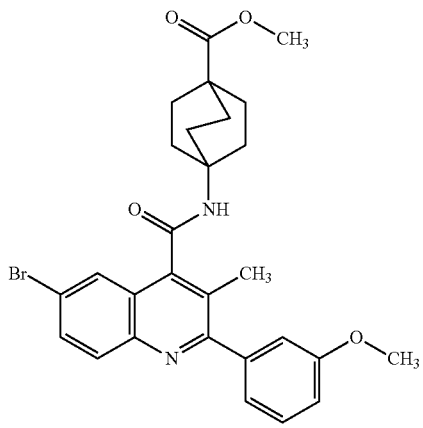 [SMILES: COC(=O)C12CCC(NC(=O)c3c(C)c(-c4cccc(OC)c4)nc4ccc(Br)cc34)(CC1)CC2]

100 mg (0.27 mmol) of the compound from Example 33A were initially charged in 1.0 ml of DMF. Successively, 70.8 mg (0.32 mmol) of methyl 4-aminobicyclo[2.2.2]octane-1-carboxylate hydrochloride, 153 mg (0.40 mmol) of HATU and 0.19 ml (1.07 mmol) of DIPEA were added to the solution, and the mixture was subsequently stirred at 60° C. overnight. After cooling to RT, the mixture, without further work-up, was purified by preparative HPLC (Method 2). This gave 98 mg (63% of theory, purity 92%) of the title compound.

$^1$H-NMR (400 Mhz, DMSO-$d_6$): δ [ppm]=8.47 (s, 1H), 7.97 (d, 1H), 7.87 (dd, 1H), 7.82 (d, 1H), 7.48-7.39 (m, 1H), 7.11 (d, 1H), 7.09-7.01 (m, 2H), 3.81 (s, 3H), 3.59 (s, 3H), 2.32 (s, 3H), 2.14-1.94 (m, 6H), 1.93-1.77 (m, 6H).

LC/MS (Method 1, ESIpos): $R_t$=1.17 min, m/z=537/539 [M+H]$^+$.

Example 68A

Methyl 4-({[6-bromo-3-(methylsulfanyl)-2-phenylquinolin-4-yl]carbonyl}amino)bicyclo[2.2.2]octane-1-carboxylate

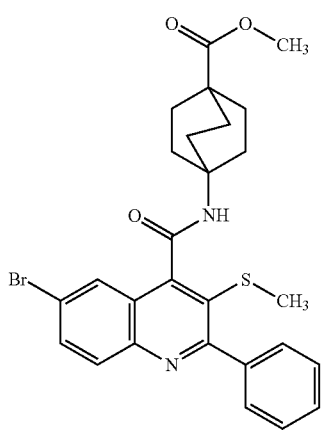 [SMILES: COC(=O)C12CCC(NC(=O)c3c(SC)c(-c4ccccc4)nc4ccc(Br)cc34)(CC1)CC2]

At RT, 68 mg (0.18 mmol) of HATU and 46 mg (0.36 mmol) of DIPEA were added to a solution of 70 mg (0.12 mmol, purity 64%) of the compound from Example 34A in 1.6 ml of DMF, and the mixture was stirred at RT for 30 min. Subsequently, 26 mg (0.12 mmol) of methyl 4-aminobicyclo[2.2.2]octane-1-carboxylate hydrochloride, dissolved in 1 ml of DMF, were added and the mixture was stirred at 60° C. overnight. After cooling to RT, the mixture was purified by preparative HPLC (Method 3). This gave 53 mg (80% of theory, purity 97%) of the title compound.

$^1$H-NMR (400 Mhz, DMSO-$d_6$): δ [ppm]=8.41 (s, 1H), 8.00 (d, 1H), 7.95 (dd, 1H), 7.84 (d, 1H), 7.73-7.67 (m, 2H), 7.56-7.45 (m, 3H), 3.59 (s, 3H), 2.09-2.00 (m, 6H), 2.01 (s, 3H), 1.92-1.81 (m, 6H).

LC/MS (Method 1, ESIpos): $R_t$=1.26 min, m/z=539/541 [M+H]$^+$.

Example 69A

Methyl 4-{[(6-bromo-3-ethyl-2-phenylquinolin-4-yl)carbonyl]amino}bicyclo[2.2.2]octane-1-carboxylate

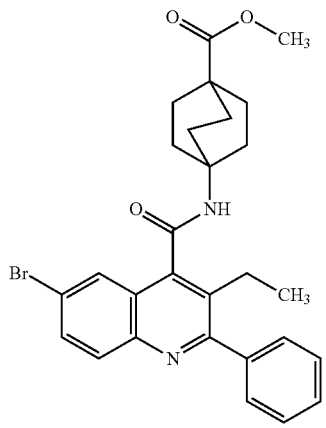 [SMILES: CCc1c(-c2ccccc2)nc2ccc(Br)cc2c1C(=O)NC12CCC(C(=O)OC)(CC1)CC2]

150 mg (0.42 mmol) of the compound from Example 35A were initially charged in 1.5 ml (20.6 mmol) of thionyl chloride and stirred at RT for 2.5 h and then at 60° C. overnight. The reaction mixture was then concentrated under reduced pressure and the residue, after drying under reduced pressure, was taken up in 1 ml of anhydrous THF. The suspension present was added slowly to a mixture of 0.28 ml (1.60 mmol) of DIPEA and 106 mg (0.48 mmol) of methyl 4-aminobicyclo[2.2.2]octane-1-carboxylate hydrochloride in 1.4 ml of anhydrous THF, and the reaction mixture was stirred at RT overnight. After addition of ethyl acetate and water, the phases were separated and the organic phase was washed with sat. sodium carbonate solution, dried over sodium sulfate, filtered and concentrated. The residue was purified by preparative HPLC (Method 2). This gave 11 mg (5% of theory, purity 99%) of the title compound.

LC/MS (Method 1, ESIpos): $R_t$=1.27 min, m/z=561/563 [M+H]$^+$.

Example 70A

Methyl 4-{[(6-bromo-3-cyclopropyl-2-phenylquinolin-4-yl)carbonyl]amino}bicyclo[2.2.2]octane-1-carboxylate

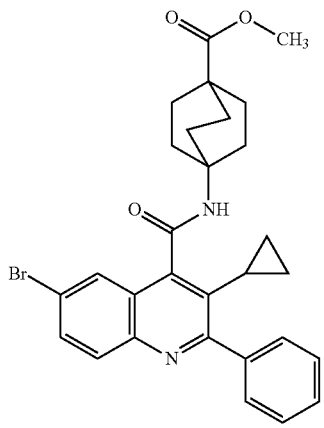 [SMILES: COC(=O)C12CCC(NC(=O)c3c(C4CC4)c(-c4ccccc4)nc4ccc(Br)cc34)(CC1)CC2]

At RT, 119 mg (0.54 mmol) of methyl 4-aminobicyclo[2.2.2]octane-1-carboxylate, 310 mg (0.82 mmol) of HATU and 0.28 ml (1.63 mmol) of DIPEA were added to a solution of 200 mg (0.54 mmol) of the compound from Example 36A in 3 ml of DMF, and the mixture was stirred at 60° C. for 5 h.

Subsequently, a further 0.19 ml (1.11 mmol) of DIPEA were added, and the mixture was stirred at 60° C. for a further 22 h. After cooling to RT, the mixture was introduced into 50 ml of 10% strength citric acid solution and extracted twice with in each case 30 ml of ethyl acetate. The combined organic phases were dried over sodium sulfate, filtered and concentrated and the residue was taken up in a little DMSO and acetonitrile and purified by preparative HPLC (Method 3). This gave 84 mg (29% of theory, purity 100%) of the title compound.

$^1$H-NMR (400 Mhz, DMSO-$d_6$): δ [ppm]=8.41 (s, 1H), 7.97 (d, 1H), 7.92 (d, 1H), 7.88 (dd, 1H), 7.72-7.66 (m, 2H), 7.54-7.42 (m, 3H), 3.60 (s, 3H), 2.30-2.17 (m, 1H), 2.13-2.00 (m, 6H), 1.93-1.79 (m, 6H), 0.72-0.58 (m, 2H), 0.38-0.22 (m, 2H).

LC/MS (Method 1, ESIpos): $R_t$=1.27 min, m/z=533/535 [M+H]$^+$.

Example 71A

Methyl 4-{[(6-bromo-3-chloro-2-phenylquinolin-4-yl)carbonyl]amino}bicyclo[2.2.2]octane-1-carboxylate

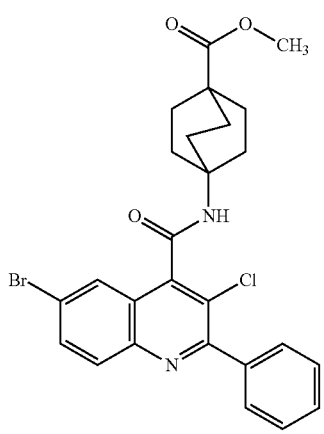 [SMILES: COC(=O)C12CCC(NC(=O)c3c(Cl)c(-c4ccccc4)nc4ccc(Br)cc34)(CC1)CC2]

At RT, 645 mg (1.70 mmol) of HATU and 438 mg (3.39 mmol) of DIPEA were added to a solution of 500 mg (1.13 mmol, purity 82%) of the compound from Example 37A in 6.5 ml of DMF, and the mixture was stirred at RT for 30 min. Subsequently, 248 mg (1.13 mmol) of methyl 4-aminobicyclo[2.2.2]octane-1-carboxylate hydrochloride, dissolved in 1 ml of DMF, were added and the mixture was stirred at 60° C. overnight. After cooling to RT, the mixture was purified by preparative HPLC (Method 4). This gave 226 mg (36% of theory, purity 96%) of the title compound.

$^1$H-NMR (400 Mhz, DMSO-$d_6$): δ [ppm]=8.62 (s, 1H), 8.05 (d, 1H), 7.99 (dd, 1H), 7.83 (d, 1H), 7.73-7.67 (m, 2H), 7.59-7.52 (m, 3H), 3.59 (s, 3H), 2.08-1.98 (m, 6H), 1.91-1.82 (m, 6H).

LC/MS (Method 1, ESIpos): $R_t$=1.24 min, m/z=527/529 [M+H]$^+$.

Example 72A

Methyl 4-{[(6-bromo-2-phenyl-3-propylquinolin-4-yl)carbonyl]amino}bicyclo[2.2.2]octane-1-carboxylate

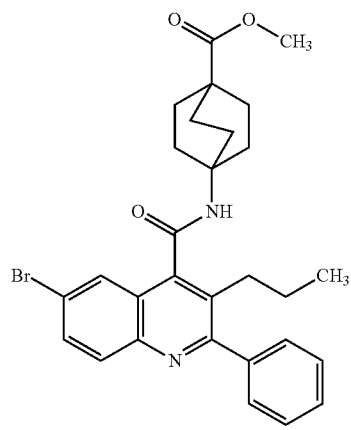 [SMILES: CCCc1c(-c2ccccc2)nc2ccc(Br)cc2c1C(=O)NC12CCC(C(=O)OC)(CC1)CC2]

150 mg (0.40 mmol) of the compound from Example 38A were dissolved in 1.4 ml (19.8 mmol) of thionyl chloride. The reaction mixture was stirred at RT for 2.5 h and then at 60° C. overnight. The reaction mixture was then concentrated under reduced pressure and the residue, after drying under reduced pressure, was taken up in 1 ml of THF. The suspension present was added slowly to a mixture of 0.27 ml (1.54 mmol) of DIPEA and 102 mg (0.46 mmol) of methyl 4-aminobicyclo[2.2.2]octane-1-carboxylate hydrochloride in 1.4 ml of THF, and the reaction mixture was stirred at RT overnight. After addition of ethyl acetate and water, the phases were separated and the aqueous phase was extracted three times with ethyl acetate. The combined organic phases were dried over sodium sulfate, filtered and concentrated and the residue was purified by preparative HPLC (Method 2). This gave 98 mg (47% of theory, purity 99%) of the title compound.

LC/MS (Method 1, ESIpos): $R_t$=1.33 min, m/z=535/537 [M+H]$^+$.

Example 73A

Methyl 4-{[(3-chloro-6-iodo-2-phenylquinolin-4-yl)carbonyl]amino}bicyclo[2.2.2]octane-1-carboxylate

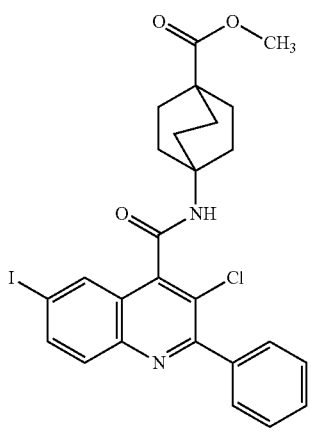 [SMILES: COC(=O)C12CCC(NC(=O)c3c(Cl)c(-c4ccccc4)nc4ccc(I)cc34)(CC1)CC2]

At RT, 376 mg (0.99 mmol) of HATU and 256 mg (1.98 mmol) of DIPEA were added to a solution of 500 mg (0.66 mmol, purity 54%) of the compound from Example 39A in 4 ml of DMF, and the mixture was stirred at RT for 30 min. Subsequently, 145 mg (0.66 mmol) of methyl 4-aminobicyclo[2.2.2]octane-1-carboxylate hydrochloride, dissolved in 1 ml of DMF, were added and the mixture was stirred at 60° C. overnight. After cooling to RT, the mixture was purified twice by preparative HPLC (Method 4). This gave 74 mg (19% of theory, purity 98%) of the title compound.

$^1$H-NMR (400 Mhz, DMSO-$d_6$): δ [ppm]=8.60 (s, 1H), 8.11 (dd, 1H), 8.06 (d, 1H), 7.87 (d, 1H), 7.73-7.66 (m, 2H), 7.57-7.51 (m, 3H), 3.59 (s, 3H), 2.07-1.99 (m, 6H), 1.91-1.83 (m, 6H).

LC/MS (Method 1, ESIpos): $R_t$=1.33 min, m/z=575 [M+H]$^+$.

Example 74A

Methyl 4-{[(3-cyclopropyl-6-iodo-2-phenylquinolin-4-yl)carbonyl]amino}bicyclo[2.2.2]octane-1-carboxylate

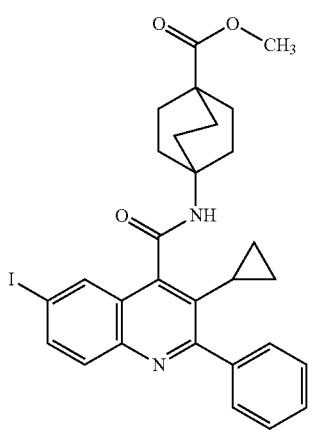 [SMILES: COC(=O)C12CCC(NC(=O)c3c(C4CC4)c(-c4ccccc4)nc4ccc(I)cc34)(CC1)CC2]

At RT, 137 mg (0.36 mmol) of HATU and 93 mg (0.72 mmol) of DIPEA were added to a solution of 100 mg (0.24 mmol) of the compound from Example 40A in 3.2 ml of DMF, and the mixture was stirred at RT for 30 min. Subsequently, 53 mg (0.24 mmol) of methyl 4-aminobicyclo[2.2.2]octane-1-carboxylate hydrochloride, dissolved in 1 ml of DMF, were added and the mixture was stirred at 60° C. overnight. After cooling to RT, the mixture was purified twice by preparative HPLC (Method 4). This gave 58 mg (40% of theory, purity 96%) of the title compound.

$^1$H-NMR (400 Mhz, DMSO-$d_6$): δ [ppm]=8.39 (s, 1H), 8.15 (d, 1H), 8.00 (dd, 1H), 7.79 (d, 1H), 7.72-7.66 (m, 2H), 7.54-7.43 (m, 3H), 3.60 (s, 3H), 2.28-2.16 (m, 1H), 2.12-2.01 (m, 6H), 1.93-1.82 (m, 6H), 0.70-0.58 (m, 2H), 0.35-0.24 (m, 2H).

LC/MS (Method 7, ESIpos): $R_t$=1.60 min, m/z=581 [M+H]$^+$.

Example 75A

Methyl 4-({[3-methyl-2-phenyl-6-(trifluoromethyl)quinolin-4-yl]carbonyl}amino)bicyclo[2.2.2]octane-1-carboxylate

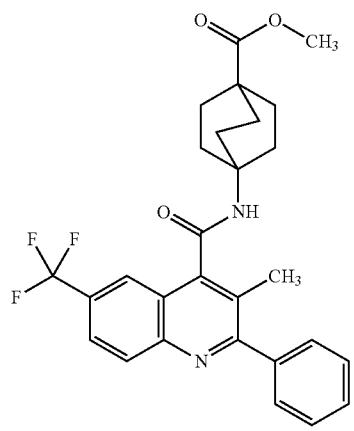 [SMILES: COC(=O)C12CCC(NC(=O)c3c(C)c(-c4ccccc4)nc4ccc(C(F)(F)F)cc34)(CC1)CC2]

10 mg (0.03 mmol; purity 94%) of the compound from Example 41A were initially charged in 0.1 ml of DMF. Successively, 8 mg (0.036 mmol) of methyl 4-aminobicyclo[2.2.2]octane-1-carboxylate hydrochloride, 17 mg (0.045 mmol) of HATU and 0.021 ml (0.12 mmol) of DIPEA were added to the solution, and the mixture was subsequently stirred at 60° C. overnight. After cooling to RT, ethyl acetate and water were added to the mixture. The phases were separated, and the organic phase was washed with saturated sodium carbonate solution and dried over sodium sulfate, filtered and concentrated. The residue was purified by column chromatography (silica gel, mobile phase cyclohexane/ethyl acetate 2:1). This gave 14 mg (94% of theory, purity 100%) of the title compound.

LC/MS (Method 1, ESIpos): $R_t$=1.27 min, m/z=497 [M+H]$^+$.

Example 76A

Methyl 4-{[(6-bromo-3-hydroxy-2-phenylquinolin-4-yl)carbonyl]amino}bicyclo [2.2.2]octane-1-carboxylate

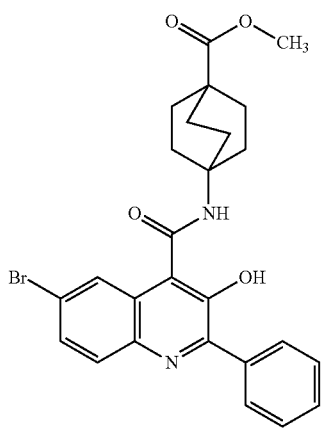

At RT, 447 mg (1.18 mmol) of HATU and 410 ml (2.35 mmol) of DIPEA were added in succession to a solution of 300 mg (0.78 mmol, purity 90%) of the compound from Example 42A in 5 ml of DMF, and the mixture was stirred at RT for 30 min. Subsequently, 172 mg (0.78 mmol) of methyl 4-aminobicyclo[2.2.2]octane-1-carboxylate hydrochloride, dissolved in DMF, were added and the mixture was stirred at 60° C. overnight. After cooling to RT, the mixture was purified directly (without further work-up) by preparative HPLC (Method 4). This gave 51 mg (12% of theory, purity 97%) of the title compound.

$^1$H-NMR (400 Mhz, DMSO-$d_6$): δ [ppm]=9.90 (br. s, 1H), 8.32 (s, 1H), 7.97-7.87 (m, 3H), 7.81 (d, 1H), 7.71 (dd, 1H), 7.56-7.40 (m, 3H), 3.59 (s, 3H), 2.09-1.99 (m, 6H), 1.90-1.79 (m, 6H).

LC/MS (Method 1, ESIpos): $R_t$=1.27 min, m/z=509/511 [M+H]$^+$.

Example 77A

Methyl 4-{[(6-bromo-3-methyl-2-phenylquinolin-3-yl)carbonyl]amino}bicyclo[1.1.1]pentane-1-carboxylate

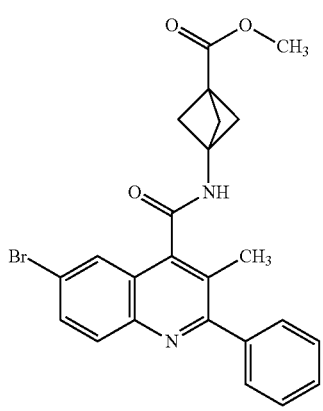 [SMILES: COC(=O)C12CC(NC(=O)c3c(C)c(-c4ccccc4)nc4ccc(Br)cc34)(C1)C2]

221 mg (0.92 mmol) of methyl 3-[(tert-butoxycarbonyl)amino]bicyclo[1.1.1]pentane-1-carboxylate (preparation described in *Eur. J. Org. Chem.* 2004, 3, 493-498) were stirred in 2 ml of a 1:1 mixture of dichloromethane and trifluoroacetic acid at RT for 2 h, and the mixture was subsequently concentrated. The residue was added to a solution of 157 mg (0.46 mmol) of the compound from Example 3A in 2.0 ml of DMF. 262 mg (0.69 mmol) of HATU and 0.32 ml (1.84 mmol) of DIPEA were then added, and the mixture was subsequently stirred at 60° C. overnight. After cooling to RT, ethyl acetate and water were added to the mixture, and the phases were separated. The organic phase was washed once with saturated sodium carbonate solution, dried over sodium sulfate, filtered and concentrated and the residue was taken up in a little DMF and purified by preparative HPLC (Method 5). This gave 105 mg (34% of theory, purity 70%) of the title compound.

$^1$H-NMR (400 Mhz, DMSO-$d_6$): δ [ppm]=9.50 (s, 1H), 7.99 (d, 1H), 7.90 (dd, 1H), 7.80 (d, 1H), 7.61-7.47 (m, 5H), 3.65 (s, 3H), 2.42 (s, 6H), 2.33 (s, 3H).

LC/MS (Method 1, ESIpos): $R_t$=1.12 min, m/z=465/467 [M+H]$^+$.

Example 78A

Methyl 4-{[(6-iodo-3-methyl-2-phenylquinolin-4-yl)carbonyl]amino}bicyclo [2.2.1]heptane-1-carboxylate

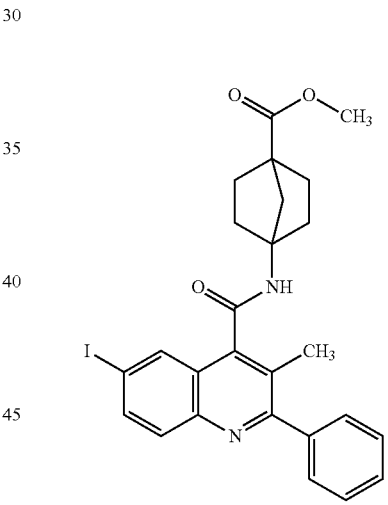

141 mg (0.35 mmol) of the compound from Example 13A were initially charged in 1.8 ml (24.7 mmol) of thionyl chloride and stirred under reflux for 2 h. The reaction mixture was then concentrated under reduced pressure and the residue, after drying under reduced pressure, was taken up in 1 ml of anhydrous THF. The suspension present was added slowly to a mixture of 0.24 ml (1.39 mmol) of DIPEA and 71 mg (0.35 mmol) of methyl 4-aminobicyclo[2.2.1]heptane-1-carboxylate hydrochloride (preparation described in US2010/267738 A1, p. 33) in 2 ml of anhydrous THF, and the reaction mixture was stirred at RT overnight. After addition of ethyl acetate and water, the phases were separated and the organic phase was washed with sat. sodium carbonate solution, dried over sodium sulfate, filtered and concentrated. The residue was purified by preparative HPLC (Method 2). This gave 103 mg (48% of theory, purity 87%) of the title compound.

¹H-NMR (400 Mhz, DMSO-d₆): δ [ppm]=9.06 (s, 1H), 8.10-7.96 (m, 2H), 7.81 (d, 1H), 7.63-7.36 (m, 5H), 2.33 (s, 3H), 2.13-1.57 (m, 10H).

LC/MS (Method 1, ESIpos): $R_t$=1.20 min, m/z=541 [M+H]⁺.

Example 79A

Ethyl 5-{[(6-bromo-3-methyl-2-phenylquinolin-4-yl)carbonyl]amino}bicyclo[3.2.2]nonane-1-carboxylate

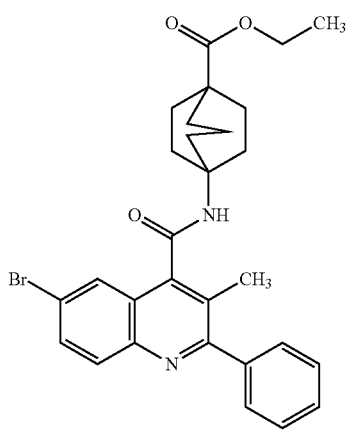 [SMILES: CCOC(=O)C12CCCC(NC(=O)c3c(C)c(-c4ccccc4)nc4ccc(Br)cc34)(CC1)CC2]

At RT, 250 mg (0.66 mmol) of HATU and 170 mg (1.32 mmol) of DIPEA were added to a solution of 150 mg (0.44 mmol) of the compound from Example 3A in 3 ml of DMF, and the mixture was stirred at RT for 30 min. Subsequently, 163 mg (0.66 mmol) of commercially available (Spirochem) ethyl 5-aminobicyclo[3.2.2]nonane-1-carboxylate hydrochloride, dissolved in 1 ml of DMF, were added and the mixture was stirred at 60° C. overnight. After cooling to RT, the mixture was purified by preparative HPLC (Method 3). This gave 171 mg (55% of theory, purity 75%) of the title compound.

LC/MS (Method 1, ESIpos): $R_t$=1.36 min, m/z=535/537 [M+H]⁺.

Example 80A

Ethyl 5-{[(6-bromo-3-chloro-2-phenylquinolin-4-yl)carbonyl]amino}bicyclo[3.2.2]nonane-1-carboxylate

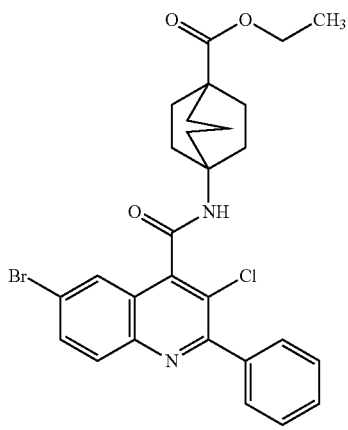 [SMILES: CCOC(=O)C12CCCC(NC(=O)c3c(Cl)c(-c4ccccc4)nc4ccc(Br)cc34)(CC1)CC2]

At RT, 193 mg (0.51 mmol) of HATU and 131 mg (1.02 mmol) of DIPEA were added to a solution of 150 mg (0.34 mmol, purity 82%) of the compound from Example 37A in 2.3 ml of DMF, and the mixture was stirred at RT for 30 min. Subsequently, 126 mg (0.51 mmol) of commercially available (Spirochem) ethyl 5-aminobicyclo[3.2.2]nonane-1-carboxylate hydrochloride, dissolved in 1 ml of DMF, were added and the mixture was stirred at 60° C. overnight. After cooling to RT, the mixture was purified by preparative HPLC (Method 4). This gave 85 mg (33% of theory, purity 75%) of the title compound.

LC/MS (Method 1, ESIpos): $R_t$=1.39 min, m/z=555/557 [M+H]⁺.

Example 81A

Ethyl 5-{[(3-chloro-6-iodo-2-phenylquinolin-4-yl)carbonyl]amino}bicyclo[3.2.2]nonane-1-carboxylate

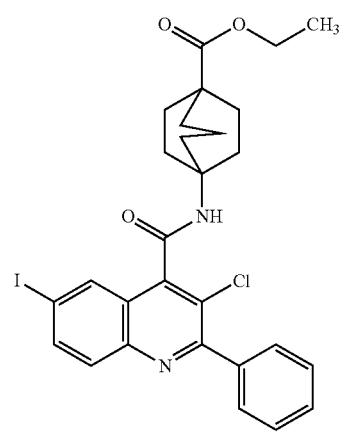 [SMILES: CCOC(=O)C12CCCC(NC(=O)c3c(Cl)c(-c4ccccc4)nc4ccc(I)cc34)(CC1)CC2]

At RT, 189 mg (0.49 mmol) of HATU and 128 mg (0.99 mmol) of DIPEA were added to a solution of 250 mg (0.33 mmol, purity 54%) of the compound from Example 39A in 2.5 ml of DMF, and the mixture was stirred at RT for 30 min. Subsequently, 122 mg (0.49 mmol) of ethyl 5-aminobicyclo[3.2.2]nonane-1-carboxylate hydrochloride, dissolved in 1 ml of DMF, were added and the mixture was stirred at 60° C. overnight. After cooling to RT, the mixture was purified by preparative HPLC (Method 4). This gave 76 mg (34% of theory, purity 90%) of the title compound.

LC/MS (Method 8, ESIpos): $R_t$=4.65 min, m/z=603 [M+H]⁺.

Example 82A

Ethyl 5-{[(3-cyclopropyl-6-iodo-2-phenylquinolin-4-yl)carbonyl]amino}bicyclo [3.2.2]nonane-1-carboxylate

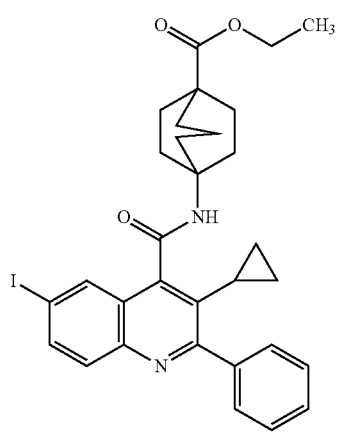 [SMILES: CCOC(=O)C12CCCC(NC(=O)c3c(C4CC4)c(-c4ccccc4)nc4ccc(I)cc34)(CC1)CC2]

At RT, 155 mg (0.41 mmol) of HATU and 105 mg (0.82 mmol) of DIPEA were added to a solution of 100 mg (0.27 mmol) of the compound from Example 40A in 2.5 ml of DMF, and the mixture was stirred at RT for 30 min. Subsequently, 101 mg (0.41 mmol) of ethyl 5-aminobicyclo [3.2.2]nonane-1-carboxylate hydrochloride, dissolved in 1 ml of DMF, were added and the mixture was stirred at 60° C. overnight. After cooling to RT, the mixture was purified by preparative HPLC (Method 3). This gave 57 mg (20% of theory, purity 58%) of the title compound.

LC/MS (Method 8, ESIpos): $R_t$=4.70 min, m/z=609 $[M+H]^+$.

Example 83A

Methyl 4-{[(6-bromo-3-methyl-2-phenylquinolin-4-yl)carbonyl]amino}cubane-1-carboxylate

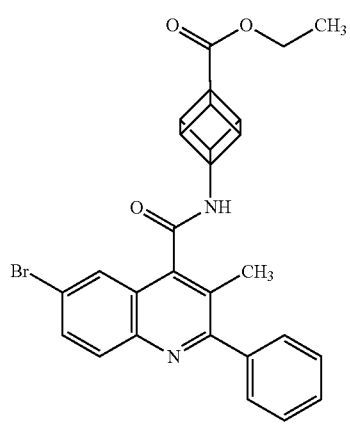 [SMILES: CCOC(=O)C12C3C4C1C1C2C3C41NC(=O)c1c(C)c(-c2ccccc2)nc2ccc(Br)cc12]

121 mg (0.33 mmol, purity 93%) of the compound from Example 3A were initially charged in 1.0 ml (13.7 mmol) of thionyl chloride and stirred at RT for 2 h. The reaction mixture was then concentrated under reduced pressure and the residue, after drying under reduced pressure, was taken up in 1 ml of anhydrous THF. The suspension present was added slowly to a mixture of 0.23 ml (1.31 mmol) of DIPEA and 70 mg (0.33 mmol) of the compound from Example 2A in 2 ml of THF, and the reaction mixture was stirred at RT overnight. After addition of ethyl acetate and water, the phases were separated and the organic phase was washed with sat. sodium carbonate solution, dried over sodium sulfate, filtered and concentrated. The residue was purified by preparative HPLC (Method 2). This gave 93 mg (51% of theory, purity 91%) of the title compound.

$^1$H-NMR (400 Mhz, DMSO-$d_6$): δ [ppm]=9.68 (s, 1H), 8.00 (d, 1H), 7.91 (dd, 1H), 7.86 (d, 1H), 7.63-7.57 (m, 2H), 7.57-7.47 (m, 3H), 4.27-4.22 (m, 3H), 4.21-4.17 (m, 3H), 3.65 (s, 3H), 2.36 (s, 3H).

LC/MS (Method 1, ESIpos): $R_t$=1.07 min, m/z=501/503 $[M+H]^+$.

Example 84A

Methyl 4-{[(6-iodo-3-methyl-2-phenylquinolin-4-yl)carbonyl]amino}cubane-1-carboxylate

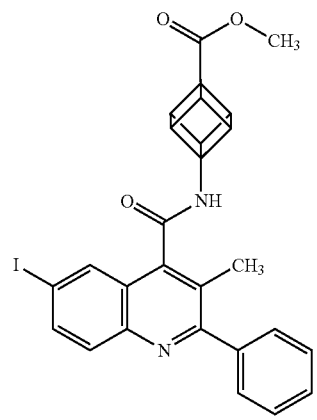 [SMILES: COC(=O)C12C3C4C1C1C2C3C41NC(=O)c1c(C)c(-c2ccccc2)nc2ccc(I)cc12]

150 mg (0.35 mmol, purity 90%) of the compound from Example 13A were initially charged in 1.8 ml (24.7 mmol) of thionyl chloride and stirred under reflux for 2 h. The reaction mixture was then concentrated under reduced pressure and the residue, after drying under reduced pressure, was taken up in 1 ml of anhydrous THF. The suspension present was added slowly to a mixture of 0.24 ml (1.39 mmol) of DIPEA and 74 mg (0.35 mmol) of the compound from Example 2A in 2.1 ml of anhydrous THF, and the reaction mixture was stirred at RT overnight. After addition of ethyl acetate and water, the phases were separated and the organic phase was washed with sat. sodium carbonate solution, dried over sodium sulfate, filtered and concentrated. The residue was purified by preparative HPLC (Method 2). This gave 96 mg (48% of theory, purity 95%) of the title compound.

$^1$H-NMR (400 Mhz, DMSO-$d_6$): δ [ppm]=9.67 (s, 1H), 8.09-8.00 (m, 2H), 7.83 (d, 1H), 7.57-7.62 (m, 2H), 7.57-7.47 (m, 3H), 4.28-4.22 (m, 3H), 4.22-4.17 (m, 3H), 3.65 (s, 3H), 2.35 (s, 3H).

LC/MS (Method 1, ESIpos): $R_t$=1.16 min, m/z=548 $[M+H]^+$.

Example 85A

Methyl 4-{[(6-bromo-3-chloro-2-phenylquinolin-4-yl)carbonyl]amino}cubane-1-carboxylate

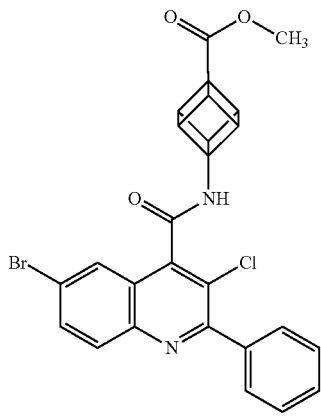 [SMILES: COC(=O)C12C3C4C1C1C2C3C41NC(=O)c1c(Cl)c(-c2ccccc2)nc2ccc(Br)cc12]

150 mg (0.34 mmol, purity 82%) of the compound from Example 37A were initially charged in 2.5 ml (34.3 mmol) of thionyl chloride and stirred under reflux for 2 h. The reaction mixture was then concentrated under reduced pressure, and the residue, after drying under reduced pressure, was taken up in 1 ml of anhydrous THF. The suspension present was added slowly to a mixture of 0.24 ml (1.36 mmol) of DIPEA and 72 mg (0.34 mmol) of the compound from Example 2A in 2 ml of anhydrous THF, and the reaction mixture was stirred at RT overnight. After addition of ethyl acetate and water, the phases were separated and the organic phase was washed with sat. sodium carbonate solution, dried over sodium sulfate, filtered and concentrated. The residue was purified by preparative HPLC (Method 2). This gave 113 mg (53% of theory, purity 83%) of the title compound.

$^1$H-NMR (400 Mhz, DMSO-d$_6$): δ [ppm]=9.82 (s, 1H), 8.11-7.99 (m, 2H), 7.88 (d, 1H), 7.75-7.69 (m, 2H), 7.60-7.52 (m, 3H), 4.28-4.23 (m, 3H), 4.22-4.17 (m, 3H), 3.65 (s, 3H).

LC/MS (Method 1, ESIpos): R$_t$=1.19 min, m/z=521/523 [M+H]$^+$.

Example 86A

4-{[(6-Bromo-3-methyl-2-phenylquinolin-4-yl)carbonyl]amino}bicyclo[2.2.2]octane-1-carbonyl chloride

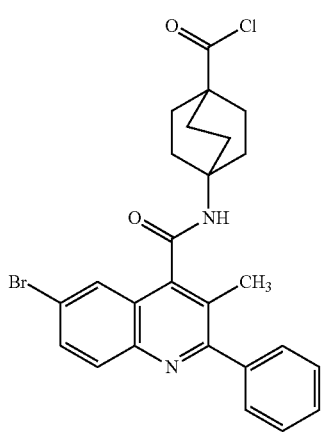

At RT, a drop of DMF and then, slowly, 0.14 ml (1.60 mmol) of oxalyl chloride were added to a suspension of 395 mg (0.80 mmol) of the compound from Example 1 in 10 ml of dichloromethane, and the mixture was then stirred at RT for 1 h. The mixture was then concentrated under reduced pressure, the residue was once more taken up in dichloromethane and the mixture was then re-concentrated under reduced pressure. This procedure was repeated several times. The residue was finally dried under reduced pressure. This gave 410 mg (100% of theory) of the title compound, which were used directly in the subsequent chemical conversions.

Example 87A

6-Bromo-2-(4-bromo-2-thienyl)-3-methylquinoline-4-carboxylic acid

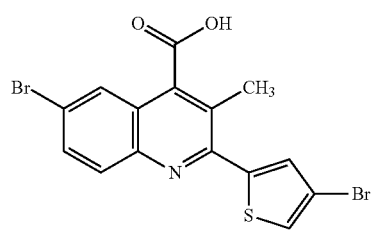 [SMILES: Cc1c(-c2cc(Br)cs2)nc2ccc(Br)cc2c1C(=O)O]

5.00 g (22.12 mmol) of 5-bromo-1H-indole-2,3-dione were initially charged in 61.2 ml of acetic acid, and 4.85 mg (22.12 mmol) of 1-(4-bromo-2-thienyl)propan-1-one (preparation described in *Journal of Organic Chemistry* 1997, 62, 2782-2785) were added. The reaction mixture was stirred at 75° C. for 5 min. Subsequently, 20.4 ml (244 mmol) of conc. hydrochloric acid were added, and stirring of the mixture was continued at 105° C. overnight. After cooling to RT, the reaction mixture was concentrated under reduced pressure, 200 ml of toluene were added and the mixture was concentrated again. Addition of toluene and concentration were repeated twice. The resulting residue was then dissolved in a warm mixture of 250 ml of acetonitrile, methanol, DMSO, dioxane and formic acid and purified by preparative HPLC [column: Kinetix C18, 5 µm, 150×21.2 mm; flow rate: 30 ml/min; detection: 210 nm; injection volume: 1.3 ml; mobile phase: 35% water/60% acetonitrile/5% formic acid (1% in water)→95% acetonitrile/5% formic acid (1% in water), run time: 7.0 min]. 3.44 g (36% of theory, 100% purity) of the title compound was obtained.

$^1$H-NMR (400 Mhz, DMSO-d$_6$): δ [ppm]=14.52 (br. s, 1H), 8.00-7.75 (m, 5H), 2.67 (s, 3H).

LC/MS (Method 1, ESIpos): R$_t$=1.10 min, m/z=425/427/429 [M+H]$^+$.

Example 88A

Methyl 4-({[6-bromo-2-(4-bromo-2-thienyl)-3-methylquinolin-4-yl]carbonyl}amino)bicyclo[2.2.2]octane-1-carboxylate

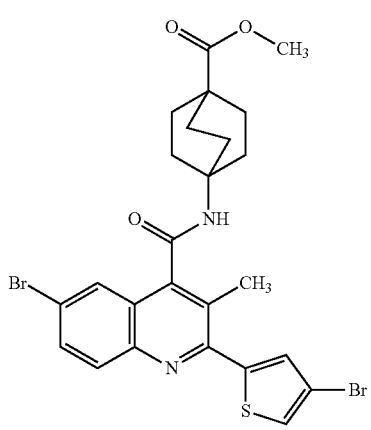 [SMILES: COC(=O)C12CCC(NC(=O)c3c(C)c(-c4cc(Br)cs4)nc4ccc(Br)cc34)(CC1)CC2]

At RT, 401 mg (0.15 mmol) of HATU and 0.37 ml (2.11 mmol) of DIPEA were added to a solution of 300 mg (0.70 mmol) of the compound from Example 87A in 3 ml of DMF, and the mixture was then stirred at RT for 30 min. Subsequently, 231 mg (1.05 mmol) of methyl 4-aminobicyclo[2.2.2]octane-1-carboxylate hydrochloride, dissolved in 1 ml of DMF, were added and the mixture was then stirred at 60° C. overnight. After cooling to RT, the mixture was purified by preparative HPLC (Method 3). This gave 206 mg (47% of theory, purity 95%) of the title compound.

$^1$H-NMR (400 Mhz, DMSO-d$_6$): δ [ppm]=8.50 (s, 1H), 7.97-7.90 (m, 2H), 7.90-7.83 (m, 1H), 7.76 (dd, 2H), 3.60 (s, 3H), 2.60 (s, 3H), 2.12-1.98 (m, 6H), 1.95-1.75 (m, 6H).

LC/MS (Method 1, ESIpos): R$_t$=2.57 min, m/z=591/593/595 [M+H]$^+$.

Example 89A

6-Bromo-3-methyl-2-(5-methyl-2-thienyl)quinoline-4-carboxylic acid

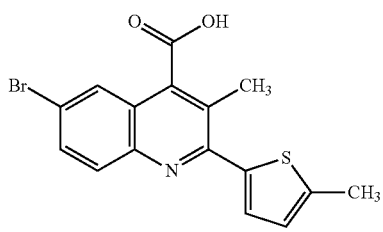 [SMILES: Cc1ccc(-c2nc3ccc(Br)cc3c(C(=O)O)c2C)s1]

5.00 g (22.12 mmol) of 5-bromo-1H-indole-2,3-dione were initially charged in 61.2 ml of acetic acid, and 4.85 g (22.12 mmol) of 1-(5-methyl-2-thienyl)propan-1-one were added. The reaction mixture was stirred at 75° C. for 5 min. Subsequently, 20.4 ml (244 mmol) of conc. hydrochloric acid were added, and stirring of the mixture was continued at 105° C. overnight. After cooling to RT, the reaction mixture was concentrated under reduced pressure, 200 ml of toluene were added and the mixture was concentrated again. Addition of toluene and concentration were repeated twice. The resulting residue was then dissolved in 150 ml of methanol and purified by preparative HPLC [column: Chromatorex Spring Column C18, 10 μm, 370 mm×100 mm; flow rate: 250 ml/min; detection: 210 nm; temperature: 20° C.; gradient acetonitrile/(water+0.2% TFA) 20:80→95:5; run time 35 min]. 5.90 g (74% of theory, 100% purity) of the title compound was obtained.

$^1$H-NMR (400 Mhz, DMSO-d$_6$): δ [ppm]=14.44 (br. s, 1H), 7.94-7.80 (m, 3H), 7.59 (d, 1H), 6.94 (dd, 1H), 2.65 (s, 3H), 2.54 (s, 3H).

LC/MS (Method 1, ESIpos): R$_t$=1.02 min, m/z=362/364 [M+H]$^+$.

Example 90A

Methyl 4-({[6-bromo-3-methyl-2-(5-methyl-2-thienyl)quinolin-4-yl]carbonyl}amino)bicyclo[2.2.2]octane-1-carboxylate

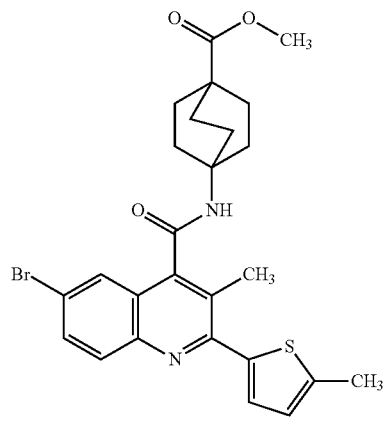 [SMILES: COC(=O)C12CCC(NC(=O)c3c(C)c(-c4ccc(C)s4)nc4ccc(Br)cc34)(CC1)CC2]

At RT, 236 mg (0.62 mmol) of HATU and 0.22 ml (1.24 mmol) of DIPEA were added to a solution of 150 mg (0.41 mmol) of the compound from Example 89A in 1.5 ml of DMF, and the mixture was then stirred at RT for 30 min. Subsequently, 136 mg (0.62 mmol) of methyl 4-aminobicyclo[2.2.2]octane-1-carboxylate hydrochloride, dissolved in 1 ml of DMF, were added and the mixture was stirred at 60° C. overnight. After cooling to RT, the mixture was purified by preparative HPLC (Method 3). This gave 16 mg (7% of theory, purity 100%) of the title compound.

LC/MS (Method 1, ESIpos): R$_t$=2.49 min, m/z=527/529 [M+H]$^+$.

Example 91A

6-Bromo-2-(5-chloro-2-thienyl)-3-methylquinoline-4-carboxylic acid

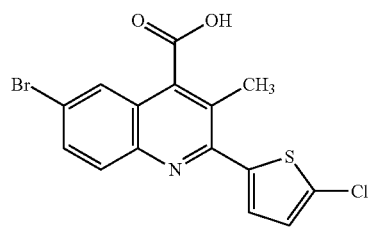 [SMILES: Cc1c(-c2ccc(Cl)s2)nc2ccc(Br)cc2c1C(=O)O]

5.00 g (22.12 mmol) of 5-bromo-1H-indole-2,3-dione were initially charged in 61.2 ml of acetic acid, and 3.83 g (22.12 mmol) of 1-(5-chloro-2-thienyl)propan-1-one were added. The reaction mixture was stirred at 75° C. for 5 min. Subsequently, 20.4 ml (244 mmol) of conc. hydrochloric acid were added, and stirring of the mixture was continued at 105° C. overnight. After cooling to RT, the reaction mixture was concentrated under reduced pressure, 200 ml of toluene were added and the mixture was then concentrated again. Addition of toluene and concentration were repeated twice. The resulting residue was dissolved in a warm mixture of 100 ml of methanol and 50 ml of THF and purified by preparative HPLC [column: Chromatorex Spring Column C18, 10 μm, 290 mm×100 mm; flow rate: 250 ml/min; detection: 210 nm; temperature: 22° C.; injection: 30 ml, gradient methanol/(water+0.1% formic acid) 50:50→90:10; run time 39 min)]. 6.27 g (74% of theory, 100% purity) of the title compound was obtained.

$^1$H-NMR (400 Mhz, DMSO-d$_6$): δ [ppm]=14.47 (br. s, 1H), 7.96-7.89 (m, 2H), 7.86 (d, 1H), 7.68 (d, 1H), 7.26 (d, 1H), 2.67 (s, 3H).

LC/MS (Method 9, ESIpos): R$_t$=2.23 min, m/z=384/382 [M+H]$^+$.

Example 92A

Methyl 4-({[6-bromo-2-(5-chloro-2-thienyl)-3-methylquinolin-4-yl]carbonyl}amino)bicyclo[2.2.2]octane-1-carboxylate

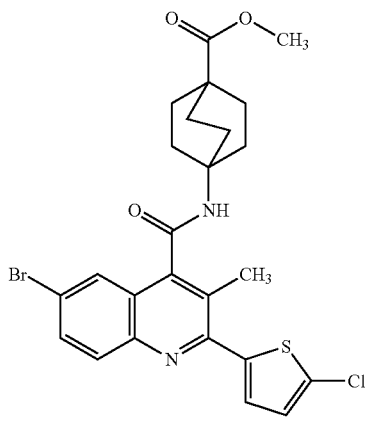

At RT, 224 mg (0.59 mmol) of HATU and 0.20 ml (1.18 mmol) of DIPEA were added to a solution of 150 mg (0.39 mmol) of the compound from Example 91A in 1.5 ml of DMF, and the mixture was stirred at RT for 30 min. Subsequently, 129 mg (0.59 mmol) of methyl 4-aminobicyclo[2.2.2]octane-1-carboxylate hydrochloride, dissolved in 1 ml of DMF, were added and the mixture was stirred at 60° C. overnight. After cooling to RT, the mixture was purified by preparative HPLC (Method 3). This gave 16 mg (7% of theory, purity 100%) of the title compound.

LC/MS (Method 9, ESIpos): R$_t$=2.63 min, m/z=549 [M+H]$^+$.

Example 93A

6-Bromo-2-(5-bromo-2-thienyl)-3-methylquinoline-4-carboxylic acid

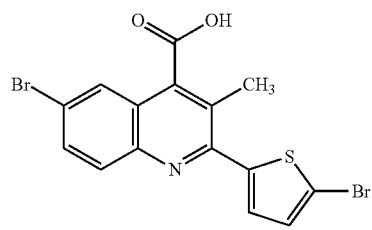 [SMILES: Cc1c(-c2ccc(Br)s2)nc2ccc(Br)cc2c1C(=O)O]

5.00 g (22.12 mmol) of 5-bromo-1H-indole-2,3-dione were initially charged in 61.2 ml of acetic acid, and 4.85 g (22.12 mmol) of 1-(5-bromo-2-thienyl)propan-1-one were added. The reaction mixture was stirred at 75° C. for 5 min. Subsequently, 20.4 ml (244 mmol) of conc. hydrochloric acid were added, and stirring of the mixture was continued at 105° C. overnight. After cooling to RT, the reaction mixture was concentrated under reduced pressure, 200 ml of toluene were added and the mixture was concentrated again. Addition of toluene and concentration were repeated twice. The resulting residue was dissolved with heating in a mixture of 100 ml of methanol and 50 ml of THF/DMSO/DMF and purified by preparative HPLC [column: Chromatorex Spring Column C18, 10 μm, 290 mm×100 mm; flow rate: 250 ml/min; detection: 210 nm; temperature: 22° C.; injection: 30 ml, gradient methanol/(water+0.1% formic acid) 50:50→90:10; run time 39 min)]. 6.77 g (72% of theory, 100% purity) of the title compound was obtained.

$^1$H-NMR (400 Mhz, DMSO-d$_6$): δ [ppm]=14.50 (br. s, 1H), 7.97-7.88 (m, 2H), 7.86 (d, 1H), 7.63 (d, 1H), 7.36 (d, 1H), 2.66 (s, 3H).

LC/MS (Method 9, ESIpos): R$_t$=2.26 min, m/z=425/427/429 [M+H]$^+$.

Example 94A

Methyl 4-({[6-bromo-2-(5-bromo-2-thienyl)-3-methylquinolin-4-yl]carbonyl}amino)bicyclo[2.2.2]octane-1-carboxylate

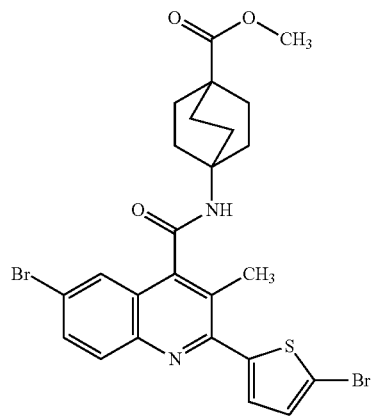 [SMILES: COC(=O)C12CCC(NC(=O)c3c(C)c(-c4ccc(Br)s4)nc4ccc(Br)cc34)(CC1)CC2]

At RT, 200 mg (0.53 mmol) of HATU and 0.18 ml (1.05 mmol) of DIPEA were added to a solution of 150 mg (0.35 mmol) of the compound from Example 93A in 1.0 ml of DMF, and the mixture was then stirred at RT for 30 min. Subsequently, 116 mg (0.53 mmol) of methyl 4-aminobicyclo[2.2.2]octane-1-carboxylate hydrochloride, dissolved in 1 ml of DMF, were added and the mixture was stirred at 60° C. overnight. After cooling to RT, the mixture was purified by preparative HPLC (Method 3). This gave 14 mg (7% of theory, purity 100%) of the title compound.

LC/MS (Method 9, ESIpos): $R_t$=2.65 min, m/z=591/593/595 [M+H]$^+$.

Example 95A

Methyl 6-bromo-3-methyl-2-phenylquinoline-4-carboxylate

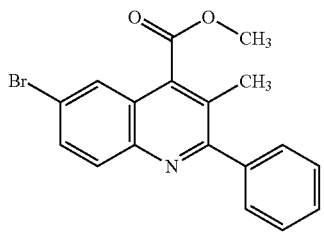 [SMILES: COC(=O)c1c(C)c(-c2ccccc2)nc2ccc(Br)cc12]

In an atmosphere of argon, a mixture of 100.0 g (292.3 mmol) of the compound from Example 3A and 339.0 g (2.85 mol) of thionyl chloride was heated at the boil for 2.5 h. After cooling to RT, the mixture was allowed to stand overnight and then concentrated under reduced pressure. The residue was taken up in 200 ml of dichloromethane, and 400 ml (9.87 mol) of methanol were slowly (initially dropwise) added at RT. After 2 h of stirring at RT, the mixture was concentrated and the residue was taken up in 1 l of dichloromethane. 500 ml of saturated aqueous sodium bicarbonate solution were added and the mixture was then stirred at RT for 4 min. The phases were subsequently separated and the aqueous phase was extracted once with 250 ml of dichloromethane. The combined organic phases were dried over magnesium sulfate, filtered and concentrated under reduced pressure. The residue was taken up in 150 ml of dichloromethane, diluted with 150 ml of cyclohexane and purified by column chromatography (15 kg of silica gel, dichloromethane/cyclohexane 1:1, then dichloromethane). This gave 86.68 g (83% of theory, 100% purity) of a first batch of the title compound and 5.50 g (5% of theory, 97% purity) of a second batch of the title compound.

$^1$H-NMR (400 Mhz, DMSO-d$_6$): δ [ppm]=8.05-7.90 (m, 3H), 7.66-7.58 (m, 2H), 7.57-7.47 (m, 3H), 4.08 (s, 3H), 2.36 (s, 3H).

LC/MS (Method 1, ESIpos): $R_t$=1.24 min, m/z=356/358 [M+H]$^+$.

Example 96A

Methyl 6-ethynyl-3-methyl-2-phenylquinoline-4-carboxylate

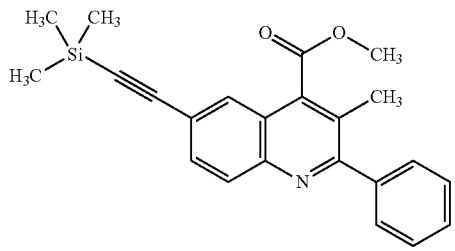 [SMILES: COC(=O)c1c(C)c(-c2ccccc2)nc2ccc(C#C[Si](C)(C)C)cc12]

Under argon and at RT, 214 mg (1.12 mmol) of copper(I) iodide, 2.45 g (25.0 mmol) of ethynyl(trimethyl)silane and 649 mg (0.56 mmol) of tetrakis(triphenylphosphine)palladium(0) were added in succession to a mixture of 4.0 g (11.23 mmol) of the compound from Example 95A in 155 ml (1.12 mol) of triethylamine, and the mixture was stirred at 110° C. for 4 h. After cooling to RT, 20 g of kieselguhr were added and the mixture was concentrated. The residue was purified by column chromatography (silica gel, cyclohexane/ethyl acetate 95:5). 3.10 g (74% of theory, 94% purity) of the title compound was obtained.

$^1$H-NMR (400 Mhz, DMSO-d$_6$): δ [ppm]=8.04 (d, 1H), 7.84 (d, 1H), 7.78 (d, 1H), 7.66-7.59 (m, 2H), 7.58-7.47 (m, 3H), 4.08 (s, 3H), 2.35 (s, 3H), 0.28 (s, 9H).

LC/MS (Method 9, ESIpos): $R_t$=2.77 min, m/z=374 [M+H]$^+$.

Example 97A

6-Ethynyl-3-methyl-2-phenylquinoline-4-carboxylic acid

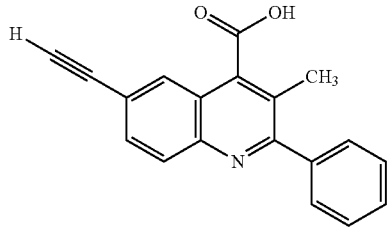 [SMILES: C#Cc1ccc2nc(-c3ccccc3)c(C)c(C(=O)O)c2c1]

8.0 ml (8.0 mmol) of a 1 M aqueous sodium hydroxide solution were added to a solution of 500 mg (1.34 mmol) of the compound from Example 96A in a mixture of 37 ml THF and 8 ml of methanol, and the mixture was stirred initially at RT for 16 h, then at 50° C. for 16 h and subsequently at 70° C. for 24 h. After cooling to RT, 0.72 ml (9.37 mmol) of TFA was added and the mixture was stirred at RT for 1 h and then concentrated. The residue was taken up in DMSO and the solid present was filtered off, rinsing with acetonitrile. The filtrate was concentrated under reduced pressure and the residue obtained by concentration of the filtrate was dissolved in a mixture of 38 ml DMSO and water and purified by preparative HPLC [column: Chromatorex C18 125 mm×30 mm; flow rate: 100 ml/min; detection: 210 nm; injection 1 ml; gradient acetonitrile/water/(water+0.1% TFA) 10:85:5→60:35:5; run time 6.5 min)]. This gave 173 mg (45% of theory, purity 100%) of the title compound.

$^1$H-NMR (400 Mhz, DMSO-d$_6$): δ [ppm]=14.38 (br. s, 1H), 8.05 (d, 1H), 7.87 (s, 1H), 7.80 (dd, 1H), 7.65-7.59 (m, 2H), 7.58-7.46 (m, 3H), 4.45 (s, 1H), 2.39 (s, 3H).

LC/MS (Method 1, ESIpos): $R_t$=0.65 min, m/z=288 [M+H]$^+$.

Example 98A

Methyl 4-{[(6-ethynyl-3-methyl-2-phenylquinolin-4-yl)carbonyl]amino}bicyclo[2.2.2]octane-1-carboxylate

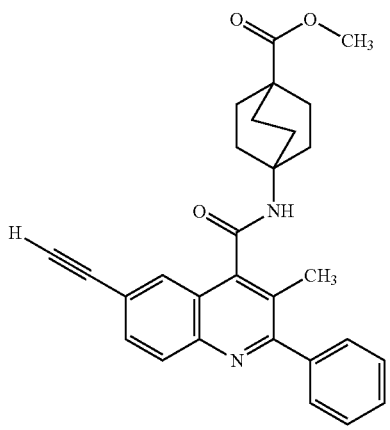 [SMILES: C#Cc1ccc2nc(-c3ccccc3)c(C)c(C(=O)NC34CCC(C(=O)OC)(CC3)CC4)c2c1]

At RT, 343 mg (0.90 mmol) of HATU and 0.31 ml (1.81 mmol) of DIPEA were added to a solution of 173 mg (0.60 mmol) of the compound from Example 97A in 1.5 ml of DMF, and the mixture was stirred at RT for 30 min. Subsequently, 198 mg (0.90 mmol) of methyl 4-aminobicyclo[2.2.2]octane-1-carboxylate hydrochloride, dissolved in 1.5 ml of DMF, were added and the mixture was stirred at 60° C. overnight. After cooling to RT, the mixture was purified by preparative HPLC (Method 3). This gave 207 mg (74% of theory, purity 98%) of the title compound.

$^1$H-NMR (500 Mhz, DMSO-d$_6$): δ [ppm]=8.47 (s, 1H), 8.01 (d, 1H), 7.84-7.71 (m, 2H), 7.63-7.43 (m, 4H), 4.42 (s, 1H), 3.59 (s, 3H), 2.32 (s, 3H), 2.13-1.99 (m, 6H), 1.92-1.81 (m, 6H).

LC/MS (Method 9, ESIpos): $R_t$=2.14 min, m/z=453 [M+H]$^+$.

Example 99A

Ethyl 4-{[(6-bromo-3-methyl-2-phenylquinolin-4-yl)carbonyl]amino}-2-oxobicyclo[2.2.2]octane-1-carboxylate

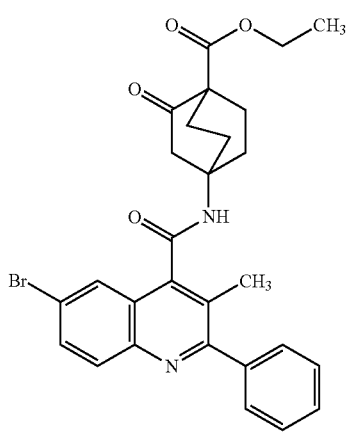 [SMILES: CCOC(=O)C12CCC(NC(=O)c3c(C)c(-c4ccccc4)nc4ccc(Br)cc34)(CC1)CC2=O]

At RT, 1.30 g (3.78 mmol) of the compound from Example 3A, 2.16 g (5.68 mmol) of HATU and 1.98 ml (11.35 mmol) of DIPEA were added in succession to a solution of 863 mg (3.78 mmol, purity 93%) of ethyl 4-amino-2-oxobicyclo[2.2.2]octane-1-carboxylate (preparation described in WO2014/18891 A1, pp. 147-148) in 10 ml of DMF, and the mixture was then stirred at 60° C. for 17 h. After cooling to RT, the mixture was added to 250 ml of a 10% strength aqueous citric acid solution and extracted twice with in each case 200 ml of ethyl acetate. The combined organic phases were washed once with 300 ml of saturated aqueous sodium chloride solution, dried over sodium sulfate, filtered and concentrated. The residue was then taken up in dichloromethane and purified by column chromatography (340 g of silica gel, Biotage, cyclohexane/ethyl acetate 7:3). This gave 960 mg (44% of theory, purity 94%) of the title compound.

$^1$H-NMR (400 Mhz, DMSO-d$_6$): δ [ppm]=8.84 (s, 1H), 7.99 (d, 1H), 7.90 (dd, 1H), 7.84 (d, 1H), 7.61-7.48 (m, 5H), 4.12 (q, 2H), 2.98 (br. s, 2H), 2.35 (s, 3H), 2.25-1.99 (m, 8H), 1.20 (t, 3H).

LC/MS (Method 9, ESIpos): $R_t$=2.19 min, m/z=535/537 [M+H]$^+$.

Example 100A

Ethyl 4-{[(6-bromo-3-methyl-2-phenylquinolin-4-yl)carbonyl]amino}-2,2-difluorobicyclo[2.2.2]octane-1-carboxylate

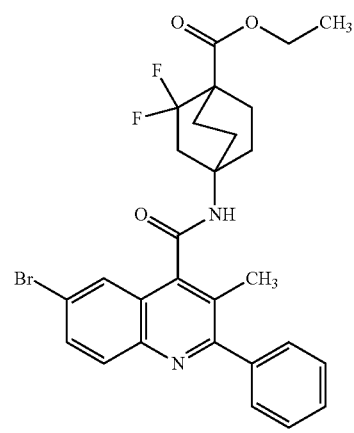 [SMILES: CCOC(=O)C12CCC(NC(=O)c3c(C)c(-c4ccccc4)nc4ccc(Br)cc34)(CC1)CC2(F)F]

At RT, 0.004 ml (0.075 mmol) of ethanol and 0.49 ml (3.74 mmol) of DAST were added to a solution of 200 mg (0.37 mmol) of the compound from Example 99A in 4.9 ml of 1,2-dichloroethane, and the mixture was stirred at 60° C. for 20 h. A further 0.49 ml (3.74 mmol) of DAST were then added, and the mixture was stirred at 60° C. for a further 5 days. A further 0.49 ml (3.74 mmol) of DAST were added, and the mixture was stirred at 60° C. for a further day. After cooling to RT, the mixture was diluted with 80 ml of water and 80 ml of dichloromethane and adjusted to pH 7 with about 20 ml of saturated aqueous sodium bicarbonate solution. After phase separation, the aqueous phase was extracted once with 80 ml of dichloromethane, and the combined organic phases were dried over sodium sulfate, filtered and concentrated. The residue was taken up in dichloromethane and purified by column chromatography (100 g of silica gel, Biotage, cyclohexane/ethyl acetate 7:3). This gave 89 mg (43% of theory; purity 100% by LC/MS) of the title compound.

$^1$H-NMR (400 Mhz, DMSO-$d_6$): δ [ppm]=8.81 (s, 1H), 7.98 (d, 1H), 7.89 (dd, 1H), 7.82 (d, 1H), 7.63-7.46 (m, 5H), 4.14 (q, 2H), 2.77-2.60 (m, 2H), 2.34 (s, 3H), 2.19-2.05 (m, 4H), 1.98-1.89 (m, 4H), 1.20 (t, 3H).

LC/MS (Method 9, ESIpos): $R_t$=2.38 min, m/z=557/559 [M+H]$^+$.

Example 101A

Ethyl 4-{[(6-bromo-3-methyl-2-phenylquinolin-4-yl)carbonyl]amino}-2-hydroxybicyclo[2.2.2]octane-1-carboxylate (racemate)

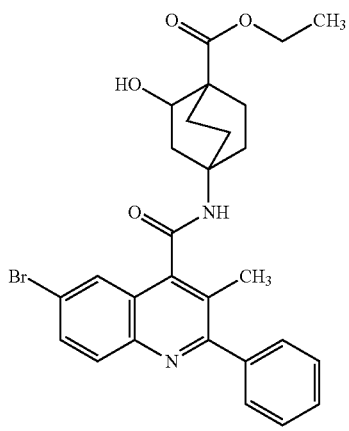 [SMILES: CCOC(=O)C12CCC(NC(=O)c3c(C)c(-c4ccccc4)nc4ccc(Br)cc34)(CC1)CC2O]

At RT, 1.49 g (4.37 mmol) of the compound from Example 3A, 2.49 g (6.55 mmol) of HATU and 3.0 ml (17.46 mmol) of DIPEA were added in succession to a solution of 1.09 g (4.37 mmol) of ethyl 4-amino-2-hydroxybicyclo[2.2.2]octane-1-carboxylate (preparation described in WO2014/18891 A1, p. 148) in 15 ml of DMF, and the mixture was stirred at 60° C. for 17 h. After cooling to RT, the mixture was added to 250 ml of a 10% strength aqueous citric acid solution. The resulting precipitate was filtered off, washed three times with 25 ml of water in each case and dried under reduced pressure. The solid was then taken up in dichloromethane and purified by column chromatography (100 g of silica gel, Biotage, cyclohexane/ethyl acetate 7:3). 1.10 g (45% of theory, 97% purity) of the title compound was obtained.

$^1$H-NMR (400 Mhz, DMSO-$d_6$): δ [ppm]=8.49 (s, 1H), 7.97 (d, 1H), 7.88 (dd, 1H), 7.82 (d, 1H), 7.60-7.46 (m, 5H), 4.96 (d, 1H), 4.20-4.11 (br. d, 1H), 4.04 (m, 2H), 2.49-2.39 (m, 1H, partially obscured), 2.33 (s, 3H), 2.24-1.62 (m, 9H), 1.17 (t, 3H).

LC/MS (Method 9, ESIpos): $R_t$=2.07 min, m/z=537/539 [M+H]$^+$.

Example 102A

Ethyl 4-{[(6-bromo-3-methyl-2-phenylquinolin-4-yl)carbonyl]amino}-2-fluorobicyclo[2.2.2]octane-1-carboxylate (racemate)

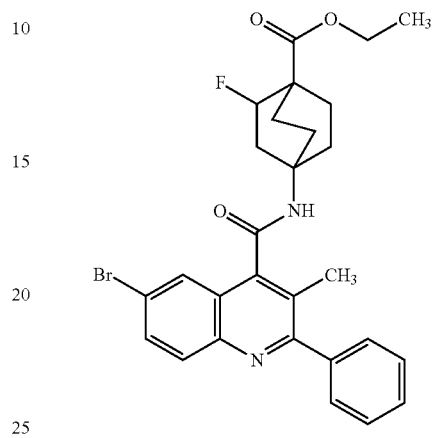

With cooling in an ice/acetone bath, 0.15 ml (1.13 mmol) of DAST was added to a solution of 550 mg (1.02 mmol) of the compound from Example 101A in 11 ml of dichloromethane, and the mixture was stirred with ice/acetone cooling for 3 h. A further 0.03 ml (0.23 mmol) of DAST were then added with ice/acetone cooling, and the mixture was stirred at RT for a further day. 100 ml of dichloromethane were then added, and the mixture was extracted once with 100 ml of saturated aqueous sodium bicarbonate solution. The aqueous phase was extracted once with 80 ml of dichloromethane. The combined organic phases were dried over sodium sulfate, filtered and concentrated. The residue was combined with 50 mg of a pre-purified crude product from a preliminary experiment carried out in a similar manner, taken up in dichloromethane and pre-purified by column chromatography (50 g of silica gel, Biotage, cyclohexane/ethyl acetate 8:2). The pre-purified product was then re-purified by preparative HPLC (column: Chiralpak ID, 5 μm 250 mm×20 mm; flow rate: 42.5 ml/min; detection: 250 nm; temperature: 25° C.; isohexane/ethanol 9:1 isocratic; run time 30 min). This gave 74 mg (13% of theory, based on 1.02 mmol, purity 100%) of the title compound.

$^1$H-NMR (400 Mhz, DMSO-$d_6$): δ [ppm]=8.64 (s, 1H), 7.98 (d, 1H), 7.89 (dd, 1H), 7.82 (d, 1H), 7.63-7.47 (m, 5H), 5.23 (dd, 1H), 4.11 (q, 2H), 2.69-2.55 (m, 1H, partially obscured), 2.33 (s, 3H), 2.29-1.68 (m, 9H), 1.19 (t, 3H).

LC/MS (Method 1, ESIpos): $R_t$=1.24 min, m/z=539/541 [M+H]$^+$.

Separation of the Enantiomers:

70 mg of the racemic compound from Example 102A were separated into the enantiomers by preparative HPLC on a chiral phase (see Examples 103A and 104A) [column: Daicel Chiralpak ID, 5 μm 250 mm×20 mm; flow rate: 42.5 ml/min; detection: 250 nm; temperature: 25° C.; mobile phase: 90% isohexane/10% ethanol; run time 30 min].

Example 103A

Ethyl 4-{[(6-bromo-3-methyl-2-phenylquinolin-4-yl)carbonyl]amino}-2-fluorobicyclo[2.2.2]octane-1-carboxylate (enantiomer 1)

Yield: 31 mg; chem. purity=100%; ee=100%

$^1$H-NMR (400 Mhz, DMSO-$d_6$): δ [ppm]=8.65 (s, 1H), 7.98 (d, 1H), 7.89 (dd, 1H), 7.82 (d, 1H), 7.62-7.46 (m, 5H), 5.23 (dd, 1H), 4.11 (q, 2H), 2.68-2.54 (m, 1H, partially obscured), 2.33 (s, 3H), 2.29-1.71 (m, 9H), 1.19 (t, 3H).

LC/MS (Method 1, ESIpos): $R_t$=1.23 min, m/z=539/541 [M+H]$^+$.

Example 104A

Ethyl 4-{[(6-bromo-3-methyl-2-phenylquinolin-4-yl)carbonyl]amino}-2-fluorobicyclo[2.2.2]octane-1-carboxylate (enantiomer 2)

Yield: 28 mg; chem. purity=100%; ee=95%

$^1$H-NMR (400 Mhz, DMSO-$d_6$): δ [ppm]=8.64 (s, 1H), 7.98 (d, 1H), 7.89 (dd, 1H), 7.82 (d, 1H), 7.62-7.43 (m, 5H), 5.23 (dd, 1H), 4.11 (q, 2H), 2.74-2.55 (m, 1H), 2.33 (s, 3H), 2.30-1.68 (m, 9H), 1.19 (t, 3H).

LC/MS (Method 1, ESIpos): $R_t$=1.23 min, m/z=539/541 [M+H]$^+$.

Example 105A tert-Butyl 3,5-dihydroxy-4-nitrobicyclo[2.2.2]octane-1-carboxylate

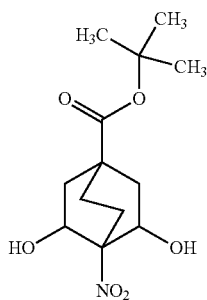 [SMILES: CC(C)(C)OC(=O)C12CCC([N+](=O)[O-])(C(O)C1)C(O)C2]

21.50 g (74.83 mmol) of a cis/trans isomer mixture of the title compound (preparation described in *Bioorganic & Medicinal Chemistry Letters* 1999, 9, 611-614) were dissolved in 150 of hot isopropanol and separated into the isomers by preparative SFC (column: Chiralpak IC, 5 μm 400 mm×50 mm; flow rate: 400 ml/min; detection: 210 nm; injection volume 10 ml, temperature: 20° C.; 85% $CO_2$/15% isopropanol isocratic; run time 14 min). This gave 7.80 g (27.15 mmol, first fraction, purity 100%) of the trans isomers and 9.0 g (31.32 mmol, second fraction, purity about 90%) of the cis isomers of the title compound.

Trans-Isomer (Racemate)

$^1$H-NMR (400 Mhz, DMSO-$d_6$): δ [ppm]=5.52 (d, 1H), 5.26 (d, 1H), 4.78-4.68 (m, 1H), 4.22-4.05 (m, 1H), 2.29-2.10 (m, 3H), 1.99-1.86 (m, 1H), 1.83-1.48 (m, 4H), 1.38 (s, 9H).

Cis-Isomer:

$^1$H-NMR (400 Mhz, DMSO-$d_6$): δ [ppm]=5.52 (d, 2H), 4.23 (ddd, 2H), 2.25-2.11 (m, 4H), 1.82-1.72 (m, 2H), 1.60-1.49 (m, 2H), 1.37 (s, 9H).

Example 106A trans-tert-Butyl 4-amino-3,5-dihydroxybicyclo[2.2.2]octane-1-carboxylate (racemate)

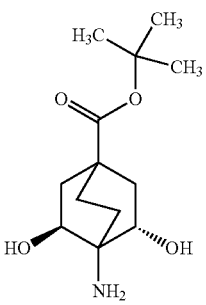 [SMILES: CC(C)(C)OC(=O)C12CCC(N)([C@@H](O)C1)[C@@H](O)C2]

Under an atmosphere of argon, 185 mg (0.17 mmol) of palladium (10% on activated carbon) were added to a solution of 2.50 g (8.70 mmol) of the compound from Example 105A (trans-isomer) in 117 ml of ethanol, and the mixture was stirred at 4 bar of hydrogen for 24 h. A further 185 mg (0.17 mmol) of palladium (10% on activated carbon) were then added, and the mixture was stirred at 4 bar of hydrogen for a further 48 h. The mixture was then filtered through kieselguhr and the filter was washed twice with ethanol. The filtrate was concentrated and twice taken up in dichloromethane and re-concentrated again and subsequently briefly dried under reduced pressure. This gave 1.73 g (contaminated) of the title compound.

$^1$H-NMR (400 Mhz, DMSO-$d_6$): δ [ppm]=4.62 (d, 1H), 4.40 (d, 1H), 3.71-3.64 (m, 1H), 3.58-3.50 (m, 1H), 2.11-1.98 (m, 3H), 1.74-1.33 (m, >13H), 1.03-0.92 (m, 1H).

Example 107A trans-tert-Butyl 4-{[(6-bromo-3-methyl-2-phenylquinolin-4-yl)carbonyl]amino}-3,5-dihydroxybicyclo[2.2.2]octane-1-carboxylate (racemate)

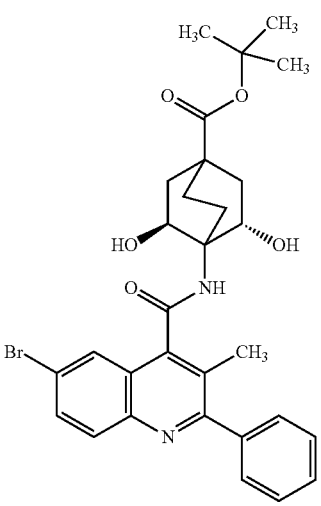 [SMILES: Cc1c(-c2ccccc2)nc2ccc(Br)cc2c1C(=O)NC12CCC(C(=O)OC(C)(C)C)(C[C@@H]1O)C[C@@H]2O]

At RT, 2.28 g (6.66 mmol) of the compound from Example 3A, 3.80 g (9.99 mmol) of HATU and 4.6 ml (26.63 mmol) of DIPEA were added in succession to a solution of 1.73 g (<6.66 mmol, contaminated) of the compound from Example 106A in 50 ml of DMF, and the mixture was stirred at 60° C. for one day. After cooling to RT, the mixture was added to 550 ml of 10% strength aqueous citric acid solution and extracted twice with in each case 250 ml of ethyl acetate. The combined organic phases were washed in each case once with 500 ml of water, dilute aqueous sodium bicarbonate solution and water, dried over sodium sulfate, filtered and concentrated. The residue was applied to Isolute® HM-N (Biotage) and purified by column chromatography (600 g of silica gel, cyclohexane/ethyl acetate 9:1). This gave 1.02 g (22% of theory, 84% purity) of a first batch of the title compound and 410 mg (10% of theory, 94% purity) of a second batch of the title compound (yields based on 6.66 mmol).

$^1$H-NMR (400 Mhz, DMSO-$d_6$): δ [ppm]=8.18 (br. s, 1H), 7.96 (d, 1H), 7.87 (dd, 1H), 7.62-7.46 (m, 5H), 5.29 (br. d, 1H), 4.78 (br. d, 1H), 4.65 (br. s, 1H), 4.31-4.23 (m, 1H), 2.37 (s, 3H), 2.29-1.49 (m, 8H), 1.39 (s, 9H).

LC/MS (Method 9, ESIpos): $R_t$=2.19 min, m/z=581/583 [M+H]$^+$.

Example 108A tert-Butyl 4-{[(6-bromo-3-methyl-2-phenylquinolin-4-yl)carbonyl]amino}-3,5-dioxobicyclo[2.2.2]octane-1-carboxylate

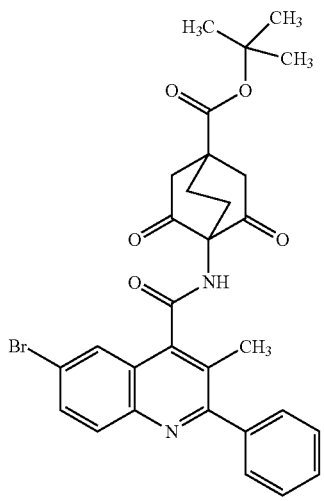 [SMILES: Cc1c(-c2ccccc2)nc2ccc(Br)cc2c1C(=O)NC12CCC(C(=O)OC(C)(C)C)(CC1=O)CC2=O]

At RT, 292 mg (0.69 mmol) of Dess-Martin periodinane (1,1,1-triacetoxy-1,1-dihydro-1,2-benziodoxol-3(1H)-one) were added to a solution of 100 mg (0.17 mmol) of the compound from Example 107A in 1.7 ml of dichloromethane, and the mixture was stirred at RT for 1.5 h. 20 ml each of 10% strength aqueous sodium thiosulfate solution and tert-butyl methyl ether were then added, and the mixture was shaken. After phase separation, the organic phase was washed once with 20 ml of saturated aqueous sodium hydrogencarbonate solution und dried over sodium sulfate, filtered and concentrated. The residue was then taken up in dichloromethane and purified by column chromatography (25 g of silica gel, Biotage, cyclohexane/ethyl acetate 7:3). This gave 68 mg (68% of theory, purity 100%) of the title compound.

$^1$H-NMR (400 Mhz, DMSO-$d_6$): δ [ppm]=9.03 (br. s, 1H), 8.73 (br. s, 1H), 7.96 (d, 1H), 7.88 (dd, 1H), 7.64-7.46 (m, 5H), 3.05-2.85 (m, 4H), 2.53-2.46 (m, obscured), 2.13 (br. s, 3H), 1.46 (s, 9H).

LC/MS (Method 9, ESIpos): $R_t$=2.29 min, m/z=577/579 [M+H]$^+$.

Example 109A

4-[(tert-Butoxycarbonyl)amino]-2-oxabicyclo[2.2.2]octane-1-carboxylic acid

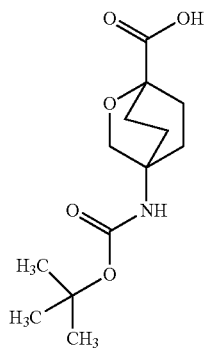 [SMILES: CC(C)(C)OC(=O)NC12CCC(C(=O)O)(CC1)OC2]

At RT, 5.9 ml (11.75 mmol) of 2-methyl-2-butene and a solution of 1.06 g (11.75 mmol) of sodium chlorite and 1.83 g (11.75 mmol) of sodium dihydrogen phosphate in 15 ml of water were added to a solution of 1.0 g (3.92 mmol) of tert-butyl (1-formyl-2-oxabicyclo[2.2.2]oct-4-yl)carbamate (preparation described in *ACS Medicinal Chemistry Letters* 2014, 5, 609-614 and WO2013/3383 A1, p. 76) in 30 ml of THF, and the mixture was stirred at RT. The course of the reaction was monitored by thin-layer chromatography. After 4 h of stirring at RT, the mixture was diluted with water and extracted with dichloromethane. The organic phase was dried over sodium sulfate, filtered and concentrated. This gave 1.06 g (99% of theory, purity not determined) of the title compound.

Example 110A

2-[(4-Methylphenyl)sulfonyl]ethyl-4-[(tert-butoxycarbonyl)amino]-2-oxabicyclo[2.2.2]octane-1-carboxylate

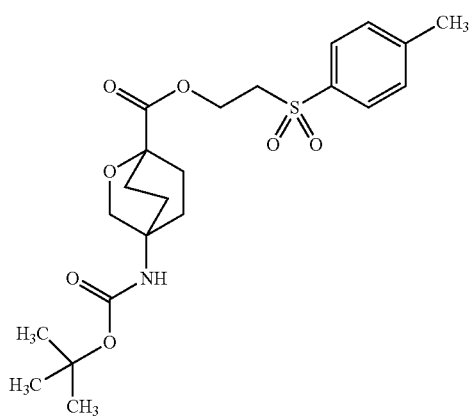 [SMILES: Cc1ccc(S(=O)(=O)CCOC(=O)C23CCC(NC(=O)OC(C)(C)C)(CC2)CO3)cc1]

At RT, 908 mg (5.53 mmol) of CDI were added to a solution of 1.0 g (3.69 mmol) of the compound from Example 109A in 21 ml of dichloromethane, and the mixture was stirred at 40° C. for 30 min. 1.11 g (5.53 mmol) of 2-(4-toluenesulfonyl)ethanol were then added, and the mixture was stirred at 55° C. overnight. After cooling to RT, the mixture was diluted with ethyl acetate, washed with 1 M hydrochloric acid, dried over sodium sulfate, filtered and concentrated, and the residue was purified by preparative HPLC (Method 4). This gave 643 mg (38% of theory, purity 98%) of the title compound.

$^1$H-NMR (400 Mhz, DMSO-$d_6$): δ [ppm]=7.78 (d, 2H), 7.48 (d, 2H), 6.66 (br s, 1H), 4.27 (t, 2H), 3.74 (s, 2H), 3.70 (t, 2H), 2.44 (s, 3H), 1.95-1.48 (m, 8H), 1.36 (s, 9H).

LC/MS (Method 9, ESIpos): $R_t$=1.84 min, m/z=398.

Example 111A

2-[(4-Methylphenyl)sulfonyl]ethyl-4-amino-2-oxabicyclo[2.2.2]octane-1-carboxylate

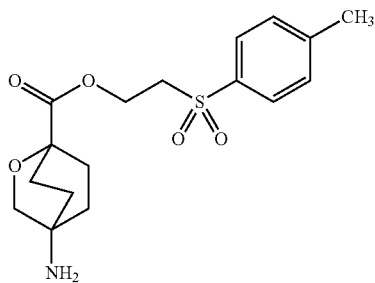 [SMILES: Cc1ccc(S(=O)(=O)CCOC(=O)C23CCC(N)(CC2)CO3)cc1]

At RT, 9.5 ml (123.5 mmol) of TFA were added to a suspension of 560 mg (1.24 mmol) of the compound from Example 110A in 28 ml of dichloromethane, and the mixture was stirred at 40° C. for 2 h, followed by 48 h at RT. The mixture was then concentrated and repeatedly dichloromethane was added and the mixture was concentrated again. The residue was purified by preparative HPLC (Method 3). This gave 466 mg (about 100% of theory, purity about 95%) of the title compound.

LC/MS (Method 9, ESIpos): $R_t$=0.67 min, m/z=354 [M+H]$^+$.

Example 112A

2-[(4-Methylphenyl)sulfonyl]ethyl 4-{[(6-iodo-3-methyl-2-phenylquinolin-4-yl)carbonyl]amino}-2-oxabicyclo[2.2.2]octane-1-carboxylate

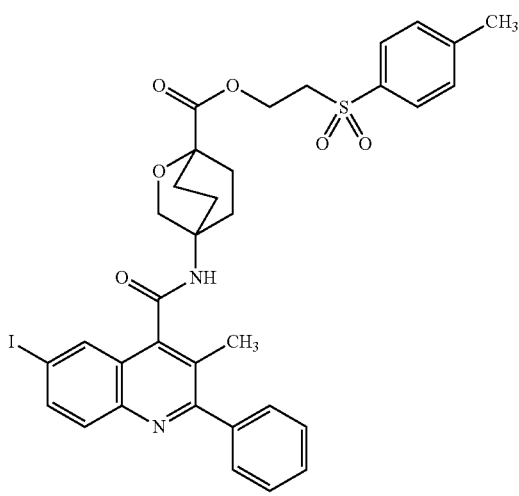 [SMILES: Cc1ccc(S(=O)(=O)CCOC(=O)C23CCC(NC(=O)c4c(C)c(-c5ccccc5)nc5ccc(I)cc45)(CC2)CO3)cc1]

At RT, 176 mg (0.46 mmol) of HATU and 0.16 ml (0.93 mmol) of DIPEA were added to a solution of 120 mg (0.31 mmol) of the compound from Example 13A in 1.5 ml of DMF, and the mixture was stirred at RT for 30 min. 172 mg (0.46 mmol, purity 95%) of the compound from Example 111A, dissolved in 1 ml of DMF, were added, and the mixture was stirred at 60° C. overnight. After cooling to RT, the mixture was purified by preparative HPLC (Method 3). This gave 99 mg (43% of theory, purity 98%) of the title compound.

$^1$H-NMR (400 Mhz, DMSO-$d_6$): δ [ppm]=8.62 (s, 1H), 8.09-7.94 (m, 2H), 7.86-7.75 (m, 3H), 7.63-7.43 (m, 7H), 4.32 (t, 2H), 4.03 (br. s, 2H), 3.74 (t, 2H), 2.47 (s, 3H), 2.31 (s, 3H), 2.24-1.56 (m, 8H).

LC/MS (Method 9, ESIpos): $R_t$=2.19 min, m/z=725 [M+H]$^+$.

Example 113A

Ethyl 8-aminobicyclo[3.2.1]octane-3-carboxylate

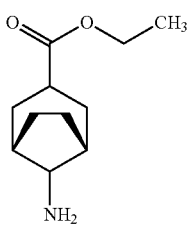

1.0 g (4.28 mmol) of a diastereomer mixture of the title compound (preparation described in *Bioorganic & Medicinal Chemistry Letters* 2006, 16, 5408-5413) were dissolved in a mixture of 10 ml of ethanol and 0.5 ml of diethylamine and separated into the diastereomers by preparative HPLC [column: Daicel Chiralpak IF, 5 μm, 250 mm×20 mm; flow rate: 15 ml/min; detection: 215 nm; temperature: 30° C.; injection volume 0.3 ml; mobile phase: 70% isohexane/(30% ethanol+0.2% diethylamine); run time 15 min]. This gave 348 mg (1.44 mmol, purity 97%) of the earlier-eluting diastereomer (diastereomer 1) and 546 mg (2.22 mmol, purity 95%) of the later-eluting diastereomer (diastereomer 2).

Earlier-eluting Diastereomer

Ethyl (3-exo,8-anti)-8-aminobicyclo[3.2.1]octane-3-carboxylate (diastereomer 1)

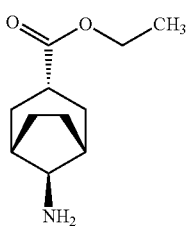

$^1$H-NMR (500 Mhz, DMSO-$d_6$): δ [ppm]=4.09 (q, 2H), 2.77 (br. s, 1H), 2.49-2.45 (m, 1H, partially obscured), 2.23

(dd, 2H), 1.89-1.81 (m, 2H), 1.79-1.58 (m, 4H), 1.37-1.27 (m, 2H), 1.20 (t, 3H).

Later-eluting Diastereomer

Ethyl (3-exo,8-syn)-8-aminobicyclo[3.2.1]octane-3-carboxylate (diastereomer 2)

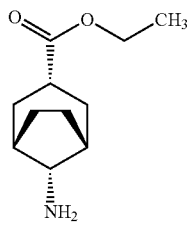

$^1$H-NMR (500 Mhz, DMSO-$d_6$): δ [ppm]=4.11 (q, 2H), 2.99 (t, 1H), 2.56-2.48 (m, 1H, obscured), 2.11-1.99 (m, 6H), 1.68-1.57 (m, 2H), 1.48-1.39 (m, 2H), 1.23-1.16 (m, 3H).

Example 114A

Ethyl (3-exo,8-anti)-8-{[(6-bromo-3-methyl-2-phenylquinolin-4-yl)carbonyl]amino}bicyclo [3.2.1]octane-3-carboxylate

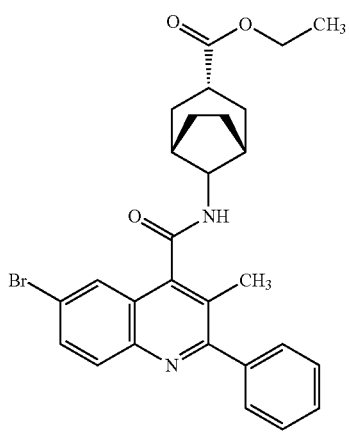 [SMILES: CCOC(=O)[C@@H]1C[C@H]2CC[C@@H](C1)C2NC(=O)c1c(C)c(-c2ccccc2)nc2ccc(Br)cc12]

At RT, 488 mg (1.28 mmol) of HATU and 0.45 ml (2.57 mmol) of DIPEA were added to a solution of 293 mg (0.86 mmol) of the compound from Example 3A in 2.5 ml of DMF, and the mixture was stirred at RT for 30 min. 300 mg (1.28 mmol) of the compound from Example 113A (diastereomer 1), dissolved in 2.5 ml of DMF, were added, and the mixture was stirred at 60° C. overnight. After cooling to RT, the mixture was purified by preparative HPLC (Method 3). This gave 360 mg (80% of theory, purity 99%) of the title compound.

$^1$H-NMR (400 Mhz, DMSO-$d_6$): δ [ppm]=8.56 (br. d, 1H), 8.02-7.94 (m, 1H), 7.92-7.76 (m, 2H), 7.62-7.43 (m, 5H), 4.12 (q, 2H), 3.95-3.82 (m, 1H), 2.62 (br. t, 1H), 2.40-2.22 (m, 7H), 1.93 (br. dd, 2H), 1.82-1.68 (m, 2H), 1.48 (br. d, 2H), 1.22 (t, 3H).

LC/MS (Method 9, ESIpos): R$_t$=2.32 min, m/z=521/523 [M+H]$^+$.

Example 115A

6-Bromo-3-cyano-2-phenylquinoline-4-carboxylic acid

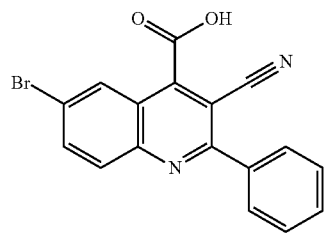 [SMILES: N#Cc1c(-c2ccccc2)nc2ccc(Br)cc2c1C(=O)O]

A mixture of 1.85 g (8.18 mmol) of 5-bromo-1H-indole-2,3-dione in 10 ml of water and 9.0 ml (9.0 mmol) of 1 M aqueous potassium hydroxide solution was stirred at 40° C. for 2 h. After cooling to RT, the solid present was filtered off and the filtrate was concentrated on a rotary evaporator to a volume of about 5 ml. This concentrate was added to a solution of 1.19 g (8.18 mmol) of 3-oxo-3-phenylpropanenitrile in 10 ml of ethanol and the mixture was stirred at 100° C. overnight. After cooling to RT, the solid present was filtered off, stirred in a diethyl ether/acetone mixture (3:1), filtered off again and dried under reduced pressure. 1.18 g (41% of theory, 100% purity) of the title compound were obtained.

LC/MS (Method 1, ESIpos): R$_t$=0.84 min, m/z=353/355 [M+H]$^+$.

Example 116A

Methyl 4-{[(6-bromo-3-cyano-2-phenylquinolin-4-yl)carbonyl]amino}bicyclo [2.2.2]octane-1-carboxylate

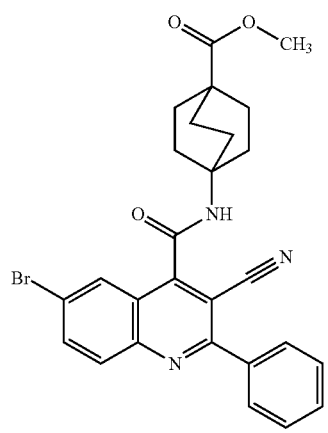 [SMILES: COC(=O)C12CCC(NC(=O)c3c(C#N)c(-c4ccccc4)nc4ccc(Br)cc34)(CC1)CC2]

At RT, 75 mg (0.34 mmol) of methyl 4-aminobicyclo [2.2.2]octane-1-carboxylate hydrochloride, 161 mg (0.43 mmol) of HATU and 0.15 ml (0.85 mmol) of DIPEA were added in succession to a solution of 100 mg (0.28 mmol) of the compound from Example 115A in 1.0 ml of DMF, and the mixture was stirred at 60° C. overnight. After cooling to RT, the mixture, without further work-up, was purified directly by preparative HPLC (Method 2). This gave 75 mg (51% of theory, purity 99%) of the title compound.

¹H-NMR (400 Mhz, DMSO-d₆): δ [ppm]=8.84 (s, 1H), 8.20-8.09 (m, 2H), 7.99 (d, 1H), 7.94-7.87 (m, 2H), 7.66-7.57 (m, 3H), 3.60 (s, 3H), 2.12-2.00 (m, 6H), 1.93-1.81 (m, 6H).

LC/MS (Method 1, ESIpos): R$_t$=1.21 min, m/z=518/520 [M+H]⁺.

Example 117A

9-Bromo-5-phenyl-3,4-dihydro-1H-pyrano [4,3-c] quinolin-1-one

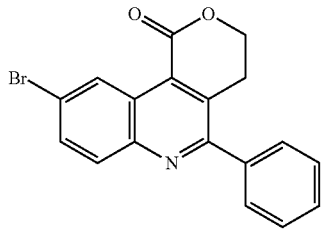 [SMILES: O=C1OCCc2c(-c3ccccc3)nc3ccc(Br)cc3c21]

1.0 g (4.34 mmol, 98% purity) of 5-bromo-1H-indole-2,3-dione were initially charged in 12 ml of acetic acid, and 712 mg (4.34 mmol) of 4-hydroxy-1-phenylbutan-1-one (preparation described in WO2006/44825 A2, p. 62) were added. The reaction mixture was stirred at 75° C. for 5 min. Subsequently, 4.0 ml (47.90 mmol) of conc. hydrochloric acid were added, and stirring of the mixture was continued at 105° C. overnight. After cooling to RT, the reaction mixture was added to water and the precipitate present was filtered off and dried under reduced pressure. The solid was then purified by column chromatography (silica gel, cyclohexane/ethyl acetate 2:1). This gave 270 mg (16% of theory, purity 90%) of the title compound.

¹H-NMR (500 Mhz, DMSO-d₆): δ [ppm]=9.13 (d, 1H), 8.07 (d, 1H), 7.97 (dd, 1H), 7.79-7.70 (m, 2H), 7.62-7.47 (m, 3H), 4.47 (t, 2H), 3.22 (t, 2H).

LC/MS (Method 1, ESIpos): R$_t$=1.12 min, m/z=354/356 [M+H]⁺.

Example 118A

6-Bromo-3-(2-hydroxyethyl)-2-phenylquinoline-4-carboxylic acid

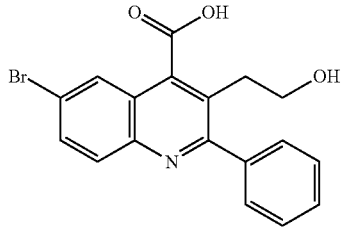 [SMILES: O=C(O)c1c(CCO)c(-c2ccccc2)nc2ccc(Br)cc12]

0.71 ml (0.71 mmol) of 1 M potassium tert-butoxide solution (in THF) was added to a solution of 100 mg (0.28 mmol) of the compound from Example 117A, and the mixture was stirred at 105° C. for four days. After cooling to RT, the mixture was added to water and extracted with dichloromethane. The organic phase was dried over sodium sulfate, filtered and concentrated under reduced pressure, and the residue was dried under reduced pressure. This gave 50 mg (23% of theory, purity 49%) of the title compound.

LC/MS (Method 1, ESIpos): R$_t$=1.10 min, m/z=372/374 [M+H]⁺.

Example 119A

Methyl 4-{[(6-bromo-2-phenyl-3-vinylquinolin-4-yl)carbonyl]amino}bicyclo [2.2.2]octane-1-carboxylate

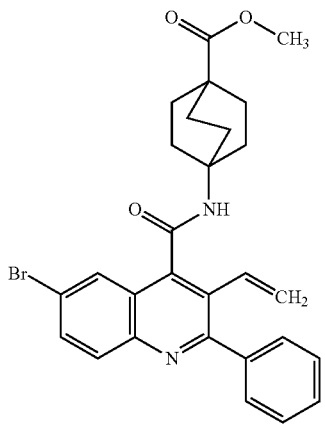 [SMILES: C=Cc1c(-c2ccccc2)nc2ccc(Br)cc2c1C(=O)NC12CCC(C(=O)OC)(CC1)CC2]

At RT, 29 mg (0.13 mmol) of methyl 4-aminobicyclo [2.2.2]octane-1-carboxylate hydrochloride, 76 mg (0.20 mmol) of HATU and 0.07 ml (0.40 mmol) of DIPEA were added in succession to a solution of 50 mg (0.056 mmol, purity 49%) of the compound from Example 118A in 2.0 ml of DMF, and the mixture was stirred at 60° C. for four days. After cooling to RT, the mixture, without further work-up, was purified directly by preparative HPLC (Method 4). This gave 36 mg ("100% of theory", purity 85%, with solvent) of the title compound.

¹H-NMR (500 Mhz, DMSO-d₆): δ [ppm]=8.40 (s, 1H), 8.00 (d, 1H), 7.95-7.86 (m, 2H), 7.63-7.58 (m, 2H), 7.55-7.47 (m, 3H), 6.57 (dd, 1H), 5.66 (dd, 1H), 5.49 (dd, 1H), 3.58 (s, 3H, partially obscured), 2.03-1.93 (m, 6H), 1.91-1.79 (m, 6H).

LC/MS (Method 9, ESIpos): R$_t$=2.38 min, m/z=519/521 [M+H]⁺.

WORKING EXAMPLES

Example 1

4-{[(6-Bromo-3-methyl-2-phenylquinolin-4-yl)carbonyl]amino}bicyclo[2.2.2]octane-1-carboxylic acid

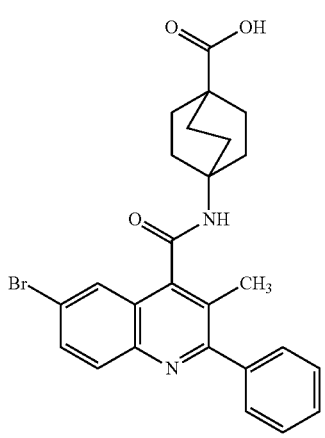 [SMILES: Cc1c(-c2ccccc2)nc2ccc(Cl)cc2c1C(=O)NC12CCC(C(=O)O)(CC1)CC2]

Method A:

At RT, 2.6 ml (2.6 mmol) of 1 M aqueous sodium hydroxide solution were added to a solution of 260 mg (0.51 mmol) of the compound from Example 43A in 7.7 ml of THF/methanol (5:1), and the mixture was stirred under reflux for 1 h. After cooling to RT, the mixture was purified directly (without further work-up) by preparative HPLC (Method 2). This gave 134 mg (53% of theory, purity 100%) of the title compound.

$^1$H-NMR (400 Mhz, DMSO-d$_6$): δ [ppm]=8.33 (s, 1H), 7.97 (d, 1H), 7.87 (dd, 1H), 7.84 (d, 1H), 7.60-7.46 (m, 5H), 2.32 (s, 3H), 2.00-1.91 (m, 6H), 1.79-1.70 (m, 6H).

LC/MS (Method 1, ESIpos): R$_t$=1.03 min, m/z=493/495 [M+H]$^+$.

Method B:

At RT, 150 ml (150 mmol) of 1 M aqueous sodium hydroxide solution were added to a solution of 15.23 g (30.01 mmol) of the compound from Example 43A in 444 ml of THF and 88 ml of methanol, and the mixture was stirred under reflux for 2.5 h. After cooling to RT, 200 ml of water were added to the mixture and the pH was adjusted to 2 with conc. hydrochloric acid, resulting in the precipitation of a solid. The mixture was extracted three times with ethyl acetate (without prior removal of the solid) and the combined organic phases were then washed twice with saturated aqueous sodium chloride solution and concentrated under reduced pressure. The residue was then suspended in 200 ml of water and stirred at 120° C. for 2 h. After cooling to RT, the solid was filtered off and then re-suspended in 200 ml of water, and the mixture was stirred at 120° C. for a further 1 h. The solid formed was subsequently directly filtered off from the cooled reaction solution and then dried under reduced pressure. 13.48 g (90% of theory, 99% purity) of the title compound was obtained.

Example 2

4-{[(6-Chloro-3-methyl-2-phenylquinolin-4-yl)carbonyl]amino}bicyclo[2.2.2]octane-1-carboxylic acid

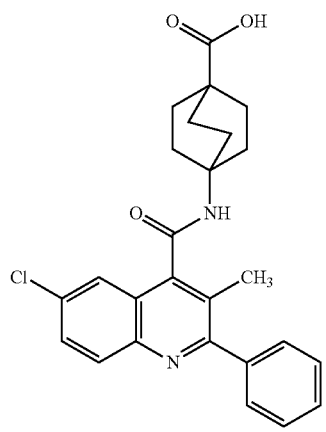

At RT, 1.9 ml (1.9 mmol) of 1 M aqueous sodium hydroxide solution were added to a solution of 304 mg (0.66 mmol) of the compound from Example 44A in a mixture of 6.0 ml of THF and 1.1 ml of methanol, and the mixture was stirred under reflux for 2 h. After cooling to RT, 0.15 ml (1.90 mmol) of TFA were added, and the mixture was purified by preparative HPLC (Method 3). This gave 281 mg (95% of theory, purity 100%) of the title compound.

$^1$H-NMR (400 Mhz, DMSO-d$_6$): δ [ppm]=11.94 (br. s, 1H), 8.46 (s, 1H), 8.05 (d, 1H), 7.77 (dd, 1H), 7.66 (d, 1H), 7.60-7.46 (m, 5H), 2.33 (s, 3H), 2.08-1.98 (m, 6H), 1.89-1.78 (m, 6H).

LC/MS (Method 1, ESIpos): R$_t$=0.96 min, m/z=449 [M+H]$^+$.

Example 3

4-{[(6,7-Dichloro-3-methyl-2-phenylquinolin-4-yl)carbonyl]amino}bicyclo[2.2.2]octane-1-carboxylic acid

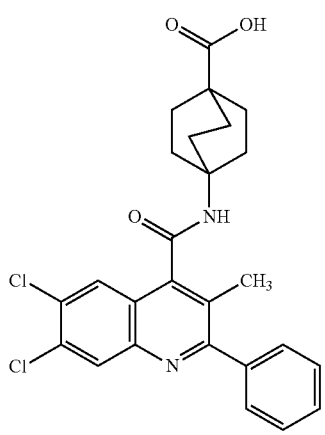 [SMILES: Cc1c(-c2ccccc2)nc2cc(Cl)c(Cl)cc2c1C(=O)NC12CCC(C(=O)O)(CC1)CC2]

0.41 ml (0.41 mmol) of 1 M aqueous lithium hydroxide solution were added to a solution of 41 mg (0.08 mmol) of the compound from Example 45A in 2.0 ml of THF/methanol (5:1), and the mixture was then stirred at 50° C. for 3 h. After cooling to RT, the mixture was adjusted to pH 1-2 using 4 M hydrochloric acid and, without further work-up, was purified directly by preparative HPLC (Method 2). This gave, after lyophilization, 28 mg (70% of theory, purity 99%) of the title compound.

$^1$H-NMR (400 Mhz, DMSO-d$_6$): δ [ppm]=12.10 (br. s, 1H), 8.49 (s, 1H), 8.34 (s, 1H), 7.83 (s, 1H), 7.67-7.43 (m, 5H), 2.33 (s, 3H), 2.11-1.93 (m, 6H), 1.93-1.70 (m, 6H).

LC/MS (Method 1, ESIpos): R$_t$=1.11 min, m/z=483 [M+H]$^+$.

Example 4

4-{[(6-tert-Butyl-3-methyl-2-phenylquinolin-4-yl)carbonyl]amino}bicyclo[2.2.2]octane-1-carboxylic acid

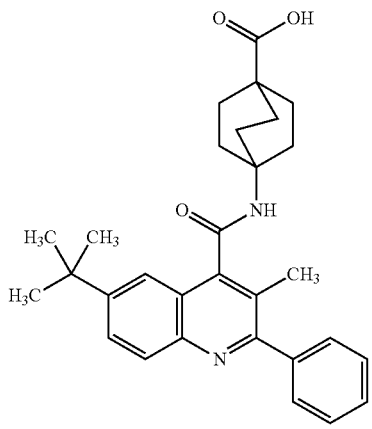 [SMILES: Cc1c(-c2ccccc2)nc2ccc(C(C)(C)C)cc2c1C(=O)NC12CCC(C(=O)O)(CC1)CC2]

3.2 ml (3.2 mmol) of 1 M aqueous sodium hydroxide solution were added to a solution of 300 mg (0.62 mmol) of the compound from Example 46A in a mixture of 12.5 ml of THF and 2.5 ml of methanol, and the mixture was stirred under reflux for 1 h. After cooling to RT, the mixture was concentrated under reduced pressure. The residue was then taken up in water and the mixture was adjusted to pH 1-2 using 1 M hydrochloric acid. The solid formed was filtered off, washed with water and dried under reduced pressure. This gave 227 mg (78% of theory, purity 100%) of the title compound.

$^1$H-NMR (400 Mhz, DMSO-$d_6$): δ [ppm]=12.08 (br. s, 1H), 8.41 (s, 1H), 7.96 (d, 1H), 7.88 (dd, 1H), 7.69 (d, 1H), 7.58-7.43 (m, 5H), 2.30 (s, 3H), 2.08-2.00 (m, 6H), 1.88-1.79 (m, 6H), 1.38 (s, 9H).

LC/MS (Method 1, ESIpos): $R_t$=1.02 min, m/z=485 [M+H]$^+$.

Example 5

4-({[6-Bromo-3-methyl-2-(2-thienyl)quinolin-4-yl]carbonyl}amino)bicyclo[2.2.2]octane-1-carboxylic acid

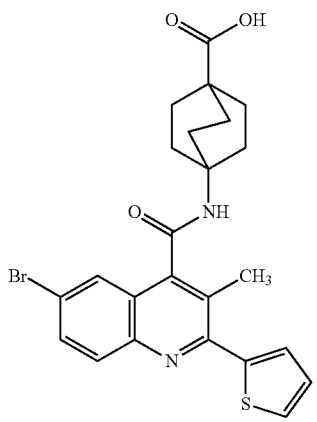 [SMILES: Cc1c(-c2cccs2)nc2ccc(Br)cc2c1C(=O)NC12CCC(C(=O)O)(CC1)CC2]

0.73 ml (0.73 mmol) of 1 M aqueous lithium hydroxide solution were added to a solution of 91.6 mg (0.15 mmol, purity 82%) of the compound from Example 47A in 4.3 ml of THF/methanol (5:1), and the mixture was then stirred at 50° C. for 1 h. After cooling to RT, the mixture was adjusted to pH 1-2 using 4 M hydrochloric acid and then, without further work-up, was purified directly by preparative HPLC (Method 2). This gave 68 mg (89% of theory, purity 95%) of the title compound.

$^1$H-NMR (400 Mhz, DMSO-$d_6$): δ [ppm]=12.10 (br. s, 1H), 8.47 (s, 1H), 7.92 (d, 1H), 7.85 (dd, 1H), 7.82-7.76 (m, 2H), 7.75 (d, 1H), 7.24 (dd, 1H), 2.60 (s, 3H), 2.13-1.95 (m, 6H), 1.93-1.73 (m, 6H).

LC/MS (Method 1, ESIpos): $R_t$=1.06 min, m/z=499/501 [M+H]$^+$.

Example 6

4-({[6-Bromo-2-(2-fluorophenyl)-3-methylquinolin-4-yl]carbonyl}amino)bicyclo[2.2.2]octane-1-carboxylic acid

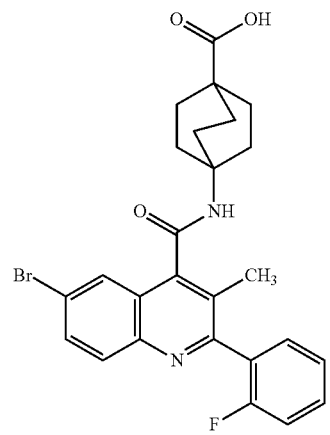 [SMILES: Cc1c(-c2ccccc2F)nc2ccc(Br)cc2c1C(=O)NC12CCC(C(=O)O)(CC1)CC2]

0.04 ml (0.18 mmol) of 5 M aqueous lithium hydroxide solution were added to a solution of 19 mg (0.04 mmol) of the compound from Example 48A in 4.3 ml of THF/methanol (5:1), and the mixture was then stirred at 50° C. for 1 h. After cooling to RT, the mixture was adjusted to pH 1-2 using 4 M hydrochloric acid and then, without further work-up, was purified directly by preparative HPLC (Method 2). This gave 17 mg (94% of theory, purity 100%) of the title compound.

$^1$H-NMR (400 Mhz, DMSO-$d_6$): δ [ppm]=12.09 (s, 1H), 8.54 (s, 1H), 7.99 (d, 1H), 7.91 (dd, 1H), 7.85 (d, 1H), 7.63-7.54 (m, 1H), 7.47 (td, 1H), 7.42-7.34 (m, 2H), 2.21 (s, 3H), 2.09-1.97 (m, 6H), 1.90-1.77 (m, 6H).

LC/MS (Method 1, ESIpos): $R_t$=1.01 min, m/z=511/513 [M+H]$^+$.

Example 7

4-({[6-Bromo-2-(3-fluorophenyl)-3-methylquinolin-4-yl]carbonyl}amino)bicyclo[2.2.2]octane-1-carboxylic acid

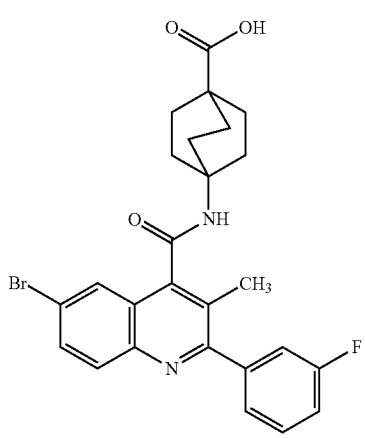 [SMILES: Cc1c(-c2cccc(F)c2)nc2ccc(Br)cc2c1C(=O)NC12CCC(C(=O)O)(CC1)CC2]

0.60 ml (0.60 mmol) of 1 M aqueous lithium hydroxide solution were added to a solution of 63 mg (0.11 mmol, purity 90%) of the compound from Example 49A in 2.0 ml of THF/methanol (5:1), and the mixture was then stirred at 50° C. for 3 h. After cooling to RT, the mixture was adjusted to pH 1-2 using 4 M hydrochloric acid and then, without further work-up, was purified directly by preparative HPLC (Method 2). This gave, after lyophilization, 46 mg (83% of theory, purity 99%) of the title compound.

$^1$H-NMR (400 Mhz, DMSO-$d_6$): δ [ppm]=12.09 (br. s, 1H), 8.45 (s, 1H), 7.99 (d, 1H), 7.90 (dd, 1H), 7.84 (d, 1H), 7.58 (td, 1H), 7.46-7.38 (m, 2H), 7.35 (td, 1H), 2.33 (s, 3H), 2.09-1.95 (m, 6H), 1.93-1.73 (m, 6H).

LC/MS (Method 1, ESIpos): $R_t$=1.04 min, m/z=511/513 [M+H]$^+$.

Example 8

4-({[6-Bromo-2-(4-fluorophenyl)-3-methylquinolin-4-yl]carbonyl}amino)bicyclo[2.2.2]octane-1-carboxylic acid

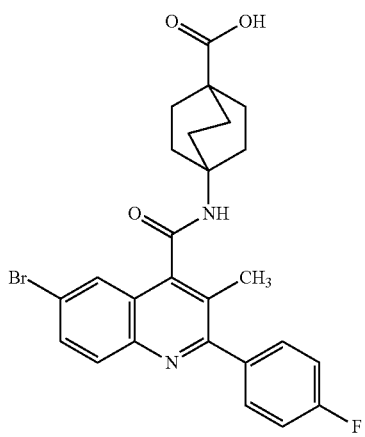 [SMILES: Cc1c(-c2ccc(F)cc2)nc2ccc(Br)cc2c1C(=O)NC12CCC(C(=O)O)(CC1)CC2]

0.55 ml (0.55 mmol) of 1 M aqueous lithium hydroxide solution was added to a solution of 58 mg (0.11 mmol) of the compound from Example 50A in 2.0 ml of THF/methanol (5:1), and the mixture was then stirred at 50° C. for 3 h. After cooling to RT, the mixture was adjusted to pH 1-2 using 4 M hydrochloric acid and, without further work-up, was purified directly by preparative HPLC (Method 2). This gave, after lyophilization, 37 mg (62% of theory, purity 95%) of the title compound.

$^1$H-NMR (400 Mhz, DMSO-$d_6$): δ [ppm]=12.10 (br. s, 1H), 8.45 (s, 1H), 7.97 (d, 1H), 7.88 (dd, 1H), 7.83 (d, 1H), 7.71-7.59 (m, 2H), 7.35 (t, 2H), 2.33 (s, 3H), 2.07-1.95 (m, 6H), 1.91-1.77 (m, 6H).

LC/MS (Method 1, ESIpos): $R_t$=1.03 min, m/z=511/513 [M+H]$^+$.

Example 9

4-({[6-Bromo-2-(3,5-difluorophenyl)-3-methylquinolin-4-yl]carbonyl}amino)bicyclo[2.2.2]octane-1-carboxylic acid

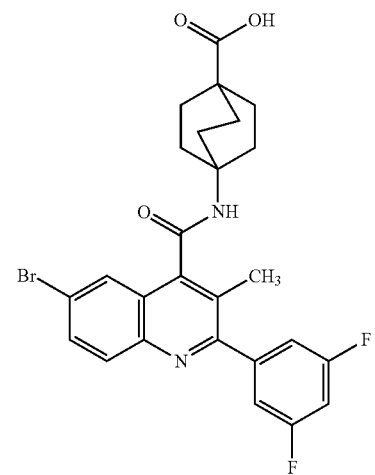 [SMILES: Cc1c(-c2cc(F)cc(F)c2)nc2ccc(Br)cc2c1C(=O)NC12CCC(C(=O)O)(CC1)CC2]

0.52 ml (0.52 mmol) of 1 M aqueous lithium hydroxide solution was added to a solution of 57 mg (0.11 mmol) of the compound from Example 51A in 1.5 ml of THF/methanol (5:1), and the mixture was then stirred at 50° C. for 3 h. After cooling to RT, the mixture was adjusted to pH 1-2 using 4 M hydrochloric acid and then, without further work-up, was purified directly by preparative HPLC (Method 2). This gave, after lyophilization, 44 mg (79% of theory, purity 99%) of the title compound.

$^1$H-NMR (400 Mhz, DMSO-$d_6$): δ [ppm]=12.10 (br. s, 1H), 8.45 (s, 1H), 8.00 (d, 1H), 7.91 (dd, 1H), 7.84 (d, 1H), 7.41 (tt, 1H), 7.36-7.25 (m, 2H), 2.34 (s, 3H), 2.10-1.95 (m, 6H), 1.90-1.75 (m, 6H).

LC/MS (Method 1, ESIpos): $R_t$=1.04 min, m/z=529/531 [M+H]$^+$.

Example 10

4-({[6-Bromo-2-(2-chlorophenyl)-3-methylquinolin-4-yl]carbonyl}amino)bicyclo[2.2.2]octane-1-carboxylic acid

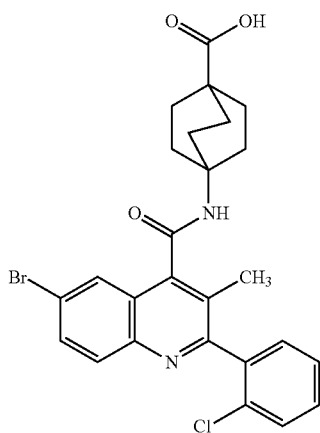 [SMILES: Cc1c(-c2ccccc2Cl)nc2ccc(Br)cc2c1C(=O)NC12CCC(C(=O)O)(CC1)CC2]

0.44 ml (0.44 mmol) of 1 M aqueous lithium hydroxide solution was added to a solution of 48 mg (0.089 mmol) of the compound from Example 52A in 2 ml of THF/methanol (5:1), and the mixture was then stirred at 50° C. for 3 h. After cooling to RT, the mixture was adjusted to pH 1-2 using 4 M hydrochloric acid and, without further work-up, was purified directly by preparative HPLC (Method 2). This gave 42 mg (85% of theory, purity 95%) of the title compound.

$^1$H-NMR (400 Mhz, DMSO-$d_6$): δ [ppm]=12.10 (br. s, 1H), 8.51 (br. s, 1H), 7.98 (d, 1H), 7.90 (dd, 1H), 7.86 (d, 1H), 7.68-7.59 (m, 1H), 7.58-7.47 (m, 2H), 7.39 (br. m, 1H), 2.13 (s, 3H), 2.07-1.96 (m, 6H), 1.90-1.77 (m, 6H).

LC/MS (Method 1, ESIpos): $R_t$=1.00 min, m/z=527/529 [M+H]$^+$.

Example 11

4-({[6-Bromo-2-(3-chlorophenyl)-3-methylquinolin-4-yl]carbonyl}amino)bicyclo[2.2.2]octane-1-carboxylic acid

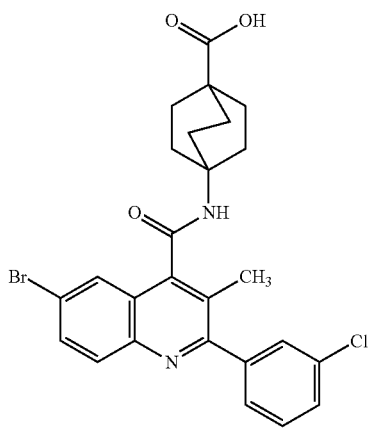 [SMILES: Cc1c(-c2cccc(Cl)c2)nc2ccc(Br)cc2c1C(=O)NC12CCC(C(=O)O)(CC1)CC2]

0.65 ml (0.65 mmol) of 1 M aqueous lithium hydroxide solution was added to a solution of 70 mg (0.13 mmol) of the compound from Example 53A in 1.8 ml of THF/methanol (5:1), and the mixture was then stirred at 50° C. for 3 h. After cooling to RT, the mixture was adjusted to pH 1-2 using 4 M hydrochloric acid and, without further work-up, was purified directly by preparative HPLC (Method 2), and then lyophilized. This gave 57 mg (83% of theory, purity 99%) of the title compound.

$^1$H-NMR (400 Mhz, DMSO-$d_6$): δ [ppm]=12.10 (br. s, 1H), 8.44 (s, 1H), 7.99 (d, 1H), 7.89 (dd, 1H), 7.84 (d, 1H), 7.65-7.61 (m, 1H), 7.61-7.50 (m, 3H), 2.33 (s, 3H), 2.12-1.94 (m, 6H), 1.94-1.70 (m, 6H).

LC/MS (Method 1, ESIpos): $R_t$=1.07 min, m/z=527/529 [M+H]$^+$.

Example 12

4-{[(6-Bromo-3-fluoro-2-phenylquinolin-4-yl)carbonyl]amino}bicyclo[2.2.2]octane-1-carboxylic acid

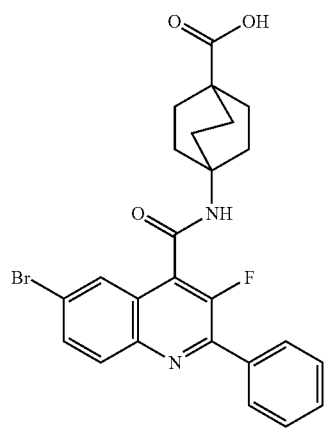

At RT, 1.8 ml (1.8 mmol) of 1 M aqueous sodium hydroxide solution were added to a solution of 195 mg (0.40 mmol, purity 97%) of the compound from Example 54A in a mixture of 5.5 ml of THF and 1.1 ml of methanol, and the mixture was stirred under reflux for 1.5 h. After cooling to RT, 0.17 ml (2.22 mmol) of TFA was added, and the mixture was purified by preparative HPLC (Method 3). This gave 30 mg (16% of theory, purity 98%) of the title compound. In addition, 131 mg (0.26 mmol, purity 100%) of the title compound from Example 13 were obtained (for analysis see Example 13).

$^1$H-NMR (400 Mhz, DMSO-$d_6$): δ [ppm]=12.10 (br. s, 1H), 8.63 (s, 1H), 8.08 (d, 1H), 8.03-7.98 (m, 2H), 7.95 (dd, 1H), 7.91 (d, 1H), 7.63-7.53 (m, 3H), 2.06-1.98 (m, 6H), 1.89-1.80 (m, 6H).

LC/MS (Method 1, ESIpos): $R_t$=1.10 min, m/z=497/499 [M+H]$^+$.

Example 13

4-{[(6-Bromo-3-methoxy-2-phenylquinolin-4-yl)carbonyl]amino}bicyclo[2.2.2]octane-1-carboxylic acid

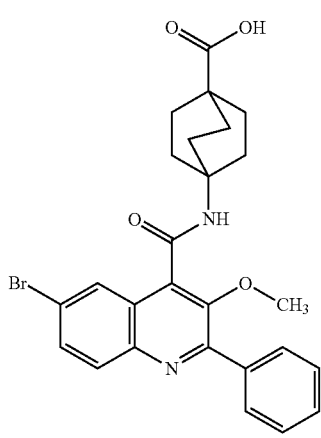

As described in the preparation of the compound from Example 12, 195 mg (0.40 mmol, purity 97%) of the compound from Example 54A were used to obtain 131 mg (0.26 mmol, purity 100%) of the title compound.

$^1$H-NMR (400 Mhz, DMSO-$d_6$): δ [ppm]=12.10 (s, 1H), 8.49 (s, 1H), 7.99 (d, 1H), 7.95-7.91 (m, 2H), 7.87-7.80 (m, 2H), 7.57-7.48 (m, 3H), 3.65 (s, 3H), 2.07-1.98 (m, 6H), 1.88-1.80 (m, 6H).

LC/MS (Method 1, ESIpos): $R_t$=1.06 min, m/z=509/511 [M+H]$^+$.

Example 14

4-{[(6-Iodo-3-methyl-2-phenylquinolin-4-yl)carbonyl]amino}bicyclo[2.2.2]octane-1-carboxylic acid

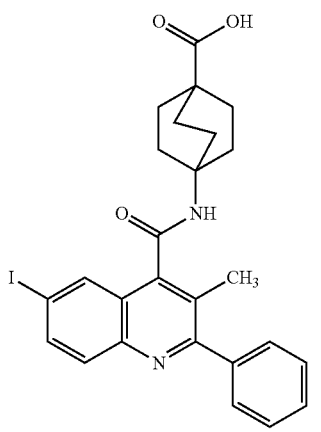 [SMILES: Cc1c(-c2ccccc2)nc2ccc(I)cc2c1C(=O)NC12CCC(C(=O)O)(CC1)CC2]

129 mg (0.23 mmol) of the compound from Example 55A were dissolved in 4.3 ml of a THF/methanol mixture (5:1), 1.16 ml (1.16 mmol) of a 1 M lithium hydroxide solution were added and the mixture was stirred at 50° C. for 3 h. After cooling to RT, the mixture was adjusted to pH 1-2 by addition of 4 M hydrochloric acid and purified by preparative HPLC (Method 2). This gave 88 mg (66% of theory, purity 95%) of the title compound.

$^1$H-NMR (400 Mhz, DMSO-$d_6$): δ [ppm]=12.09 (br. s, 1H), 8.45 (s, 1H), 8.07 (d, 1H), 8.00 (dd, 1H), 7.80 (d, 1H), 7.65-7.42 (m, 5H), 2.32 (s, 3H), 2.09-1.95 (m, 6H), 1.92-1.75 (m, 6H).

LC/MS (Method 1, ESIpos): $R_t$=1.04 min, m/z=541 [M+H]$^+$.

Example 15

4-{[(6-Cyclopropyl-3-methyl-2-phenylquinolin-4-yl)carbonyl]amino}bicyclo[2.2.2]octane-1-carboxylic acid

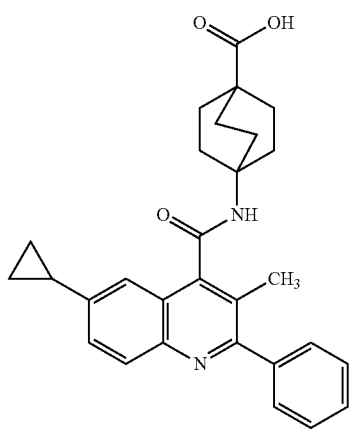 [SMILES: Cc1c(-c2ccccc2)nc2ccc(C3CC3)cc2c1C(=O)NC12CCC(C(=O)O)(CC1)CC2]

62 mg (0.13 mmol) of the compound from Example 56A were dissolved in 2.5 ml of a THF/methanol mixture (5:1), 0.66 ml (0.66 mmol) of a 1 M lithium hydroxide solution were added and the mixture was stirred at 50° C. for 3 h. After cooling to RT, the mixture was adjusted to pH 1-2 by addition of 4 M hydrochloric acid and purified by preparative HPLC (Method 2). This gave 56 mg (92% of theory, purity 99%) of the title compound.

$^1$H-NMR (400 Mhz, DMSO-$d_6$): δ [ppm]=11.62 (br. s, 1H), 8.42 (s, 1H), 7.94 (d, 1H), 7.65-7.46 (m, 6H), 7.45 (s, 1H), 2.30 (s, 3H), 2.21-2.12 (m, 1H), 2.10-1.98 (m, 6H), 1.91-1.79 (m, 6H), 1.11 (d, 2H), 0.78 (br. s, 2H).

LC/MS (Method 1, ESIpos): $R_t$=0.95 min, m/z=455 [M+H]$^+$.

Example 16

4-{[(6-Cyclobutyl-3-methyl-2-phenylquinolin-4-yl)carbonyl]amino}bicyclo [2.2.2]octane-1-carboxylic acid

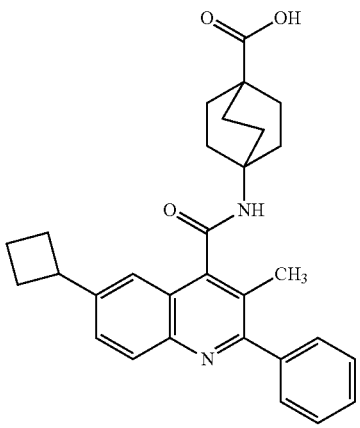 [SMILES: Cc1c(-c2ccccc2)nc2ccc(C3CCC3)cc2c1C(=O)NC12CCC(C(=O)O)(CC1)CC2]

170 mg (0.35 mmol) of the compound from Example 57A were dissolved in 6.6 ml of a THF/methanol mixture (5:1), 1.76 ml (1.76 mmol) of a 1 M lithium hydroxide solution were added and the mixture was then stirred at 60° C. for 3 h. After cooling to RT, the mixture was adjusted to pH 1-2 by addition of 4 M hydrochloric acid and purified by preparative HPLC (Method 2). This gave 120 mg (67% of theory, purity 92%) of the title compound.

$^1$H-NMR (400 Mhz, DMSO-$d_6$): δ [ppm]=12.09 (br. s, 1H), 8.40 (s, 1H), 7.96 (d, 1H), 7.66 (d, 1H), 7.61-7.37 (m, 6H), 3.80-3.69 (m, 1H), 2.45-2.36 (m, 2H), 2.31 (s, 3H), 2.22-2.07 (m, 3H), 2.07-1.97 (m, 6H), 1.94-1.75 (m, 7H).

LC/MS (Method 1, ESIpos): $R_t$=1.03 min, m/z=469 [M+H]$^+$.

Example 17

4-({[3-Methyl-2-phenyl-6-(trimethylsilyl)quinolin-4-yl]carbonyl}amino)bicyclo[2.2.2]octane-1-carboxylic acid

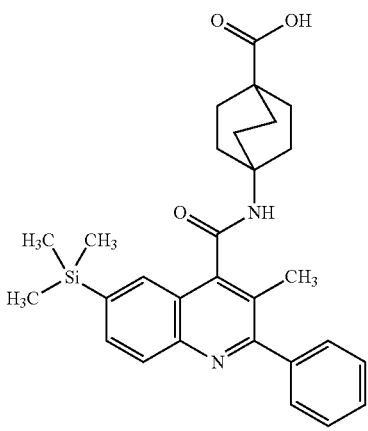 [SMILES: Cc1c(-c2ccccc2)nc2ccc([Si](C)(C)C)cc2c1C(=O)NC12CCC(C(=O)O)(CC1)CC2]

At RT, 2.0 ml (2.00 mmol) of 1 M aqueous sodium hydroxide solution were added to a mixture of 199 mg (0.40 mmol) of the compound from Example 58A in a mixture of 8.0 ml of THF and 1.5 ml of methanol, and the mixture was stirred under reflux for 1 h. After cooling to RT, the solvent was removed and the residue was triturated with a little water and 1 M hydrochloric acid. The solid was filtered off, washed twice with water and dried under reduced pressure. This gave 186 mg (86% of theory, purity 100%) of the title compound.

$^1$H-NMR (400 Mhz, DMSO-$d_6$): δ [ppm]=12.00 (br. s, 1H), 8.45 (s, 1H), 8.02 (d, 1H), 7.95 (s, 1H), 7.90 (d, 1H), 7.63-7.47 (m, 5H), 2.32 (s, 3H), 2.09-1.99 (m, 6H), 1.92-1.75 (m, 6H), 0.34 (s, 9H).

LC/MS (Method 1, ESIpos): $R_t$=1.07 min, m/z=487 [M+H]$^+$.

Example 18

4-({[6-(Difluoromethyl)-3-methyl-2-phenylquinolin-4-yl]carbonyl}amino)bicyclo[2.2.2]octane-1-carboxylic acid

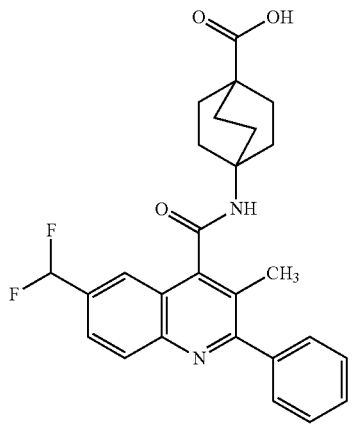 [SMILES: Cc1c(-c2ccccc2)nc2ccc(C(F)F)cc2c1C(=O)NC12CCC(C(=O)O)(CC1)CC2]

50 mg (0.10 mmol) of the compound from Example 59A were dissolved in 3.0 ml of a THF/methanol mixture (5:1), 0.1 ml (0.52 mmol) of a 5 M lithium hydroxide solution was added and the mixture was stirred at 50° C. for 3 h. After cooling to RT, the mixture was adjusted to pH 1-2 by addition of 4 M hydrochloric acid and purified by preparative HPLC (Method 2). This gave 31 mg (62% of theory, purity 98%) of the title compound.

$^1$H-NMR (400 Mhz, DMSO-$d_6$): δ [ppm]=12.10 (br. s, 1H), 8.46 (s, 1H), 8.15 (d, 1H), 7.93 (s, 1H), 7.88 (d, 1H), 7.65-7.57 (m, 2H), 7.57-7.48 (m, 3H), 7.32 (t, 1H), 2.34 (s, 3H), 2.13-1.96 (m, 6H), 1.93-1.74 (m, 6H).

LC/MS (Method 1, ESIpos): $R_t$=0.93 min, m/z=465 [M+H]$^+$.

Example 19

4-({[3-Methyl-2-phenyl-6-(trifluoromethoxy)quinolin-4-yl]carbonyl}amino)bicyclo[2.2.2]octane-1-carboxylic acid

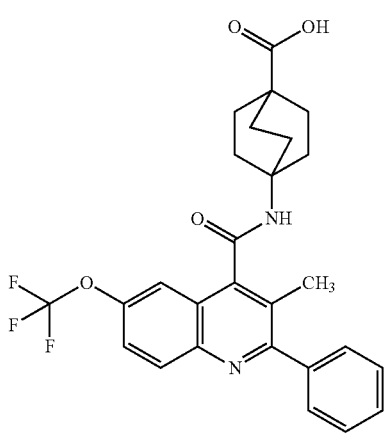 [SMILES: Cc1c(-c2ccccc2)nc2ccc(OC(F)(F)F)cc2c1C(=O)NC12CCC(C(=O)O)(CC1)CC2]

70.4 mg (0.14 mmol) of the compound from Example 60A were dissolved in 2.5 ml of a THF/methanol mixture (5:1), 0.69 ml (0.69 mmol) of a 1 M lithium hydroxide solution was added and the mixture was stirred at 60° C. for 3 h. After cooling to RT, the mixture was adjusted to pH 1-2 by addition of 4 M hydrochloric acid and purified by preparative HPLC (Method 2). This gave 43 mg (62% of theory, purity 99%) of the title compound.

$^1$H-NMR (400 Mhz, DMSO-$d_6$): δ [ppm]=12.09 (s, 1H), 8.48 (s, 1H), 8.16 (d, 1H), 7.75 (dd, 1H), 7.62-7.45 (m, 6H), 2.33 (s, 3H), 2.09-1.96 (m, 6H), 1.91-1.76 (m, 6H).

LC/MS (Method 1, ESIpos): $R_t$=1.07 min, m/z=499 [M+H]$^+$.

Example 20

4-[({3-Methyl-2-phenyl-6-[(trifluoromethyl)sulfanyl]quinolin-4-yl}carbonyl)amino]bicyclo[2.2.2]octane-1-carboxylic acid

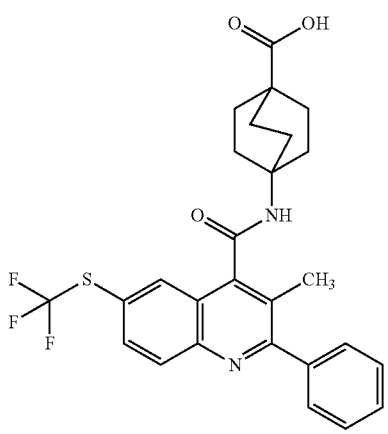 [SMILES: Cc1c(-c2ccccc2)nc2ccc(SC(F)(F)F)cc2c1C(=O)NC12CCC(C(=O)O)(CC1)CC2]

100 mg (0.19 mmol, purity 87%) of the compound from Example 61A were dissolved in 4.0 ml of a THF/methanol mixture (5:1), 0.19 ml (0.95 mmol) of a 5 M lithium hydroxide solution was added and the mixture was stirred at 50° C. for 3 h. After cooling to RT, the mixture was adjusted to pH 1-2 by addition of 4 M hydrochloric acid and purified by preparative HPLC (Method 2). This gave 72 mg (85% of theory, purity >99%) of the title compound.

$^1$H-NMR (400 Mhz, DMSO-$d_6$): δ [ppm]=12.10 (br. s, 1H), 8.50 (s, 1H), 8.15 (d, 1H), 8.08 (d, 1H), 7.95 (dd, 1H), 7.64-7.47 (m, 5H), 2.34 (s, 3H), 2.11-1.96 (m, 6H), 1.93-1.77 (m, 6H).

LC/MS (Method 1, ESIpos): $R_t$=1.06 min, m/z=515 [M+H]$^+$.

Example 21

4-{[(6-Bromo-3,8-dimethyl-2-phenylquinolin-4-yl)carbonyl]amino}bicyclo[2.2.2]octane-1-carboxylic acid

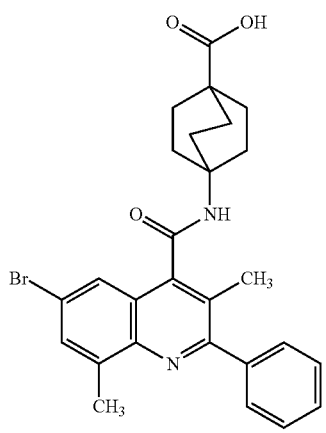 [SMILES: Cc1c(-c2ccccc2)nc2c(C)cc(Br)cc2c1C(=O)NC12CCC(C(=O)O)(CC1)CC2]

At RT, 1.37 ml (1.37 mmol) of 1 M aqueous sodium hydroxide solution were added to a solution of 212 mg (0.33 mmol, purity 80%) of the compound from Example 62A in a mixture of 4 ml of THF and 0.8 ml of methanol, and the mixture was stirred under reflux for 1.5 h. After cooling to RT, the mixture was adjusted to pH 3 by addition of 0.15 ml (1.95 mmol) TFA and concentrated. The residue was taken up in a mixture of 10 ml of acetonitrile and 2 ml of DMSO and purified by preparative HPLC (column: Kinetix C18, 5 μm, 200 mm×21.5 mm; flow rate: 75 ml/min; detection: 210 nm; injection volume 1.0 ml; temperature: 40° C.; gradient water/acetonitrile/(acetonitrile/water+0.2% formic acid) 45:50:5→5:90:5; run time 11.5 min). This gave 85 mg (51% of theory, purity 100%) of the title compound.

$^1$H-NMR (400 Mhz, DMSO-$d_6$): δ [ppm]=12.04 (br. s, 1H), 8.41 (s, 1H), 7.78 (s, 1H), 7.69-7.58 (m, 3H), 7.57-7.46 (m, 3H), 2.68 (s, 3H), 2.34 (s, 3H), 2.07-1.98 (m, 6H), 1.88-1.80 (m, 6H).

LC/MS (Method 1, ESIpos): $R_t$=1.15 min, m/z=507/509 [M+H]$^+$.

Example 22

4-{[(6,8-Dichloro-3-methyl-2-phenylquinolin-4-yl)carbonyl]amino}bicyclo[2.2.2]octane-1-carboxylic acid

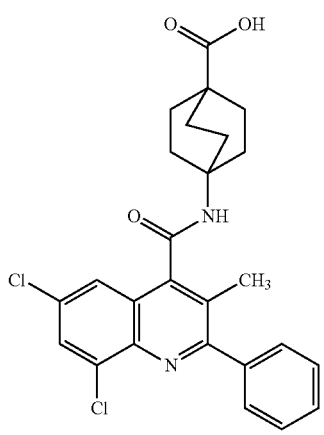 [SMILES: Cc1c(-c2ccccc2)nc2c(Cl)cc(Cl)cc2c1C(=O)NC12CCC(C(=O)O)(CC1)CC2]

130 mg (0.24 mmol, purity 90%) of the compound from Example 63A were dissolved in 4.4 ml of a THF/methanol mixture (5:1), 1.18 ml (1.18 mmol) of a 1 M lithium hydroxide solution were added and the mixture was then stirred at 50° C. for 3 h. After cooling to RT, the mixture was adjusted to pH 1-2 by addition of 4 M hydrochloric acid and purified by preparative HPLC (Method 2). This gave 67 mg (57% of theory, purity 97%) of the title compound.

$^1$H-NMR (400 Mhz, DMSO-$d_6$): δ [ppm]=12.10 (br. s, 1H), 8.48 (s, 1H), 8.10 (d, 1H), 7.66-7.59 (m, 3H), 7.59-7.49 (m, 3H), 2.36 (s, 3H), 2.09-1.95 (m, 6H), 1.92-1.73 (m, 6H).

LC/MS (Method 1, ESIpos): $R_t$=1.17 min, m/z=483 [M+H]$^+$.

Example 23

4-{[(3,6,7-Trimethyl-2-phenylquinolin-4-yl carbonyl]amino}bicyclo[2.2.2]octane-1-carboxylic acid

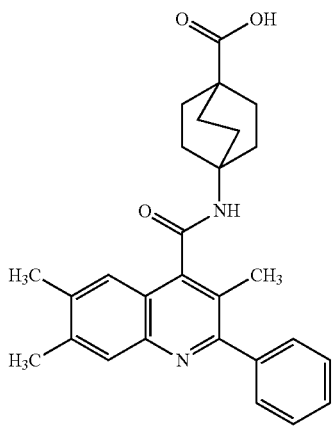 [SMILES: Cc1cc2nc(-c3ccccc3)c(C)c(C(=O)NC34CCC(C(=O)O)(CC3)CC4)c2cc1C]

175 mg (0.30 mmol, purity 78%) of the compound from Example 64A were dissolved in 5.6 ml of a THF/methanol mixture (5:1), 1.50 ml (1.50 mmol) of a 1 M lithium hydroxide solution were added and the mixture was stirred at 60° C. for 3 h. After cooling to RT, the mixture was adjusted to pH 1-2 by addition of 4 M hydrochloric acid and purified by preparative HPLC (Method 2). This gave 146 mg (99% of theory, purity 90%) of the title compound.

$^1$H-NMR (400 Mhz, DMSO-$d_6$): δ [ppm]=12.07 (br. s, 1H), 8.41 (s, 1H), 7.84 (s, 1H), 7.66-7.47 (m, 6H), 2.46 (s, 3H), 2.45 (s, 3H), 2.30 (s, 3H), 2.10-2.00 (m, 6H), 1.89-1.78 (m, 6H).

LC/MS (Method 1, ESIpos): $R_t$=0.86 min, m/z=443 [M+H]$^+$.

Example 24

4-({[6-Bromo-3-methyl-2-(2-methylphenyl)quinolin-4-yl]carbonyl}amino)bicyclo[2.2.2]octane-1-carboxylic acid

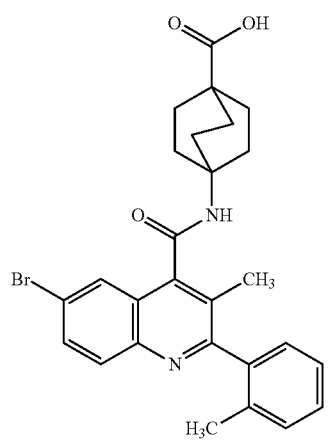 [SMILES: Cc1ccccc1-c1nc2ccc(Br)cc2c(C(=O)NC23CCC(C(=O)O)(CC2)CC3)c1C]

140 mg (0.268 mmol) of the compound from Example 65A were dissolved in 5 ml of a THF/methanol mixture (5:1), 1.34 ml (1.34 mmol) of a 1 M lithium hydroxide solution were added and the mixture was stirred at 50° C. for 2 h. After cooling to RT, the mixture was adjusted to pH 1-2 by addition of 4 M hydrochloric acid and purified by preparative HPLC (Method 2). This gave 118 mg (83% of theory, purity 95%) of the title compound.

$^1$H-NMR (400 Mhz, DMSO-$d_6$): δ [ppm]=12.09 (br. s, 1H), 8.48 (s, 1H), 7.94 (d, 1H), 7.91-7.79 (m, 2H), 7.44-7.25 (m, 3H), 7.18 (d, 1H), 2.09 (s, 3H), 2.08-1.99 (m, 9H), 1.90-1.76 (m, 6H).

LC/MS (Method 1, ESIpos): $R_t$=1.06 min, m/z=507/509 [M+H]$^+$.

Example 25

4-({[6-Bromo-2-(2,6-difluorophenyl)-3-methylquinolin-4-yl]carbonyl}amino)bicyclo[2.2.2]octane-1-carboxylic acid

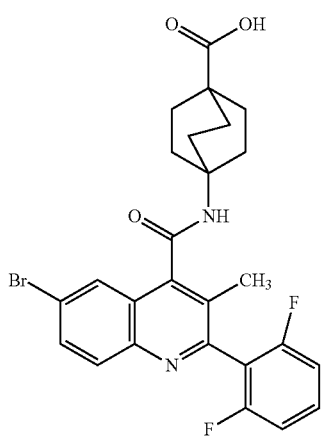 [SMILES: Cc1c(-c2c(F)cccc2F)nc2ccc(Br)cc2c1C(=O)NC12CCC(C(=O)O)(CC1)CC2]

58.6 mg (0.11 mmol) of the compound from Example 66A were dissolved in 2.0 ml of a THF/methanol mixture (5:1), 0.54 ml (0.54 mmol) of a 1 M lithium hydroxide solution was added and the mixture was stirred at 60° C. for 3 h. After cooling to RT, the mixture was adjusted to pH 1-2 by addition of 4 M hydrochloric acid and purified by preparative HPLC (Method 2). This gave 44 mg (71% of theory, purity 93%) of the title compound.

$^1$H-NMR (400 Mhz, DMSO-$d_6$): δ [ppm]=12.10 (br. s, 1H), 8.61 (s, 1H), 8.01 (d, 1H), 7.93 (dd, 1H), 7.87 (d, 1H), 7.71-7.58 (m, 1H), 7.31 (t, 2H), 2.19 (s, 3H), 2.10-1.95 (m, 6H), 1.94-1.73 (m, 6H).

LC/MS (Method 1, ESIpos): $R_t$=1.04 min, m/z=529/531 [M+H]$^+$.

Example 26

4-({[6-Bromo-2-(3-methoxyphenyl)-3-methylquinolin-4-yl]carbonyl}amino)bicyclo[2.2.2]octane-1-carboxylic acid

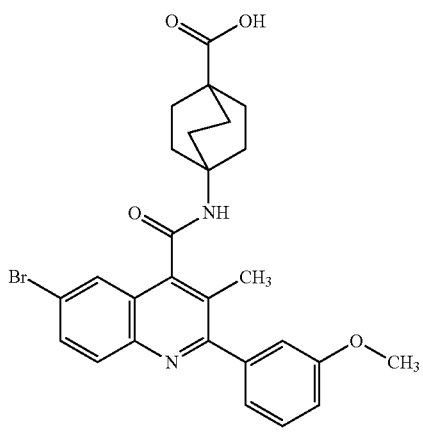 [SMILES: COc1cccc(-c2nc3ccc(Br)cc3c(C(=O)NC34CCC(C(=O)O)(CC3)CC4)c2C)c1]

83 mg (0.14 mmol, purity 92%) of the compound from Example 67A were dissolved in 2.8 ml of a THF/methanol mixture (5:1), 0.14 ml (0.71 mmol) of a 5 M lithium hydroxide solution was added and the mixture was stirred at 50° C. for 5 h. After cooling to RT, the mixture was adjusted to pH 1-2 by addition of 4 M hydrochloric acid and purified by preparative HPLC (Method 2). This gave 75 mg (99% of theory, purity 98%) of the title compound.

$^1$H-NMR (400 Mhz, DMSO-$d_6$): δ [ppm]=12.10 (br. s, 1H), 8.45 (s, 1H), 7.97 (d, 1H), 7.88 (dd, 1H), 7.83 (d, 1H), 7.49-7.39 (m, 1H), 7.11 (d, 1H), 7.09-7.02 (m, 2H), 3.82 (s, 3H), 2.32 (s, 3H), 2.16-1.93 (m, 6 H), 1.91-1.72 (m, 6 H).

LC/MS (Method 1, ESIpos): $R_t$=1.01 min, m/z=523/525 [M+H]$^+$.

Example 27

4-({[6-Bromo-3-(methylsulfanyl)-2-phenylquinolin-4-yl]carbonyl}amino)bicyclo[2.2.2]octane-1-carboxylic acid

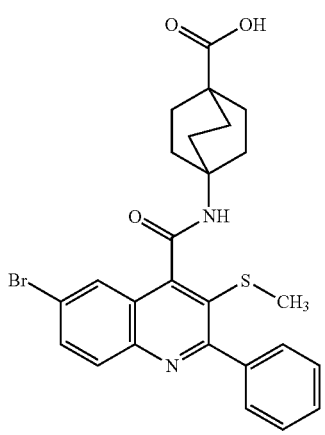 [SMILES: CSc1c(-c2ccccc2)nc2ccc(Br)cc2c1C(=O)NC12CCC(C(=O)O)(CC1)CC2]

0.56 ml (0.56 mmol) of 1 M aqueous sodium hydroxide solution were added to a solution of 50 mg (0.09 mmol) of the compound from Example 68A in a mixture of 3 ml of THF and 0.6 ml of methanol, and the mixture was stirred at RT overnight. The mixture was then adjusted to pH 3 by addition of 0.05 ml (0.65 mmol) of TFA and purified by preparative HPLC (Method 3). This gave 43 mg (87% of theory, purity 97%) of the title compound.

$^1$H-NMR (400 Mhz, DMSO-$d_6$): δ [ppm]=12.04 (br. s, 1H), 8.40 (s, 1H), 8.03-7.92 (m, 2H), 7.85 (d, 1H), 7.74-7.68 (m, 2H), 7.57-7.45 (m, 3H), 2.09-1.96 (m, 6H), 2.01 (s, 3H), 1.91-1.76 (m, 6H).

LC/MS (Method 1, ESIpos): $R_t$=1.08 min, m/z=525/527 [M+H]$^+$.

Example 28

4-{[(6-Bromo-3-ethyl-2-phenylquinolin-4-yl)carbonyl]amino}bicyclo[2.2.2]octane-1-carboxylic acid

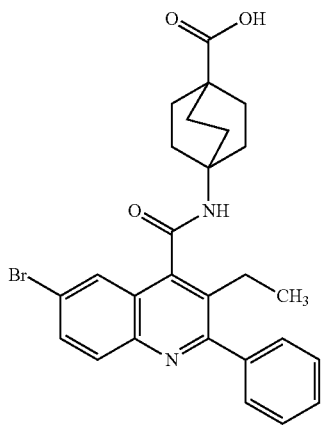 [SMILES: CCc1c(-c2ccccc2)nc2ccc(Br)cc2c1C(=O)NC12CCC(C(=O)O)(CC1)CC2]

11 mg (0.02 mmol) of the compound from Example 69A were dissolved in 0.4 ml of a THF/methanol mixture (5:1), 0.11 ml (0.11 mmol) of a 1 M lithium hydroxide solution was added and the mixture was stirred at 60° C. overnight. After cooling to RT, the mixture was adjusted to pH 1-2 by addition of 4 M hydrochloric acid and pre-purified by preparative HPLC (Method 2). The pre-purified product was dissolved in 1 ml of DMSO and purified by preparative HPLC (column XBridge C18, 5 μm, 75×30 mm; flow rate: 75 ml/min; detection: 210 nm; injection volume: 1.0 ml; temperature: 40° C.; water/acetonitrile/(acetonitrile/water 80:20+1% TFA) gradient 95/0/5 (0-1 min)→50/45/5 (13.30 min)→5/90/5 (13.50 min)). This gave 4 mg (35% of theory, purity 92%) of the title compound.

$^1$H-NMR (400 Mhz, DMSO-$d_6$): δ [ppm]=12.10 (br. s, 1H), 8.50 (s, 1H), 7.96 (d, 1H), 7.89 (dd, 1H), 7.84 (d, 1H), 7.57-7.47 (m, 5H), 2.81-2.64 (m, 2H), 2.14-1.94 (m, 6H), 1.92-1.78 (m, 6H), 0.96 (t, 3H).

LC/MS (Method 1, ESIpos): $R_t$=1.06 min, m/z=507/509 [M+H]$^+$.

Example 29

4-{[(6-Bromo-3-cyclopropyl-2-phenylquinolin-4-yl)carbonyl]amino}bicyclo[2.2.2]octane-1-carboxylic acid

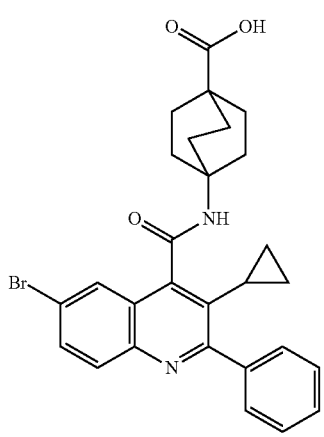 [SMILES: O=C(NC12CCC(C(=O)O)(CC1)CC2)c1c(C2CC2)c(-c2ccccc2)nc2ccc(Br)cc12]

0.65 ml (0.65 mmol) of 1 M aqueous sodium hydroxide solution were added to a solution of 69 mg (0.13 mmol) of the compound from Example 70A in a mixture of 1.5 ml of THF and 0.35 ml of methanol, and the mixture was allowed to stand at RT for three days. The mixture was then adjusted to pH 3 by addition of TFA and purified by preparative HPLC (Method 3). This gave 65 mg (96% of theory, purity 100%) of the title compound.

$^1$H-NMR (400 Mhz, DMSO-$d_6$): δ [ppm]=12.06 (br. s, 1H), 8.39 (s, 1H), 7.97 (d, 1H), 7.92 (d, 1H), 7.88 (dd, 1H), 7.73-7.65 (m, 2H), 7.55-7.44 (m, 3H), 2.29-2.16 (m, 1H), 2.11-2.01 (m, 6H), 1.90-1.80 (m, 6H), 0.70-0.59 (m, 2H), 0.35-0.26 (m, 2H).

LC/MS (Method 1, ESIpos): $R_t$=1.08 min, m/z=519/521 [M+H]$^+$.

Example 30

4-{[(6-Bromo-3-chloro-2-phenylquinolin-4-yl)carbonyl]amino}bicyclo[2.2.2]octane-1-carboxylic acid

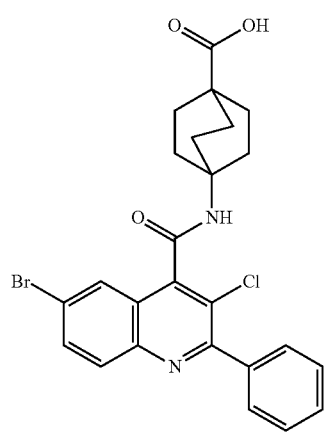 [SMILES: O=C(NC12CCC(C(=O)O)(CC1)CC2)c1c(Cl)c(-c2ccccc2)nc2ccc(Br)cc12]

2.08 ml (2.08 mmol) of 1 M aqueous sodium hydroxide solution were added to a solution of 220 mg (0.42 mmol) of the compound from Example 71A in a mixture of 5.5 ml of THF and 1.1 ml of methanol, and the mixture was stirred at RT overnight. The mixture was then adjusted to pH 3 by addition of about 0.19 ml (2.50 mmol) of TFA and purified by preparative HPLC (Method 3). This gave 190 mg (87% of theory, purity 98%) of the title compound.

$^1$H-NMR (400 Mhz, DMSO-$d_6$): δ [ppm]=12.08 (br. s, 1H), 8.60 (s, 1H), 8.05 (d, 1H), 7.99 (dd, 1H), 7.83 (d, 1H), 7.73-7.67 (m, 2H), 7.59-7.51 (m, 3H), 2.07-1.97 (m, 6H), 1.88-1.80 (m, 6H).

LC/MS (Method 1, ESIpos): $R_t$=1.09 min, m/z=513/515 [M+H]$^+$.

Example 31

4-{[(6-Bromo-2-phenyl-3-propylquinolin-4-yl)carbonyl]amino}bicyclo[2.2.2]octane-1-carboxylic acid

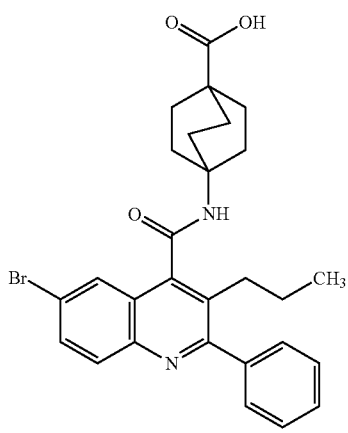 [SMILES: CCCc1c(-c2ccccc2)nc2ccc(Br)cc2c1C(=O)NC12CCC(C(=O)O)(CC1)CC2]

98 mg (0.18 mmol) of the compound from Example 72A were dissolved in 3.2 ml of a THF/methanol mixture (5:1), 0.91 ml (0.91 mmol) of a 1 M lithium hydroxide solution was added and the mixture was stirred at 50° C. for 2 h. After cooling to RT, the mixture was adjusted to pH 1-2 by addition of 4 M hydrochloric acid and purified by preparative HPLC (Method 2). This gave 53 mg (95% of theory, purity 98%) of the title compound.

$^1$H-NMR (400 Mhz, DMSO-$d_6$): δ [ppm]=12.06 (br. s, 1H), 8.50 (s, 1H), 7.96 (d, 1H), 7.88 (dd, 1H), 7.84 (d, 1H), 7.58-7.44 (m, 5H), 2.80-2.59 (m, 2H), 2.11-1.94 (m, 6H), 1.94-1.72 (m, 6H), 1.47-1.24 (m, 2H), 0.69 (t, 3H).

LC/MS (Method 1, ESIpos): $R_t$=1.07 min, m/z=521/523 [M+H]$^+$.

Example 32

4-{[(3-Chloro-6-iodo-2-phenylquinolin-4-yl)carbonyl]amino}bicyclo[2.2.2]octane-1-carboxylic acid

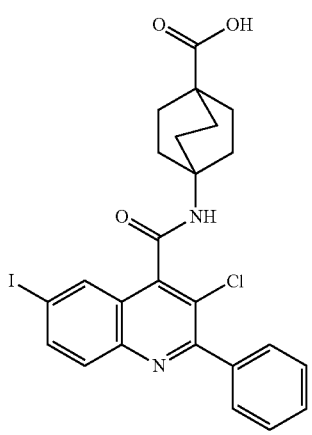 [SMILES: O=C(NC12CCC(C(=O)O)(CC1)CC2)c1c(Cl)c(-c2ccccc2)nc2ccc(I)cc12]

0.73 ml (0.73 mmol) of 1 M aqueous sodium hydroxide solution was added to a solution of 70 mg (0.12 mmol) of the compound from Example 73A in a mixture of 4 ml of THF and 0.7 ml of methanol, and the mixture was stirred at RT overnight. The mixture was then adjusted to pH 3 by addition of 0.07 ml (0.85 mmol) of TFA and purified by preparative HPLC (Method 3). This gave 50 mg (70% of theory, purity 96%) of the title compound.

$^1$H-NMR (400 Mhz, DMSO-$d_6$): δ [ppm]=12.13 (br. s, 1H), 8.58 (s, 1H), 8.11 (dd, 1H), 8.06 (d, 1H), 7.87 (d, 1H), 7.72-7.66 (m, 2H), 7.58-7.51 (m, 3H), 2.07-1.96 (m, 6H), 1.89-1.79 (m, 6H).

LC/MS (Method 1, ESIpos): $R_t$=1.12 min, m/z=561 [M+H]$^+$.

Example 33

4-{[(3-Cyclopropyl-6-iodo-2-phenylquinolin-4-yl)carbonyl]amino}bicyclo[2.2.2]octane-1-carboxylic acid

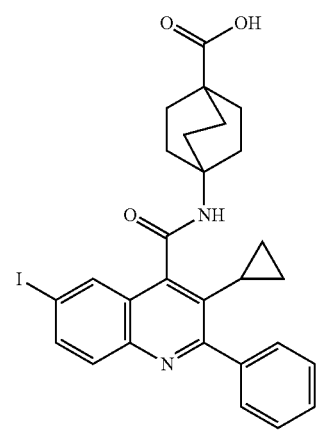 [SMILES: O=C(NC12CCC(C(=O)O)(CC1)CC2)c1c(C2CC2)c(-c2ccccc2)nc2ccc(I)cc12]

0.60 ml (0.60 mmol) of 1 M aqueous sodium hydroxide solution was added to a solution of 58 mg (0.10 mmol) of the compound from Example 74A in a mixture of 3 ml of THF and 0.6 ml of methanol, and the mixture was stirred at RT overnight. The mixture was then adjusted to pH 3 by addition of 0.053 ml (0.70 mmol) of TFA and purified by preparative HPLC (Method 3). This gave 14 mg (25% of theory, purity 98%) of the title compound.

$^1$H-NMR (400 Mhz, DMSO-$d_6$): δ [ppm]=12.10 (br. s, 1H), 8.37 (s, 1H), 8.15 (d, 1H), 8.00 (dd, 1H), 7.79 (d, 1H), 7.72-7.66 (m, 2H), 7.54-7.43 (m, 3H), 2.27-2.16 (m, 1H), 2.10-2.00 (m, 6H), 1.90-1.79 (m, 6H), 0.70-0.58 (m, 2H), 0.36-0.23 (m, 2H).

LC/MS (Method 1, ESIpos): $R_t$=1.08 min, m/z=567 [M+H]$^+$.

Example 34

4-({[3-Methyl-2-phenyl-6-(trifluoromethyl)quinolin-4-yl]carbonyl}amino)bicyclo[2.2.2]octane-1-carboxylic acid

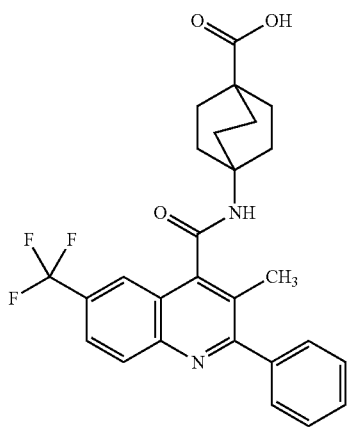 [SMILES: Cc1c(-c2ccccc2)nc2ccc(C(F)(F)F)cc2c1C(=O)NC12CCC(C(=O)O)(CC1)CC2]

14 mg (0.028 mmol) of the compound from Example 75A were dissolved in 3.5 ml of a THF/methanol mixture (5:1), 0.028 ml (0.14 mmol) of a 5 M lithium hydroxide solution were added and the mixture was stirred at 50° C. for 1 h. After cooling to RT, the mixture was adjusted to pH 1-2 by addition of 4 M hydrochloric acid and purified by preparative HPLC (Method 2). This gave 9 mg (63% of theory, purity 95%) of the title compound.

$^1$H-NMR (500 Mhz, DMSO-d$_6$): δ [ppm]=8.43 (s, 1H), 8.23 (d, 1H), 8.06 (s, 1H), 8.00 (dd, 1H), 7.63-7.58 (m, 2H), 7.57-7.49 (m, 3H), 2.36 (s, 3H), 2.01-1.93 (m, 6H), 1.82-1.74 (m, 6H).

LC/MS (Method 1, ESIpos): R$_t$=1.00 min, m/z=483 [M+H]$^+$.

Example 35

4-{[(6-Bromo-3-hydroxy-2-phenylquinolin-4-yl)carbonyl]amino}bicyclo[2.2.2]octane-1-carboxylic acid

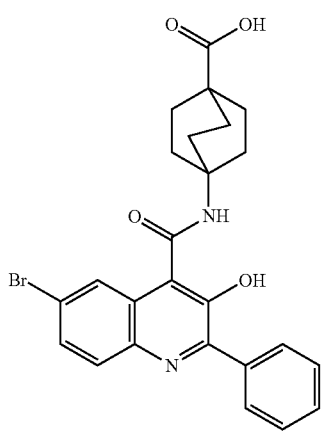

0.54 ml (0.54 mmol) of 1 M aqueous sodium hydroxide solution were added to a solution of 46 mg (0.09 mmol) of the compound from Example 76A in a mixture of 1.5 ml of THF and 0.3 ml of methanol, and the mixture was stirred at RT overnight. The mixture was then adjusted to about pH 2 by addition of 1 M hydrochloric acid and purified by preparative HPLC (Method 4). This gave 27 mg (57% of theory, purity 95%) of the title compound.

$^1$H-NMR (400 Mhz, DMSO-d$_6$): δ [ppm]=12.07 (br. s, 1H), 9.90 (br. s, 1H), 8.31 (s, 1H), 7.96-7.88 (m, 3H), 7.81 (d, 1H), 7.70 (dd, 1H), 7.56-7.44 (m, 3H), 2.08-1.97 (m, 6H), 1.88-1.78 (m, 6H).

LC/MS (Method 1, ESIpos): R$_t$=1.09 min, m/z=495/497 [M+H]$^+$.

Example 36

6-Bromo-N-(4-carbamoylbicyclo[2.2.2]oct-1-yl)-3-methyl-2-phenylquinoline-4-carboxamide

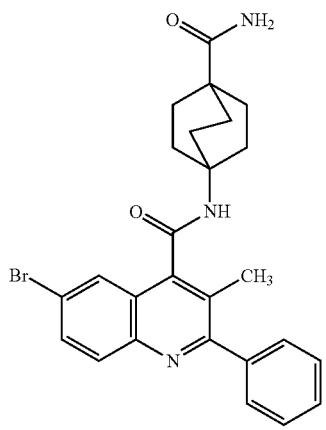 [SMILES: Cc1c(-c2ccccc2)nc2ccc(Br)cc2c1C(=O)NC12CCC(C(N)=O)(CC1)CC2]

4.5 ml (38.1 mmol) of a 33% strength aqueous ammonia solution were added slowly to a solution of 300 mg (0.59 mmol) of the compound from Example 86A in 6 ml of THF, and the mixture was stirred at RT overnight. 50 ml of water were then added. The solid formed was then filtered off, washed twice with water and dried under reduced pressure. This gave 205 mg (71% of theory, purity 100%) of the title compound.

$^1$H-NMR (400 Mhz, DMSO-d$_6$): δ [ppm]=8.43 (s, 1H), 7.97 (d, 1H), 7.91-7.79 (m, 2H), 7.61-7.44 (m, 5H), 6.97 (br. s, 1H), 6.75 (br. s, 1H), 2.33 (s, 3H), 2.08-1.93 (m, 6H), 1.89-1.72 (m, 6H).

LC/MS (Method 1, ESIpos): R$_t$=0.87 min, m/z=492/494 [M+H]$^+$.

Example 37

3-{[(6-Bromo-3-methyl-2-phenylquinolin-4-yl)carbonyl]amino}bicyclo[1.1.1]pentane-1-carboxylic acid

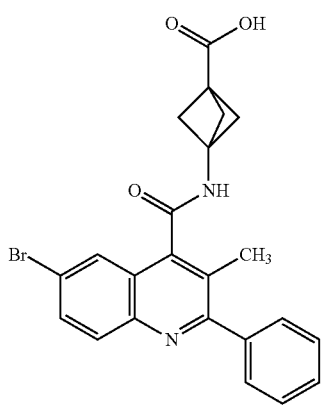 [SMILES: Cc1c(-c2ccccc2)nc2ccc(Br)cc2c1C(=O)NC12CC(C(=O)O)(C1)C2]

93 mg (0.2 mmol) of the compound from Example 77A were dissolved in 3.0 ml of a THF/methanol mixture (5:1), 1.0 ml (1.0 mmol) of a 1 M sodium hydroxide solution and the mixture was stirred under reflux for 1 h. After cooling to RT, the mixture was introduced into 20 ml of water and adjusted to pH 1-2 by addition of 4 M hydrochloric acid. The solid present was filtered off and washed twice with water and once with tert-butyl methyl ether. This gave 62 mg (65% of theory, purity 95%) of the title compound.

$^1$H-NMR (400 Mhz, DMSO-$d_6$): δ [ppm]=12.51 (br. s, 1H), 9.46 (s, 1H), 7.99 (d, 1H), 7.90 (dd, 1H), 7.80 (d, 1H), 7.61-7.48 (m, 5H), 2.37 (s, 6H), 2.33 (s, 3H).

LC/MS (Method 1, ESIpos): $R_t$=0.93 min, m/z=451/453 [M+H]$^+$.

Example 38

4-{[(6-Iodo-3-methyl-2-phenylquinolin-4-yl)carbonyl]amino}bicyclo[2.2.1]heptane-1-carboxylic acid

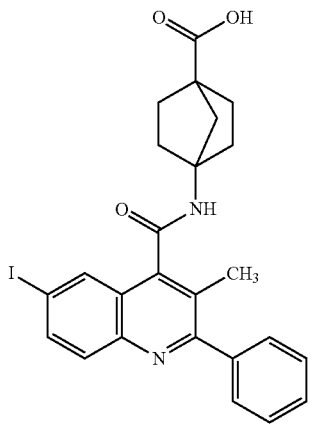 [SMILES: Cc1c(-c2ccccc2)nc2ccc(I)cc2c1C(=O)NC12CCC(C(=O)O)(CC1)C2]

100 mg (0.16 mmol, purity 87%) of the compound from Example 78A were dissolved in 3.0 ml of a THF/methanol mixture (5:1), 0.80 ml (0.80 mmol) of a 1 M lithium hydroxide solution was added and the mixture was stirred at 60° C. for 3 h. After cooling to RT, the mixture was adjusted to pH 1-2 by addition of 4 M hydrochloric acid and purified by preparative HPLC (Method 2). This gave 87 mg (93% of theory, purity 90%) of the title compound.

$^1$H-NMR (400 Mhz, DMSO-$d_6$): δ [ppm]=12.0 (br. s, 1H), 9.05 (s, 1H), 8.08-7.98 (m, 2H), 7.82 (d, 1H), 7.62-7.46 (m, 5H), 2.33 (s, 3H), 2.12-1.54 (m, 10H).

LC/MS (Method 1, ESIpos): $R_t$=1.02 min, m/z=527 [M+H]$^+$.

Example 39

5-{[(6-Bromo-3-methyl-2-phenylquinolin-4-yl)carbonyl]amino}bicyclo[3.2.2]nonane-1-carboxylic acid

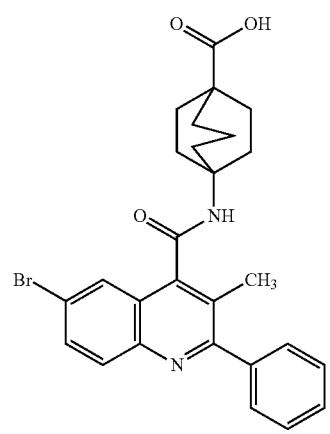 [SMILES: Cc1c(-c2ccccc2)nc2ccc(Br)cc2c1C(=O)NC12CCCC(C(=O)O)(CC1)CC2]

1.4 ml (1.4 mmol) of 1 M aqueous sodium hydroxide solution were added to a solution of 171 mg (0.24 mmol, purity 75%) of the compound from Example 79A in a mixture of 7.3 ml of THF and 1.5 ml of methanol, and the mixture was stirred at RT overnight. The mixture was then adjusted to pH 3 by addition of TFA and purified by preparative HPLC (Method 3). The pre-purified product was dissolved in 25 ml of a methanol/acetonitrile mixture and re-purified by preparative SFC (column: Chiralpak ADH, 5 µm, 250 mm×20 mm; flow rate: 80 ml/min; detection: 210 nm; injection volume 2.0 ml; temperature: 40° C.; 85% $CO_2$/15% ethanol isocratic; run time 13 min). This gave 64 mg (53% of theory, purity 100%) of the title compound.

$^1$H-NMR (400 Mhz, DMSO-$d_6$): δ [ppm]=12.02 (br. s, 1H), 8.50 (s, 1H), 7.97 (d, 1H), 7.90-7.81 (m, 2H), 7.60-7.46 (m, 5H), 2.33 (s, 3H), 2.35-2.15 (m, 4H), 1.98-1.69 (m, 10H).

LC/MS (Method 1, ESIpos): $R_t$=1.03 min, m/z=507/509 [M+H]$^+$.

Example 40

5-{[(6-Bromo-3-chloro-2-phenylquinolin-4-yl)carbonyl]amino}bicyclo[3.2.2]nonane-1-carboxylic acid

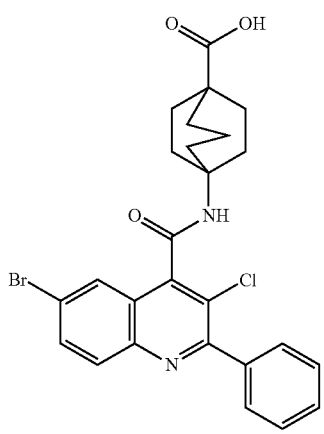 [SMILES: O=C(NC12CCCC(C(=O)O)(CC1)CC2)c1c(Cl)c(-c2ccccc2)nc2ccc(Br)cc12]

0.7 ml (0.7 mmol) of 1 M aqueous sodium hydroxide solution were added to a solution of 85 mg (0.12 mmol, purity 85%) of the compound from Example 80A in a mixture of 3.5 ml of THF and 0.7 ml of methanol, and the mixture was stirred at RT overnight. The mixture was then adjusted to pH 3 by addition of TFA and purified by preparative HPLC (Method 3). This gave 41 mg (66% of theory, purity 98%) of the title compound.

$^1$H-NMR (400 Mhz, DMSO-$d_6$): δ [ppm]=11.98 (s, 1H), 8.64 (s, 1H), 8.10-7.93 (m, 2H), 7.88-7.79 (m, 1H), 7.76-7.66 (m, 2H), 7.60-7.51 (m, 3H), 2.33-2.11 (m, 4H), 2.00-1.62 (m, 10H).

LC/MS (Method 1, ESIpos): $R_t$=1.13 min, m/z=527/529 [M+H]$^+$.

Example 41

5-{[(3-Chloro-6-iodo-2-phenylquinolin-4-yl)carbonyl]amino}bicyclo[3.2.2]nonane-1-carboxylic acid

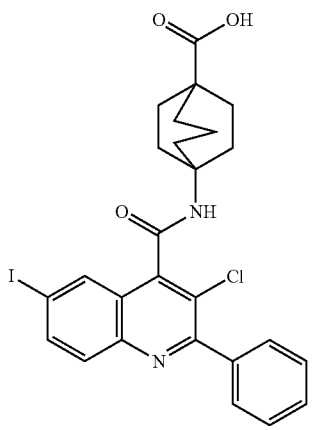 [SMILES: O=C(NC12CCCC(C(=O)O)(CC1)CC2)c1c(Cl)c(-c2ccccc2)nc2ccc(I)cc12]

0.68 ml (0.68 mmol) of 1 M aqueous sodium hydroxide solution were added to a solution of 86 mg (0.11 mmol, purity 90%) of the compound from Example 81A in a mixture of 3.5 ml of THF and 0.7 ml of methanol, and the mixture was stirred at RT overnight. The mixture was then adjusted to pH 3 by addition of TFA and purified by preparative HPLC (Method 3). This gave 46 mg (69% of theory, purity 98%) of the title compound.

$^1$H-NMR (400 Mhz, DMSO-$d_6$): δ [ppm]=12.02 (br. s, 1H), 8.62 (s, 1H), 8.11 (dd, 1H), 8.07 (d, 1H), 7.87 (d, 1H), 7.72-7.67 (m, 2H), 7.59-7.48 (m, 3H), 2.31-2.15 (m, 4H), 1.98-1.68 (m, 10H).

LC/MS (Method 1, ESIpos): $R_t$=1.15 min, m/z=575 [M+H]$^+$.

Example 42

5-{[(3-Cyclopropyl-6-iodo-2-phenylquinolin-4-yl)carbonyl]amino}bicyclo[3.2.2]nonane-1-carboxylic acid

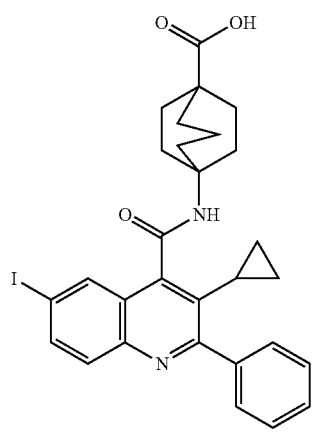 [SMILES: O=C(NC12CCCC(C(=O)O)(CC1)CC2)c1c(C2CC2)c(-c2ccccc2)nc2ccc(I)cc12]

0.32 ml (0.32 mmol) of 1 M aqueous sodium hydroxide solution were added to a solution of 55 mg (0.05 mmol, purity 58%) of the compound from Example 82A in a mixture of 1.6 ml of THF and 0.3 ml of methanol, and the mixture was stirred at RT overnight. The mixture was then adjusted to pH 3 by addition of TFA and purified by preparative HPLC (Method 3). This gave 21 mg (66% of theory, purity 96%) of the title compound.

$^1$H-NMR (400 Mhz, DMSO-$d_6$): δ [ppm]=12.01 (br. s, 1H), 8.39 (s, 1H), 8.17 (d, 1H), 7.99 (dd, 1H), 7.79 (d, 1H), 7.72-7.66 (m, 2H), 7.54-7.42 (m, 3H), 2.35-2.16 (m, 5H), 2.06-1.69 (m, 10H), 0.70-0.59 (m, 2H), 0.35-0.22 (m, 2H).

LC/MS (Method 1, ESIpos): $R_t$=1.16 min, m/z=581 [M+H]$^+$.

Example 43

4-{[(6-Bromo-3-methyl-2-phenylquinolin-4-yl)carbonyl]amino}cubane-1-carboxylic acid

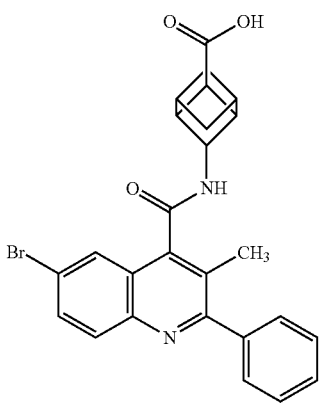 [SMILES: Cc1c(-c2ccccc2)nc2ccc(Br)cc2c1C(=O)NC1C2C3CC(C3)C1C2C(=O)O]

93.4 mg (0.17 mmol, purity 91%) of the compound from Example 83A were dissolved in 4.9 ml of a THF/methanol mixture (5:1), 0.84 ml (0.84 mmol) of a 1 M lithium hydroxide solution was added and the mixture was stirred at 50° C. for 1 h. After cooling to RT, the mixture was adjusted to pH 1-2 by addition of 4 M hydrochloric acid and purified by preparative HPLC (Method 2). The solid obtained was stirred in boiling water for 3 h, filtered whilst hot and dried under reduced pressure. This gave 52 mg (63% of theory, purity 99%) of the title compound. $^1$H-NMR (400 Mhz, DMSO-d$_6$): δ [ppm]=12.34 (br. s, 1H), 9.66 (s, 1H), 8.00 (d, 1H), 7.91 (dd, 1H), 7.86 (d, 1H), 7.64-7.46 (m, 5H), 4.28-4.18 (m, 3H), 4.18-4.08 (m, 3H), 2.36 (s, 3H).

LC/MS (Method 1, ESIpos): R$_t$=0.94 min, m/z=487/489 [M+H]$^+$.

Example 44

4-{[(6-Iodo-3-methyl-2-phenylquinolin-4-yl)carbonyl]amino}cubane-1-carboxylic acid

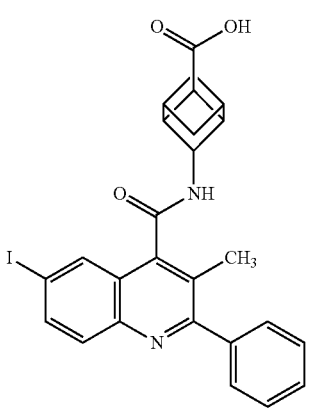 [SMILES: Cc1c(-c2ccccc2)nc2ccc(I)cc2c1C(=O)NC1C2C3CC(C3)C1C2C(=O)O]

83 mg (0.14 mmol, purity 95%) of the compound from Example 84A were dissolved in 2.7 ml of a THF/methanol mixture (5:1), 0.72 ml (0.72 mmol) of a 1 M lithium hydroxide solution was added and the mixture was stirred at 60° C. for 6 h. After cooling to RT, the mixture was adjusted to pH 1-2 by addition of 4 M hydrochloric acid and purified by preparative HPLC (Method 2). This gave 54 mg (64% of theory, purity 92%) of the title compound.

$^1$H-NMR (400 Mhz, DMSO-d$_6$): δ [ppm]=12.34 (br. s, 1H), 9.65 (s, 1H), 8.06 (d, 1H), 8.03 (dd, 1H), 7.83 (d, 1H), 7.62-7.56 (m, 2H), 7.56-7.48 (m, 3H), 4.24-4.18 (m, 3H), 4.18-4.11 (m, 3H), 2.35 (s, 3H).

LC/MS (Method 1, ESIpos): R$_t$=0.98 min, m/z=535 [M+H]$^+$.

Example 45

4-{[(6-Bromo-3-chloro-2-phenylquinolin-4-yl)carbonyl]amino}cubane-1-carboxylic acid

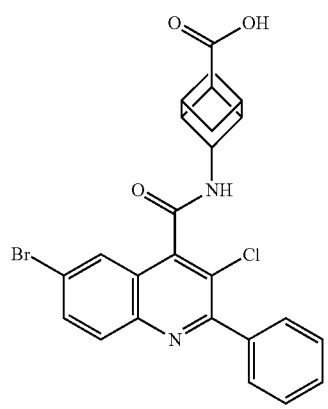 [SMILES: O=C(NC1C2C3CC(C3)C1C2C(=O)O)c1c(Cl)c(-c2ccccc2)nc2ccc(Br)cc12]

107 mg (0.17 mmol, purity 83%) of the compound from Example 85A were dissolved in 3.1 ml of a THF/methanol mixture (5:1), 0.85 ml (0.85 mmol) of a 1 M lithium hydroxide solution was added and the mixture was stirred at 60° C. for 3 h. After cooling to RT, the mixture was adjusted to pH 1-2 by addition of 4 M hydrochloric acid and purified by preparative HPLC (Method 2). This gave 24 mg (22% of theory, purity 79%) of the title compound.

$^1$H-NMR (400 Mhz, DMSO-d$_6$): δ [ppm]=12.34 (br. s, 1H), 9.80 (s, 1H), 8.14-7.98 (m, 2H), 7.88 (d, 1H), 7.77-7.66 (m, 2H), 7.61-7.50 (m, 3H), 4.26-4.19 (m, 3H), 4.18-4.11 (m, 3H).

LC/MS (Method 1, ESIpos): R$_t$=0.98 min, m/z=507/509 [M+H]$^+$.

Example 46

Sodium 4-{[(6-bromo-3-methyl-2-phenylquinolin-4-yl)carbonyl]amino}bicyclo[2.2.2]octane-1-carboxylate

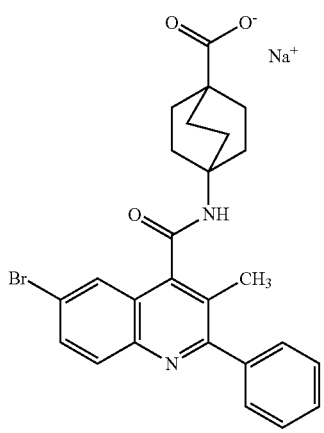 [SMILES: Cc1c(-c2ccccc2)nc2ccc(Br)cc2c1C(=O)NC12CCC(C(=O)[O-])(CC1)CC2 ; [Na+]]

100 ml of ethanol were added to 2.0 g (4.05 mmol) of the compound from Example 1, and the mixture was heated to the boil. 4.1 ml (4.1 mmol) of a 0.1 M aqueous sodium hydroxide solution were added to the hot mixture. After cooling to RT, the solution was left to stand at RT under air until the solvent had evaporated. Decanting gave 2.23 g (quant., purity 99%, contains ethanol) of the title compound.

$^1$H-NMR (500 Mhz, DMSO-$d_6$): δ [ppm]=8.33 (s, 1H), 7.96 (d, 1H), 7.88-7.82 (m, 2H), 7.60-7.46 (m, 5H), 2.32 (s, 3H), 1.98-1.90 (m, 6H), 1.77-1.70 (m, 6H).

LC/MS (Method 1, ESIpos): $R_t$=1.03 min, m/z=493/495 [M+H]$^+$.

Example 47

Potassium 4-{[(6-bromo-3-methyl-2-phenylquinolin-4-yl)carbonyl]amino}bicyclo[2.2.2]octane-1-carboxylate

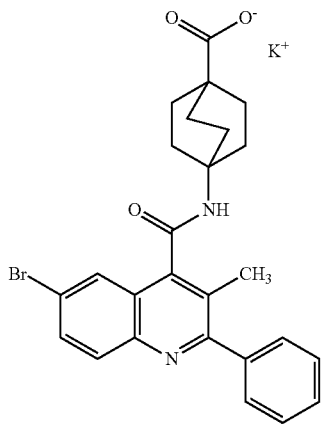 [SMILES: Cc1c(-c2ccccc2)nc2ccc(Br)cc2c1C(=O)NC12CCC(C(=O)[O-])(CC1)CC2 ; [K+]]

100 ml of ethanol were added to 2.0 g (4.05 mmol) of the compound from Example 1, and the mixture was heated to the boil. 4.1 ml (4.1 mmol) of a 0.1 M aqueous potassium hydroxide solution were added to the hot mixture. After cooling to RT, the solution was left to stand at RT under air until the solvent had evaporated. Decanting gave 2.25 g (quant., purity 97%, contains ethanol) of the title compound.

$^1$H-NMR (500 Mhz, DMSO-$d_6$): δ [ppm]=8.32 (s, 1H), 7.96 (d, 1H), 7.88-7.82 (m, 2H), 7.59-7.46 (m, 5H), 2.32 (s, 3H), 1.95-1.88 (m, 6H), 1.73-1.65 (m, 6H).

LC/MS (Method 1, ESIpos): $R_t$=1.03 min, m/z=493/495 [M+H]$^+$.

Example 48

4-{[(6-Bromo-3-methyl-2-phenylquinolin-4-yl)carbonyl]amino}bicyclo[2.2.2]octane-1-carboxylic acid 2-amino-2-(hydroxymethyl)propane-1,3-diole salt

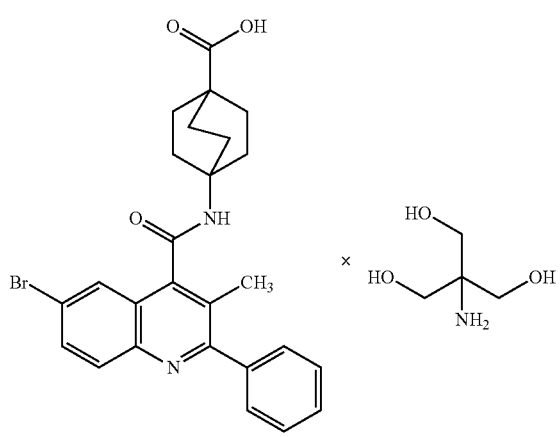 [SMILES: Cc1c(-c2ccccc2)nc2ccc(Br)cc2c1C(=O)NC12CCC(C(=O)O)(CC1)CC2 ; NC(CO)(CO)CO]

Method A:

100 ml of ethanol were added to 2.0 g (4.05 mmol) of the compound from Example 1, and the mixture was heated to the boil. A solution of 492 mg (4.06 mmol) of 2-amino-2-(hydroxymethyl)propane-1,3-diol (TRIS) in 10 ml of water was added to the hot solution. After cooling to RT, the mixture was left to stand at RT under air until the solvent had evaporated. Decanting gave 2.60 g (quant., purity 100%, contains ethanol) of the title compound.

$^1$H-NMR (500 Mhz, DMSO-$d_6$): δ [ppm]=8.43 (s, 1H), 7.97 (d, 1H), 7.87 (dd, 1H), 7.83 (d, 1H), 7.60-7.47 (m, 5H), 3.29 (s, 6H), 2.33 (s, 3H), 2.05-1.96 (m, 6H), 1.85-1.78 (m, 6H).

LC/MS (Method 1, ESIpos): $R_t$=1.03 min, m/z=493/495 [M+H]$^+$.

Method B:

340 ml of ethanol were added to 5.0 g (10.13 mmol) of the compound from Example 1, and the mixture was heated to an internal temperature of 65° C. with stirring. Slowly, with stirring, the solution was allowed to cool and, at about 38° C., a seed crystal (obtained according to Method A) was added. The mixture was then allowed to cool further, and stirring was continued at RT overnight. The precipitate present was filtered off and washed twice with in each case 10 ml of ethanol. Drying under reduced pressure gave 4.25 g (68% of theory, 100% of theory, contains ethanol) of the title compound.

Example 49

4-{[(6-Bromo-3-methyl-2-phenylquinolin-4-yl)carbonyl]amino}bicyclo[2.2.2]octane-1-carboxylic acid L-lysine salt

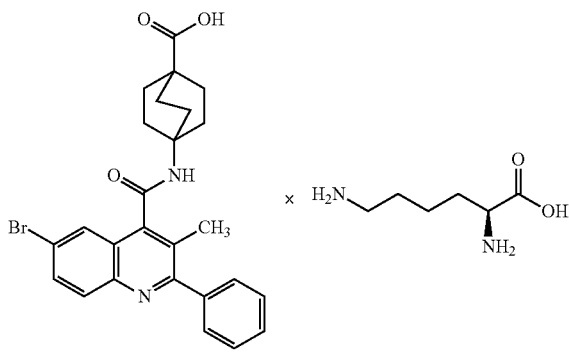 [SMILES: Cc1c(-c2ccccc2)nc2ccc(Br)cc2c1C(=O)NC12CCC(C(=O)O)(CC1)CC2 ; NCCCC[C@H](N)C(=O)O]

100 ml of ethanol were added to 2.0 g (4.05 mmol) of the compound from Example 1, and the mixture was heated to the boil. A solution of 593 mg (4.06 mmol) of L-lysine in 10 ml of water was added to the hot solution. After cooling to RT, the mixture was left to stand at RT under air until the solvent had evaporated. Decanting gave 2.58 g (quant., purity 100%, contains ethanol) of the title compound.

$^1$H-NMR (500 Mhz, DMSO-$d_6$): δ [ppm]=8.42 (s, 1H), 7.97 (d, 1H), 7.90-7.80 (m, 2H), 7.61-7.45 (m, 5H), 3.14 (t, 1H), 2.65 (t, 2H), 2.32 (s, 3H), 2.04-1.95 (m, 6H), 1.85-1.74 (m, 6H), 1.73-1.64 (m, 1H), 1.63-1.52 (m, 1H), 1.51-1.30 (m, 4H).

LC/MS (Method 1, ESIpos): $R_t$=1.03 min, m/z=493/495 [M+H]$^+$.

Example 50

2-Hydroxy-N,N,N-trimethylethanaminium 4-{[(6-bromo-3-methyl-2-phenylquinolin-4-yl)carbonyl]amino}bicyclo[2.2.2]octane-1-carboxylate

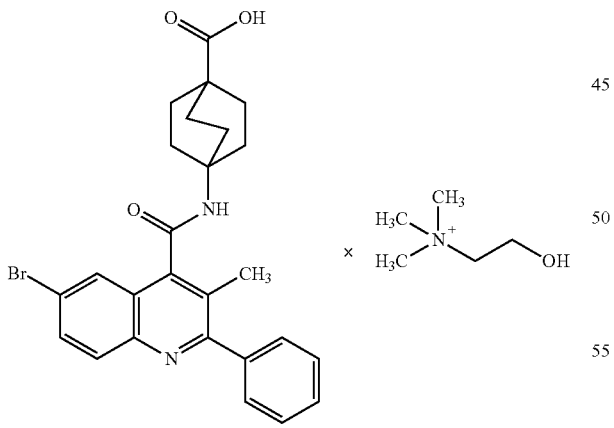

100 ml of ethanol were added to 2.0 g (4.05 mmol) of the compound from Example 1, and the mixture was heated to the boil. A solution of 500 mg (4.13 mmol) of 2-hydroxy-N,N,N-trimethylethanaminium hydroxide (choline hydroxide) in 500 mg of water was added to the hot mixture. After cooling to RT, the mixture was left to stand at RT under air until the solvent had evaporated. Decanting gave 2.59 g (quant., purity 99%, contains ethanol) of the title compound.

$^1$H-NMR (500 Mhz, DMSO-$d_6$): δ [ppm]=8.29 (s, 1H), 7.96 (d, 1H), 7.88-7.82 (m, 2H), 7.59-7.46 (m, 5H), 3.88-3.81 (m, 2H), 3.43-3.39 (m, 2H), 3.12 (s, 9H), 2.32 (s, 3H), 1.95-1.88 (m, 6H), 1.72-1.65 (m, 6H).

LC/MS (Method 1, ESIpos): $R_t$=1.03 min, m/z=493/495 [M+H]$^+$.

Example 51

4-{[(6-Bromo-3-methyl-2-phenylquinolin-4-yl)carbonyl]amino}bicyclo[2.2.2]octane-1-carboxylic acid L-arginine salt

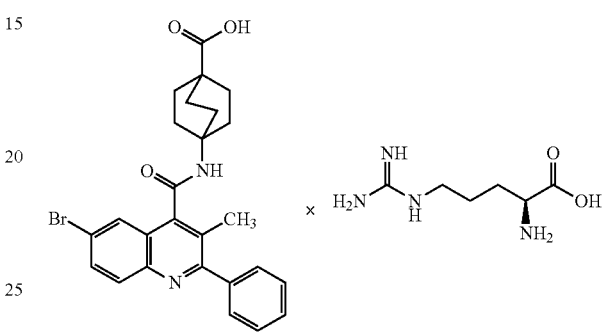

100 ml of ethanol were added to 2.0 g (4.05 mmol) of the compound from Example 1, and the mixture was heated to the boil. A solution of 706 mg (4.05 mmol) of L-(+)-arginine in 10 ml of water was added to the hot solution. After cooling to RT, the mixture was left to stand at RT under air until the solvent had evaporated. After decanting, 2.81 g of the title compound were obtained (quant., purity 100%, contains ethanol).

$^1$H-NMR (500 Mhz, DMSO-$d_6$): δ [ppm]=8.38 (s, 1H), 8.24 (br. s, ~2H), 7.97 (d, 1H), 7.89-7.81 (m, 2H), 7.60-7.46 (m, 5H), 3.22-3.17 (m, 1H), 3.13-2.98 (m, 3H), 2.32 (s, 3H), 2.01-1.92 (m, 6H), 1.81-1.73 (m, 6H), 1.73-1.49 (m, 4H).

LC/MS (Method 1, ESIpos): $R_t$=1.03 min, m/z=493/495 [M+H]$^+$.

Example 52

4-({[6-Bromo-2-(4-bromo-2-thienyl)-3-methylquinolin-4-yl]carbonyl}amino)bicyclo[2.2.2]octane-1-carboxylic acid

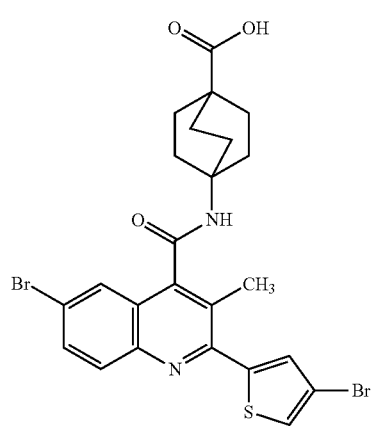 [SMILES: Cc1c(-c2cc(Br)cs2)nc2ccc(Br)cc2c1C(=O)NC12CCC(C(=O)O)(CC1)CC2]

1.8 ml (1.8 mmol) of 1 M aqueous sodium hydroxide solution were added to a solution of 180 mg (0.30 mmol) of the compound from Example 88A in a mixture of 9.7 ml of THF and 1.9 ml of methanol, and the mixture was allowed to stand at RT overnight. 0.16 ml (2.13 mmol) of TFA was then added, and the mixture was purified by preparative HPLC (Method 4). This gave 171 mg (95% of theory, purity 97%) of the title compound.

$^1$H-NMR (400 Mhz, DMSO-$d_6$): δ [ppm]=12.01 (br. s, 1H), 8.48 (s, 1H), 7.97-7.90 (m, 2H), 7.90-7.85 (m, 1H), 7.76 (dd, 2H), 2.60 (s, 3H), 2.09-1.96 (m, 6H), 1.92-1.76 (m, 6H).

LC/MS (Method 9, ESIpos): $R_t$=2.20 min, m/z=577/579/581 [M+H]$^+$.

Example 53

4-({[6-Bromo-3-methyl-2-(5-methyl-2-thienyl)qui-nolin-4-yl]carbonyl}amino)bicyclo[2.2.2]octane-1-carboxylic acid

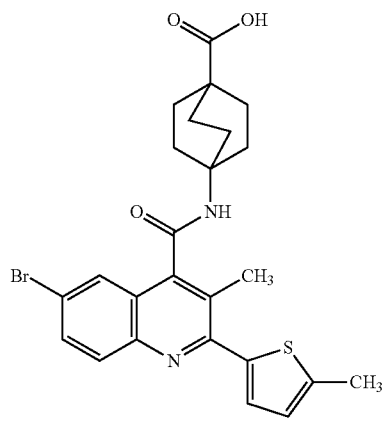 [SMILES: Cc1ccc(-c2nc3ccc(Br)cc3c(C(=O)NC34CCC(C(=O)O)(CC3)CC4)c2C)s1]

0.18 ml (0.18 mmol) of 1 M aqueous sodium hydroxide solution was added to a solution of 16 mg (0.031 mmol) of the compound from Example 90A in a mixture of 1.0 ml of THF and 0.2 ml of methanol, and the mixture was allowed to stand at RT overnight. 0.016 ml (0.21 mmol) of TFA was then added, and the mixture was purified by preparative HPLC (Method 3). This gave 1.5 mg (9% of theory, purity 98%) of the title compound.

$^1$H-NMR (400 Mhz, DMSO-$d_6$): δ [ppm]=12.10 (br. s, 1H), 8.46 (s, 1H), 7.87 (d, 1H), 7.84 (dd, 1H), 7.75 (d, 1H), 7.55 (d, 1H), 6.93 (dd, 1H), 2.57 (s, 3H), 2.09-1.93 (m, 6H), 1.91-1.76 (m, 6H).

LC/MS (Method 9, ESIpos): $R_t$=2.11 min, m/z=513/515 [M+H]$^+$.

Example 54

4-({[6-Bromo-2-(5-chloro-2-thienyl)-3-methylquino-lin-4-yl]carbonyl}amino)bicyclo[2.2.2]octane-1-carboxylic acid

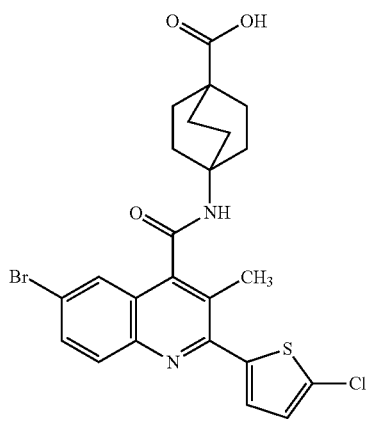 [SMILES: Cc1c(-c2ccc(Cl)s2)nc2ccc(Br)cc2c1C(=O)NC12CCC(C(=O)O)(CC1)CC2]

0.17 ml (0.17 mmol) of 1 M aqueous sodium hydroxide solution was added to a solution of 16 mg (0.028 mmol) of the compound from Example 92A in a mixture of 0.9 ml of THF and 0.2 ml of methanol, and the mixture was allowed to stand at RT overnight. 0.015 ml (0.20 mmol) of TFA was then added, and the mixture was purified by preparative HPLC (Method 3). This gave 6 mg (38% of theory, purity 92%) of the title compound.

$^1$H-NMR (400 Mhz, DMSO-$d_6$): δ [ppm]=12.09 (br. s, 1H), 8.47 (s, 1H), 7.94-7.83 (m, 2H), 7.77 (d, 1H), 7.65 (d, 1H), 7.24 (d, 1H), 2.59 (s, 3H), 2.08-1.96 (m, 6H), 1.91-1.79 (m, 6H).

LC/MS (Method 9, ESIpos): $R_t$=2.28 min, m/z=535 [M+H]$^+$.

Example 55

4-({[6-Bromo-2-(5-bromo-2-thienyl)-3-methylqui-nolin-4-yl]carbonyl}amino)bicyclo[2.2.2]octane-1-carboxylic acid

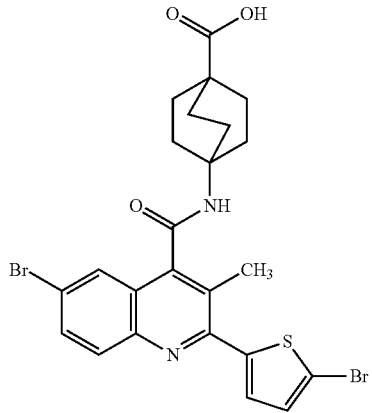 [SMILES: Cc1c(-c2ccc(Br)s2)nc2ccc(Br)cc2c1C(=O)NC12CCC(C(=O)O)(CC1)CC2]

0.14 ml (0.14 mmol) of 1 M aqueous sodium hydroxide solution was added to a solution of 14 mg (0.024 mmol) of the compound from Example 94A in a mixture of 0.8 ml of THF and 0.15 ml of methanol, and the mixture was allowed to stand at RT overnight. 0.013 ml (0.17 mmol) of TFA was then added, and the mixture was purified by preparative HPLC (Method 3). This gave 7 mg (42% of theory, purity 88%) of the title compound.

¹H-NMR (400 Mhz, DMSO-d₆): δ [ppm]=12.09 (s, 1H), 8.47 (s, 1H), 7.95-7.82 (m, 2H), 7.77 (d, 1H), 7.60 (d, 1H), 7.35 (d, 1H), 2.59 (s, 3H), 2.10-1.95 (m, 6H), 1.91-1.77 (m, 6H).

LC/MS (Method 9, ESIpos): R$_t$=2.30 min, m/z=577/579/581 [M+H]⁺.

Example 56

4-{[(6-Ethynyl-3-methyl-2-phenylquinolin-4-yl)carbonyl]amino}bicyclo[2.2.2]octane-1-carboxylic acid

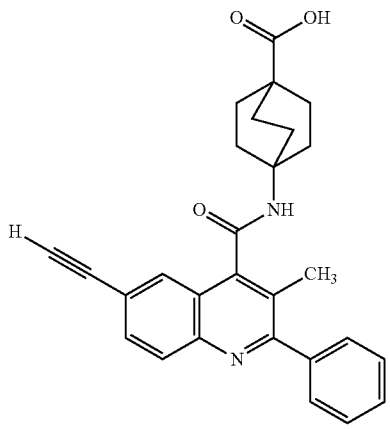 [SMILES: C#Cc1ccc2nc(-c3ccccc3)c(C)c(C(=O)NC34CCC(C(=O)O)(CC3)CC4)c2c1]

0.4 ml (0.4 mmol) of 1 M aqueous sodium hydroxide solution were added to a solution of 30 mg (0.066 mmol) of the compound from Example 98A in a mixture of 0.3 ml of THF and 0.14 ml of methanol, and the mixture was allowed to stand at RT overnight. 0.036 ml (0.46 mmol) of TFA was then added, and the mixture was purified by preparative HPLC (Method 4). This gave 20 mg (67% of theory, purity 98%) of the title compound.

¹H-NMR (400 Mhz, DMSO-d₆): δ [ppm]=12.09 (br. s, 1H), 8.45 (s, 1H), 8.00 (d, 1H), 7.82-7.70 (m, 2H), 7.61-7.45 (m, 5H), 4.42 (s, 1H), 2.32 (s, 3H), 2.09-1.95 (m, 6H), 1.91-1.78 (m, 6H).

LC/MS (Method 9, ESIpos): R$_t$=1.77 min, m/z=439 [M+H]⁺.

Example 57

4-{[(6-Bromo-3-methyl-2-phenylquinolin-4-yl)carbonyl]amino}-2-oxobicyclo[2.2.2]octane-1-carboxylic acid

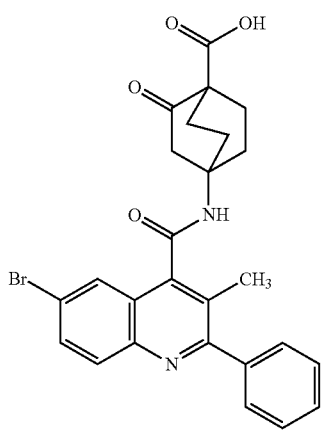 [SMILES: Cc1c(-c2ccccc2)nc2ccc(Br)cc2c1C(=O)NC12CCC(C(=O)O)(CC1)C(=O)C2]

0.35 ml (0.35 mmol) of 1 M aqueous sodium hydroxide solution was added to a solution of 31 mg (0.058 mmol) of the compound from Example 99A in a mixture of 1.5 ml of THF and 0.3 ml of methanol, and the mixture was allowed to stand at RT overnight. The mixture was then concentrated under reduced pressure and the residue obtained was adjusted to pH 3 using water and 0.031 ml (0.40 mmol) of TFA. The mixture was then concentrated once more. The residue was taken up in a mixture of DMSO, water and acetonitrile and purified by preparative HPLC (Method 3). This gave 28 mg (96% of theory, purity 100%) of the title compound.

¹H-NMR (500 Mhz, DMSO-d₆): δ [ppm]=12.58 (br. s, 1H), 8.83 (s, 1H), 7.99 (d, 1H), 7.89 (dd, 1H), 7.84 (d, 1H), 7.61-7.47 (m, 5H), 2.96 (br. s, 2H), 2.35 (s, 3H), 2.25-1.95 (m, 8H).

LC/MS (Method 9, ESIpos): R$_t$=1.75 min, m/z=507/509 [M+H]⁺.

Example 58

4-{[(6-Bromo-3-methyl-2-phenylquinolin-4-yl)carbonyl]amino}-2,2-difluorobicyclo[2.2.2]octane-1-carboxylic acid

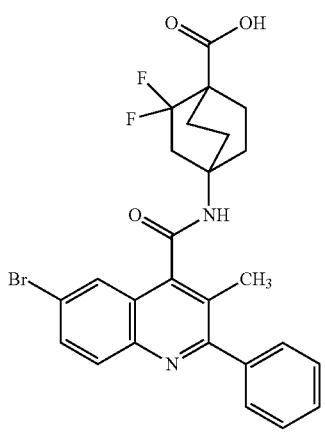 [SMILES: Cc1c(-c2ccccc2)nc2ccc(Br)cc2c1C(=O)NC12CCC(C(=O)O)(CC1)C(F)(F)C2]

0.73 ml (0.73 mmol) of 1 M aqueous sodium hydroxide solution were added to a solution of 68 mg (0.12 mmol) of the compound from Example 100A in a mixture of 3.9 ml of THF and 0.8 ml of methanol, and the mixture was allowed to stand at RT overnight. The mixture was then stirred at 60° C. for 18 h. After cooling to RT, 0.065 ml (0.85 mmol) of TFA were added, and the mixture was purified by preparative HPLC (Method 3). This gave 56 mg (88% of theory, purity 100%) of the title compound.

¹H-NMR (400 Mhz, DMSO-d₆): δ [ppm]=12.77 (br. s, 1H), 8.79 (s, 1H), 7.98 (d, 1H), 7.89 (dd, 1H), 7.82 (d, 1H), 7.62-7.45 (m, 5H), 2.78-2.56 (m, 2H), 2.34 (s, 3H), 2.17-2.02 (m, 4H), 1.93 (m, 4H).

LC/MS (Method 1, ESIpos): R$_t$=1.01 min, m/z=529/531 [M+H]⁺.

Example 59

4-{[(6-Bromo-3-methyl-2-phenylquinolin-4-yl)carbonyl]amino}-2-hydroxybicyclo[2.2.2]octane-1-carboxylic acid (racemate)

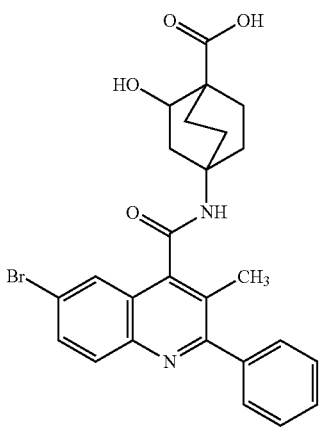 [SMILES: Cc1c(-c2ccccc2)nc2ccc(Br)cc2c1C(=O)NC12CCC(C(=O)O)(CC1)C(O)C2]

0.67 ml (0.67 mmol) of 1 M aqueous sodium hydroxide solution was added to a solution of 60 mg (0.11 mmol) of the compound from Example 101A in a mixture of 3.4 ml of THF and 0.7 ml of ethanol, and the mixture was allowed to stand at RT overnight. 0.060 ml (0.78 mmol) of TFA was then added, and the mixture was purified by preparative HPLC (Method 3). This gave 47 mg (83% of theory, purity 100%) of the title compound.

$^1$H-NMR (400 Mhz, DMSO-$d_6$): δ [ppm]=12.05 (br. s, 1H), 8.48 (s, 1H), 7.97 (d, 1H), 7.88 (dd, 1H), 7.83 (d, 1H), 7.65-7.44 (m, 5H), 4.14 (d, 1H), 2.49-2.38 (m, 1H, partially obscured), 2.33 (s, 3H), 2.23-1.54 (m, 10H).

LC/MS (Method 9, ESIpos): $R_t$=1.64 min, m/z=509/511 [M+H]$^+$.

Example 60

4-{[(6-Bromo-3-methyl-2-phenylquinolin-4-yl)carbonyl]amino}-2-fluorobicyclo[2.2.2]octane-1-carboxylic acid (racemate)

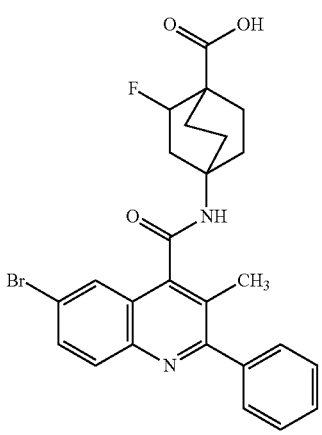 [SMILES: Cc1c(-c2ccccc2)nc2ccc(Br)cc2c1C(=O)NC12CCC(C(=O)O)(CC1)C(F)C2]

0.94 ml (0.94 mmol) of 1 M aqueous sodium hydroxide solution was added to a solution of 94 mg (0.16 mmol, purity 90%) of the compound from Example 102A in a mixture of 5.0 ml of THF and 1.0 ml of methanol, and the mixture was allowed to stand at RT for two days. 0.085 ml (1.10 mmol) of TFA was then added, and the mixture was purified by preparative HPLC (Method 3). This gave 80 mg (100% of theory, purity 100%, with solvent) of the title compound.

$^1$H-NMR (400 Mhz, DMSO-$d_6$): δ [ppm]=12.53 (br. s, 1H), 8.63 (s, 1H), 7.98 (d, 1H), 7.89 (dd, 1H), 7.83 (d, 1H), 7.64-7.41 (m, 5H), 5.21 (dd, 1H), 2.33 (s, 2H), 2.67-1.67 (m, 10H, partially obscured).

LC/MS (Method 9, ESIpos): $R_t$=1.87 min, m/z=511/513 [M+H]$^+$.

Example 61

(−)-4-{[(6-Bromo-3-methyl-2-phenylquinolin-4-yl)carbonyl]amino}-2-fluorobicyclo[2.2.2]octane-1-carboxylic acid (enantiomer 1)

0.3 ml (0.3 mmol) of 1 M aqueous sodium hydroxide solution was added to a solution of 27 mg (0.05 mmol) of the compound from Example 103A in a mixture of 1.6 ml of THF and 0.3 ml of methanol, and the mixture was allowed to stand at RT overnight. 0.027 ml (0.35 mmol) of TFA was then added, and the mixture was purified by preparative HPLC (Method 3). This gave 20 mg (79% of theory, purity 100%) of the title compound.

$[α]_D^{20}$=−13.5°, 589 nm, c=0.22 g/100 ml, DMSO $^1$H-NMR (400 Mhz, DMSO-$d_6$): δ [ppm]=12.66 (br. s, 1H), 8.63 (s, 1H), 7.98 (d, 1H), 7.89 (dd, 1H), 7.83 (d, 1H), 7.62-7.46 (m, 5H), 5.21 (dd, 1H), 2.70-2.55 (m, 1H), 2.33 (s, 3H), 2.28-1.68 (m, 9H).

LC/MS (Method 9, ESIpos): $R_t$=1.86 min, m/z=511/513 [M+H]$^+$.

Example 62

(+)-4-{[(6-Bromo-3-methyl-2-phenylquinolin-4-yl)carbonyl]amino}-2-fluorobicyclo[2.2.2]octane-1-carboxylic acid (enantiomer 2)

0.3 ml (0.3 mmol) of 1 M aqueous sodium hydroxide solution was added to a solution of 24 mg (0.04 mmol) of the compound from Example 104A in a mixture of 1.4 ml of THF and 0.3 ml of methanol, and the mixture was allowed to stand at RT overnight. 0.024 ml (0.31 mmol) of TFA was then added, and the mixture was purified by preparative HPLC (Method 3). This gave 11 mg (48% of theory, purity 100%) of the title compound.

$[α]_D^{20}$=+28.5°, 436 nm, c=0.22 g/100 ml, DMSO $^1$H-NMR (400 Mhz, DMSO-$d_6$): δ [ppm]=12.53 (br. s, 1H), 8.63 (s, 1H), 7.98 (d, 1H), 7.89 (dd, 1H), 7.83 (d, 1H), 7.66-7.41 (m, 5H), 5.21 (dd, 1H), 2.70-2.54 (m, 1H), 2.33 (s, 3H), 2.30-1.69 (m, 9H).

LC/MS (Method 9, ESIpos): $R_t$=1.86 min, m/z=511/513 [M+H]$^+$.

Example 63

4-{[(6-Bromo-3-methyl-2-phenylquinolin-4-yl)carbonyl]amino}-3,5-dioxobicyclo [2.2.2]octane-1-carboxylic acid

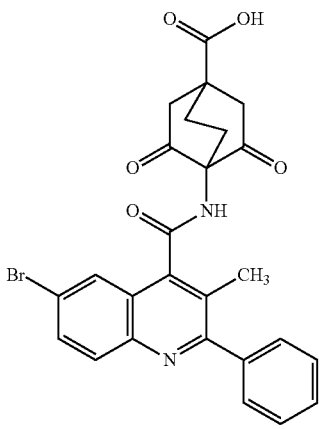 [SMILES: Cc1c(-c2ccccc2)nc2ccc(Br)cc2c1C(=O)NC12CCC(C(=O)O)(CC1=O)CC2=O]

At RT, 0.82 ml (10.70 mmol) of TFA was added to a solution of 62 mg (0.11 mmol) of the compound from Example 108A in 2.3 ml of dichloromethane, and the mixture was stirred for 2 h. The mixture was then concentrated and repeatedly dichloromethane was added and the mixture was concentrated again. The residue was purified by preparative HPLC (Method 3). This gave 36 mg (65% of theory, purity 100%) of the title compound.

$^1$H-NMR (400 Mhz, DMSO-$d_6$): δ [ppm]=12.95 (br. s, 1H), 9.03 (br. s, 1H), 8.73 (br. s, 1H), 7.97 (d, 1H), 7.89 (dd, 1H), 7.63-7.40 (m, 5H), 3.07-2.83 (m, 4H), 2.54-2.46 (m, obscured), 2.15 (br. s, 3H).

LC/MS (Method 9, ESIpos): $R_t$=1.71 min, m/z=521/523 [M+H]$^+$.

Example 64

4-{[(6-Iodo-3-methyl-2-phenylquinolin-4-yl)carbonyl]amino}-2-oxabicyclo [2.2.2]octane-1-carboxylic acid

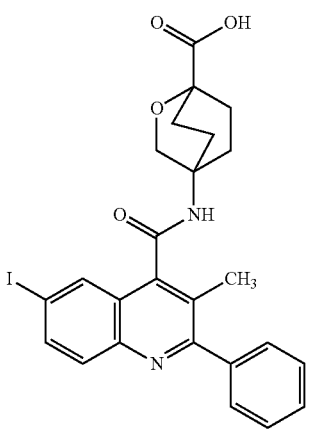 [SMILES: Cc1c(-c2ccccc2)nc2ccc(I)cc2c1C(=O)NC12CCC(C(=O)O)(CC1)OC2]

0.8 ml (0.8 mmol) of 1 M aqueous sodium hydroxide solution were added to a solution of 98 mg (0.14 mmol) of the compound from Example 112A in a mixture of 4.3 ml of THF and 0.9 ml of methanol, and the mixture was stirred at RT for 2 h. 2 ml of 10% strength aqueous citric acid solution were then added, and the mixture was allowed to stand at RT overnight. The mixture was then, without further work-up, pre-purified directly by preparative HPLC (Method 3). The pre-purified product was then purified once more by preparative HPLC (column: Kinetix C18, 5 μm, 100×30 mm; mobile phase: acetonitrile/water gradient]. This gave 37 mg (49% of theory, purity 98%) of the title compound.

$^1$H-NMR (400 Mhz, DMSO-$d_6$): δ [ppm]=12.57 (br. s, 1H), 8.63 (s, 1H), 8.08-7.96 (m, 2H), 7.81 (d, 1H), 7.61-7.44 (m, 5H), 4.12 (br. s, 2H), 2.32 (s, 3H), 2.29-1.95 (m, 8H).

LC/MS (Method 1, ESIpos): $R_t$=0.93 min, m/z=543 [M+H]$^+$.

Example 65

(3-exo,8-anti)-8-{[(6-Bromo-3-methyl-2-phenylquinolin-4-yl)carbonyl]amino}bicyclo[3.2.1]octane-3-carboxylic acid

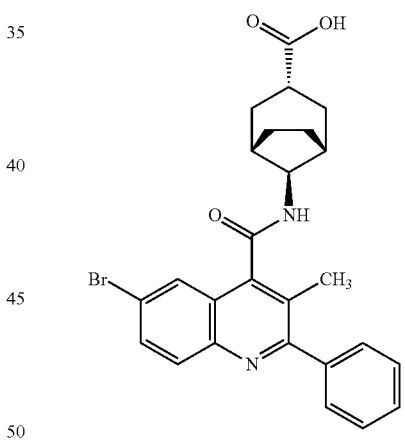

4.0 ml (4.0 mmol) of 1 M aqueous sodium hydroxide solution were added to a solution of 350 mg (0.67 mmol) of the compound from Example 114A in a mixture of 11.3 ml of THF and 2.3 ml of methanol, and the mixture was stirred at RT overnight. Subsequently, the mixture was acidified with 1 M hydrochloric acid and, without further work-up, purified directly by preparative HPLC (Method 4). This gave 289 mg (86% of theory, purity 98%) of the title compound.

$^1$H-NMR (500 Mhz, DMSO-$d_6$): δ [ppm]=11.00 (br. s, 1H), 8.61 (d, 1H), 7.99 (d, 1H), 7.93-7.81 (m, 2H), 7.67-7.40 (m, 5H), 3.91 (d, 1H), 2.56-2.46 (m, 1H, partially obscured), 2.40-2.35 (m, 2H, partially obscured), 2.33 (s, 3H), 1.97-1.44 (m, 8H).

LC/MS (Method 9, ESIpos): $R_t$=1.79 min, m/z=493/495 [M+H]$^+$.

Example 66

4-{[(6-Bromo-3-cyano-2-phenylquinolin-4-yl)carbonyl]amino}bicyclo[2.2.2]octane-1-carboxylic acid

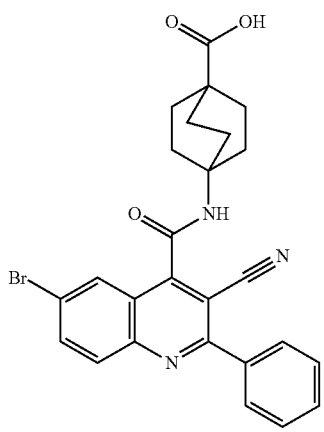 [SMILES: N#Cc1c(-c2ccccc2)nc2ccc(Br)cc2c1C(=O)NC12CCC(C(=O)O)(CC1)CC2]

At RT, 0.4 ml (0.4 mmol) of 1 M aqueous sodium hydroxide solution were added to a solution of 38 mg (0.073 mmol) of the compound from Example 116A in 1.0 ml of THF/methanol (5:1), and the mixture was stirred at RT for 50 min. Subsequently, the mixture was purified directly (without further work-up) by preparative HPLC (Method 2). This gave 4 mg (9% of theory, purity 90%) of the title compound.

$^1$H-NMR (500 Mhz, DMSO-$d_6$): δ [ppm]=12.11 (br. s, 1H), 8.82 (s, 1H), 8.22-8.08 (m, 2H), 7.99 (d, 1H), 7.94-7.89 (m, 2H), 7.64-7.60 (m, 3H), 2.09-2.00 (m, 6H), 1.89-1.82 (m, 6H).

LC/MS (Method 9, ESIpos): $R_t$=1.95 min, m/z=504/506 [M+H]$^+$.

Example 67

4-{[(6-Bromo-2-phenyl-3-vinylquinolin-4-yl)carbonyl]amino}bicyclo[2.2.2]octane-1-carboxylic acid

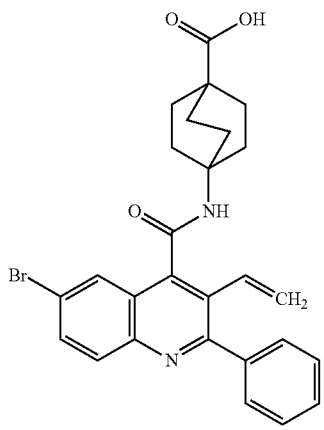 [SMILES: C=Cc1c(-c2ccccc2)nc2ccc(Br)cc2c1C(=O)NC12CCC(C(=O)O)(CC1)CC2]

0.35 ml (0.35 mmol) of 1 M aqueous sodium hydroxide solution were added to a solution of 30 mg (0.058 mmol) of the compound from Example 119A in a mixture of 0.25 ml of THF and 1.3 ml of methanol, and the mixture was allowed to stand at RT overnight. 0.031 ml (0.40 mmol) of TFA was then added, and the mixture was purified by preparative HPLC (Method 4). This gave 4 mg (13% of theory, purity 95%) of the title compound.

$^1$H-NMR (500 Mhz, DMSO-$d_6$): δ [ppm]=12.09 (br. s, 1H), 8.38 (s, 1H), 8.00 (d, 1H), 7.94-7.90 (m, 2H), 7.63-7.57 (m, 2H), 7.56-7.47 (m, 3H), 6.57 (dd, 1H), 5.66 (dd, 1H), 5.49 (dd, 1H), 2.01-1.93 (m, 6H), 1.89-1.76 (m, 6H).

LC/MS (Method 9, ESIpos): $R_t$=1.97 min, m/z=505/507 [M+H]$^+$.

B. Assessment of Pharmacological Efficacy

The pharmacological activity of the compounds of the invention can be demonstrated by in vitro and in vivo studies as known to the person skilled in the art. The application examples which follow describe the biological action of the compounds of the invention, without restricting the invention to these examples.

Abbreviations and Acronyms:
CRTH2 chemoattractant receptor-homologous molecule expressed on T helper type 2 cells
DMEM Dulbecco's modified Eagle's medium
DMSO dimethyl sulfoxide
DP PGD2 receptor
$EC_{50}$ half-maximum effective concentration
Em emission
EP PGE2 receptor
Ex excitation
from Company (source)
FCS fetal calf serum
FP PGF2α receptor
HEPES 2-[4-(2-hydroxyethyl)piperazin-1-yl]ethanesulfonic acid
$IC_{50}$ half-maximum inhibitory concentration
IP PGI2 receptor
MES 2-(N-morpholino)ethanesulfonic acid
Pen/Strep penicillin/streptomycin
PGD2 prostaglandin D2
PGE2 prostaglandin E2
PGF2α prostaglandin F2α
PGI2 prostaglandin I2
TC tissue culture
TP thromboxane A2 receptor
Tris tris(hydroxymethyl)aminomethane
v/v volume to volume ratio (of a solution)
w/w weight to weight ratio (of a solution)

B-1. In Vitro Test of Inhibition of Human FP Receptor Activity

For the characterization of test substances in respect of FP antagonism, PGF2α-induced calcium flux in FP-expressing CHEM1 cells (Millipore, HTS093C) was used.

3000 cells in 25 µl of full medium [DMEM F12, 10% FCS, 1.35 mM sodium pyruvate, 20 mM HEPES, 4 mM GlutaMAX™, 2% sodium bicarbonate, 1% Pen/Strep, 1% 100× non-essential amino acids] are sown per well of a 384 multititer plate (from Greiner, TC plate, black with clear base) and incubated at 37° C./5% $CO_2$ for 24 hours. Prior to the measurement, the medium is replaced by 30 µl of Fluo-8 AM loading buffer [calcium-free Tyrode (130 mM NaCl, 5 mM KCl, 20 mM HEPES, 1 mM $MgCl_2$, 4.8 mM $NaHCO_3$, pH 7.4), 2 mM $CaCl_2$, 1× SmartBlock (from CANDOR Bioscience GmbH), 4.5 mM Probenecid, 5 µM Fluo-8 AM, 0.016% Pluronic®, 0.04% Brilliant black] and incubated at 37° C./5% $CO_2$ for 30 minutes. The test substance is prepared in DMSO in various concentrations as a dose-response curve (starting concentration 10 mM, dilution factor 3.16) and prediluted 1:50 with calcium-free Tyrode/2 mM $CaCl_2$. 10 µl of the prediluted substance solution are added to the Fluo-8-laden cells and incubated at 37° C./5% $CO_2$ for 10 minutes. The FP receptor is activated by adding 20 µl of 3 nM (final concentration) PGF2α in calcium-free Tyrode/2 mM $CaCl_2$/0.04% Brilliant black, and the calcium flux is determined by measuring the fluorescence at ex. 470 nm/em. 525 nm in a fluorescence measuring instrument (FLIPR Tetra®, Molecular Devices) for 120 seconds.

Table 1 below lists the $IC_{50}$ values from this assay for individual working examples of the invention (some as mean values from multiple independent individual determinations):

TABLE 1

| Example No. | FP receptor activity $IC_{50}$ [µmol/l] |
|---|---|
| 1 | 0.074 |
| 2 | 0.259 |
| 3 | 0.142 |
| 4 | 0.456 |
| 5 | 0.113 |
| 6 | 0.240 |
| 7 | 0.181 |
| 8 | 0.180 |
| 9 | 0.386 |
| 10 | 0.128 |
| 11 | 0.129 |
| 12 | 0.139 |
| 13 | 0.153 |
| 14 | 0.033 |
| 15 | 0.326 |
| 16 | 0.589 |
| 17 | 0.214 |
| 18 | 0.543 |
| 19 | 0.917 |
| 20 | 0.521 |
| 21 | 0.214 |
| 22 | 0.677 |
| 23 | 0.306 |
| 24 | 0.129 |
| 25 | 0.494 |
| 26 | 0.114 |
| 27 | 0.074 |
| 28 | 0.220 |
| 29 | 0.051 |
| 30 | 0.052 |
| 31 | 0.351 |
| 32 | 0.022 |
| 33 | 0.051 |
| 34 | 0.505 |
| 35 | 0.430 |
| 36 | 0.553 |
| 37 | 0.723 |
| 38 | 1.280 |
| 39 | 0.230 |
| 40 | 0.195 |
| 41 | 0.048 |
| 42 | 0.033 |
| 43 | 0.198 |
| 44 | 0.073 |
| 45 | 0.161 |
| 46 | 0.068 |
| 47 | 0.068 |
| 48 | 0.093 |
| 49 | 0.091 |
| 50 | 0.066 |
| 51 | 0.093 |
| 52 | 0.058 |
| 53 | 0.235 |
| 54 | 0.240 |
| 55 | 0.383 |
| 56 | 0.148 |
| 57 | 0.637 |
| 58 | 0.668 |
| 59 | 0.435 |
| 60 | 0.197 |
| 61 | 0.083 |
| 62 | 0.193 |
| 63 | 0.082 |
| 64 | 0.762 |
| 65 | 0.824 |
| 66 | 0.762 |
| 67 | 0.440 |

B-2. In Vitro FP Receptor Binding Inhibition Test

For the FP receptor binding test, human recombinant prostanoid FP receptors, expressed in HEK293 cells, in modified MES buffer, pH 6.0, are used. This test is conducted commercially (at Eurofins Panlabs, catalog #268510). 80 µg of membrane are incubated with 1 nM [$^3$H]-PGF2α at 25° C. for 60 minutes. The amount of membrane protein can vary from batch to batch and is adjusted if required. Unspecific binding is determined in the presence of 1 µM cloprostenol. The membranes are filtered, washed and then analyzed in order to determine the specific binding of [$^3$H]-PGF2α. Substances are tested for inhibitory activity at a concentration of 10 µM or in the form of a dose-response curve [lit.: Abramovitz et al., *J. Biol. Chem.* 1994, 269 (4): 2632].

B-3. In Vitro CRTH2 Receptor Binding Inhibition Test

For this test, human recombinant prostanoid CRTH2 receptors, expressed in CHO-K1 cells, in modified Tris-HCl buffer, pH 7.4, are used. This test is conducted commercially (at Eurofins Panlabs, catalog #268030). 4 µg of membrane are incubated with 1 nM [$^3$H]-PGD2 at 25° C. for 120 minutes. The amount of membrane protein can vary from batch to batch and is adjusted if required. Unspecific binding is determined in the presence of 1 µM PGD2. The membranes are filtered, washed and then analyzed in order to determine the specific binding of [$^3$H]-PGD2. Substances are tested for inhibitory activity at a concentration of 10 µM or in the form of a dose-response curve [lit.: Sugimoto et al., *J. Pharmacol. Exp. Ther.* 2003, 305 (1): 347].

B-4. In Vitro DP Receptor Binding Inhibition Test

For this test, human recombinant prostanoid DP receptors, expressed in Chem-1 cells, in modified HEPES buffer, pH 7.4, are used. This test is conducted commercially (at Eurofins Panlabs, catalog #268060). 10 µg of membrane are incubated with 2 nM [$^3$H]-PGD2 at 25° C. for 120 minutes. The amount of membrane protein can vary from batch to batch and is adjusted if required. Unspecific binding is determined in the presence of 1 µM PGD2. The membranes are filtered, washed and then analyzed in order to determine the specific binding of [$^3$H]-PGD2. Substances are tested for inhibitory activity at a concentration of 10 µM or in the form of a dose-response curve [lit.: Wright et al., *Br. J. Pharmacol.* 1998, 123 (7): 1317; Sharif et al., *Br. J. Pharmacol.* 2000, 131 (6): 1025].

B-5. In Vitro EP1 Receptor Binding Inhibition Test

For this test, human recombinant prostanoid EP1 receptors, expressed in HEK293 cells, in modified MES buffer, pH 6.0, are used. This test is conducted commercially (at Eurofins Panlabs, catalog #268110). 14 µg of membrane are incubated with 1 nM [$^3$H]-PGE2 at 25° C. for 60 minutes. The amount of membrane protein can vary from batch to batch and is adjusted if required. Unspecific binding is determined in the presence of 10 µM PGE2. The membranes are filtered, washed and then analyzed in order to determine the specific binding of [$^3$H]-PGE2. Substances are tested for inhibitory activity at a concentration of 10 μM or in the form of a dose-response curve [lit.: Abramovitz et al., *Biochim. Biophys. Acta* 2000, 1483 (2): 285; Funk et al., *J. Biol. Chem.* 1993, 268 (35): 26767].

B-6. In Vitro EP2 Receptor Binding Inhibition Test

For this test, human recombinant prostanoid EP2 receptors, expressed in HEK293 cells, in modified MES/KOH buffer, pH 6.0, are used. This test is conducted commercially (at Eurofins Panlabs, catalog #268200). 25 mg/ml of membrane are incubated with 4 nM [$^3$H]-PGE2 at 25° C. for 120 minutes. The amount of membrane protein can vary from batch to batch and is adjusted if required. Unspecific binding is determined in the presence of 10 μM PGE2. The membranes are filtered, washed and then analyzed in order to determine the specific binding of [$^3$H]-PGE2. Substances are tested for inhibitory activity at a concentration of 10 μM or in the form of a dose-response curve [lit.: Bastien et al., *J. Biol. Chem.* 1994, 269 (16): 11873; Boie et al., *Eur. J. Pharmacol.* 1997, 340 (2-3): 227].

B-7. In Vitro EP3 Receptor Binding Inhibition Test

For this test, human recombinant prostanoid EP3 receptors, expressed in HEK293 cells, in modified MES buffer, pH 6.0, are used. This test is conducted commercially (at Eurofins Panlabs, catalog #268310). 3 μg of membrane are incubated with 0.5 nM [$^3$H]-PGE2 at 25° C. for 120 minutes. The amount of membrane protein can vary from batch to batch and is adjusted if required. Unspecific binding is determined in the presence of 10 μM PGE2. The membranes are filtered, washed and then analyzed in order to determine the specific binding of [$^3$H]-PGE2. Substances are tested for inhibitory activity at a concentration of 10 μM or in the form of a dose-response curve [lit.: Schmidt et al., *Eur. J. Biochem.* 1995, 228 (1): 23].

B-8. In Vitro EP4 Receptor Binding Inhibition Test

For this test, human recombinant prostanoid EP4 receptors, expressed in Chem-1 cells, in modified MES buffer, pH 6.0, are used. This test is conducted commercially (at Eurofins Panlabs, catalog #268420). 3 μg of membrane are incubated with 1 nM [$^3$H]-PGE2 at 25° C. for 120 minutes. The amount of membrane protein can vary from batch to batch and is adjusted if required. Unspecific binding is determined in the presence of 10 μM PGE2. The membranes are filtered, washed and then analyzed in order to determine the specific binding of [$^3$H]-PGE2. Substances are tested for inhibitory activity at a concentration of 10 μM or in the form of a dose-response curve [lit.: Davis et al., *Br. J. Pharmacol.* 2000, 130 (8): 1919].

B-9. In Vitro IP Receptor Binding Inhibition Test

For this test, human recombinant prostanoid IP receptors, expressed in HEK293 cells, in modified HEPES buffer, pH 6.0, are used. This test is conducted commercially (at Eurofins Panlabs, catalog #268600). 15 μg of membrane are incubated with 5 nM [$^3$H]-iloprost at 25° C. for 60 minutes. The amount of membrane protein can vary from batch to batch and is adjusted if required. Unspecific binding is determined in the presence of 10 μM iloprost. The membranes are filtered, washed and then analyzed in order to determine the specific binding of [$^3$H]-iloprost. Substances are tested for inhibitory activity at a concentration of 10 μM or in the form of a dose-response curve [lit.: Armstrong et al., *Br. J. Pharmacol.* 1989, 97 (3): 657; Boie et al., *J. Biol. Chem.* 1994, 269 (16): 12173].

B-10. In Vitro TP Receptor Binding Inhibition Test

For this test, human recombinant prostanoid TP receptors, expressed in HEK-293 EBNA cells, in modified Tris/HCl buffer, pH 7.4, are used. This test is conducted commercially (at Eurofins Panlabs, catalog #285510). 18.4 μg of membrane are incubated with 5 nM [$^3$H]-SQ-29 548 at 25° C. for 30 minutes. The amount of membrane protein can vary from batch to batch and is adjusted if required. Unspecific binding is determined in the presence of 1 μM SQ-29 548. The membranes are filtered, washed and then analyzed in order to determine the specific binding of [$^3$H]-SQ-29 548. Substances are tested for inhibitory activity at a concentration of 10 μM or in the form of a dose-response curve [lit.: Saussy Jr. et al., *J. Biol. Chem.* 1986, 261: 3025; Hedberg et al., *J. Pharmacol. Exp. Ther.* 1988, 245: 786].

B-11. In Vitro Test for DP Agonism and Antagonism

For the characterization of test substances in respect of DP agonism and antagonism, PGD2-induced calcium flux in DP-expressing CHEM1 cells (Millipore, HTS091C) was used: 3000 cells in 25 μl of full medium [DMEM, 4.5 g/l glucose, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 μl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of DP agonism, in a fluorescence measuring instrument (FLIPR Tetra®, Molecular Devices), 10 μl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of DP antagonism, the DP receptor is activated in the FLIPR Tetra® by adding 20 μl of ~76 nM (2×$EC_{50}$, final concentration) PGD2 in, for example, calcium-free Tyrode/2 mM $CaCl_2$, and the calcium flux is determined by measuring the fluorescence at ex. 470 nm/em. 525 nm for 120 seconds [lit.: T. Matsuoka et al. (2000) *Science* 287: 2013-2017; S. Narumiya and G. A. Fitzgerald (2001) *J. Clin. Invest.* 108: 25-30].

B-12. In Vitro Test for EP1 Agonism and Antagonism

For the characterization of test substances in respect of EP1 agonism and antagonism, PGE2-induced calcium flux in EP1-expressing CHEM1 cells (Millipore, HTS099C) was used: 3000 cells in 25 μl of full medium [DMEM, 4.5 g/l glucose, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 μl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP1 agonism, in a fluorescence measuring instrument (FLIPR Tetra®, Molecular Devices), 10 μl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP1 antagonism, the EP1 receptor is activated in the FLIPR Tetra® by adding 20 µl of ~6 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: Y. Matsuoka et al. (2005) *Proc. Natl. Acad. Sci. USA* 102: 16066-16071; S. Narumiya and G. A. Fitzgerald (2001) *J. Clin. Invest.* 108: 25-30; K. Watanabe et al. (1999) *Cancer Res.* 59: 5093-5096].

B-13. In Vitro Test for EP2 Agonism and Antagonism

For the characterization of test substances in respect of EP2 agonism and antagonism, PGE2-induced calcium flux in EP2-expressing CHEM9 cells (Millipore, HTS185C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP2 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP2 antagonism, the EP2 receptor is activated in the FLIPR Tetra® by adding 20 µl of ~22 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: C. R. Kennedy et al. (1999) *Nat. Med.* 5: 217-220; S. Narumiya and G. A. Fitzgerald (2001) *J. Clin. Invest.* 108: 25-30; N. Yang et al. (2003) *J. Clin. Invest.* 111: 727-735].

B-14. In Vitro Test for EP3 Agonism and Antagonism

For the characterization of test substances in respect of EP3 agonism and antagonism, PGE2-induced calcium flux in EP3 (splice variant 6)-expressing CHEM1 cells (Millipore, HTS092C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP3 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP3 antagonism, the EP3 receptor is activated in the FLIPR Tetra® by adding 20 µl of ~2 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: M. Kotani et al. (1995) *Mol. Pharmacol.* 48: 869-879; M. Kotani et al. (1997) *Genomics* 40: 425-434; T. Kunikata et al. (2005) *Nat. Immunol.* 6: 524-531; S. Narumiya and G. A. Fitzgerald (2001) *J. Clin. Invest.* 108: 25-30; F. Ushikubi et al. (1998) *Nature* 395: 281-284].

B-15. In Vitro Test for EP4 Agonism and Antagonism

For the characterization of test substances in respect of EP4 agonism and antagonism, PGE2-induced calcium flux in EP4-expressing CHEM1 cells (Millipore, HTS142C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP4 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP4 antagonism, the EP4 receptor is activated in the FLIPR Tetra® by adding 20 µl of ~26 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: S. Narumiya and G. A. Fitzgerald (2001) *J. Clin. Invest.* 108: 25-30; M. Nguyen et al. (1997) *Nature* 390: 78-81; K. Yoshida et al. (2002) *Proc. Natl. Acad. Sci. USA* 99: 4580-4585].

B-16. In Vitro Test for IP Agonism and Antagonism

For the characterization of test substances in respect of IP agonism and antagonism, iloprost-induced calcium flux in IP-expressing CHEM1 cells (Millipore, HTS131C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of IP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of IP antagonism, the IP receptor is activated in the FLIPR Tetra® by adding 20 µl of ~106 nM ($2 \times EC_{50}$, final concentration) iloprost in, for example, calcium-free Tyrode/2 mM $CaCl_2$, and the calcium flux is determined by measuring the fluorescence at ex. 470 nm/em. 525 nm for 120 seconds [lit.: S. Narumiya et al. (1999) *Physiol. Rev.* 79: 1193-1226; T. Murata et al. (1997) *Nature* 388: 678-682; Y. Cheng et al. (2002) *Science* 296: 539-541; C. H. Xiao et al. (2001) *Circulation* 104: 2210-2215; G. A. Fitzgerald (2004) *N. Engl. J. Med.* 351: 1709-1711].

B-17. In Vitro Test for TP Agonism and Antagonism

For the characterization of test substances in respect of TP agonism and antagonism, U46619-induced calcium flux in TP-expressing CHEM1 cells (Millipore, HTS081C) was used: 3000 cells in 25 µl of plating medium [DMEM, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of TP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of TP antagonism, the TP receptor is activated in the FLIPR Tetra® by adding 20 µl of ~88 nM ($2 \times EC_{50}$, final concentration) U46619 in, for example, calcium-free Tyrode/2 mM $CaCl_2$, and the calcium flux is determined by measuring the fluorescence at ex. 470 nm/em. 525 nm for 120 seconds [lit.: S. Ali et al. (1993) *J. Biol. Chem.* 268: 17397-17403; K. Hanasaki et al. (1989) *Biochem. Pharmacol.* 38: 2967-2976; M. Hirata et al. (1991) *Nature* 349: 617-620].

B-18. Animal Model of Bleomycin-induced Pulmonary Fibrosis

Bleomycin-induced pulmonary fibrosis in the mouse or rat is a widely used animal model of pulmonary fibrosis. Bleomycin is a glycopeptide antibiotic employed in oncology for the therapy of testicular tumors and Hodgkin- and Non-Hodgkin tumors. It is eliminated renally, has a half-life of about 3 hours and, as cytostatic, influences various phases of the division cycle [Lazo et al., Cancer Chemother. Biol. Response Modif., 15, 44-50 (1994)]. Its anti-neoplastic effect is based on an oxidatively damaging action on DNA [Hay et al., Arch. 65, 81-94 (1991)]. Lung tissue is at a particular risk when exposed to bleomycin since it contains only a small number of cysteine hydrolases which, in other tissues, lead to inactivation of bleomycin. Following administration of bleomycin, the animals suffer an acute respiratory distress syndrome (ARDS) with subsequent development of pulmonary fibrosis.

Administration of bleomycin may be by single or repeat intratracheal, inhalative, intravenous or intraperitoneal administration. Treatment of the animals with the test substance (by gavage, by addition to the feed or drinking water, using an osmotic minipump, by subcutaneous or intraperitoneal injection or by inhalation) starts at the day of the first bleomycin administration or therapeutically 3-14 days later and extends over a period of 2-6 weeks. At the end of the study, a bronchio-alveolar lavage to determine the cell content and the pro-inflammatory and pro-fibrotic markers and measurements of lung function and a histological assessment of pulmonary fibrosis are carried out.

B-19. Animal Model of DQ12 Quartz-induced Pulmonary Fibrosis

DQ12 quartz-induced pulmonary fibrosis in the mouse or rat is a widely used animal model of pulmonary fibrosis [Shimbori et al., *Exp. Lung Res.* 36, 292-301 (2010)]. DQ12 quartz is quartz which is highly active owing to breaking or grinding. In mice and rats, intratracheal or inhalative administration of DQ12 quartz leads to alveolar proteinosis followed by interstitial pulmonary fibrosis. The animals receive a single or repeat intratracheal or inhalative instillation of DQ12 quartz. Treatment of the animals with the test substance (by gavage, by addition to the feed or drinking water, using an osmotic minipump, by subcutaneous or intraperitoneal injection or by inhalation) starts at the day of the first silicate instillation or therapeutically 3-14 days later and extends over a period of 3-12 weeks. At the end of the study, a bronchio-alveolar lavage to determine the cell content and the pro-inflammatory and pro-fibrotic markers and measurements of lung function and a histological assessment of pulmonary fibrosis are carried out.

B-20. Animal Model of DQ12 Quartz or FITC-induced Pulmonary Inflammation

In the mouse and the rat, intratracheal administration of DQ12 quartz or fluorescein isothiocyanate (FITC) leads to an inflammation in the lung [Shimbori et al., *Exp. Lung Res.* 36, 292-301 (2010)]. At the day of the instillation of DQ12 quartz or FITC or a day later the animals are treated with the test substance for a duration of 24 h up to 7 days (by gavage, by addition to the feed or drinking water, using an osmotic minipump, by subcutaneous or intraperitoneal injection or by inhalation). At the end of the experiment, a bronchio-alveolar lavage to determine the cell content and the pro-inflammatory and pro-fibrotic markers is carried out.

C. Working Examples of Pharmaceutical Compositions

The compounds of the invention can be converted to pharmaceutical preparations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h until the swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

i.v. Solution:

The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:

1. A compound of the formula (I)

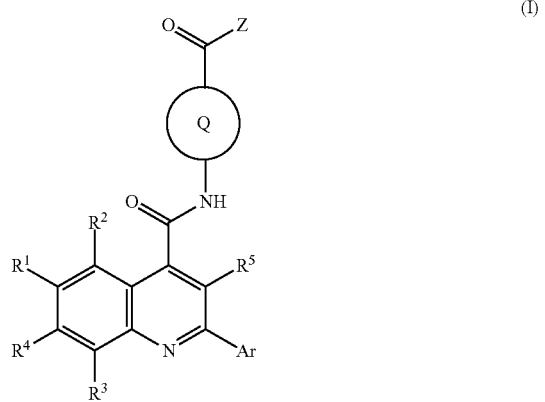

in which the ring Q represents a group of the formula

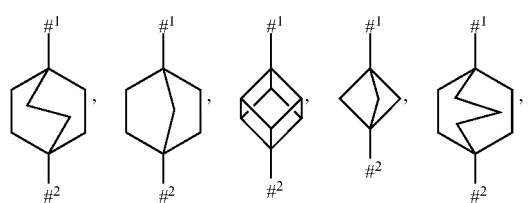

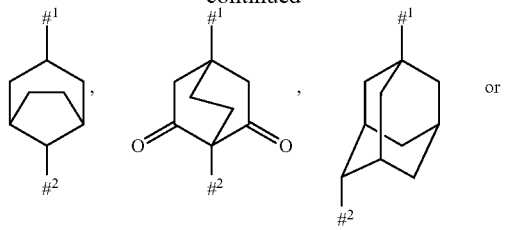

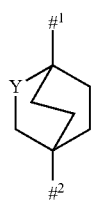

where $\#^1$ represents the point of attachment to the carbonyl group, $\#^2$ represents the point of attachment to the nitrogen atom, Y represents a group of the formula —O—, —CF$_2$—, —C(H)(OH)—, —CHF— or —C(=O)—

Z represents —OH or represents a group of the formula —NH—R$^6$ or —NH—SO$_2$—R$^7$ in which R$^6$ represents hydrogen, methyl or ethyl which is up to trisubstituted by fluorine, and R$^7$ represents (C$_1$-C$_2$)-alkyl which is up to trisubstituted by fluorine, R$^1$ represents halogen, (C$_1$-C$_4$)-alkyl which is up to pentasubstituted by fluorine, methoxy which is up to trisubstituted by fluorine, (trifluoromethyl)sulfanyl, pentafluorosulfanyl, trimethylsilyl, ethynyl, cyclopropyl or cyclobutyl, where cyclopropyl and cyclobutyl may be up to tetrasubstituted by fluorine, R$^2$, R$^3$ and R$^4$ independently of one another represent hydrogen, halogen or methyl which is up to trisubstituted by fluorine, R$^5$ represents halogen, (C$_1$-C$_4$)-alkyl which is up to pentasubstituted by fluorine, methoxy which is up to trisubstituted by fluorine, represents hydroxy, methylsulfanyl, cyano, ethenyl, cyclopropyl or cyclobutyl, where cyclopropyl and cyclobutyl may be up to tetrasubstituted by fluorine, and Ar represents phenyl which may be up to trisubstituted by identical or different substituents from the group consisting of fluorine, chlorine, methyl, which is up to trisubstituted by fluorine, and methoxy, which is up to trisubstituted by fluorine, or represents thienyl which may be mono- or disubstituted by methyl or monosubstituted by chlorine or bromine, or represents thiazolyl or pyridyl, and the N-oxides, salts, solvates, salts of the N-oxides and solvates of the N-oxides and salts thereof.

2. The compound of the formula (I) as claimed in claim 1 in which the ring Q represents a group of the formula

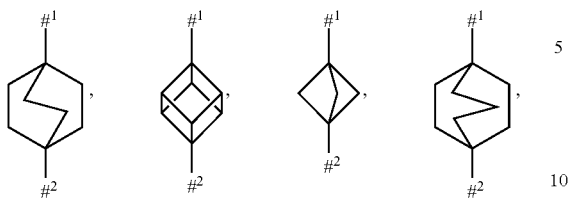

or

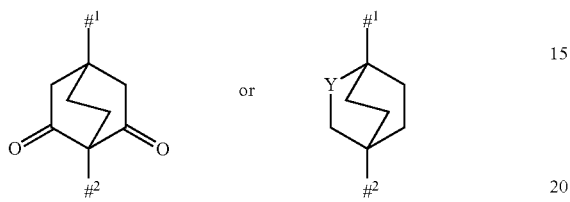

where

¹ represents the point of attachment to the carbonyl group,

² represents the point of attachment to the nitrogen atom,

Y represents a group of the formula —C(H)(OH)— or —CHF—

Z represents —OH, $R^1$ represents chlorine, bromine, iodine, methyl, isopropyl, tert-butyl, difluoromethyl, trifluoronnethyl, trifluoronnethoxy, (trifluoromethyl)sulfanyl, trimethylsilyl, ethynyl, cyclopropyl or cyclobutyl, $R^2$ represents hydrogen, $R^3$ and $R^4$ independently of one another represent hydrogen, chlorine or methyl, $R^5$ represents fluorine, chlorine, bromine, iodine, methyl, ethyl, propyl, monofluoromethyl, difluoromethyl, trifluoromethyl, methoxy, trifluoromethoxy, hydroxy, methylsulfanyl or cyclopropyl, and Ar represents phenyl which may be mono- or disubstituted by fluorine, represents thienyl which may be mono- or disubstituted by methyl or monosubstituted by chlorine or bromine or represents a group of the formula

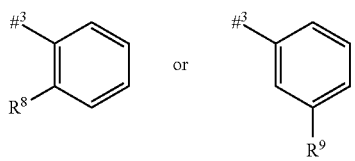

where

³ represents the point of attachment to the quinoline ring, $R^8$ represents chlorine or methyl, and $R^9$ represents chlorine or methoxy, and the salts, solvates and solvates of the salts thereof.

3. The compound of the formula (I) as claimed in claim 1, in which the ring Q represents a group of the formula

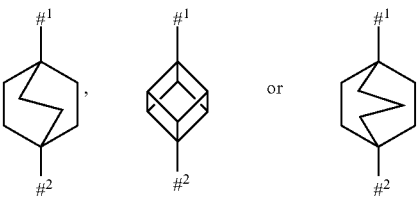

Z represents a group of the formula —OH, $R^1$ represents chlorine, bromine, iodine, methyl, tert-butyl, difluoromnethyl, trifluoromethyl, trimethylsilyl, ethynyl or cyclopropyl, $R^2$ represents hydrogen, $R^3$ and $R^4$ independently of one another represent hydrogen, chlorine or methyl, where at least one of the radicals $R^3$ and $R^4$ represents hydrogen, $R^5$ represents fluorine, chlorine, methyl, ethyl, methoxy, hydroxy, methylsulfanyl or cyclopropyl, and Ar represents phenyl which may be monosubstituted by fluorine, and the salts, solvates and solvates of the salts thereof.

4. The compound of the formula (I) as claimed in claim 1 in which the ring Q represents a group of the formula

Z represents a group of the formula —OH, $R^1$ represents ethynyl, bromine or iodine, $R^2$, $R^3$ and $R^4$ each represent hydrogen, $R^5$ represents chlorine, methyl, methylsulfanyl or cyclopropyl, and Ar represents phenyl, and the salts, solvates and solvates of the salts thereof.

5. A process for preparing a compound as defined in claim 1, wherein a compound of the formula (II)

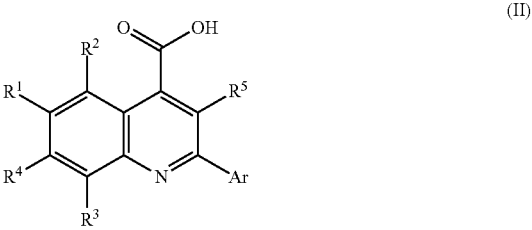

is coupled with an amine compound of the formula (III)

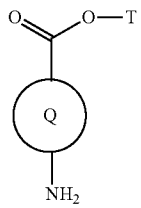

(III)

and
T represents an ester protective group,
to give a compound of the formula (IV)

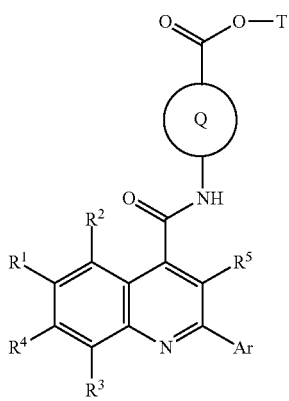

(IV)

and then the ester radical T is eliminated to give the carboxylic acid of the formula (I-A)

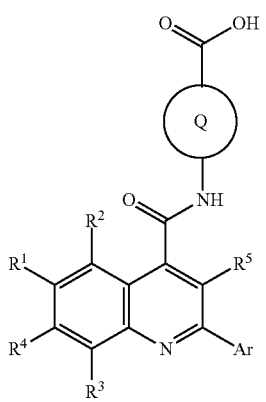

(I-A)

and the carboxylic acid (I-A) is optionally converted in a further step into the corresponding acid chloride of the formula (V)

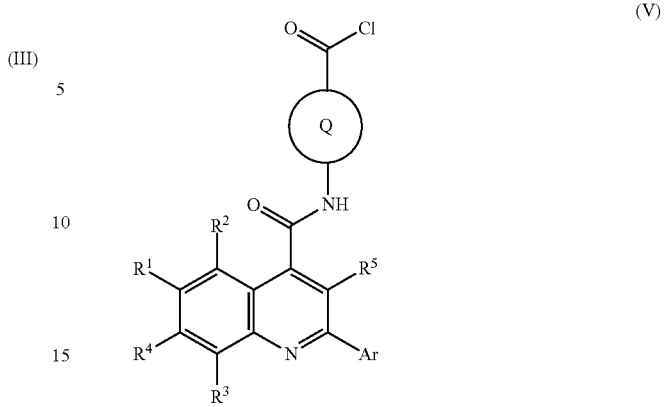

(V)

and the latter is subsequently reacted with a compound of the formula (VI)

$$H_2N-R^6$$ (VI)

to give the carboxamide of the formula (I-B)

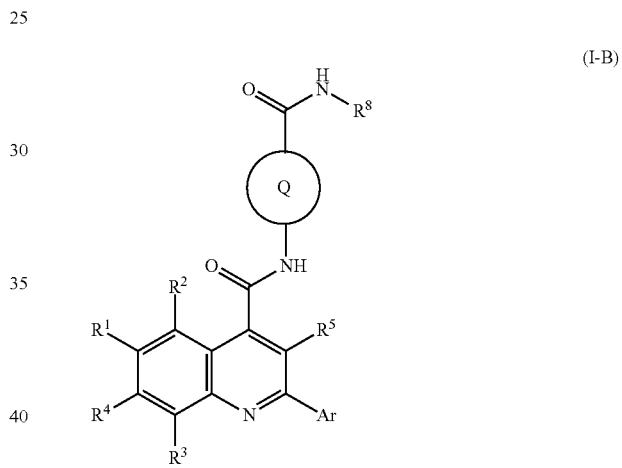

(I-B)

and the compounds of the formulae (I-A) and (I-B) thus obtained are optionally converted with the appropriate (i) solvents and/or (ii) bases or acids to the solvates, salts and/or solvates of the salts thereof.

6. A method for treatment of idiopathic pulmonary fibrosis, pulmonary hypertension, bronchiolitis obliterans syndrome, inflammatory and fibrotic skin and eye disorders and fibrotic disorders of the internal organs in humans and animals by administration of an effective amount of a medicament comprising at least one compound as defined in claim 1.

7. A medicament comprising a compound as defined in claim 1 in combination with one or more inert, nontoxic, pharmaceutically suitable excipients.

8. A medicament comprising a compound as defined in claim 1 in combination with one or more further active ingredients selected from the group consisting of PDE 5 inhibitors, sGC activators, sGC stimulators, prostacyclin analogs, IP receptor agonists, endothelin antagonists, compounds that inhibit the signal transduction cascade and pirfenidone.

9. A method for treatment of idiopathic pulmonary fibrosis, pulmonary hypertension, bronchiolitis obliterans syndrome, inflammatory and fibrotic skin and eye disorders and fibrotic disorders of the internal organs in humans and animals by administration of an effective amount of a medicament of claim 7.

10. A method for treatment of idiopathic pulmonary fibrosis, pulmonary hypertension, bronchiolitis obliterans syndrome, inflammatory and fibrotic skin and eye disorders and fibrotic disorders of the internal organs in humans and animals by administration of an effective amount of at least one compound as defined in claim 1.

11. The process of claim 5 wherein T represents $(C_1$-$C_4)$-alkyl, benzyl or 4-methylphenylsulfonylethyl.

12. A medicament comprising a compound as defined in claim 2 in combination with one or more inert, nontoxic, pharmaceutically suitable excipients.

13. A medicament comprising a compound as defined in claim 3 in combination with one or more inert, nontoxic, pharmaceutically suitable excipients.

14. A medicament comprising a compound as defined in claim 4 in combination with one or more inert, nontoxic, pharmaceutically suitable excipients.

15. A medicament comprising a compound as defined in claim 2 in combination with one or more further active ingredients selected from the group consisting of PDE 5 inhibitors, sGC activators, sGC stimulators, prostacyclin analogs, IP receptor agonists, endothelin antagonists, compounds that inhibit the signal transduction cascade and pirfenidone.

16. A medicament comprising a compound as defined in claim 3 in combination with one or more further active ingredients selected from the group consisting of PDE 5 inhibitors, sGC activators, sGC stimulators, prostacyclin analogs, IP receptor agonists, endothelin antagonists, compounds that inhibit the signal transduction cascade and pirfenidone.

17. A medicament comprising a compound as defined in claim 4 in combination with one or more further active ingredients selected from the group consisting of PDE 5 inhibitors, sGC activators, sGC stimulators, prostacyclin analogs, IP receptor agonists, endothelin antagonists, compounds that inhibit the signal transduction cascade and pirfenidone.

18. Compound according to claim 1 which is 4-{[(6-bromo-3-methyl-2-phenylquinolin-4-yl)carbonyl] amino}bicyclo[2.2.2]octane-1-carboxylic acid having the formula

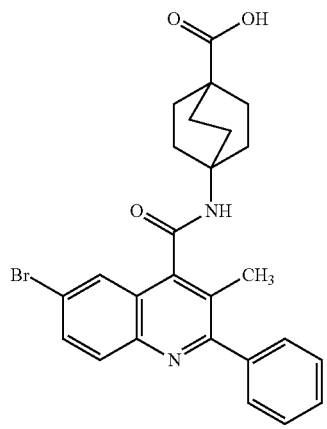

and the salts, solvates and solvates of the salts thereof.

19. Compound according to claim 1 which is 4-{[(6-bromo-3-chloro-2-phenylquinolin-4-yl)carbonyl] annino}bicyclo[2.2.2]octane-1-carboxylic acid having the formula

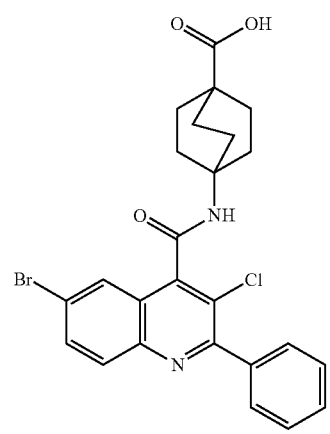

and the salts, solvates and solvates of the salts thereof.

20. Compound according to claim 1 which is 4-{[(6-bromo-3-cyclopropyl-2-phenylquinolin-4-yl)carbonyl] amino}bicyclo[2.2.2]octane-1-carboxylic acid having the formula

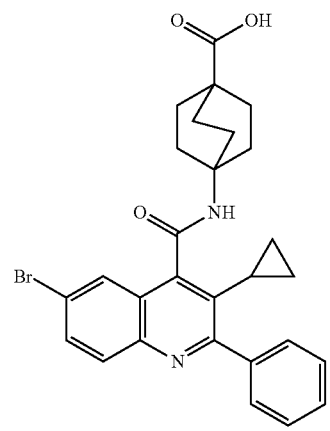 [SMILES: O=C(NC12CCC(C(=O)O)(CC1)CC2)c1c(C2CC2)c(-c2ccccc2)nc2ccc(Br)cc12]

and the salts, solvates and solvates of the salts thereof.

* * * * *